United States Patent
Lee et al.

(10) Patent No.: US 12,004,417 B2
(45) Date of Patent: Jun. 4, 2024

(54) HETEROCYCLIC COMPOUND AND LIGHT-EMITTING DEVICE INCLUDING SAME

(71) Applicant: Samsung Display Co., Ltd., Yongin-si (KR)

(72) Inventors: Yeseul Lee, Yongin-si (KR); Soobyung Ko, Yongin-si (KR); Hyeongmin Kim, Yongin-si (KR); Heechoon Ahn, Yongin-si (KR); Hyunah Um, Yongin-si (KR); Yirang Im, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 654 days.

(21) Appl. No.: 17/146,977

(22) Filed: Jan. 12, 2021

(65) Prior Publication Data

US 2021/0391546 A1  Dec. 16, 2021

(30) Foreign Application Priority Data

Jun. 9, 2020 (KR) .......................... 10-2020-0069844

(51) Int. Cl.
*H10K 85/40* (2023.01)
*C07D 401/04* (2006.01)
(Continued)

(52) U.S. Cl.
CPC ........... *H10K 85/40* (2023.02); *C07D 401/04* (2013.01); *C09K 11/06* (2013.01); *H10K 50/12* (2023.02);
(Continued)

(58) Field of Classification Search
CPC .. H10K 85/40; H10K 85/654; H10K 85/6572; H10K 85/6574; H10K 85/6576;
(Continued)

(56) References Cited

U.S. PATENT DOCUMENTS

2011/0309345 A1  12/2011  Balaganesan et al.
2020/0091436 A1  3/2020  Sun et al.

FOREIGN PATENT DOCUMENTS

CN  109206416 A    1/2019
CN  109438350 A  *  3/2019  ........... C07D 221/20
(Continued)

OTHER PUBLICATIONS

Li, Wei et al., "Adamantane-Substituted Acridine Donor for Blue Dual Fluorescence and Efficient Organic Light-Emitting Diodes", Agnew Chem. Int. Ed., 2019, p. 582-586, vol. 58 (2), Wiley Online Library.

*Primary Examiner* — Ruiyun Zhang
(74) *Attorney, Agent, or Firm* — Lewis Roca Rothgerber Christie LLP

(57) ABSTRACT

A heterocyclic compound is represented by Formula 1. A light-emitting device may include a first electrode, a second electrode facing the first electrode, and an interlayer between the first electrode and the second electrode and including an emission layer, and the light-emitting device may include at least one heterocyclic compound represented by Formula 1. In Formula 1, the substituents are the same as defined in the detailed description.

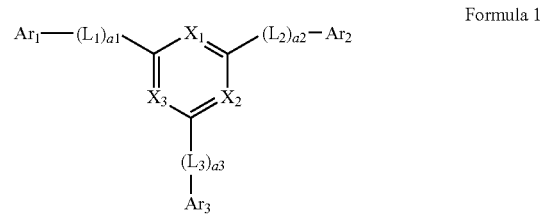

20 Claims, 3 Drawing Sheets

(51) Int. Cl.
*C09K 11/06* (2006.01)
*H10K 50/12* (2023.01)
*H10K 85/60* (2023.01)
*H10K 50/15* (2023.01)
*H10K 50/16* (2023.01)
*H10K 50/17* (2023.01)
*H10K 50/18* (2023.01)

(52) U.S. Cl.
CPC ....... *H10K 85/654* (2023.02); *H10K 85/6572* (2023.02); *H10K 85/6574* (2023.02); *H10K 85/6576* (2023.02); *C09K 2211/1029* (2013.01); *C09K 2211/1044* (2013.01); *C09K 2211/1059* (2013.01); *H10K 50/15* (2023.02); *H10K 50/16* (2023.02); *H10K 50/171* (2023.02); *H10K 50/18* (2023.02)

(58) Field of Classification Search
CPC ...... H10K 50/12; C07D 401/04; C09K 11/06; C09K 2211/1029; C09K 2211/1044; C09K 2211/1059
USPC .................................. 428/917, 670; 257/40
See application file for complete search history.

(56) References Cited

FOREIGN PATENT DOCUMENTS

| | | | | |
|---|---|---|---|---|
| CN | 109438350 A | | 3/2019 | |
| CN | 110724129 A | * | 1/2020 | ........... C07D 401/10 |
| JP | 2016-9824 A | | 1/2016 | |

* cited by examiner

HETEROCYCLIC COMPOUND AND LIGHT-EMITTING DEVICE INCLUDING SAME

CROSS-REFERENCE TO RELATED APPLICATION

This application claims priority to and the benefit of Korean Patent Application No. 10-2020-0069844, filed on Jun. 9, 2020, in the Korean Intellectual Property Office, the disclosure of which is incorporated by reference herein in its entirety.

BACKGROUND

1. Field

One or more embodiments relate to a heterocyclic compound and a light-emitting device including the heterocyclic compound.

2. Description of Related Art

Light-emitting devices are devices that convert electrical energy into light energy. Examples of such light-emitting devices include organic light-emitting devices utilizing organic materials for an emission layer, quantum dot light-emitting devices utilizing quantum dots for an emission layer, and the like.

Light-emitting devices may include a first electrode on a substrate, and a hole transport region, an emission layer, an electron transport region, and a second electrode sequentially stacked on the first electrode. Holes provided from the first electrode may move toward the emission layer through the hole transport region, and electrons provided from the second electrode may move toward the emission layer through the electron transport region. Carriers, such as holes and electrons, recombine in the emission layer to produce excitons. These excitons transit from an excited state to a ground state to thereby generate light.

SUMMARY

An aspect according to one or more embodiments is directed toward a light-emitting device having improved efficiency and high maximum quantum efficiency.

Additional aspects will be set forth in part in the description which follows and, in part, will be apparent from the description, or may be learned by practice of the presented embodiments of the disclosure.

According to one or more embodiments, a heterocyclic compound may be represented by Formula 1:

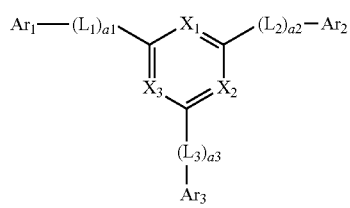

Formula 1

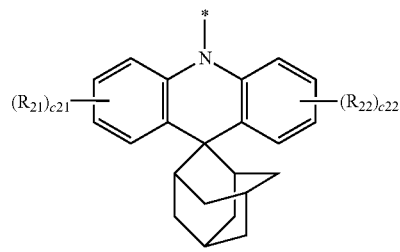

Formula 2 wherein, in Formulae 1 and 2, $X_1$ may be N or C-$(L_4)_{a4}$-$(R_1)_{c1}$, $X_2$ may be N or C-$(L_5)_{a5}$-$(R_2)_{c2}$, and $X_3$ may be N or C-$(L_6)_{a6}$-$(R_3)_{c3}$, provided that at least one of $X_1$ to $X_3$ may be N, $L_1$ to $L_6$ may each independently be a single bond, a $C_5$-$C_{60}$ carbocyclic group unsubstituted or substituted with at least one $R_{10a}$, or a $C_1$-$C_{60}$ heterocyclic group unsubstituted or substituted with at least one $R_{10a}$, a1 to a6 may each independently be an integer from 1 to 5, $Ar_1$ to $Ar_3$ may each independently be a group represented by Formula 2, hydrogen, deuterium, —F, —Cl, —Br, —I, a hydroxyl group, a cyano group, a nitro group, an amino group, an amidino group, a hydrazino group, a hydrazono group, a carboxylic acid group or a salt thereof, a sulfonic acid group or a salt thereof, a phosphoric acid group or a salt thereof, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{10}$ cycloalkyl group unsubstituted or substituted with at least one $R_{10a}$, a $C_1$-$C_{10}$ heterocycloalkyl group unsubstituted or substituted with at least one $R_{10a}$, a $C_3$-$C_{10}$ cycloalkenyl group unsubstituted or substituted with at least one $R_{10a}$, a $C_1$-$C_{10}$ heterocycloalkenyl group unsubstituted or substituted with at least one $R_{10a}$, a $C_6$-$C_{60}$ aryl group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, a $C_1$-$C_{60}$ heteroaryl group unsubstituted or substituted with at least one $R_{10a}$, a monovalent non-aromatic condensed polycyclic group unsubstituted or substituted with at least one $R_{10a}$, a monovalent non-aromatic condensed heteropolycyclic group unsubstituted or substituted with at least one $R_{10a}$, —Si($Q_1$)($Q_2$)($Q_3$), —N($Q_1$)($Q_2$), —B($Q_1$)($Q_2$), —S(=O)$_2$($Q_1$), or —P(=O)($Q_1$)($Q_2$), provided that at least one of $Ar_1$ to $Ar_3$ may be the group represented by Formula 2, $R_1$ to $R_3$, $R_{21}$, and $R_{22}$ may each independently be hydrogen, deuterium, —F, —Cl, —Br, —I, a hydroxyl group, a cyano group, a nitro group, an amino group, an amidino group, a hydrazino group, a hydrazono group, a carboxylic acid group or a salt thereof, a sulfonic acid group or a salt thereof, a phosphoric acid group or a salt thereof, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{10}$ cycloalkyl group unsubstituted or substituted with at least one $R_{10a}$, a $C_1$-$C_{10}$ heterocycloalkyl group unsubstituted or substituted with at least one $R_{10a}$, a $C_3$-$C_{10}$ cycloalkenyl group unsubstituted or substituted with at least one $R_{10a}$, a $C_1$-$C_{10}$ heterocycloalkenyl group unsubstituted or substituted with at least one $R_{10a}$, a $C_6$-$C_{60}$ aryl group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, a $C_1$-$C_{60}$ heteroaryl group unsubstituted or substituted with at least one $R_{10a}$, a monovalent non-aromatic condensed polycyclic group unsubstituted or substituted with at least one $R_{10a}$, a monovalent non-aromatic condensed heteropolycyclic group unsubstituted or substituted with at least one $R_{10a}$, —Si($Q_1$)($Q_2$)($Q_3$), —N($Q_1$)($Q_2$), —B($Q_1$)($Q_2$), —S(=O)$_2$($Q_1$), or —P(=O)($Q_1$)($Q_2$), c1 to c3 may each independently be an integer from 1 to 5, provided that when $Ar_1$ may be the group represented by Formula 2, and *-($L_2$)$_{a2}$-$Ar_2$ and *-($L_3$)$_{a3}$-$Ar_3$ may each be a substituted or unsubstituted phenyl group, $L_1$ may be a single bond, when $Ar_2$ may be the group represented by Formula 2, and *-($L_1$)$_{a1}$-$Ar_1$ and *-($L_3$)$_{a3}$-$Ar_3$ may each be a substituted or unsubstituted phenyl group, $L_2$ may be a single bond, and when $Ar_3$ may be the group represented by Formula 2, and *-($L_1$)$_{a1}$-$Ar_1$ and *-($L_2$)$_{a2}$-$Ar_2$ may each be a substituted or unsubstituted phenyl group, $L_3$ may be a single bond, and $R_{10a}$ may be:

deuterium (-D), —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), —P(=O)($Q_{11}$)($Q_{12}$), or any combination thereof;

a $C_3$-$C_{60}$ carbocyclic group, a $C_1$-$C_{60}$ heterocyclic group, a $C_6$-$C_{60}$ aryloxy group, or a $C_6$-$C_{60}$ arylthio group, each unsubstituted or substituted with deuterium, —F, —Cl, —Br, —I, a hydroxyl group, a cyano group, a nitro group, a $C_1$-$C_{30}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), —P(=O)($Q_{21}$)($Q_{22}$), or any combination thereof; or —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$), wherein $Q_1$ to $Q_3$, $Q_{11}$ to $Q_{13}$, $Q_{21}$ to $Q_{23}$, and $Q_{31}$ to $Q_{33}$ may each independently be hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; or a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{30}$ alkoxy group, a phenyl group, a biphenyl group, or any combination thereof, and

* indicates a binding site to an adjacent atom.

According to one or more embodiments, a light-emitting device may include a first electrode, a second electrode facing the first electrode, and an interlayer between the first electrode and the second electrode and including an emission layer, and the light-emitting device may include at least one heterocyclic compound.

BRIEF DESCRIPTION OF THE DRAWINGS

The above and other aspects, features, and enhancements of certain embodiments of the disclosure will be more apparent from the following description taken in conjunction with the accompanying drawings, in which.

DETAILED DESCRIPTION

Figure 1:
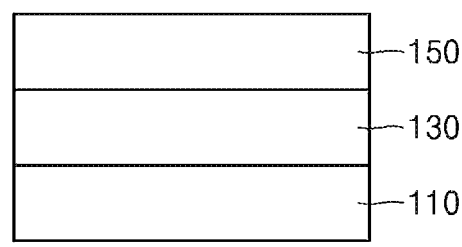
FIG. 1 is a schematic cross-sectional view of a light-emitting device according to an embodiment.

Reference will now be made in more detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Throughout the disclosure, the expression "at least one of a, b or c" indicates only a, only b, only c, both a and b, both a and c, both b and c, all of a, b, and c, or variations thereof.

As the subject matter of the present disclosure allows for various suitable changes and numerous embodiments, particular embodiments will be illustrated in the drawings and described in more detail in the written description. Effects, features, and a method of achieving the subject matter of the present disclosure will be obvious by referring to example embodiments of the present disclosure with reference to the attached drawings. The subject matter of the present disclosure may, however, be embodied in many different forms and should not be construed as being limited to the embodiments set forth herein.

Hereinafter, the subject matter of the present disclosure will be described in more detail by explaining example embodiments with reference to the attached drawings. Like reference numerals in the drawings denote like elements, and thus their description will be omitted.

In the embodiments described in the present specification, an expression used in the singular encompasses the expression of the plural, unless it has a clearly different meaning in the context.

In the present specification, it is to be understood that the terms such as "including," "having," and "comprising" are intended to indicate the existence of the features or components disclosed in the specification, and are not intended to preclude the possibility that one or more other features or components may exist or may be added.

It will be understood that when a layer, region, or component is referred to as being "on" or "onto" another layer, region, or component, it may be directly or indirectly formed over the other layer, region, or component. That is, for example, intervening layers, regions, or components may be present.

Sizes of components in the drawings may be exaggerated for convenience of explanation. In other words, because sizes and thicknesses of components in the drawings are arbitrarily illustrated for convenience of explanation, the following embodiments are not limited thereto.

The term "interlayer" as used herein refers to a single layer and/or a plurality of layers (e.g., all layers) located between a first electrode and a second electrode in a light-emitting device.

A heterocyclic compound may be represented by Formula 1:

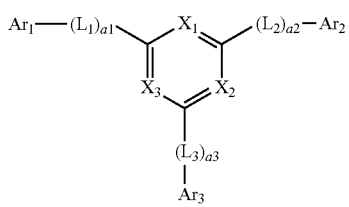

Formula 1

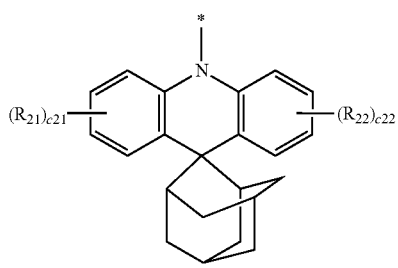

Formula 2 wherein, in Formula 1, $X_1$ may be N or $C$-$(L_4)_{a4}$-$(R_1)_{c1}$, $X_2$ may be N or $C$-$(L_5)_{a5}$-$(R_2)_{c2}$, and $X_3$ may be N or $C$-$(L_6)_{a6}$-$(R_3)_{c3}$, provided that at least one of $X_1$ to $X_3$ may be N.

In some embodiments, in Formula 1, $X_1$ to $X_3$ may each be N, $X_1$ and $X_2$ may each be N, and $X_3$ may be $C$-$(L_6)_{a6}$-$(R_3)_{c3}$, $X_1$ and $X_3$ may each be N, and $X_2$ may be $C$-$(L_5)_{a5}$-$(R_2)_{c2}$, or $X_2$ and $X_3$ may each be N, and $X_1$ may be $C$-$(L_4)_{a4}$-$(R_1)_{c1}$.

In Formula 1, $L_1$ to $L_6$ may each independently be a single bond, a $C_5$-$C_{60}$ carbocyclic group unsubstituted or substituted with at least one $R_{10a}$, or a $C_1$-$C_{60}$ heterocyclic group unsubstituted or substituted with at least one $R_{10a}$.

In an embodiment, in Formula 1, $L_1$ to $L_6$ may each independently be:

a single bond; or a benzene group, a pentalene group, an indene group, a naphthalene group, an azulene group, a heptalene group, an indacene group, an acenaphthalene group, a fluorene group, a spiro-bifluorene group, a spiro-benzofluorene-fluorene group, a benzofluorene group, a dibenzofluorene group, a phenalene group, a phenanthrene group, an anthracene group, a fluoranthene group, a pyrene group, a chrysene group, a naphthacene group, a picene group, a perylene group, a pyrrole group, a thiophene group, a furan group, a silole group, an imidazole group, a pyrazole group, a thiazole group, an isothiazole group, an oxazole group, an isoxazole group, a pyridine group, a pyrazine group, a pyrimidine group, a pyridazine group, a triazine group, a benzofuran group, a benzothiophene group, a dibenzofuran group, a dibenzothiophene group, a carbazole group, a benzosilole group, a dibenzosilole group, a quinoline group, an isoquinoline group, a benzimidazole group, an imidazopyridine group, or an imidazopyrimidine group, each unsubstituted or substituted with deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a spiro-benzofluorene-fluorenyl group, a benzofluorenyl group, a dibenzofluorenyl group, a phenalenyl group, a phenanthrenyl group, an anthracenyl group, a fluoranthenyl group, a pyrenyl group, a chrysenyl group, a naphthacenyl group, a picenyl group, a perylenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a triazinyl group, a benzofuranyl group, a benzothiophenyl group, a dibenzofuranyl group, a dibenzothiophenyl group, a carbazolyl group, a benzosilolyl group, a dibenzosilolyl group, a quinolinyl group, an isoquinolinyl group, a benzimidazolyl group, an imidazopyridinyl group, an imidazopyrimidinyl group, —Si$(Q_{31})(Q_{32})(Q_{33})$, —N$(Q_{31})(Q_{32})$, —B$(Q_{31})(Q_{32})$, —C$(=O)(Q_{31})$, —S$(=O)_2(Q_{31})$, —P$(=O)(Q_{31})(Q_{32})$, or any combination thereof, wherein $Q_{31}$ to $Q_{33}$ may each independently be a $C_1$-$C_{10}$ alkyl group, a $C_1$-$C_{10}$ alkoxy group, a phenyl group, a biphenyl group, a terphenyl group, a naphthyl group, or a phenyl group substituted with a cyano group.

In some embodiments, in Formula 1, $L_1$ to $L_6$ may each independently be a single bond or a group represented by one of Formulae 3-1 to 3-24:

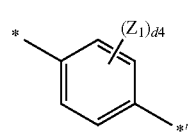

3-1

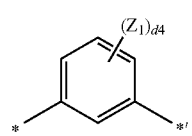

3-2

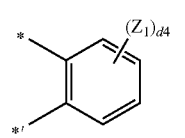

3-3

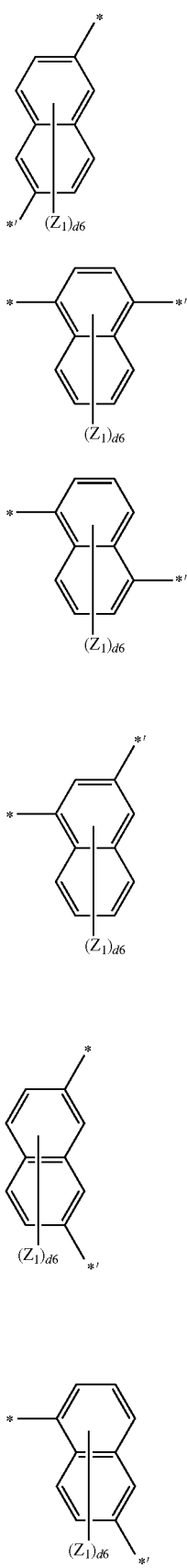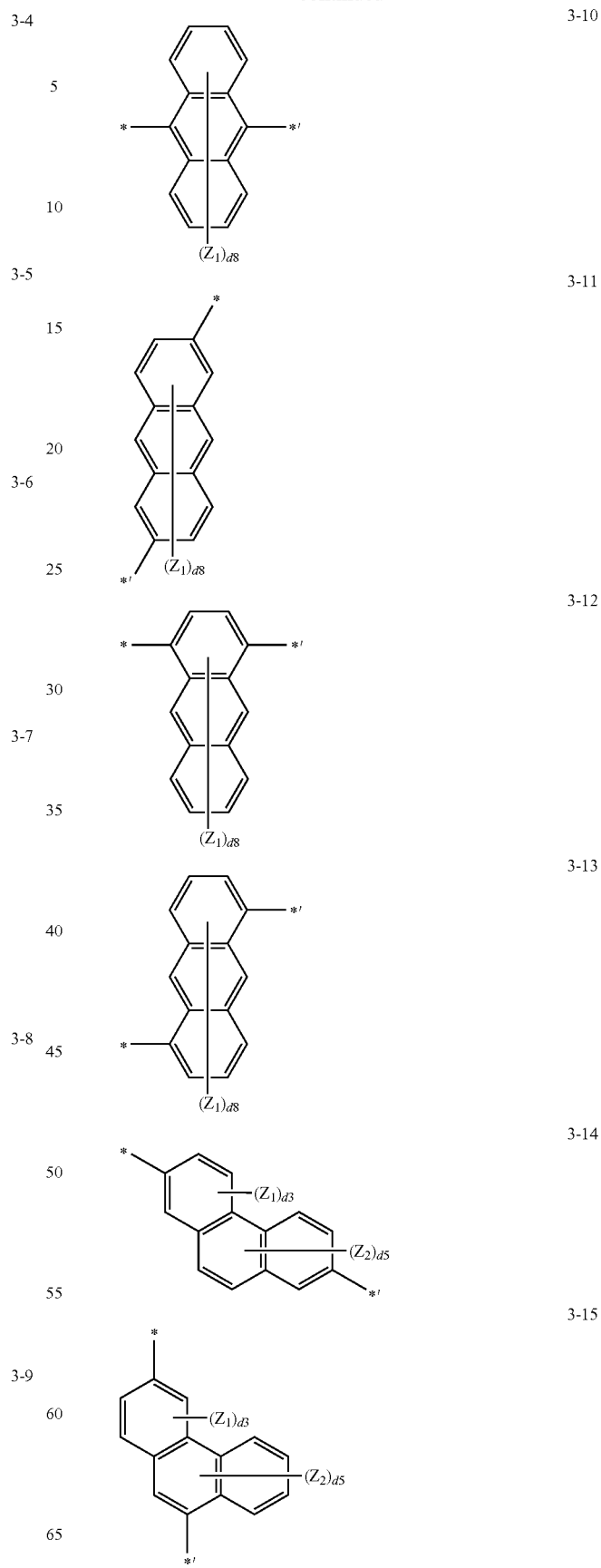

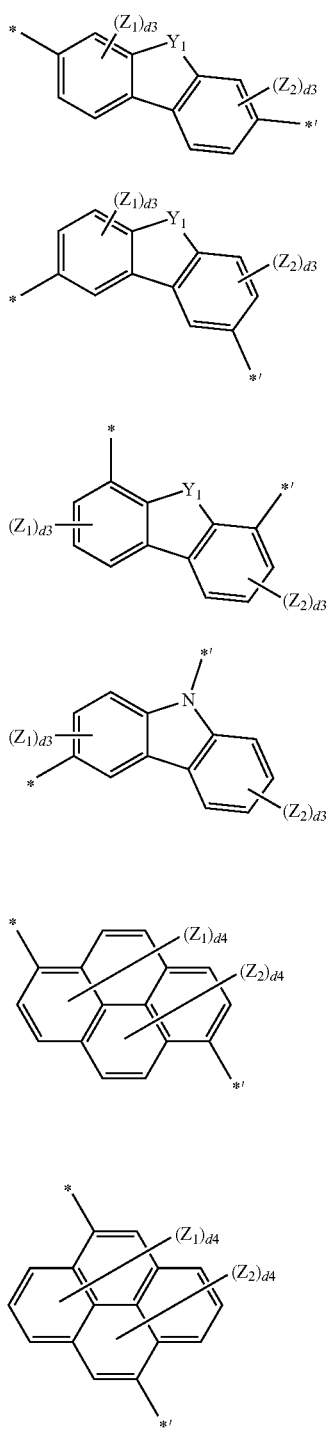

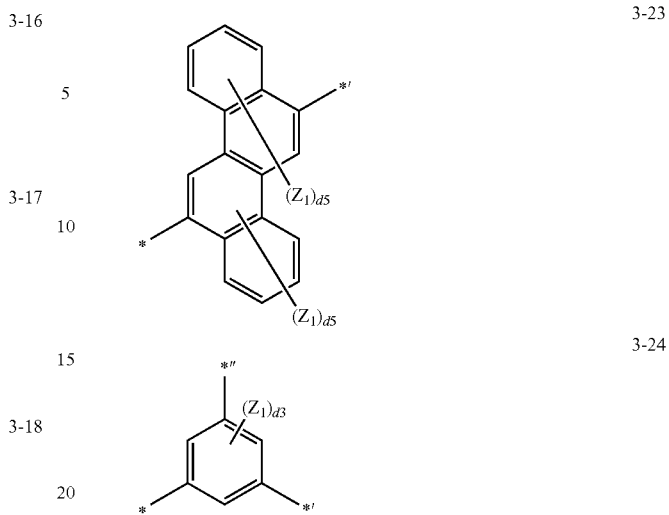

wherein, in Formulae 3-1 to 3-24,
Y$_1$ may be O, S, C(Z$_3$)(Z$_4$), N(Z$_5$), or Si(Z$_6$)(Z$_7$),
Z$_1$ to Z$_7$ may each independently be hydrogen, deuterium, —F, —Cl, —Br, —I, a hydroxyl group, a cyano group, a nitro group, an amidino group, a hydrazino group, a hydrazono group, a C$_1$-C$_{20}$ alkyl group, a C$_1$-C$_{20}$ alkoxy group, a phenyl group, a biphenyl group, a terphenyl group, a naphthyl group, a fluorenyl group, a spiro-bifluorenyl group, a spiro-benzofluorene-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a triazinyl group, a benzofuranyl group, a benzothiophenyl group, a dibenzofuranyl group, a dibenzothiophenyl group, a carbazolyl group, a benzosilolyl group, a dibenzosilolyl group, a quinolinyl group, an isoquinolinyl group, a benzimidazolyl group, —Si(Q$_{31}$)(Q$_{32}$)(Q$_{33}$), —N(Q$_{31}$)(Q$_{32}$), or —B(Q$_{31}$)(Q$_{32}$),
wherein Q$_{31}$ to Q$_{33}$ may each independently be a C$_1$-C$_{10}$ alkyl group, a C$_1$-C$_{10}$ alkoxy group, a phenyl group, a biphenyl group, a terphenyl group, a naphthyl group, or a phenyl group substituted with a cyano group,
d3 may be an integer from 0 to 3,
d4 may be an integer from 0 to 4,
d5 may be an integer from 0 to 5,
d6 may be an integer from 0 to 6,
d8 may be an integer from 0 to 8, and
and *' each indicate a binding site to an adjacent atom.

In some embodiments, in Formula 1, L$_1$ to L$_6$ may each independently be a single bond or a group represented by one of Formulae 4-1 to 4-5:

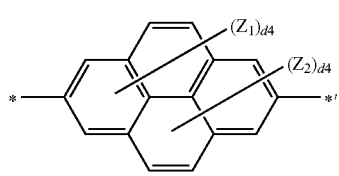

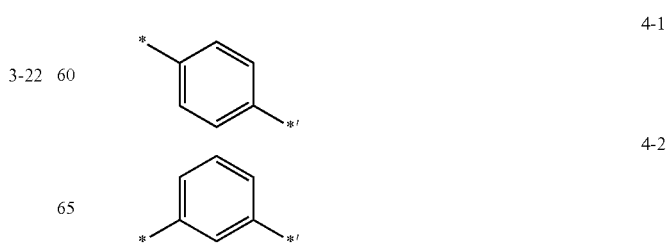

-continued

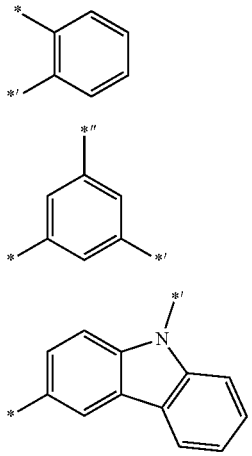

4-3

4-4

4-5 wherein, in Formulae 4-1 to 4-5,
and *' each indicate a binding site to an adjacent atom.

In some embodiments, in Formula 1, when $Ar_1$ is a group represented by Formula 2, $L_1$ may be a single bond,
when $Ar_2$ is a group represented by Formula 2, $L_2$ may be a single bond, and
when $Ar_3$ is a group represented by Formula 2, $L_3$ may be a single bond.

In Formula 1, a1 to a6 may each independently be an integer from 1 to 5. when a1 is 2 or greater, at least two $L_1(s)$ may be identical to or different from each other, when a2 is 2 or greater, at least two $L_2(s)$ may be identical to or different from each other, when a3 is 2 or greater, at least two $L_3(s)$ may be identical to or different from each other, when a4 is 2 or greater, at least two $L_4(s)$ may be identical to or different from each other, when a5 is 2 or greater, at least two $L_5(s)$ may be identical to or different from each other, and when a6 is 2 or greater, at least two $L_6(s)$ may be identical to or different from each other. For example, when a1 is 2 or greater, the two or more $L_1(s)$ may be identical to or different from each other, when a2 is 2 or greater, the two or more $L_2(s)$ may be identical to or different from each other, when a3 is 2 or greater, the two or more $L_3(s)$ may be identical to or different from each other, when a4 is 2 or greater, the two or more U(s) may be identical to or different from each other, when a5 is 2 or greater, the two or more $L_5(s)$ may be identical to or different from each other, and when a6 is 2 or greater, the two or more $L_6(s)$ may be identical to or different from each other.

In some embodiments, a1 to a6 may each independently be 0, 1, or 2.

In Formula 1, $Ar_1$ to $Ar_3$ may each independently be a group represented by Formula 2, hydrogen, deuterium, —F, —Cl, —Br, —I, a hydroxyl group, a cyano group, a nitro group, an amino group, an amidino group, a hydrazino group, a hydrazono group, a carboxylic acid group or a salt thereof, a sulfonic acid group or a salt thereof, a phosphoric acid group or a salt thereof, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{10}$ cycloalkyl group unsubstituted or substituted with at least one $R_{10a}$, a $C_1$-$C_{10}$ heterocycloalkyl group unsubstituted or substituted with at least one $R_{10a}$, a $C_3$-$C_{10}$ cycloalkenyl group unsubstituted or substituted with at least one $R_{10a}$, a $C_1$-$C_{10}$ heterocycloalkenyl group unsubstituted or substituted with at least one $R_{10a}$, a $C_6$-$C_{60}$ aryl group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, a $C_1$-$C_{60}$ heteroaryl group unsubstituted or substituted with at least one $R_{10a}$, a monovalent non-aromatic condensed polycyclic group unsubstituted or substituted with at least one $R_{10a}$, a monovalent non-aromatic condensed heteropolycyclic group unsubstituted or substituted with at least one $R_{10a}$, —Si($Q_1$)($Q_2$)($Q_3$), —N($Q_1$)($Q_2$), —B($Q_1$)($Q_2$), —S(=O)$_2$($Q_1$), or —P(=O)($Q_1$)($Q_2$), provided that at least one of $Ar_1$ to $Ar_3$ may be the group represented by Formula 2.

Provided that when $Ar_1$ may be the group represented by Formula 2, and *-$(L_2)_{a2}$-$Ar_2$ and *-$(L_3)_{a3}$-$Ar_3$ may each be a substituted or unsubstituted phenyl group, $L_1$ may be a single bond,
when $Ar_2$ may be the group represented by Formula 2, and *-$(L_1)_{a1}$-$Ar_1$ and *-$(L_3)_{a3}$-$Ar_3$ may each be a substituted or unsubstituted phenyl group, $L_2$ may be a single bond, and
when $Ar_3$ may be the group represented by Formula 2, and *-$(L_1)_{a1}$-$Ar_1$ and *-$(L_2)_{a2}$-$Ar_2$ may each be a substituted or unsubstituted phenyl group, $L_3$ may be a single bond.

In some embodiments, in Formula 1, one or two of $Ar_1$ to $Ar_3$ may each independently be the group represented by Formula 2.

In some embodiments, in Formula 1, $Ar_1$ to $Ar_3$ may each independently be the group represented by Formula 2, a $C_1$-$C_{20}$ alkyl group, a $C_1$-$C_{20}$ alkyl group substituted with at least one phenyl group, or a $C_1$-$C_{20}$ alkoxy group;

a cyclopentyl group, a cyclohexyl group, a cycloheptyl group, a cyclopentenyl group, a cyclohexenyl group, a phenyl group, a biphenyl group, a terphenyl group, a naphthyl group, a fluorenyl group, a spiro-bifluorenyl group, a spiro-fluorene-benzofluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a triazinyl group, an indolyl group, an isoindolyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a dibenzofuranyl group, a dibenzothiophenyl group, a dibenzosilolyl group, a carbazolyl group, a benzocarbazolyl group, a dibenzocarbazolyl group, an azafluorenyl group, an azaspiro-bifluorenyl group, an azacarbazolyl group, a diazacarbazolyl group, an azadibenzofuranyl group, an azadibenzothiophenyl group, an azadibenzosilolyl group, an imidazopyridinyl group, or an imidazopyrimidinyl group, each unsubstituted or substituted with deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkyl group substituted with at least one phenyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a naphthyl group, a fluorenyl group, a spiro-bifluorenyl group, a spiro-fluorene-benzofluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a triazinyl group, an indolyl group, an isoindolyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a dibenzofuranyl group, a dibenzothiophenyl group, a dibenzosilolyl group, a carbazolyl group, a benzocarbazolyl group, a dibenzocarbazolyl group, an azafluorenyl group, an azaspiro-bifluorenyl group, an azacarbazolyl group, a diazacarbazolyl group, an azadibenzofuranyl group, an azadibenzothiophenyl group, an azadibenzosilolyl group, an imidazopyridinyl group, an imidazopyrimidinyl group, $-Si(Q_{31})(Q_{32})(Q_{33})$, $-N(Q_{31})(Q_{32})$, $-B(Q_{31})(Q_{32})$, $-C(=O)(Q_{31})$, $-S(=O)_2(Q_{31})$, $-P(=O)(Q_{31})(Q_{32})$, or any combination thereof; or $-S_1(Q_1)(Q_2)(Q_3)$, $-N(Q_1)(Q_2)$, or $-B(Q_1)(Q_2)$, wherein $Q_1$ to $Q_3$ and $Q_{31}$ to $Q_{33}$ may each independently be a $C_1$-$C_{10}$ alkyl group, a $C_1$-$C_{10}$ alkoxy group, a phenyl group, a biphenyl group, a terphenyl group, a naphthyl group, or a phenyl group substituted with a cyano group.

In some embodiments, in Formula 1, $Ar_1$ to $Ar_3$ may each independently be the group represented by Formula 2, a $C_1$-$C_{20}$ alkyl group, a $C_1$-$C_{20}$ alkyl group substituted with at least one phenyl group, a $C_1$-$C_{20}$ alkoxy group, a group represented by one of Formulae 5-1 to 5-21, or $-Si(Q_1)(Q_2)(Q_3)$:

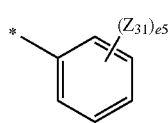
5-1

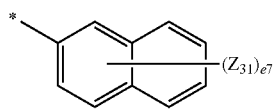
5-2

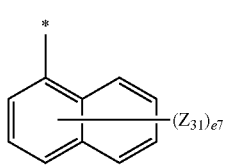
5-3

-continued

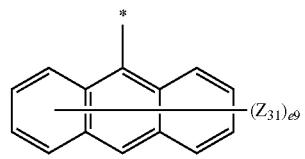
5-4

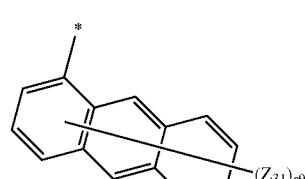
5-5

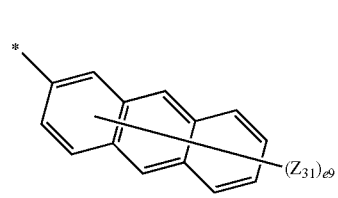
5-6

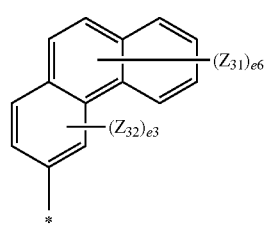
5-7

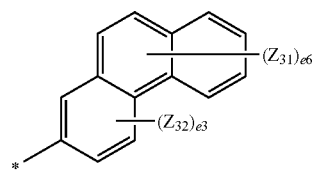
5-8

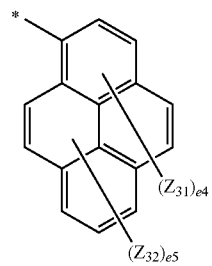
5-9

5-10

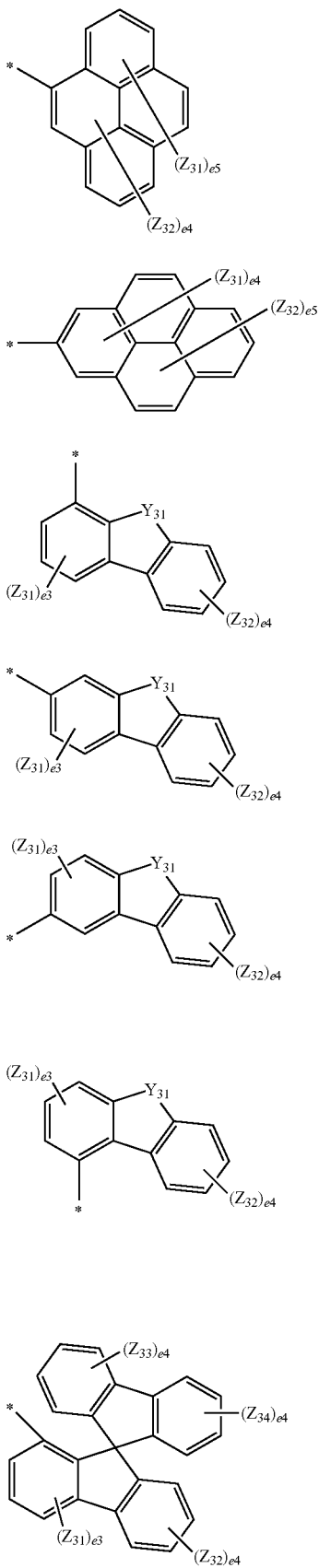
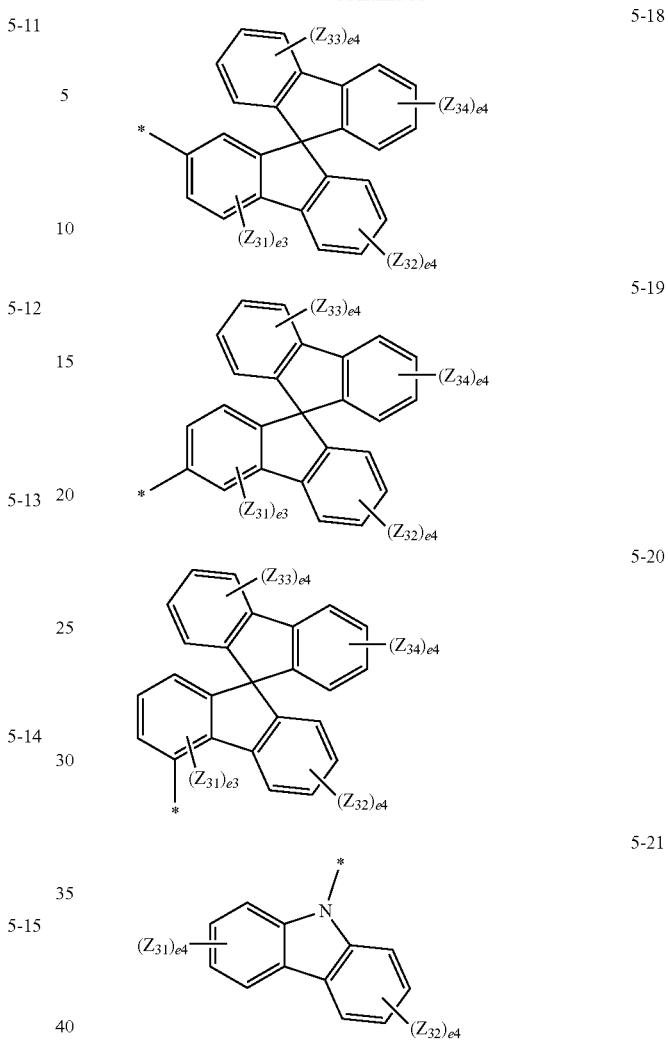

wherein, in Formulae 5-1 to 5-21, $Y_{31}$ may be O, S, $N(Z_{35})$, $C(Z_{33})(Z_{34})$, or $Si(Z_{36})(Z_{37})$, $Z_{31}$ to $Z_{37}$ may each independently be hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkyl group substituted with at least one phenyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a naphthyl group, a fluorenyl group, a spiro-bifluorenyl group, a spiro-fluorene-benzofluorenyl group, a benzofluorenyl group, a dibenzofluorenyl group, a phenalenyl group, a phenanthrenyl group, an anthracenyl group, a fluoranthenyl group, a triphenylenyl group, a pyridinyl group, a pyrimidinyl group, a pyrazinyl group, a triazinyl group, a quinolinyl group, an isoquinolinyl group, a benzoquinolinyl group, a naphthyridinyl group, a quinoxalinyl group, a quinazolinyl group, a carbazolyl group, a phenanthridinyl group, an acridinyl group, a phenanthrolinyl group, a phenazinyl group, a dibenzofuranyl group, a dibenzothiophenyl group, a dibenzosilolyl group, —$Si(Q_{31})(Q_{32})(Q_{33})$, —$N(Q_{31})(Q_{32})$, or —$B(Q_{31})(Q_{32})$, e2 may be 1 or 2, e3 may be an integer from 1 to 3, e4 may be an integer from 1 to 4, e5 may be an integer from 1 to 5, e6 may be an integer from 1 to 6, e7 may be an integer from 1 to 7, and e9 may be an integer from 1 to 9, wherein $Q_1$ to $Q_3$ and $Q_{31}$ to $Q_{33}$ may each independently be a $C_1$-$C_{10}$ alkyl group, a $C_1$-$C_{10}$ alkoxy group, a phenyl group, a biphenyl group, a terphenyl group, a naphthyl group, or a phenyl group substituted with a cyano group, and

* indicates a binding site to an adjacent atom.

In some embodiments, in Formula 1, $Ar_1$ to $Ar_3$ may each independently be the group represented by Formula 2 or a group represented by one of Formulae 6-1 to 6-61:

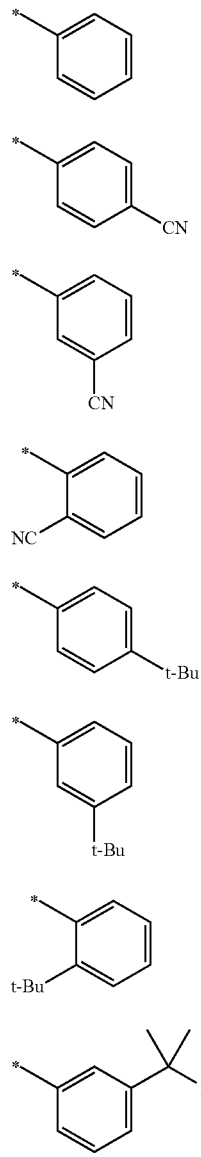

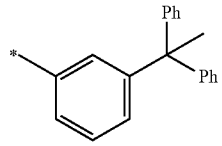

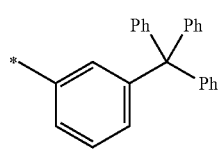

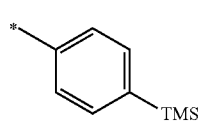

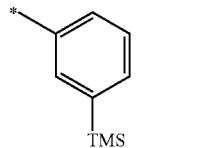

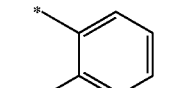

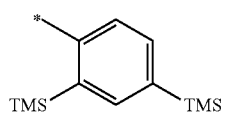

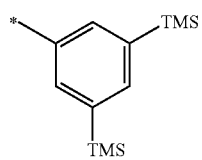

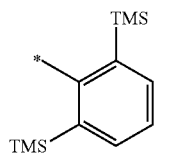

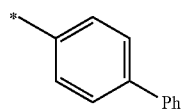

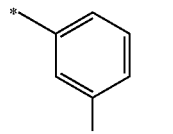

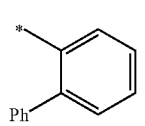

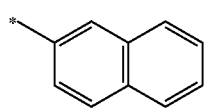 
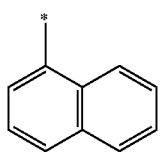 
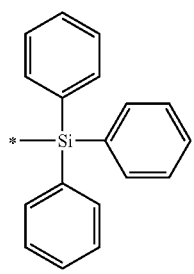 
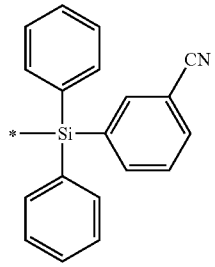 
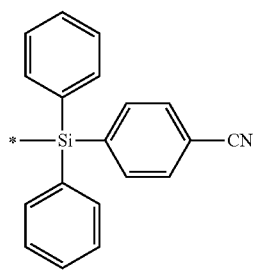 
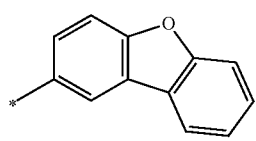 
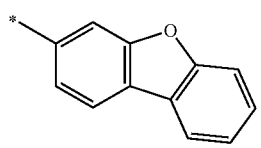 
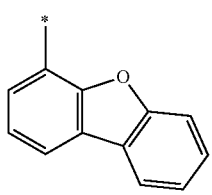 
6-20
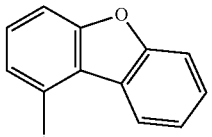
6-21
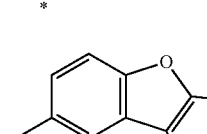
6-22
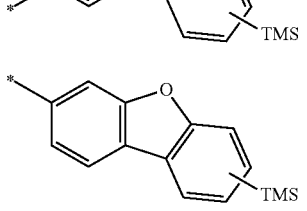
6-23
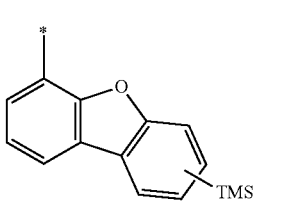
6-24
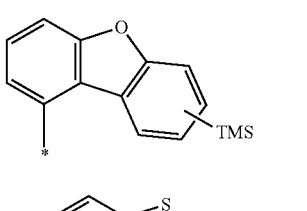
6-25
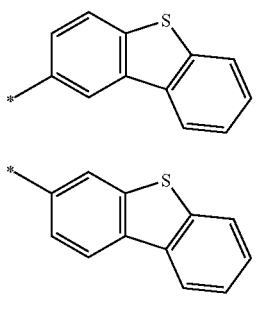
6-26
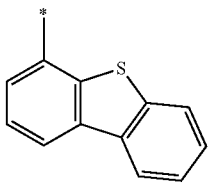
6-27
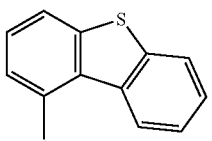
6-28
6-29
6-30
6-31
6-32
6-33
6-34
6-35
6-36
6-37
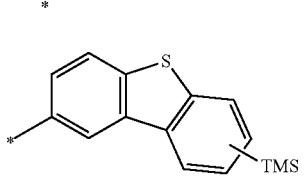

6-38, 6-39, 6-40, 6-41, 6-42, 6-43, 6-44, 6-45, 6-46, 6-47, 6-48, 6-49, 6-50, 6-51, 6-52, 6-53

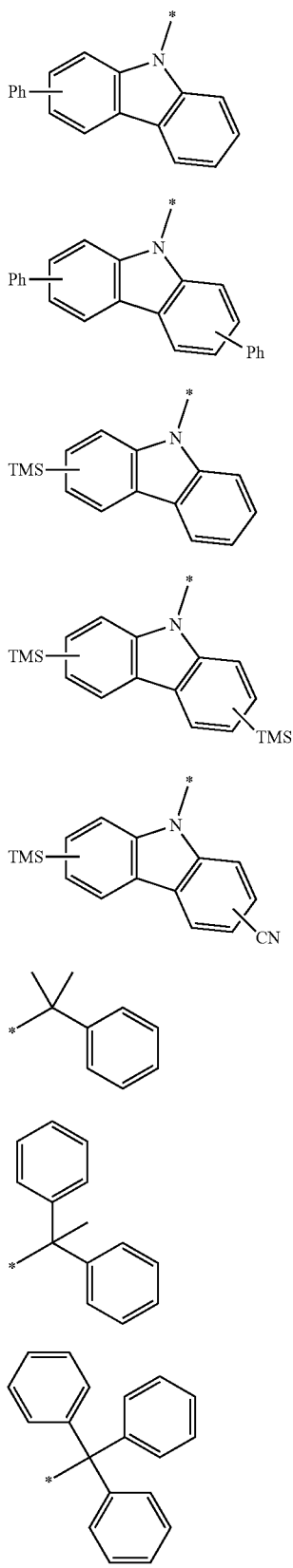

wherein, in Formulae 6-1 to 6-61,
"t-Bu" represents a tert-butyl group,

"Ph" represents a phenyl group,
"TMS" represents a trimethylsilyl group, and
* indicates a binding site to an adjacent atom.

In one or more embodiments, in Formula 1, at least one of $Ar_1$ to $Ar_3$ may be the group represented by Formula 2, at least one of the others (e.g., at least one of the remaining ones) of $Ar_1$ to $Ar_3$ may be a $C_1$-$C_{20}$ alkyl group, a $C_1$-$C_{20}$ alkyl group substituted with at least one phenyl group, or a $C_1$-$C_{20}$ alkoxy group; or a phenyl group, a dibenzofuranyl group, a dibenzothiophenyl group, or a carbazolyl group, each unsubstituted or substituted with a cyano group, a $C_1$-$C_{20}$ alkyl group, a $C_1$-$C_{20}$ alkyl group substituted with at least one phenyl group, a $C_1$-$C_{20}$ alkoxy group, a phenyl group, a dibenzofuranyl group, a dibenzothiophenyl group, a carbazolyl group, —Si($Q_{31}$)($Q_{32}$)($Q_{33}$), or any combination thereof,
wherein $Q_{31}$ to $Q_{33}$ may each independently be a $C_1$-$C_{10}$ alkyl group, a $C_1$-$C_{10}$ alkoxy group, a phenyl group, a biphenyl group, a terphenyl group, a naphthyl group, or a phenyl group substituted with a cyano group.

In Formulae 1 and 2, $R_1$ to $R_3$, $R_{21}$, and $R_{22}$ may each independently be hydrogen, deuterium, —F, —Cl, —Br, —I, a hydroxyl group, a cyano group, a nitro group, an amino group, an amidino group, a hydrazino group, a hydrazono group, a carboxylic acid group or a salt thereof, a sulfonic acid group or a salt thereof, a phosphoric acid group or a salt thereof, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{10}$ cycloalkyl group unsubstituted or substituted with at least one $R_{10a}$, a $C_1$-$C_{10}$ heterocycloalkyl group unsubstituted or substituted with at least one $R_{10a}$, a $C_3$-$C_{10}$ cycloalkenyl group unsubstituted or substituted with at least one $R_{10a}$, a $C_1$-$C_{10}$ heterocycloalkenyl group unsubstituted or substituted with at least one $R_{10a}$, a $C_6$-$C_{60}$ aryl group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, a $C_1$-$C_{60}$ heteroaryl group unsubstituted or substituted with at least one $R_{10a}$, a monovalent non-aromatic condensed polycyclic group unsubstituted or substituted with at least one $R_{10a}$, a monovalent non-aromatic condensed heteropolycyclic group unsubstituted or substituted with at least one $R_{10a}$, —Si($Q_1$)($Q_2$)($Q_3$), —N($Q_1$)($Q_2$), —B($Q_1$)($Q_2$), —S(=O)$_2$($Q_1$), or —P(=O)($Q_1$)($Q_2$).

In some embodiments, in Formulae 1 and 2, $R_1$ to $R_3$, $R_{21}$, and $R_{22}$ may each independently be hydrogen, deuterium, —F, —Cl, —Br, —I, a hydroxyl group, a cyano group, or a nitro group;
a $C_1$-$C_{20}$ alkyl group or a $C_1$-$C_{20}$ alkoxy group, each unsubstituted or substituted with deuterium, —F, —Cl, —Br, —I, a cyano group, a phenyl group, a biphenyl group, or any combination thereof;
a cyclopentyl group, a cyclohexyl group, a cycloheptyl group, a cyclopentenyl group, a cyclohexenyl group, a phenyl group, a biphenyl group, a terphenyl group, a naphthyl group, a fluorenyl group, a spiro-bifluorenyl group, a spiro-fluorene-benzofluorenyl group, a benzofluorenyl group, a dibenzofluorenyl group, a pyrenyl group, a phenalenyl group, a phenanthrenyl group, an anthracenyl group, a fluoranthenyl group, a triphenylenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzoisothiazolyl group, a benzoxazolyl group, a benzoisoxazolyl group, a triazolyl group, a tetrazolyl group, an oxadiazolyl group, a triazinyl group, a dibenzofuranyl group, a dibenzothiophenyl group, a dibenzosilolyl group, a carbazolyl group, a benzocarbazolyl group, a dibenzocarbazolyl group, a thiadiazolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, a diazacarbazolyl group, an azadibenzofuranyl group, an azadibenzothiophenyl group, or an azadibenzosilolyl group, each unsubstituted or substituted with deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a naphthyl group, a fluorenyl group, a spiro-bifluorenyl group, a spiro-fluorene-benzofluorenyl group, a benzofluorenyl group, a dibenzofluorenyl group, a pyrenyl group, a phenalenyl group, a phenanthrenyl group, an anthracenyl group, a fluoranthenyl group, a triphenylenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzoisothiazolyl group, a benzoxazolyl group, a benzoisoxazolyl group, a triazolyl group, a tetrazolyl group, an oxadiazolyl group, a triazinyl group, a dibenzofuranyl group, a dibenzothiophenyl group, a dibenzosilolyl group, a carbazolyl group, a benzocarbazolyl group, a dibenzocarbazolyl group, a thiadiazolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, a diazacarbazolyl group, an azadibenzofuranyl group, an azadibenzothiophenyl group, an azadibenzosilolyl group, or any combination thereof; or —Si($Q_1$)($Q_2$)($Q_3$), —B($Q_2$), or —B($Q_1$)($Q_2$), wherein $Q_1$ to $Q_3$ may each independently be a $C_1$-$C_{10}$ alkyl group, a $C_1$-$C_{10}$ alkoxy group, a phenyl group, a biphenyl group, a terphenyl group, or a naphthyl group.

In an embodiment, in Formula 1, $R_1$ to $R_3$ may each be hydrogen.

In an embodiment, in Formula 2, $R_{21}$ and $R_{22}$ may each be hydrogen.

In Formula 1, c1 to c3 may each independently be an integer from 1 to 5. When c1 is 2 or greater, at least two $R_1$(s) may be identical to or different from each other, when c2 is 2 or greater, at least two $R_2$(s) may be identical to or different from each other, and when c3 is 2 or greater, at least two $R_3$(s) may be identical to or different from each other. For example, when c1 is 2 or greater, the two or more $R_1$(s) may be identical to or different from each other, when c2 is 2 or greater, the two or more $R_2$(s) may be identical to or different from each other, and when c3 is 2 or greater, the two or more $R_3$(s) may be identical to or different from each other In some embodiments, c1 to c3 may each independently be 1 or 2. In some embodiments, c1 to c3 may each be 1.

In some embodiments, the heterocyclic compound may be represented by one of Formulae 1-1 to 1-6, but embodiments are not limited thereto:

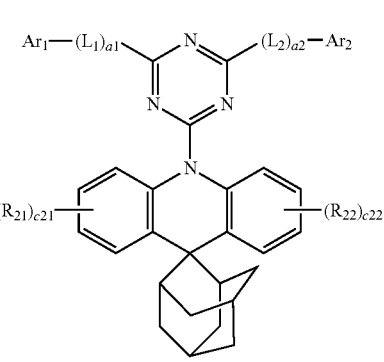

1-1

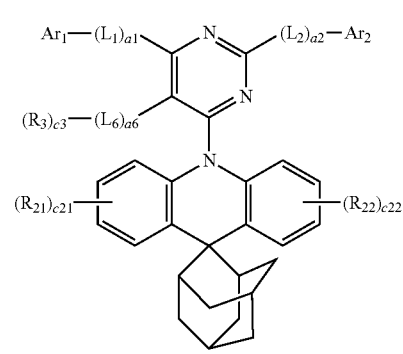

1-2

-continued 1-3
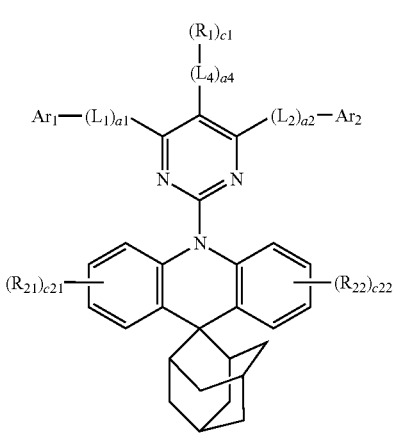

1-4
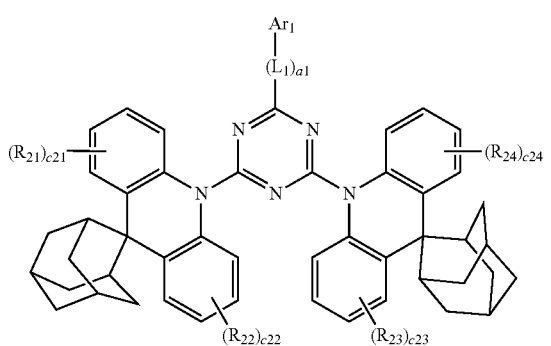

1-5
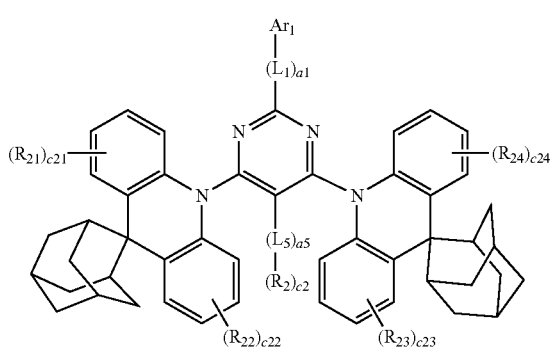

1-6
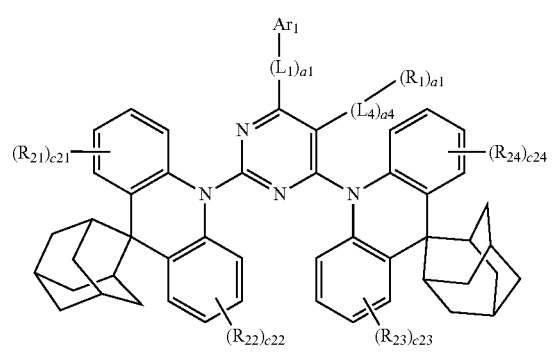

wherein, in Formulae 1-1 to 1-6, $R_{23}$ and $R_{24}$ may each independently be understood by referring to the description of $R_{21}$ provided herein, that is, $R_{23}$ and $R_{24}$ may each independently be the same as described in connection with $R_{21}$ provided herein, c23 and c24 may each independently be an integer from 1 to 4, $L_1$, $L_2$, $L_4$ to $L_6$, $Ar_1$, $Ar_2$, a1, a2, a4 to a6, $R_1$ to $R_3$, $R_{21}$, $R_{22}$, c1 to c3, c21, and c22 may respectively be understood by referring to the descriptions of $L_1$, $L_2$, $L_4$ to $L_6$, $Ar_1$, $Ar_2$, a1, a2, a4 to a6, $R_1$ to $R_3$, $R_{21}$, $R_{22}$, c1 to c3, c21, and c22 provided herein. That is, $L_1$, $L_2$, $L_4$ to $L_6$, $Ar_1$, $Ar_2$, a1, a2, a4 to a6, $R_1$ to $R_3$, $R_{21}$, $R_{22}$, c1 to c3, c21, and c22 may each independently be the same as described in connection with Formulae 1 and 2 provided herein.

In the present specification $R_{10a}$ may be:

deuterium (-D), —F, —Cl, —Br, —I, a hydroxyl group, a cyano group, or a nitro group;

a $C_1$-$C_{60}$ alkyl group, a $C_2$-$C_{30}$ alkenyl group, a $C_2$-$C_{30}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_3$-$C_{60}$ aryloxy group, a $C_3$-$C_{60}$ arylthio group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), —P(=O)($Q_{11}$)($Q_{12}$), or any combination thereof;

a $C_3$-$C_{60}$ carbocyclic group, a $C_1$-$C_{60}$ heterocyclic group, a $C_6$-$C_{60}$ aryloxy group, or a $C_6$-$C_{60}$ arylthio group, each unsubstituted or substituted with deuterium, —F, —Cl, —Br, —I, a hydroxyl group, a cyano group, a nitro group, a $C_1$-$C_{30}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), —P(=O)($Q_{21}$)($Q_{22}$), or any combination thereof; or —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$), wherein $Q_1$ to $Q_3$, $Q_{11}$ to $Q_{13}$, $Q_{21}$ to $Q_{23}$, and $Q_{31}$ to $Q_{33}$ may each independently be hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; or a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{30}$ alkoxy group, a phenyl group, a biphenyl group, or any combination thereof.

In an embodiment, the heterocyclic compound may be selected from Compounds 1 to 60, but embodiments are not limited thereto:

1
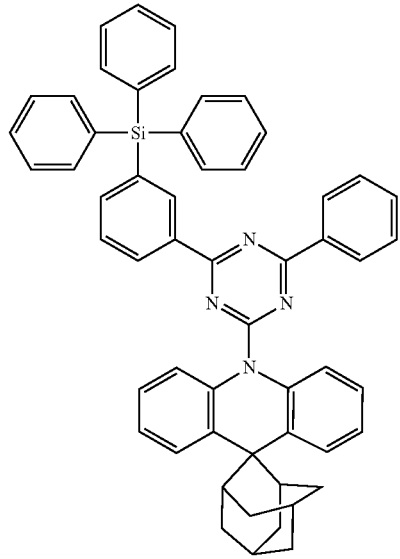
2
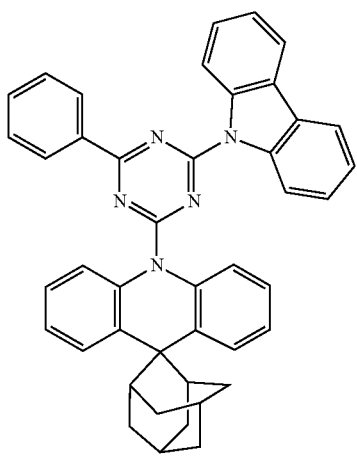
3
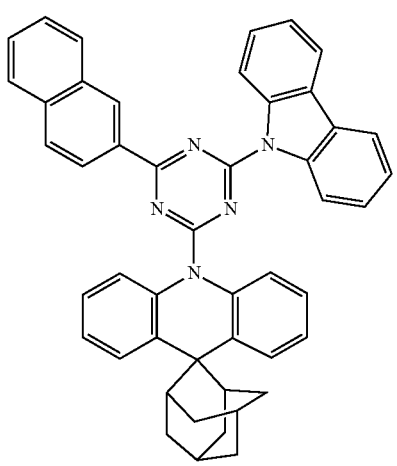
4
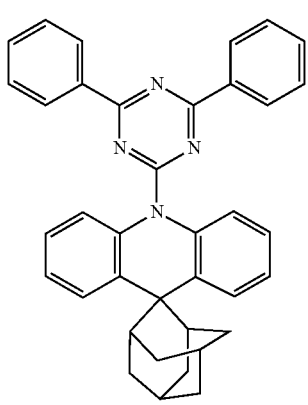
5
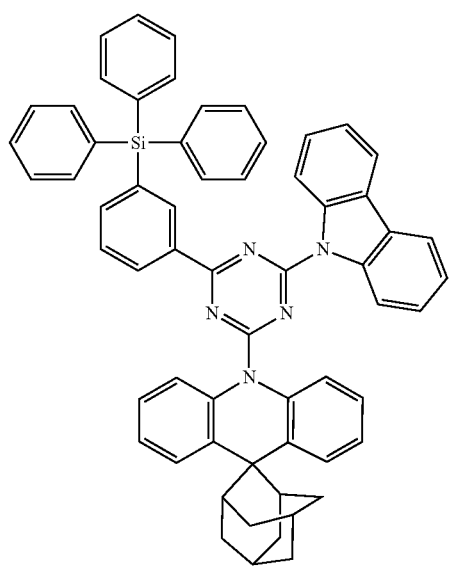

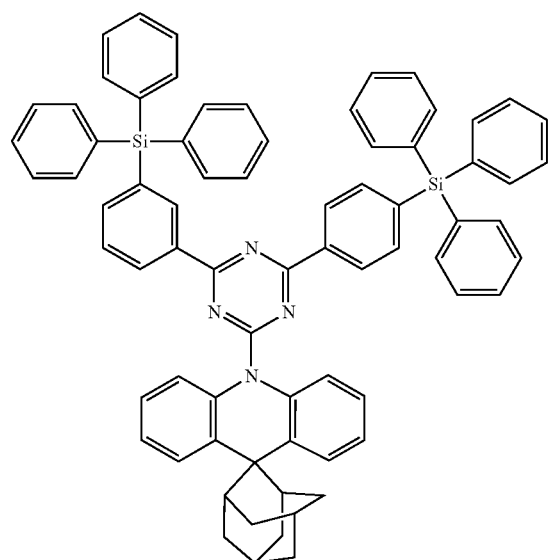
6
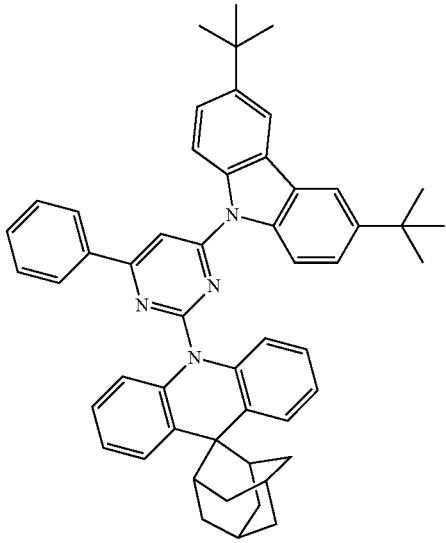
8
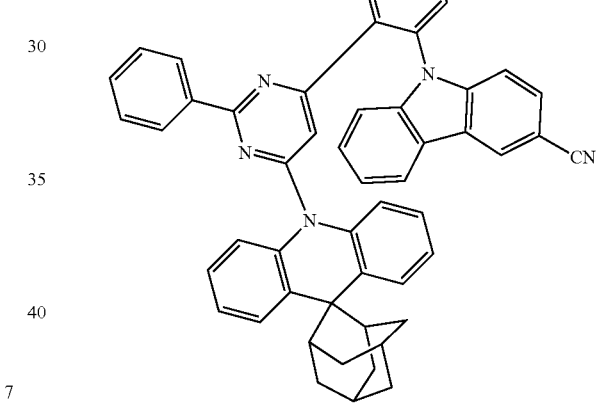
9
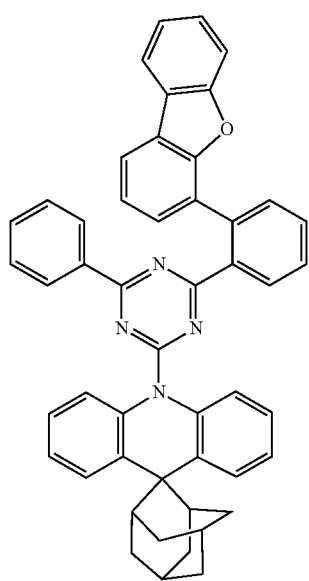
7
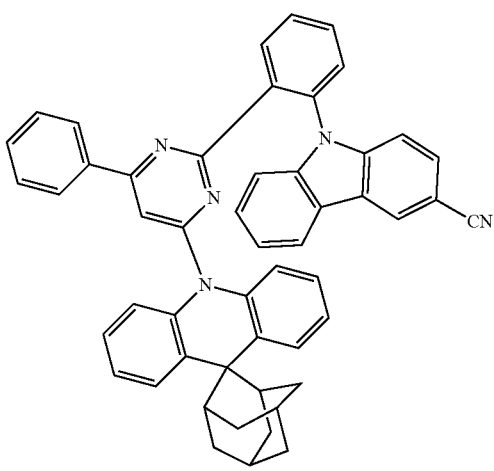
10

11
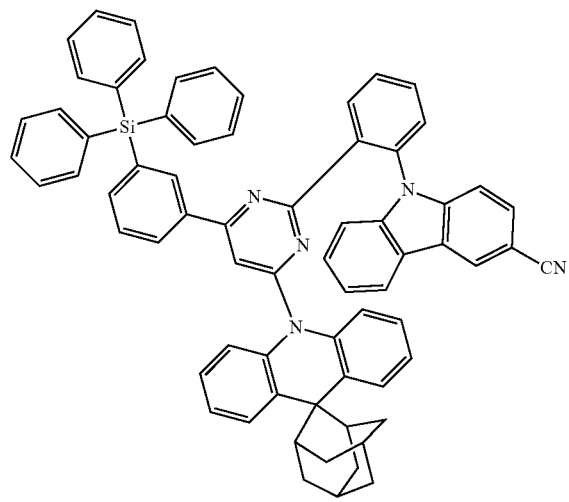
11
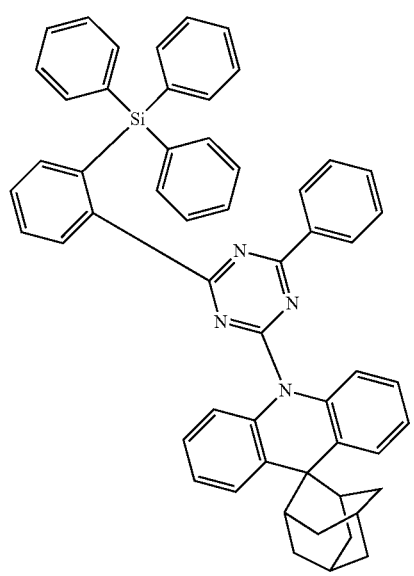
12
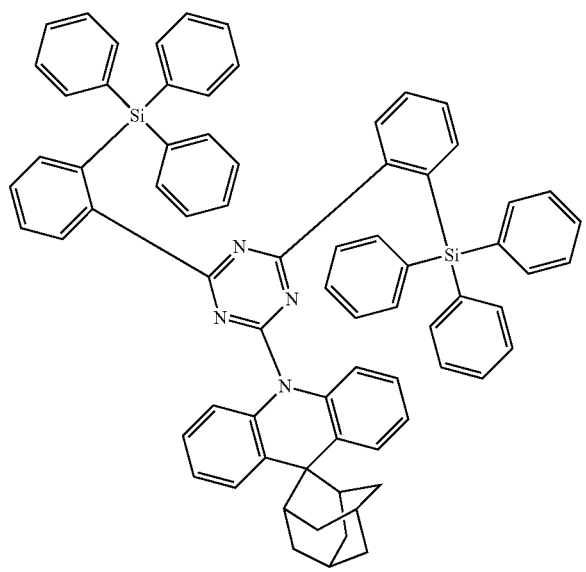
13
12
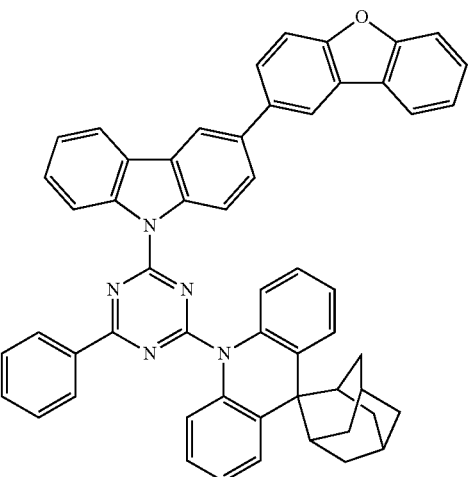
14
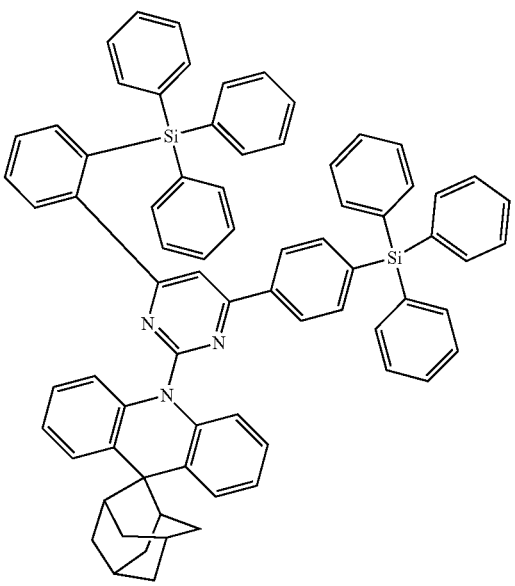
15
16

17
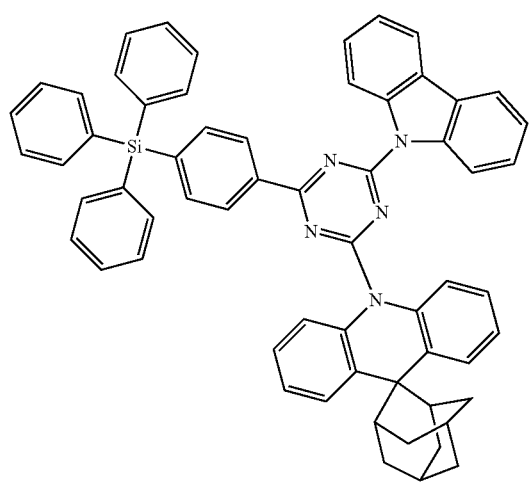
18
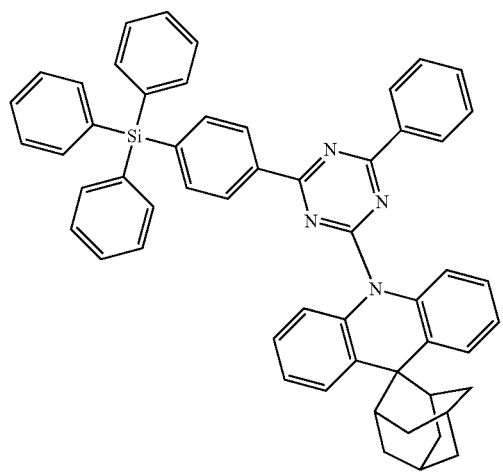
19
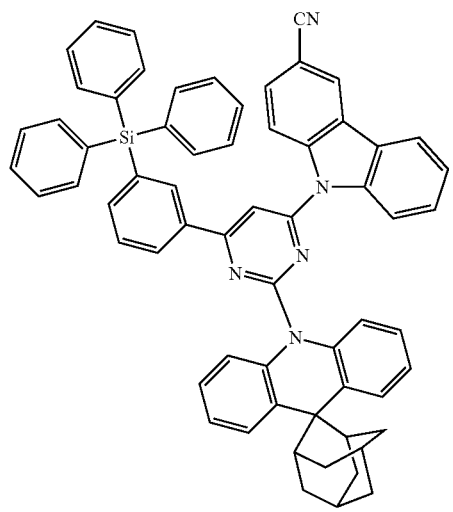
20
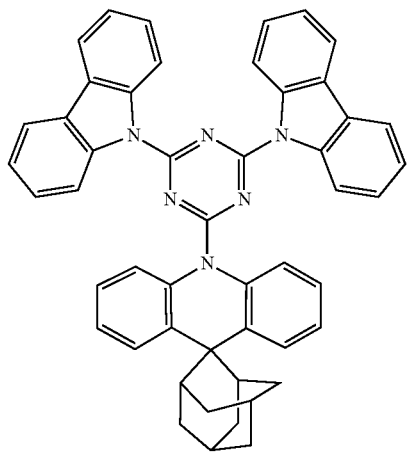
21
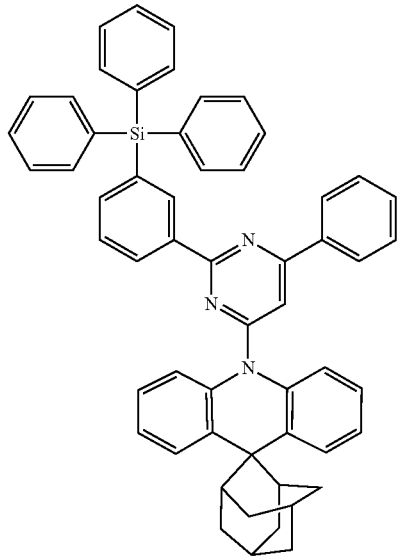
22
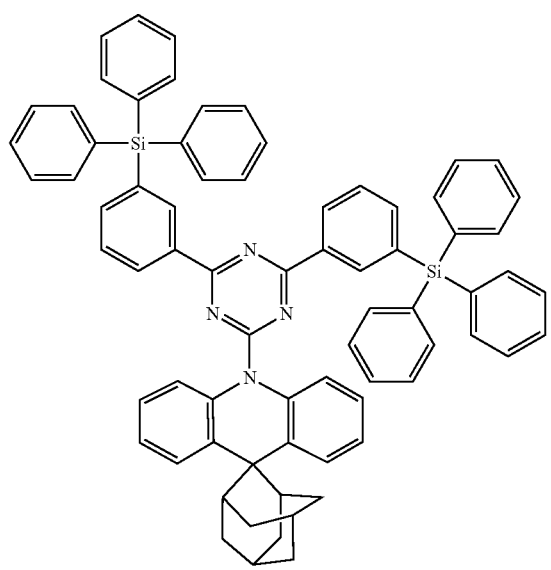

23
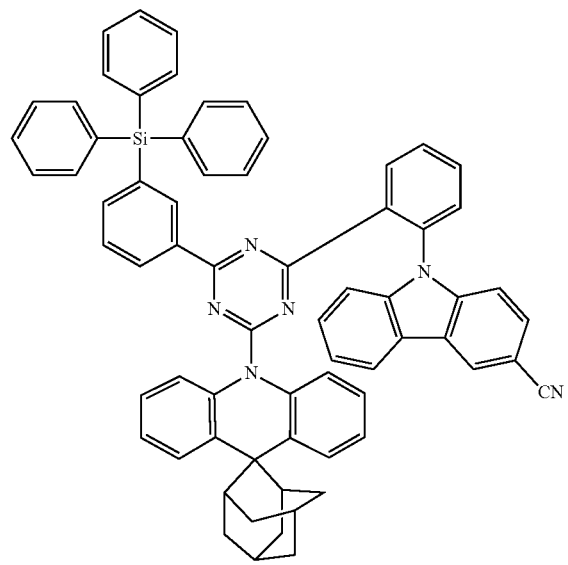
24
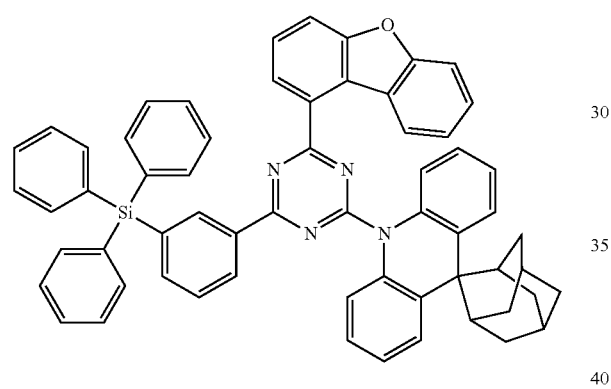
25
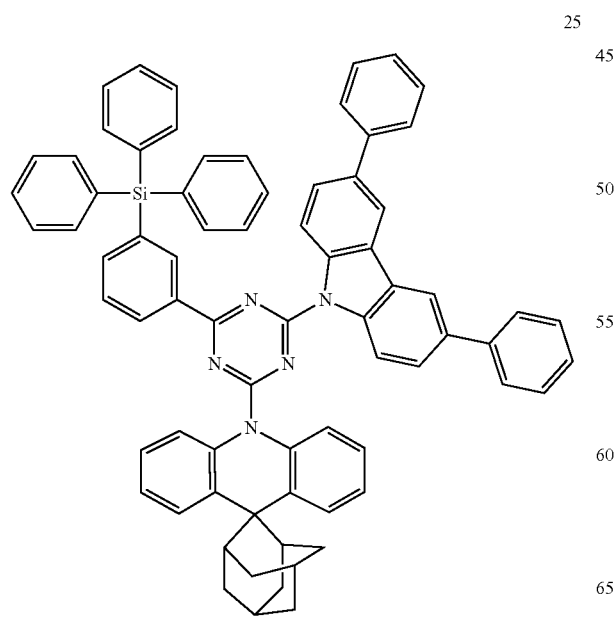
26
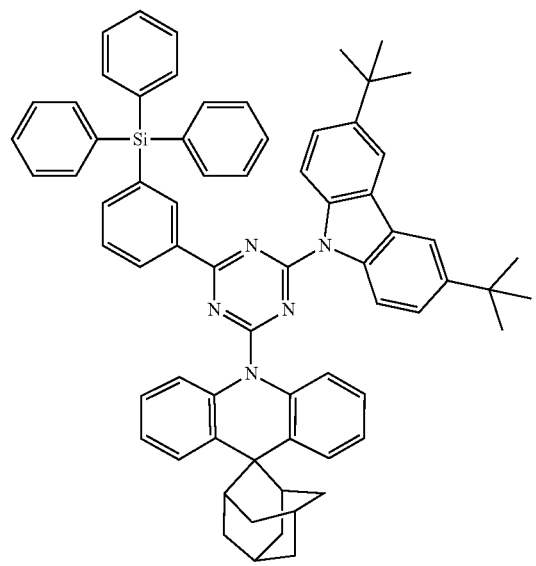
27
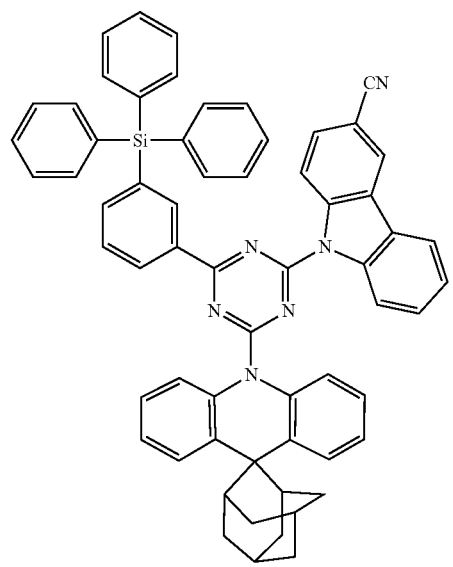

28
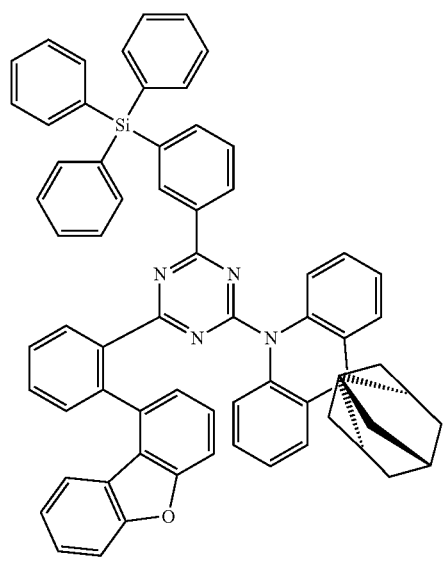
29
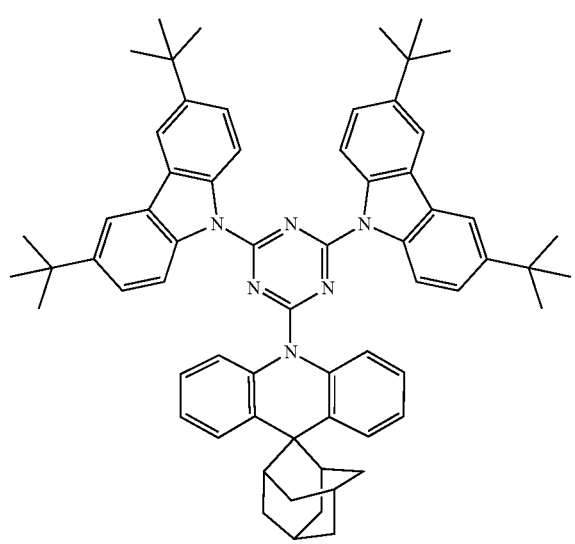
30
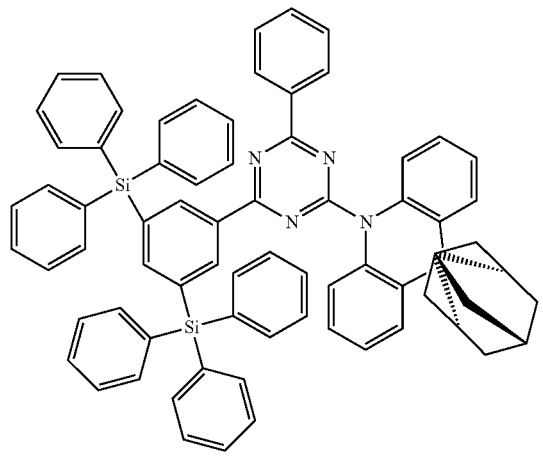
31
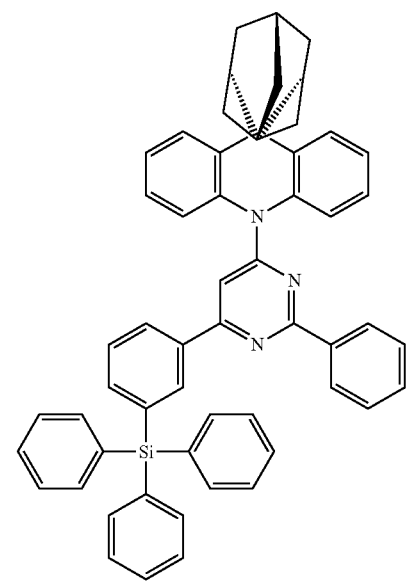
32
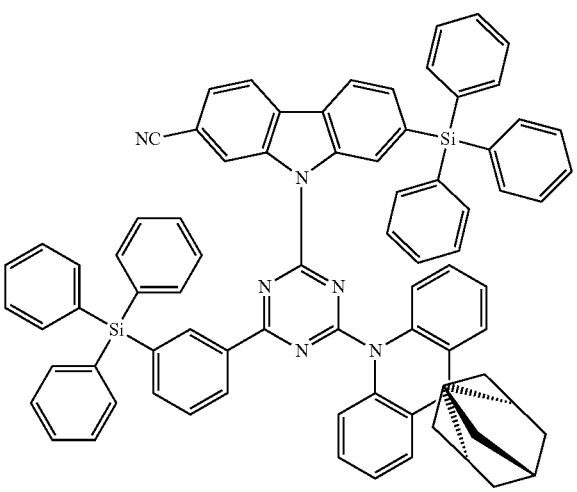
33
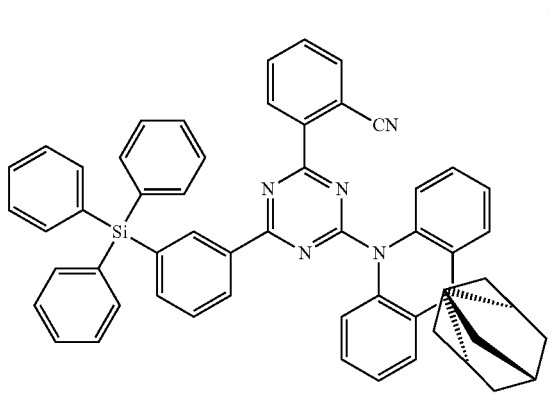

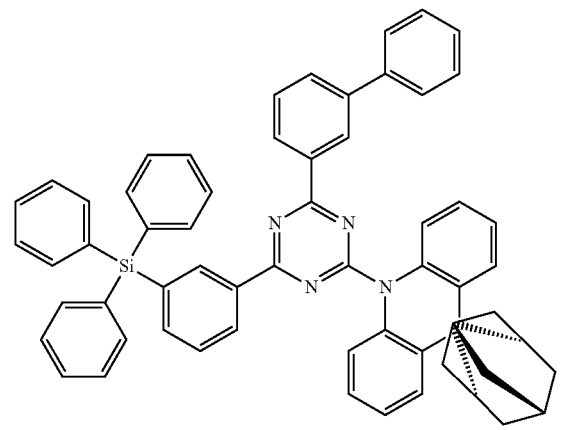
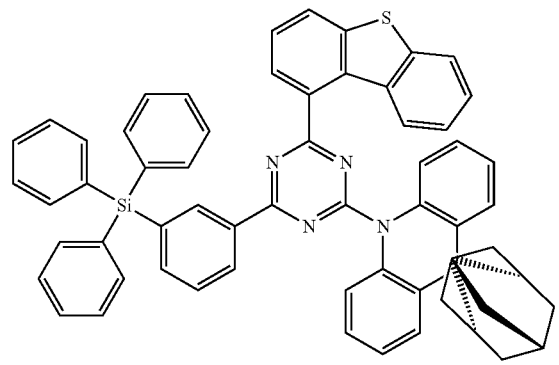
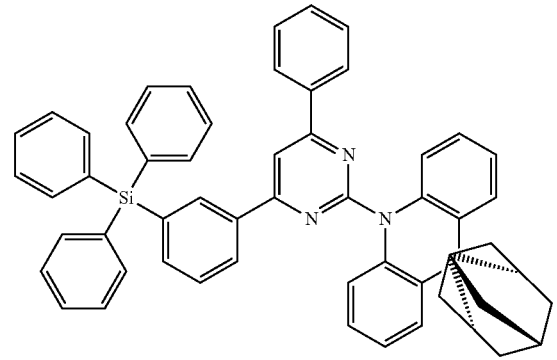
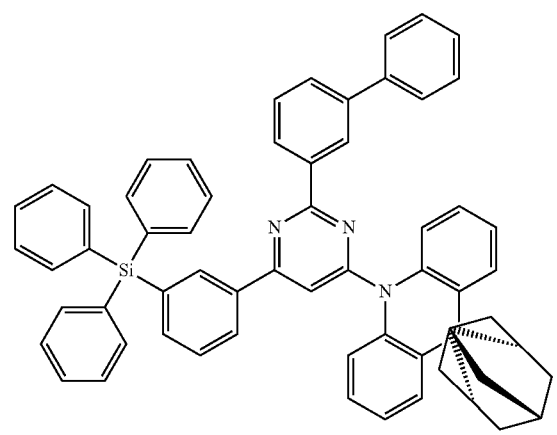
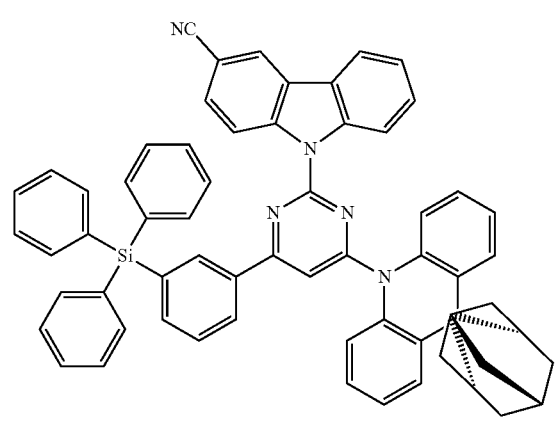

41
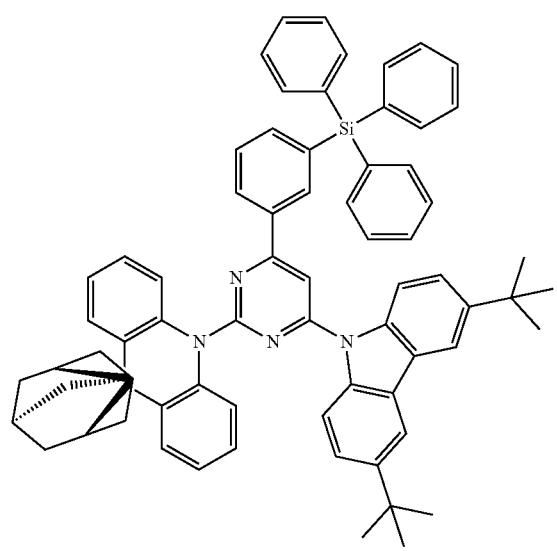
42
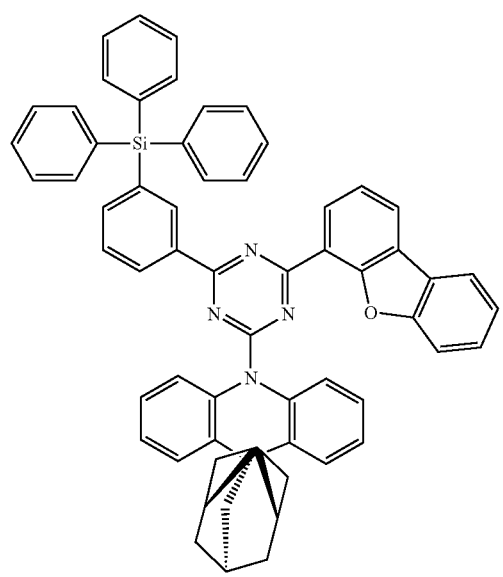
43
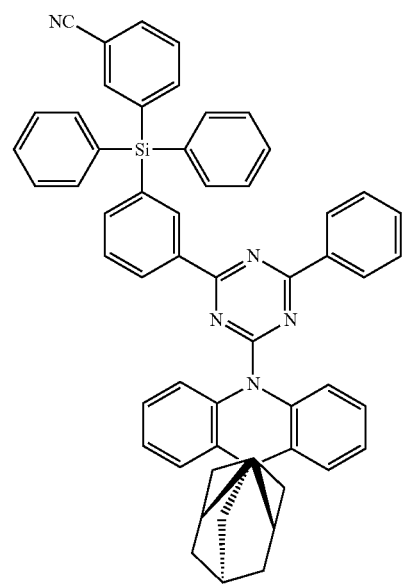
44
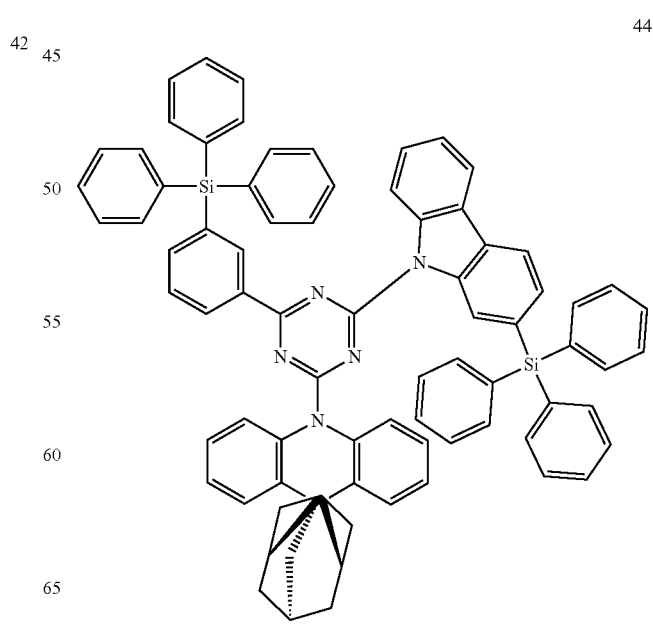

45
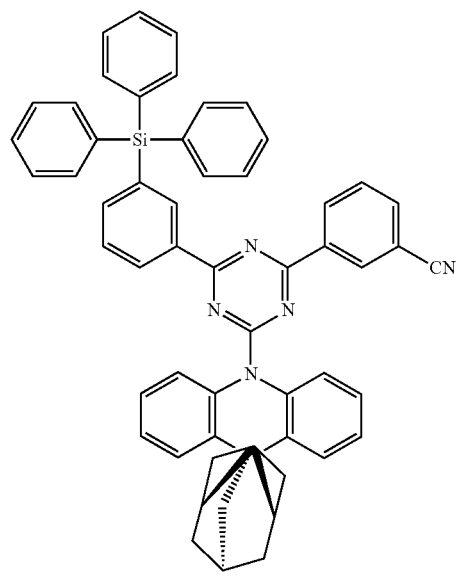
46
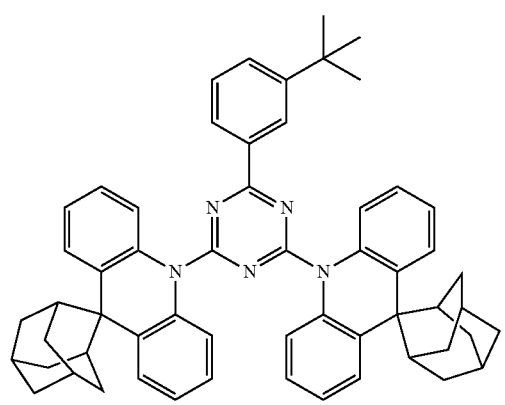
47
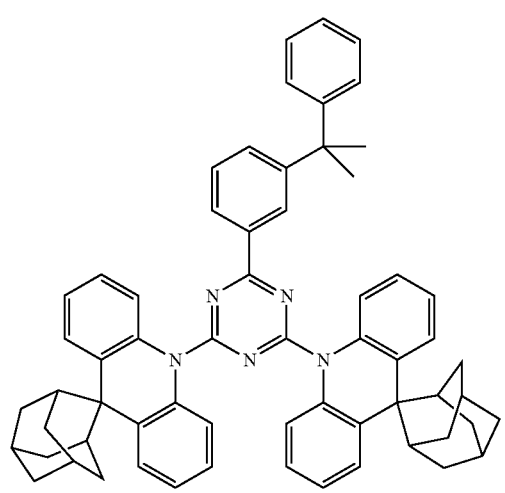
48
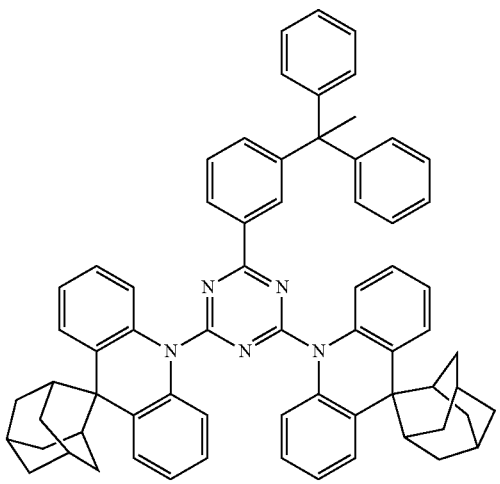
49
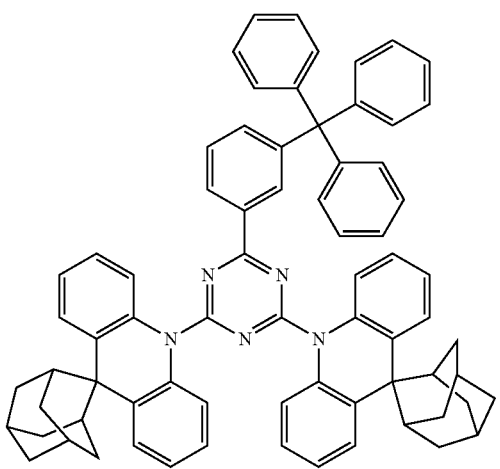
50
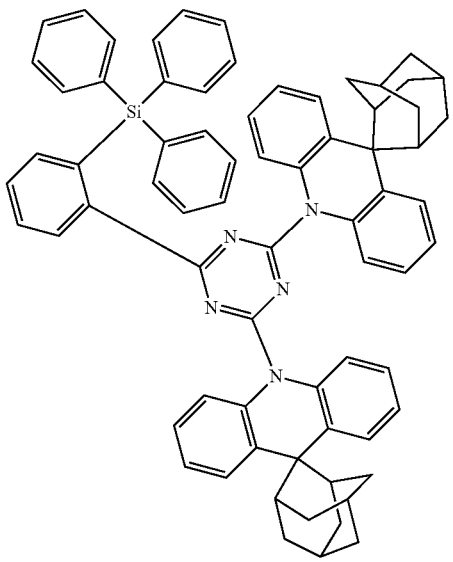

51
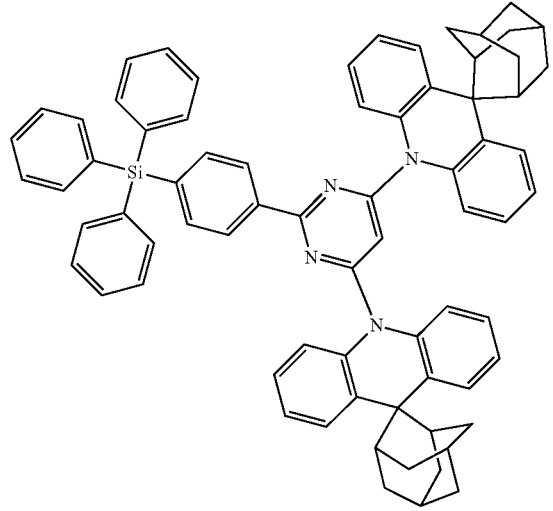
52
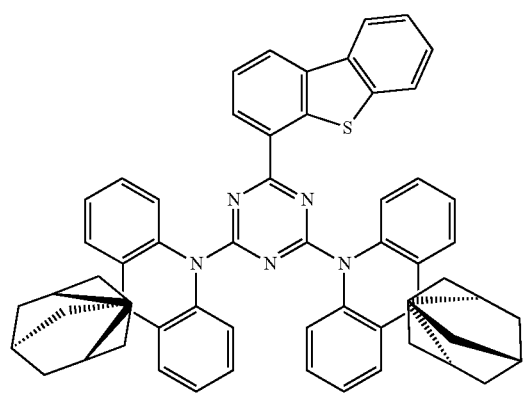
53
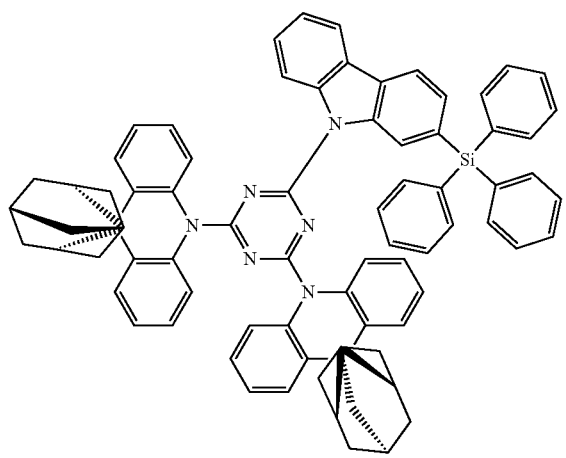
54
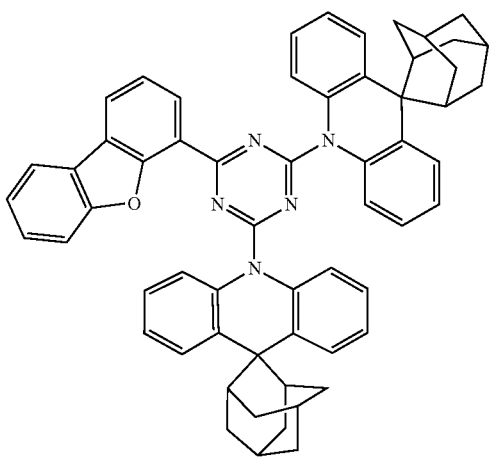
55
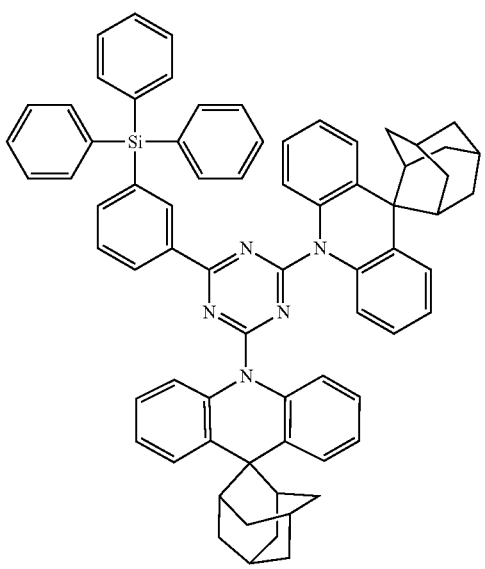
56
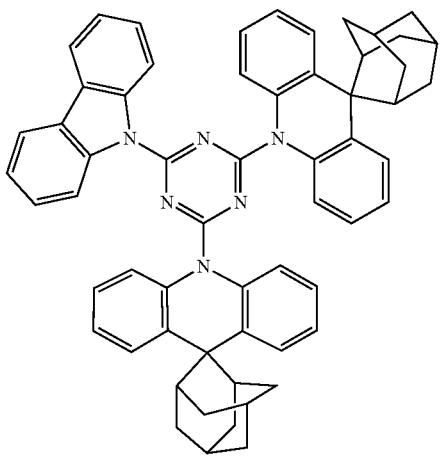

57

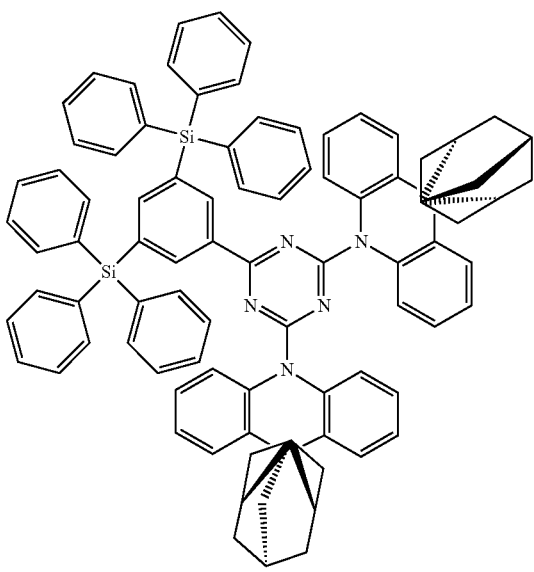

58

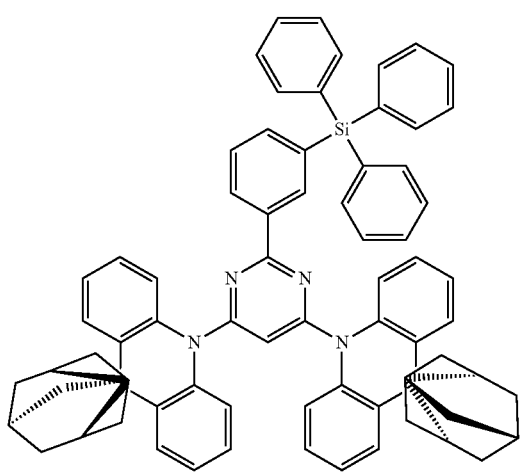

59

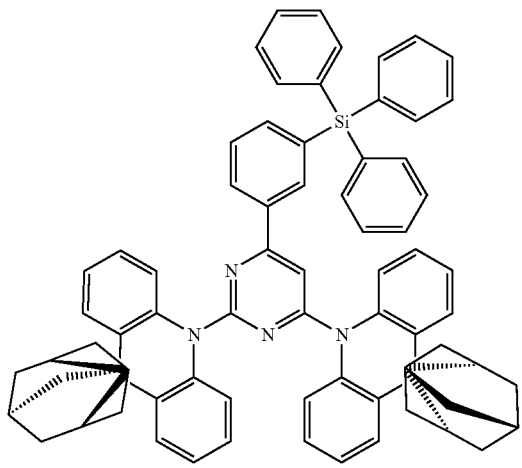

60

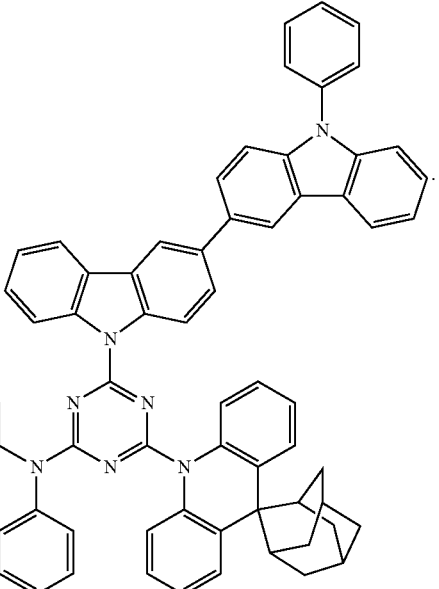

The heterocyclic compound represented by Formula 1 may include at least one group represented by Formula 2. The group represented by Formula 2 may have a high glass transition temperature by including a structure in which adamantane which is relatively large and has relatively high rigidity is condensed at a carbon-9 position of 9,9-dihydroacridine. Accordingly, the heterocyclic compound may have improved thermal stability. In addition, as the heterocyclic compound may have a bulky substituent, intermolecular interaction may be reduced due to a relatively large steric hindrance, and accordingly, the heterocyclic compound may have a relatively high triplet energy level. Thus, when the heterocyclic compound is applied to a light-emitting device, triplet excitons generated from the emission layer may be prevented or substantially prevented from being diffused to a layer close to the emission layer, e.g., a hole transport layer or an electron transport layer, thereby improving luminescence efficiency of the light-emitting device. Accordingly, the light-emitting device may have improved luminescence characteristics.

Further, as the heterocyclic compound has a relatively high triplet energy level, the heterocyclic compound may be suitable for usage as a blue host material.

In the heterocyclic compound, when at least one of $Ar_1$ to $Ar_3$ in Formula 1 may be the group represented by Formula 2, and the other substituents of the azine core are each (e.g., all) a substituted or unsubstituted phenyl group, the group represented by Formula 2 may be bound to the azine core via a single bond. In this embodiment, the heterocyclic compound may have a short conjugation length as compared with a compound, in which a linker is disposed between the group represented by Formula 2 and the azine core, and thus, the heterocyclic compound may have a relatively high triplet energy.

Therefore, an electronic device, e.g., a light-emitting device, including the heterocyclic compound represented by Formula 1 may have a low driving voltage, high efficiency, and high maximum quantum efficiency.

Methods of synthesizing the heterocyclic compound represented by Formula 1 may be easily understood by those of ordinary skill in the art by referring to Synthesis Examples and Examples described herein.

At least one heterocyclic compound represented by Formula 1 may be included between a pair of electrodes in a light-emitting device. In some embodiments, the heterocyclic compound may be included in at least one selected from a hole transport region, an electron transport region, and an emission layer. In some embodiments, the heterocyclic compound represented by Formula 1 may be utilized as a material for forming a capping layer, which is disposed on outer sides of a pair of electrodes (e.g., on the side of an electrode facing away from the other electrode) in a light-emitting device.

Accordingly, there is provided a light-emitting device including a first electrode; a second electrode facing the first electrode; an interlayer located between the first electrode and the second electrode and including an emission layer; and at least one heterocyclic compound represented by Formula 1.

In an embodiment, the interlayer in the light-emitting device may include the at least one heterocyclic compound represented by Formula 1.

In one or more embodiments, the light-emitting device may further include at least one of a first capping layer located outside a first electrode (e.g., on the side of the first electrode facing away from the second electrode) and a second capping layer located outside a second electrode (e.g., on the side of the second electrode facing away from the first electrode), and at least one of the first capping layer and the second capping layer may include the heterocyclic compound represented by Formula 1. The first capping layer and the second capping layer may respectively be understood by referring to the descriptions of the first capping layer and the second capping layer provided herein.

In some embodiments, the light-emitting device may include:
  a first capping layer located outside the first electrode and including the heterocyclic compound represented by Formula 1;
  a second capping layer located outside the second electrode and including the heterocyclic compound represented by Formula 1; or
  the first capping layer and the second capping layer.

The expression that an "(interlayer and/or a capping layer) includes at least one heterocyclic compound" as used herein may be construed as referring to that the "(interlayer and/or the capping layer) may include one heterocyclic compound of Formula 1, or two or more different heterocyclic compounds of Formula 1".

For example, the interlayer and/or the capping layer may include only Compound 1 as the heterocyclic compound. In this embodiment, Compound 1 may be included in the emission layer of the light-emitting device. In some embodiments, the interlayer may include Compounds 1 and 2 as the heterocyclic compounds. In this embodiment, Compounds 1 and 2 may be included in the same layer (for example, both Compounds 1 and 2 may be included in the emission layer) or in different layers (for example, Compound 1 may be included in the emission layer, and Compound 2 may be included in a hole transport layer).

In some embodiments, the first electrode of the light-emitting device may be an anode,
  the second electrode of the light-emitting device may be a cathode,
  the interlayer may further include a hole transport region located between the first electrode and the emission layer and an electron transport region located between the emission layer and the second electrode,
  the hole transport region may include a hole injection layer, a hole transport layer, an emission auxiliary layer, an electron blocking layer, or a combination thereof, and
  the electron transport region may include a buffer layer, a hole blocking layer, an electron control layer, an electron transport layer, an electron injection layer, or a combination thereof.

In an embodiment, the heterocyclic compound may be included in the interlayer of the light-emitting device.

In an embodiment, the heterocyclic compound may be included in the emission layer of the light-emitting device.

In an embodiment, the emission layer may include a host and a dopant, a content of the host in the emission layer may be greater than a content of the dopant in the emission layer, and the host may include the heterocyclic compound.

In some embodiments, the dopant in the emission layer may include a phosphorescent dopant or a fluorescent dopant. The fluorescent dopant may include a thermally activated delayed fluorescent (TADF) dopant.

In some embodiments, the dopant may be a phosphorescent dopant, and the phosphorescent dopant may include an organometallic complex represented by Formula 401:

Formula 401
$$M(L_{401})_{xc1}(L_{402})_{xc2}$$

Formula 402
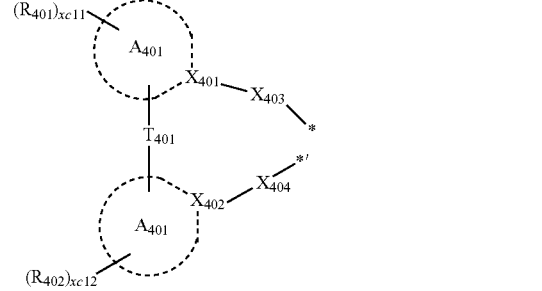

wherein, in Formulae 401 and 402,
M may be a transition metal (e.g., iridium (Ir), platinum (Pt), palladium (Pd), osmium (Os), titanium (Ti), gold (Au), hafnium (Hf), europium (Eu), terbium (Tb), rhodium (Rh), rhenium (Re), and/or thulium (Tm)),
$L_{401}$ may be a ligand represented by Formula 402, and xc1 may be 1, 2, or 3, and when xc1 is 2 or greater, at least two $L_{401}$(s) may be identical to or different from each other, for example, when xc1 is 2 or greater, the two or more $L_{401}$(s) may be identical to or different from each other,
$L_{402}$ may be an organic ligand, and xc2 may be an integer from 0 to 4, and when xc2 is 2 or greater, at least two $L_{402}$(s) may be identical to or different from each other, for example, when xc2 is 2 or greater, the two or more $L_{402}$(s) may be identical to or different from each other,
$X_{401}$ and $X_{402}$ may each independently be nitrogen or carbon,
ring $A_{401}$ and ring $A_{402}$ may each independently be a $C_3$-$C_{60}$ carbocyclic group or a $C_1$-$C_{60}$ heterocyclic group,
$T_{401}$ may be a single bond, *—O—*', *—S—*', *—C(=O)—*', *—N($Q_{411}$)-*', *—C($Q_{411}$)($Q_{412}$)-*', *—C($Q_{411}$)=C($Q_{412}$)-*', *—C($Q_{411}$)=*', or *=C=*', $X_{403}$ and $X_{404}$ may each independently be a chemical bond (e.g., a covalent bond or a coordinate bond), O, S, $N(Q_{413})$, $B(Q_{413})$, $P(Q_{413})$, $C(Q_{413})(Q_{414})$, or $Si(Q_{413})(Q_{414})$, $Q_{411}$ to $Q_{414}$ may each independently be understood by referring to the description of $Q_1$ provided herein, $R_{401}$ and $R_{402}$ may each independently be hydrogen, deuterium, —F, —Cl, —Br, —I, a hydroxyl group, a cyano group, a nitro group, a $C_1$-$C_{20}$ alkyl group unsubstituted or substituted with at least one $R_{10a}$, a $C_1$-$C_{20}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —$Si(Q_{401})(Q_{402})(Q_{403})$, —$N(Q_{401})(Q_{402})$, —$B(Q_{401})(Q_{402})$, —$C(=O)(Q_{401})$, —$S(=O)_2(Q_{401})$, or —$P(=O)(Q_{401})(Q_{402})$ $Q_{401}$ to $Q_{403}$ may each independently be understood by referring to the description of $Q_1$ provided herein, xc11 and xc12 may each independently be an integer from 0 to 10, and and *' in Formula 402 each indicate a binding site to M in Formula 401.

The heterocyclic compound may have a high triplet energy level, and thus, the heterocyclic compound may be suitable for use as a blue host. In some embodiments, the heterocyclic compound may be a blue phosphorescent host or a blue fluorescent host.

In one or more embodiments, a dopant in the emission layer may include the heterocyclic compound. A content of the dopant in the emission layer may be in a range of about 0.1 parts to about 49.99 parts by weight, based on 100 parts by weight of the emission layer.

In an embodiment, an emission layer including the heterocyclic compound may emit blue light. The blue light may have a maximum emission wavelength in a range of about 390 nanometers (nm) to about 440 nm.

In an embodiment, a hole transport region of the light-emitting device may include a charge generating material. In an embodiment, the charge generating material may include a p-dopant of which the lowest unoccupied molecular orbital (LUMO) energy level may be about −3.5 electron volts (eV) or lower.

In an embodiment, the light-emitting device may further include a metal-containing material in the electron transport region thereof.

In some embodiments, the electron transport region may further include an alkali metal, an alkaline earth metal, a rare earth metal, an alkali metal compound, an alkaline earth metal compound, a rare earth metal compound, an alkali metal complex, an alkaline earth metal complex, a rare earth metal complex, or a combination thereof.

According to one or more embodiments, an electronic apparatus may include the light-emitting device. The electronic apparatus may further include a thin-film transistor. In some embodiments, the electronic apparatus may further include a thin-film transistor including a source electrode and a drain electrode, and a first electrode of the light-emitting device may be electrically connected to the source electrode or the drain electrode. The electronic apparatus may further include a color filter, a color-conversion layer, a touchscreen layer, a polarization layer, or any combination thereof. The electronic apparatus may be understood by referring to the description of the electronic apparatus provided herein.

Description of FIG. 1

FIG. 1 is a schematic cross-sectional view of a light-emitting device 10 according to an embodiment. The light-emitting device 10 may include a first electrode 110, an interlayer 130, and a second electrode 150.

Hereinafter, the structure of the light-emitting device 10 according to an embodiment and a method of manufacturing the light-emitting device 10 according to an embodiment will be described in connection with FIG. 1.

First Electrode 110

In FIG. 1, a substrate may be additionally located under the first electrode 110 or above the second electrode 150. The substrate may be a glass substrate or a plastic substrate. The substrate may be a flexible substrate including a plastic material having excellent heat resistance and durability, for example, polyimide, polyethylene terephthalate (PET), polycarbonate, polyethylene napthalate, polyarylate (PAR), polyetherimide, or any combination thereof.

The first electrode 110 may be formed by depositing or sputtering, onto the substrate, a material for forming the first electrode 110. When the first electrode 110 is an anode, a high work function material that may suitably (e.g., easily) inject holes may be utilized as the material for the first electrode.

The first electrode 110 may be a reflective electrode, a semi-transmissive electrode, or a transmissive electrode. When the first electrode 110 is a transmissive electrode, the material for forming the first electrode 110 may be indium tin oxide (ITO), indium zinc oxide (IZO), tin oxide ($SnO_2$), zinc oxide (ZnO), or any combinations thereof. In some embodiments, when the first electrode 110 is a semi-transmissive electrode or a reflective electrode, magnesium (Mg), silver (Ag), aluminum (Al), aluminum-lithium (Al—Li), calcium (Ca), magnesium-indium (Mg-ln), magnesium-silver (Mg—Ag), or any combination thereof may be utilized as the material for forming the first electrode 110.

The first electrode 110 may have a single-layered structure including (e.g., consisting of) a single layer or a multi-layered structure including two or more layers. In some embodiments, the first electrode 110 may have a triple-layered structure of ITO/Ag/ITO.

Interlayer 130

The interlayer 130 may be (e.g., located) on the first electrode 110. The interlayer 130 may include an emission layer.

The interlayer 130 may further include a hole transport region between the first electrode 110 and the emission layer and an electron transport region between the emission layer and the second electrode 150.

The interlayer 130 may further include a metal-containing compound (such as an organometallic compound), an inorganic material (such as quantum dots), and/or the like, in addition to various suitable organic materials.

The interlayer 130 may include: i) at least two emitting units sequentially stacked between the first electrode 110 and the second electrode 150; and ii) a charge-generation layer located between the at least two emitting units. When the interlayer 130 includes the at least two emitting units and the charge-generation layer, the light-emitting device 10 may be a tandem light-emitting device.

Hole Transport Region in Interlayer 130

The hole transport region may have i) a single-layered structure including (e.g., consisting of) a single layer including (e.g., consisting of) a single material, ii) a single-layered structure including (e.g., consisting of) a single layer including a plurality of different materials, or iii) a multi-layered structure having a plurality of layers including a plurality of different materials.

The hole transport region may include a hole injection layer (HIL), a hole transport layer (HTL), an emission auxiliary layer, an electron blocking layer (EBL), or a combination thereof.

For example, the hole transport region may have a multi-layered structure, e.g., a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron blocking layer structure, wherein layers of each structure are sequentially stacked on the first electrode 110 in each stated order.

The hole transport region may include the compound represented by Formula 201, the compound represented by Formula 202, or any combination thereof:

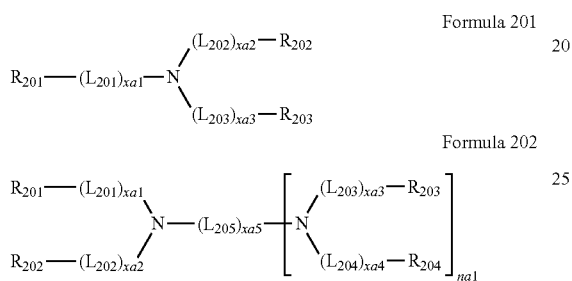

Formula 201

Formula 202 wherein, in Formulae 201 and 202, $L_{201}$ to $L_{204}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $L_{205}$ may be *—O—*', *—S—*', *—N($Q_{201}$)-*', a $C_1$-$C_{20}$ alkylene group unsubstituted or substituted with at least one $R_{10a}$, a $C_2$-$C_{20}$ alkenylene group unsubstituted or substituted with at least one $R_{10a}$, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, xa1 to xa4 may each independently be an integer from 0 to 5, xa5 may be an integer from 1 to 10, $R_{201}$ to $R_{204}$ and $Q_{201}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $R_{201}$ and $R_{202}$ may optionally be bound to each other via a single bond, a $C_1$-$C_5$ alkylene group unsubstituted or substituted with at least one $R_{10a}$, or a $C_2$-$C_5$ alkenylene group unsubstituted or substituted with at least one $R_{10a}$ to form a $C_8$-$C_{60}$ polycyclic group (e.g., a carbazole group and/or the like) unsubstituted or substituted with at least one $R_{10a}$ (e.g., Compound HT16 described herein), $R_{203}$ and $R_{204}$ may optionally be bound to each other via a single bond, a $C_1$-$C_5$ alkylene group unsubstituted or substituted with at least one $R_{10a}$, or a $C_2$-$C_5$ alkenylene group unsubstituted or substituted with at least one $R_{10a}$ to form a $C_8$-$C_{60}$ polycyclic group unsubstituted or substituted with at least one $R_{10a}$, and na1 may be an integer from 1 to 4.

In some embodiments, Formulae 201 and 202 may each include at least one of the groups represented by Formulae CY201 to CY217:

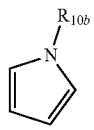

CY201

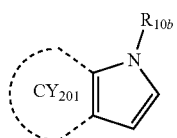

CY202

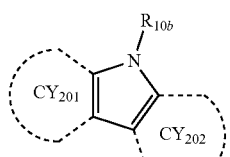

CY203

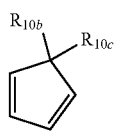

CY204

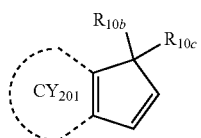

CY205

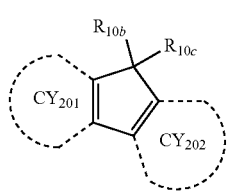

CY206

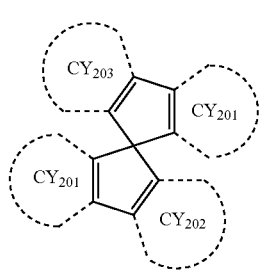

CY207

-continued

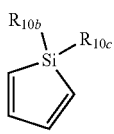

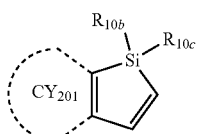

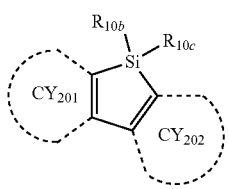

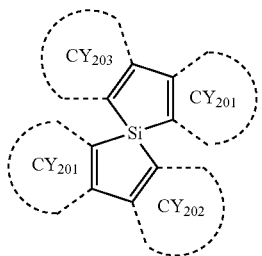

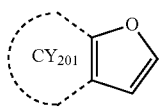

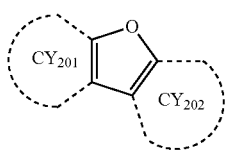

CY208 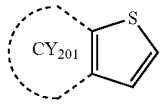 CY216

CY209

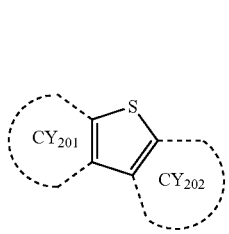 CY217

CY210

CY211

CY212

CY213

CY214

CY215

-continued wherein, in Formulae CY201 to CY217, $R_{10b}$ and $R_{10c}$ may each independently be understood by referring to the descriptions of $R_{10a}$, ring CY201 to ring CY204 may each independently be a $C_3$-$C_{20}$ carbocyclic group or a $C_1$-$C_{20}$ heterocyclic group, and at least one hydrogen in Formulae CY201 to CY217 may be unsubstituted or substituted with $R_{10a}$.

In some embodiments, in Formulae CY201 to CY217, ring CY201 to ring CY204 may each independently be a benzene group, a naphthalene group, a phenanthrene group, or an anthracene group.

In one or more embodiments, Formulae 201 and 202 may each include at least one of groups represented by Formulae CY201 to CY203.

In one or more embodiments, Formula 201 may include at least one of the groups represented by Formulae CY201 to CY203 and at least one of groups represented by Formulae CY204 to CY217.

In one or more embodiments, in Formula 201, xa1 may be 1, $R_{201}$ may be a group represented by any one of Formulae CY201 to CY203, xa2 may be 0, and $R_{202}$ may be a group represented by any one of Formulae CY204 to CY207.

In one or more embodiments, Formulae 201 and 202 may each not include the groups represented by Formulae CY201 to CY203.

In one or more embodiments, Formulae 201 and 202 may each not include the groups represented by Formulae CY201 to CY203, and include at least one of the groups represented by Formulae CY204 to CY217.

In one or more embodiments, Formulae 201 and 202 may each not include the groups represented by Formulae CY201 to CY217.

In some embodiments, the hole transport region may include one of Compounds HT1 to HT44, m-MTDATA, TDATA, 2-TNATA, NPB (NPD), β-NPB, TPD, spiro-TPD, spiro-NPB, methylated-NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphorsulfonic acid (PANI/CSA), polyaniline/poly(4-styrenesulfonate) (PANI/PSS), or any combination thereof:

HT1
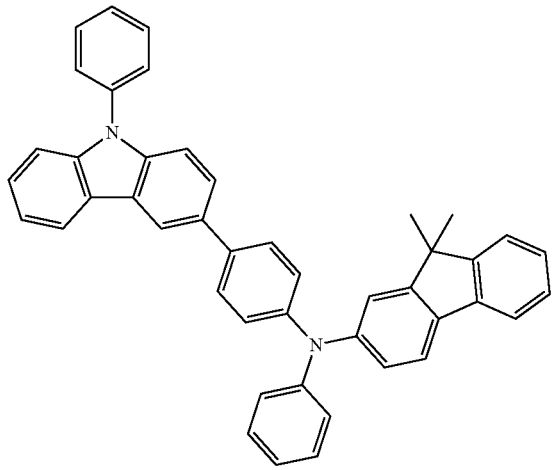
HT2
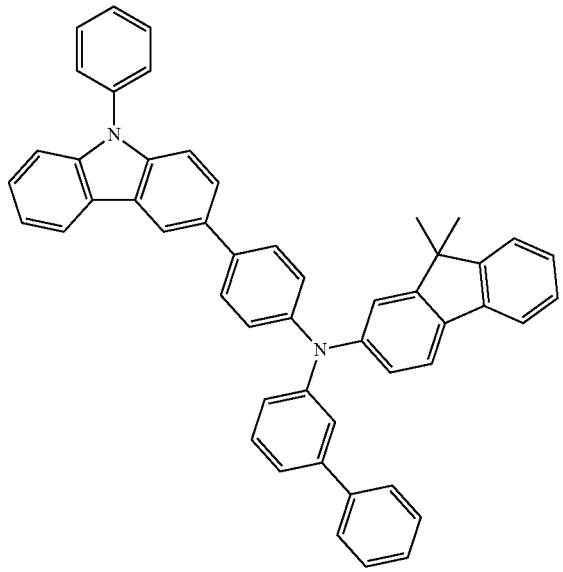
HT3
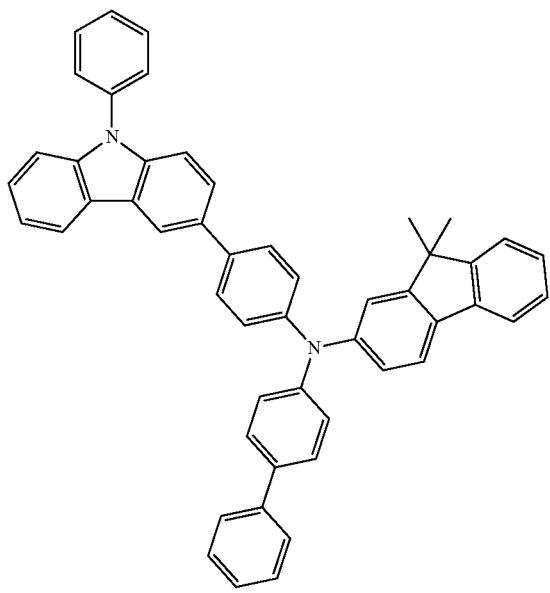
HT4
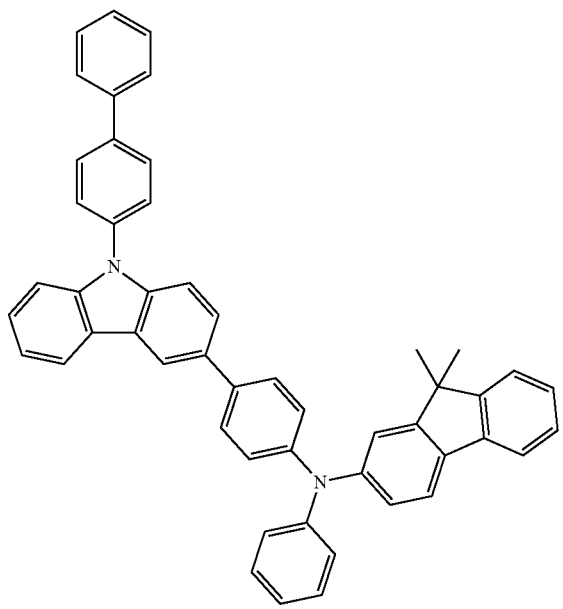

-continued
HT5
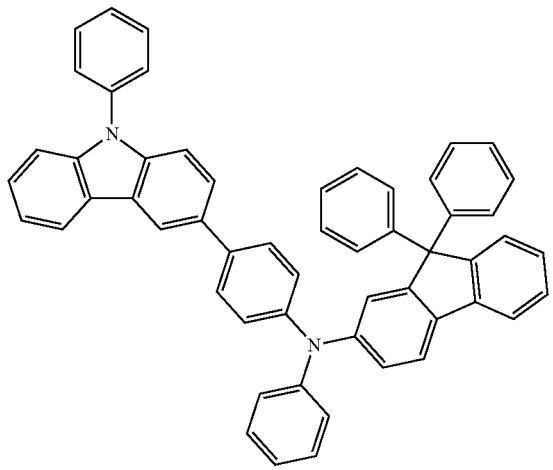
HT6
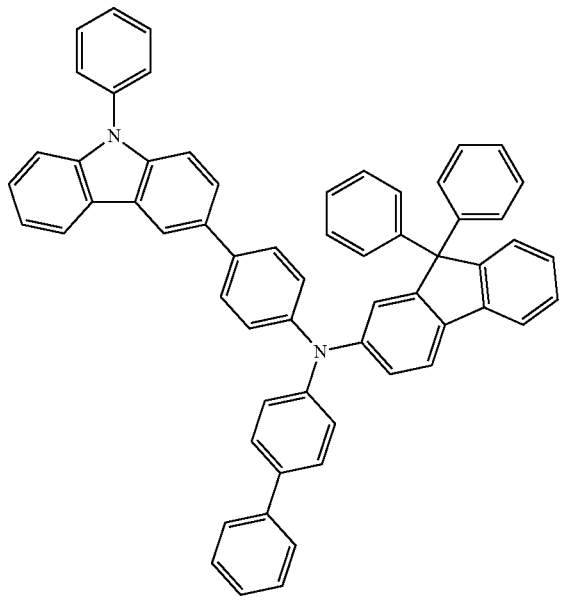
HT7
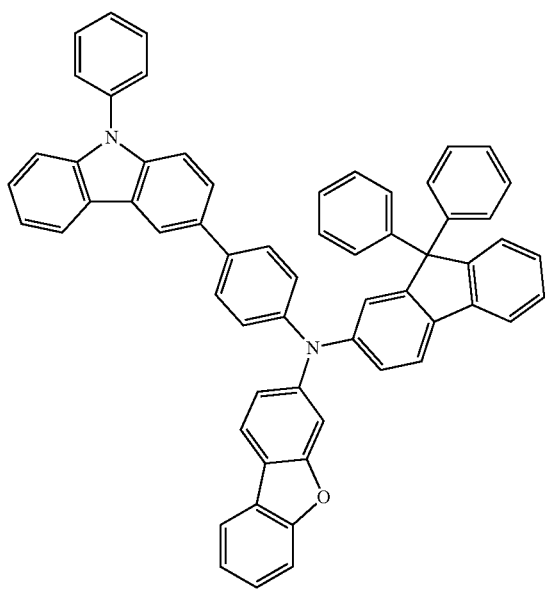
HT8
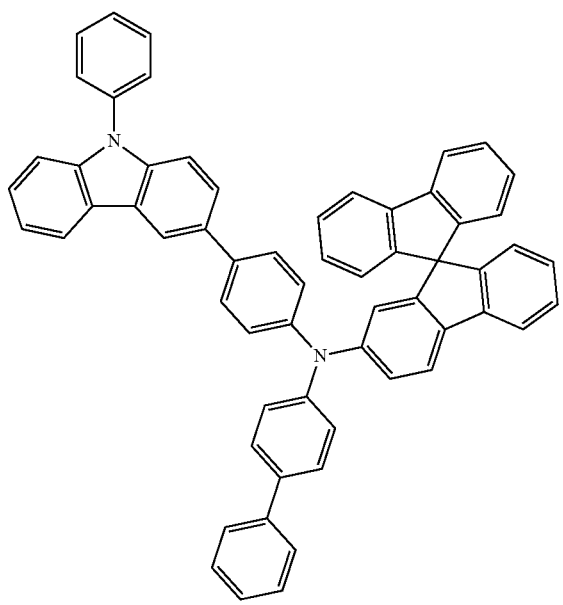

-continued
HT9
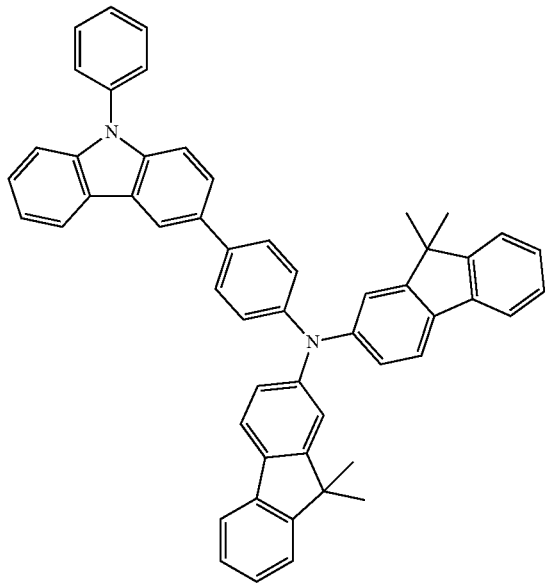
HT10
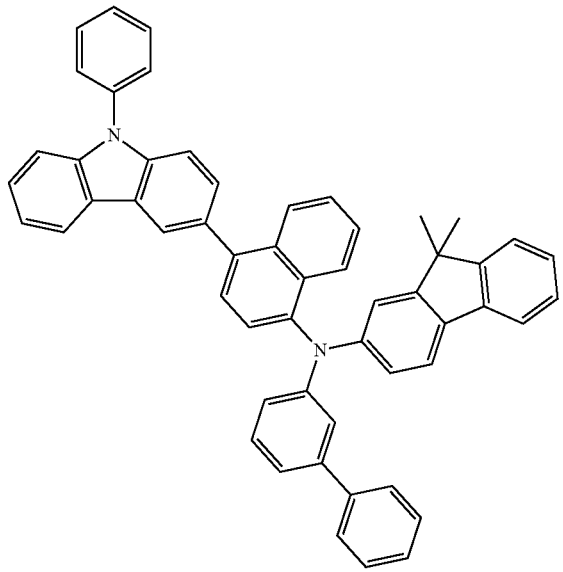
HT11
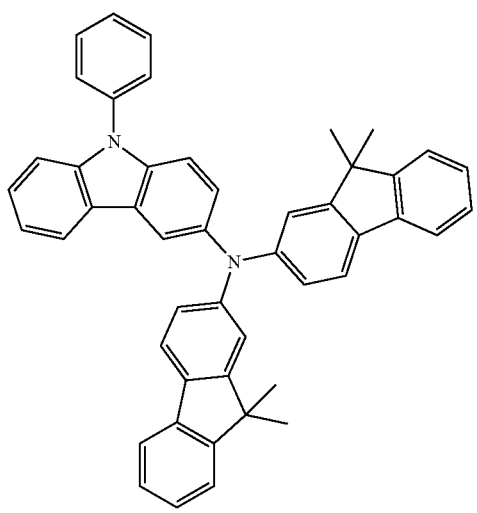
HT12
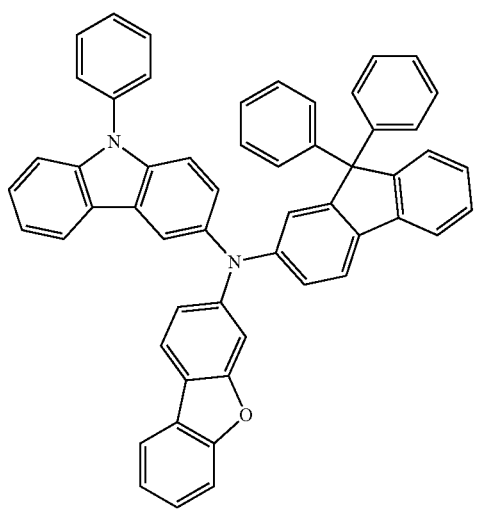

-continued
HT13
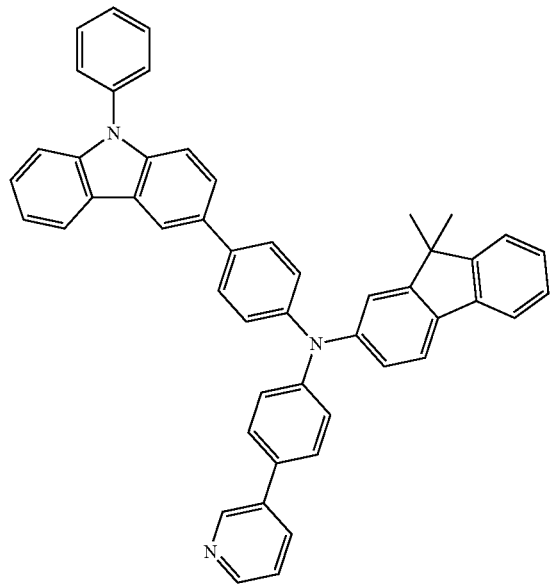
HT14
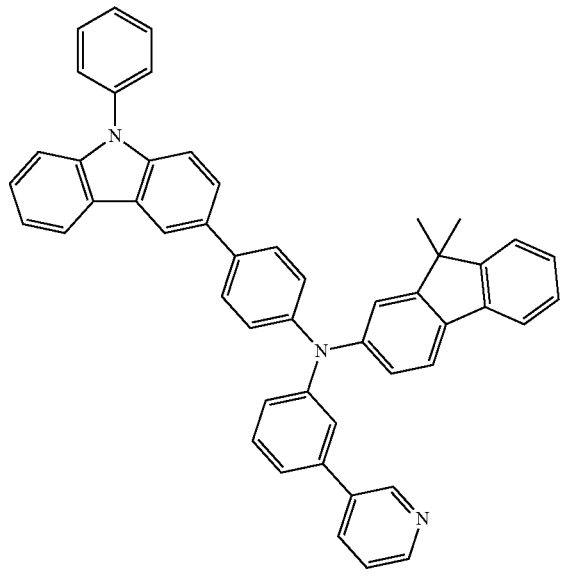
HT15
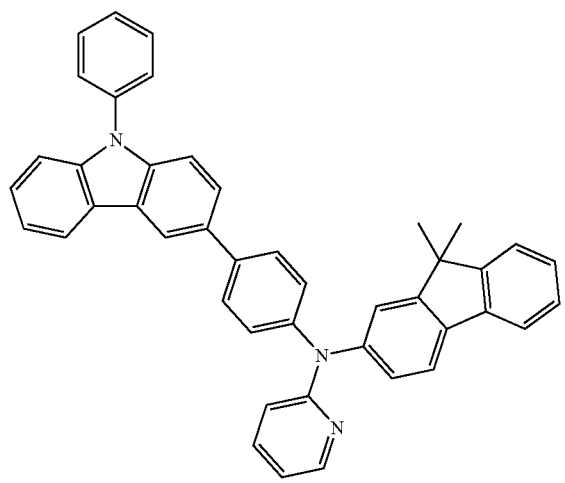
HT16
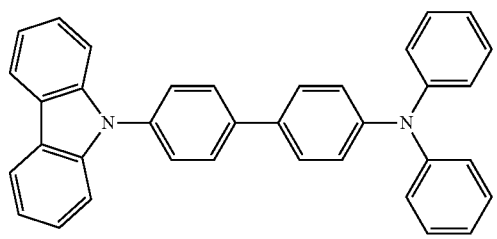
HT17
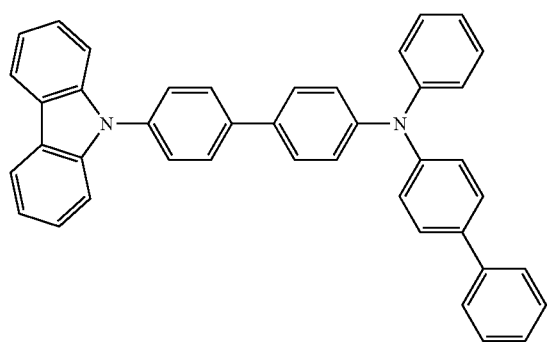
HT18
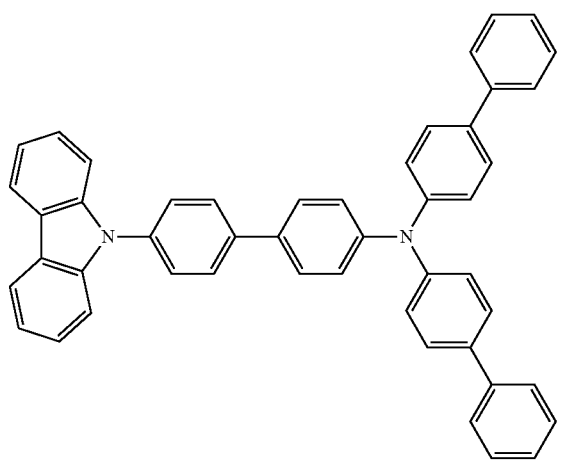

-continued
HT19
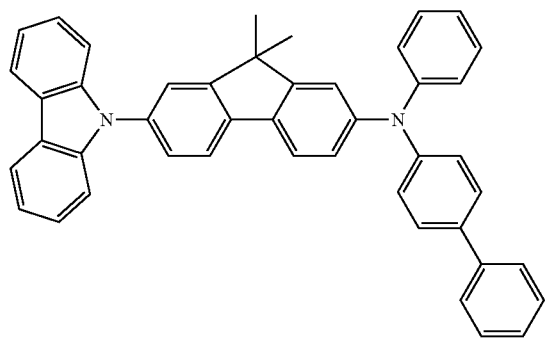
HT20
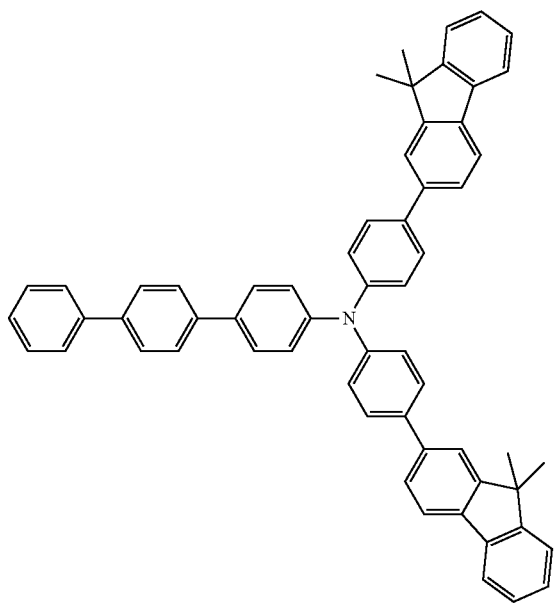
HT21
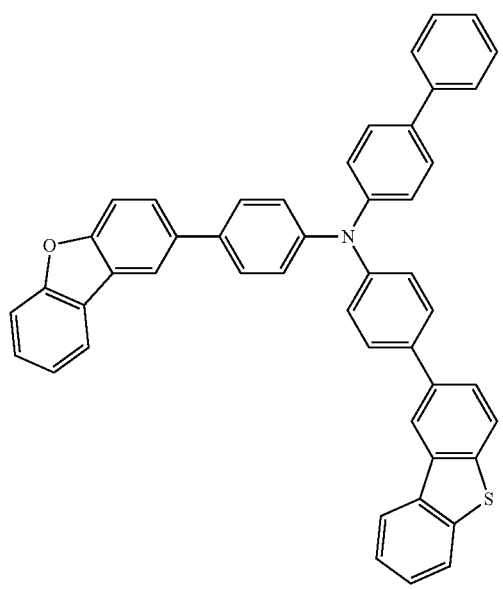
HT22
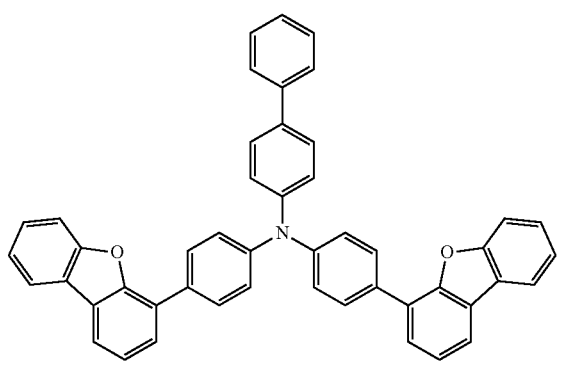

HT23
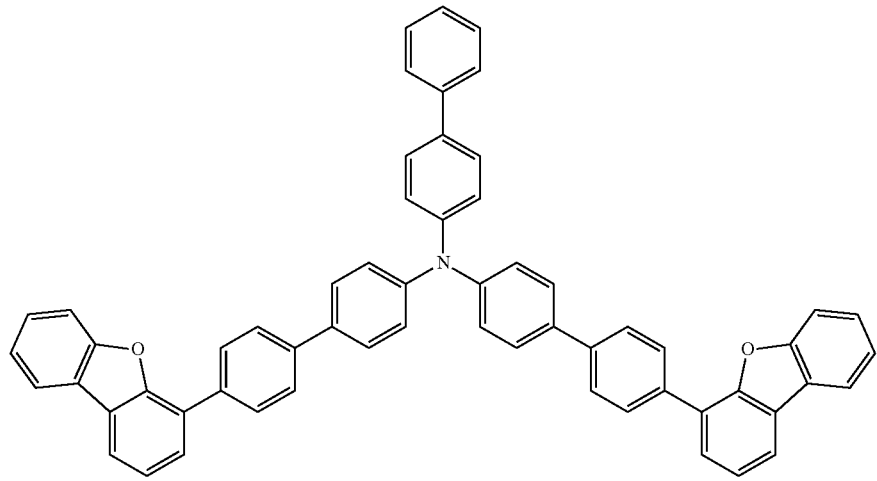
HT24
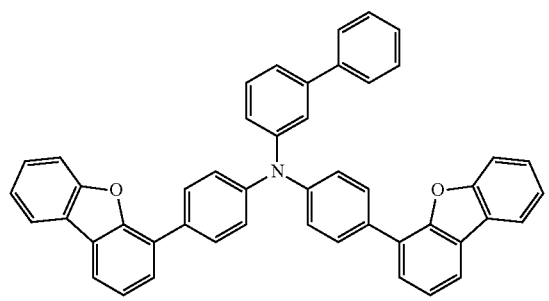
HT25
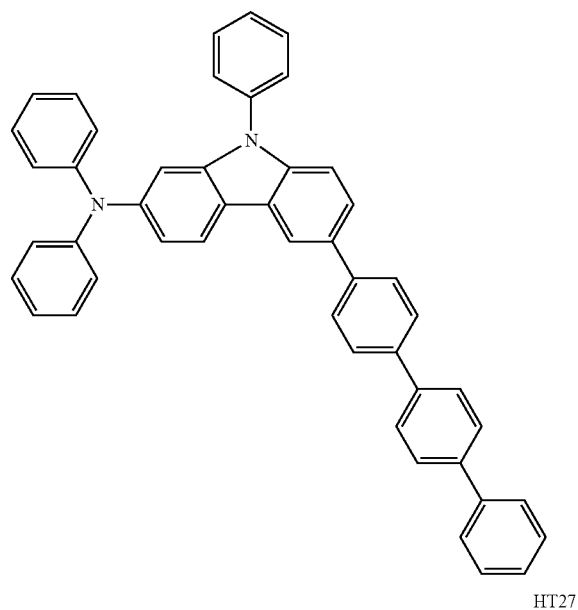
HT26
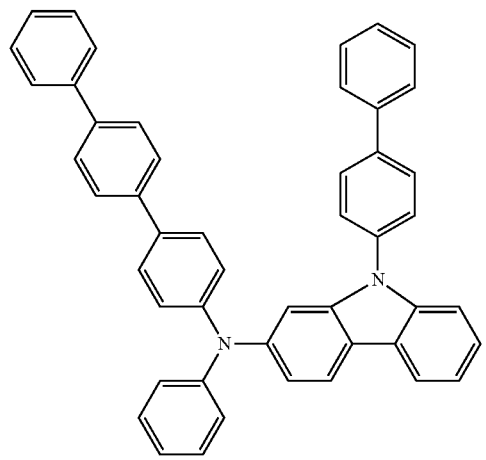
HT27
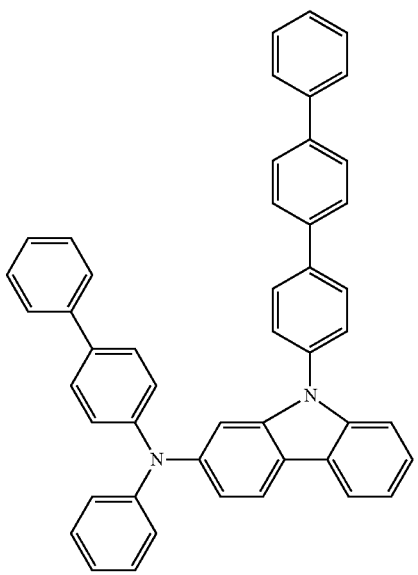

-continued
HT28
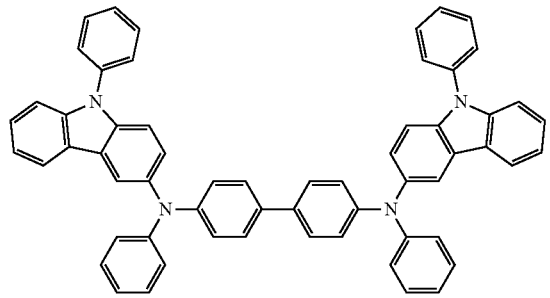
HT29
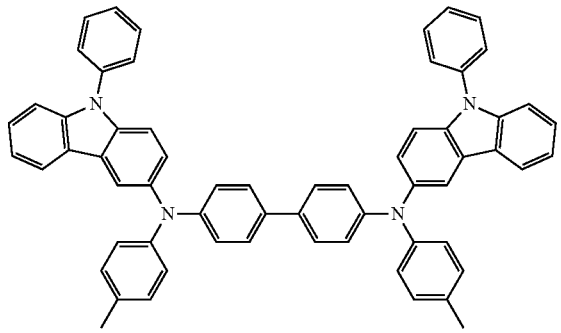
HT30
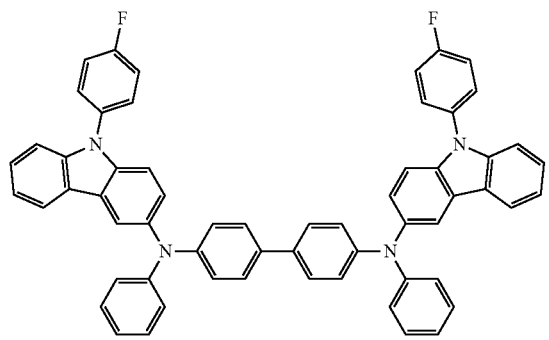
HT31
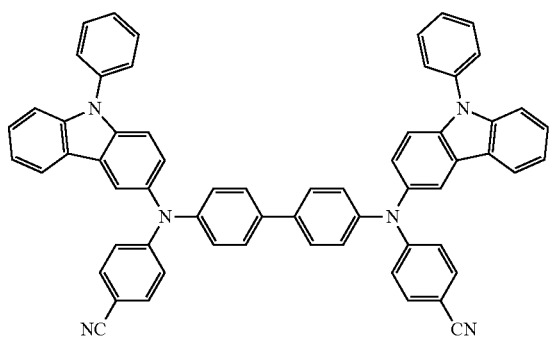
HT32
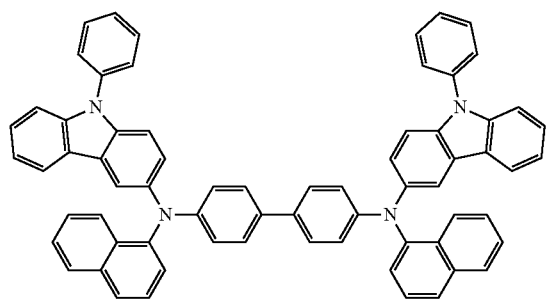
HT33
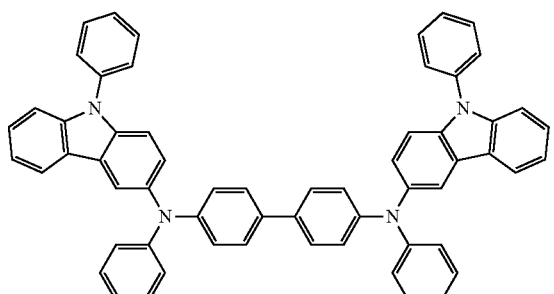
HT34
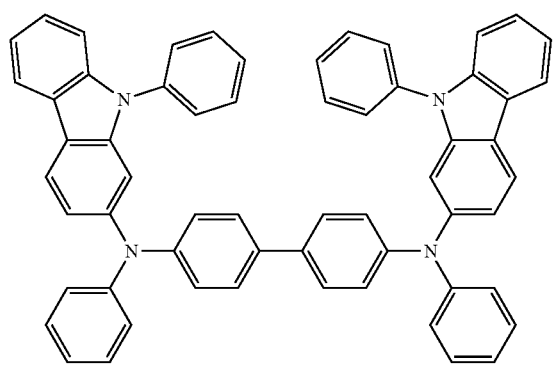
HT35
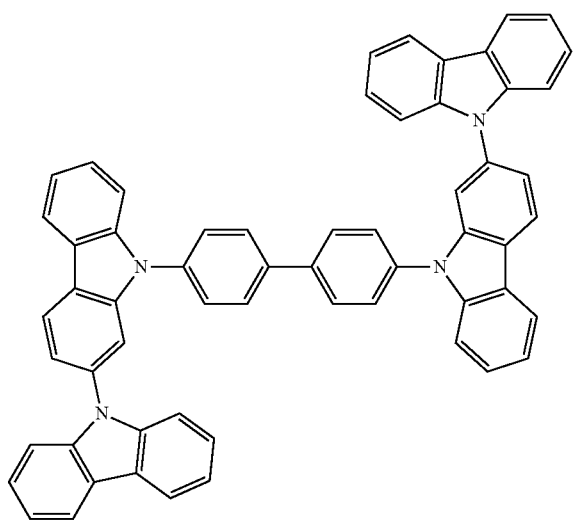

-continued
HT36
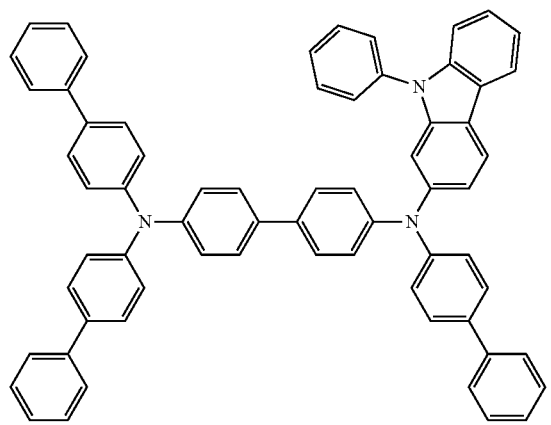
HT37
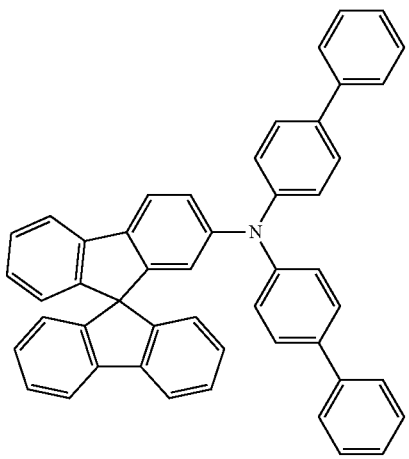
HT38
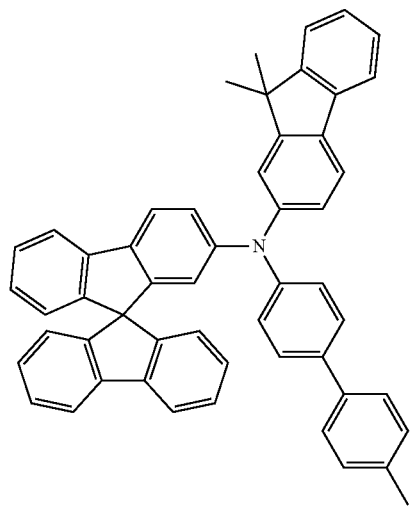
HT39
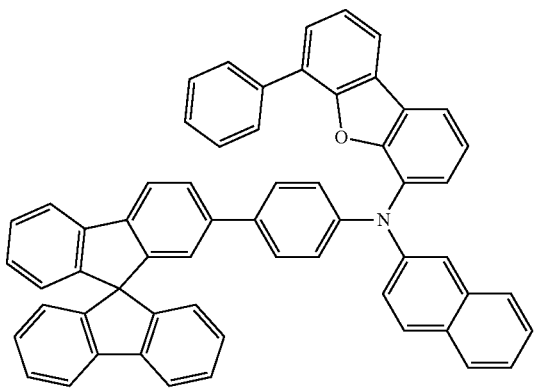
HT40
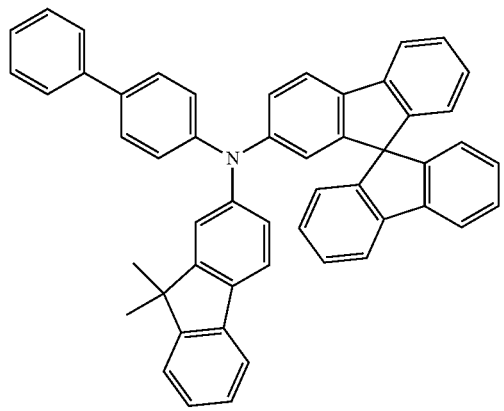
HT41
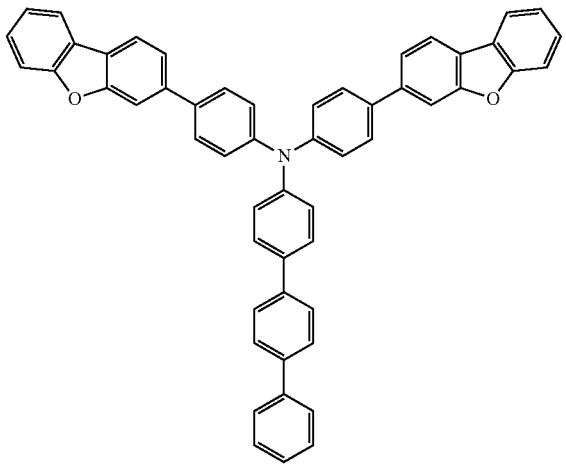

HT42
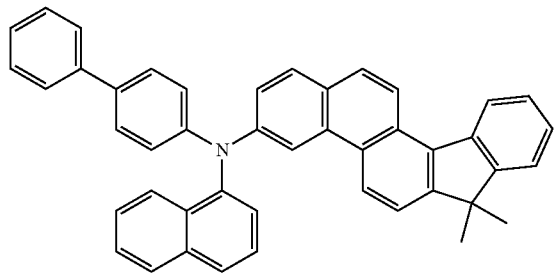
HT43
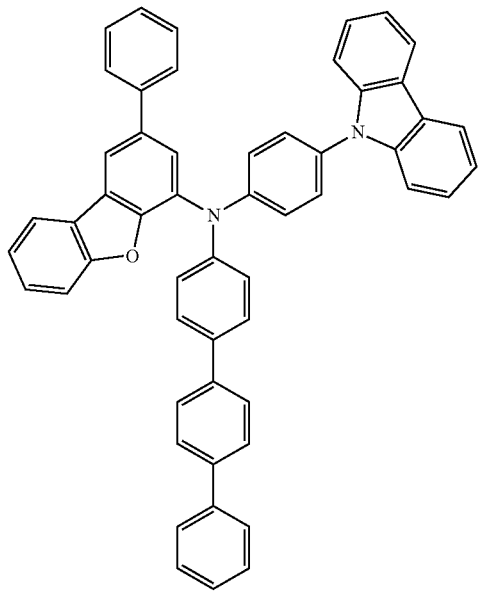
HT44
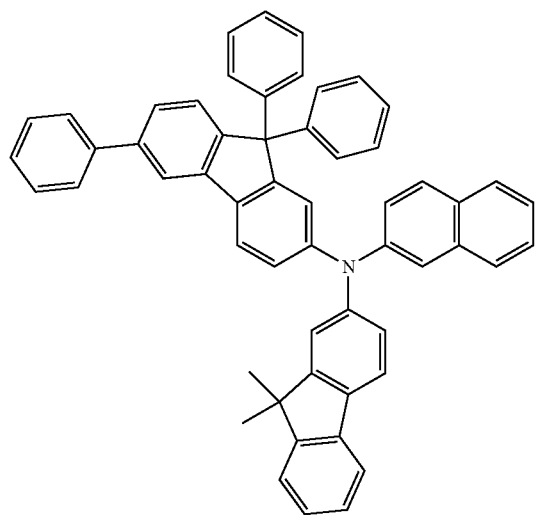
m-MTDATA
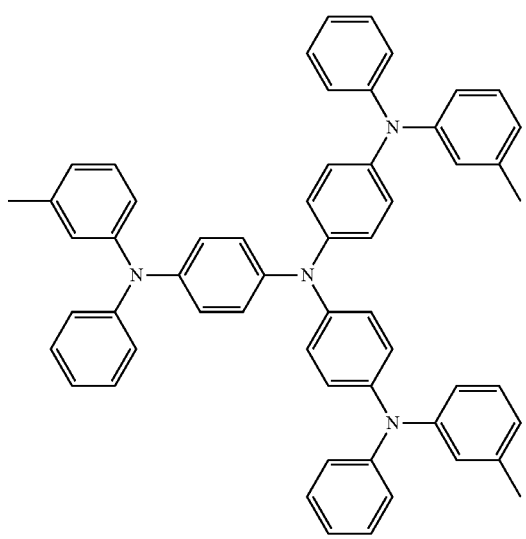

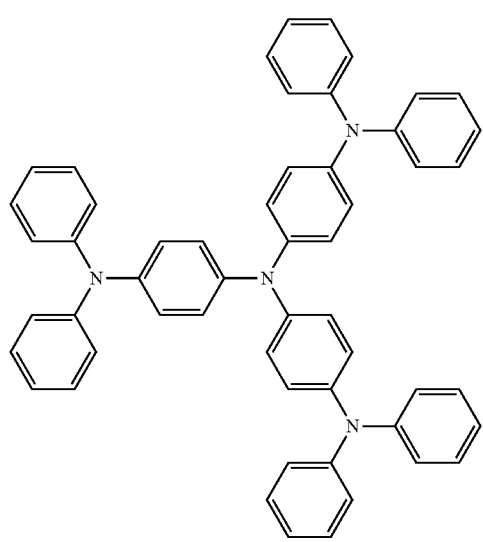
TDATA
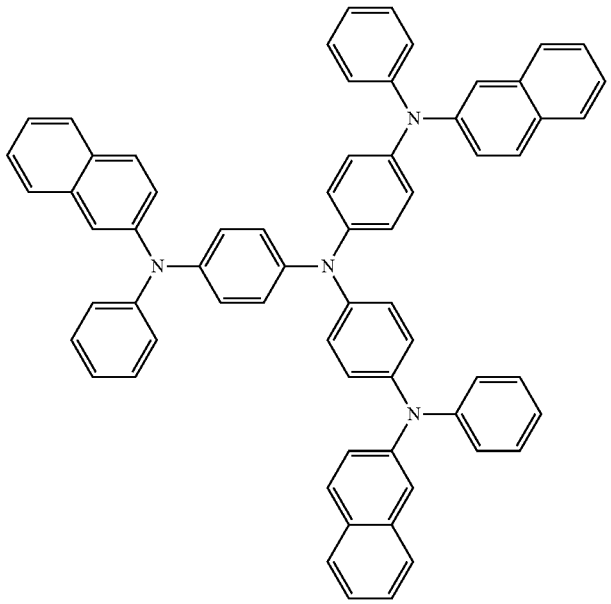
2-TNATA
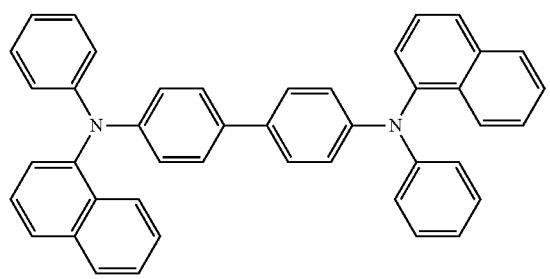
NPB
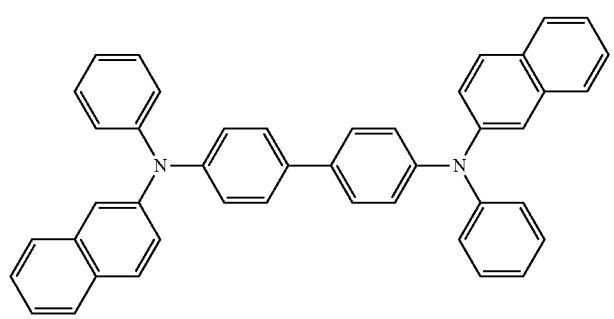
β-NPB
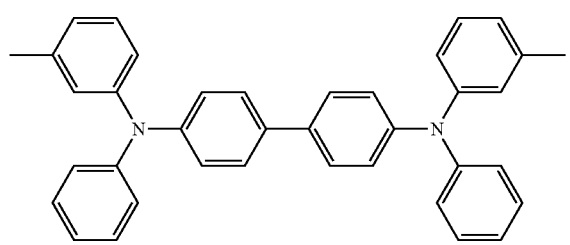
TPD
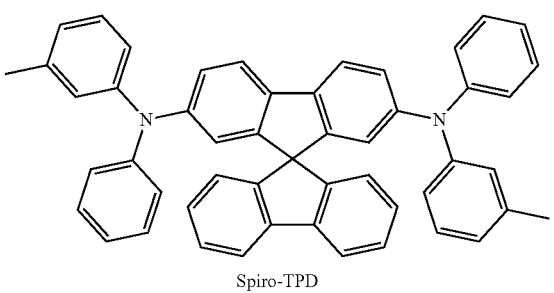
Spiro-TPD -continued

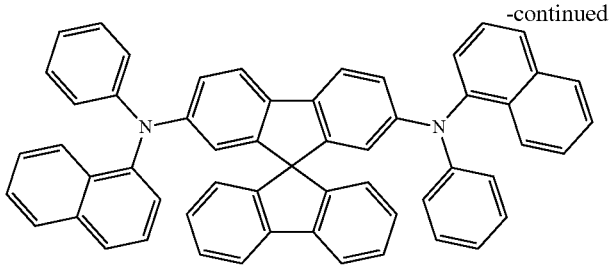
Spiro-NPB

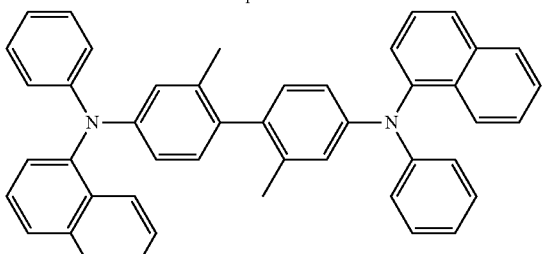
methylated-NPB

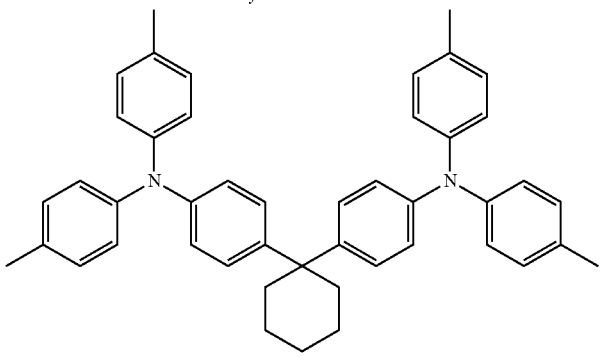
TAPC

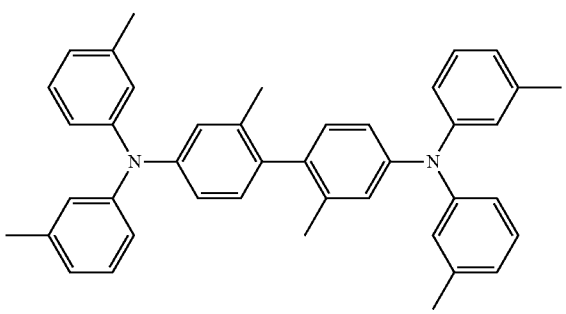
HMTPD

The thickness of the hole transport region may be in a range of about 50 (Angstroms) Å to about 10,000 Å, and in some embodiments, about 100 Å to about 4,000 Å. When the hole transport region includes a hole injection layer, a hole transport layer, or any combination thereof, the thickness of the hole injection layer may be in a range of about 100 Å to about 9,000 Å, and in some embodiments, about 100 Å to about 1,000 Å, and the thickness of the hole transport layer may be in a range of about 50 Å to about 2,000 Å, and in some embodiments, about 100 Å to about 1,500 Å. When the thicknesses of the hole transport region, the hole injection layer, and the hole transport layer are within any of these ranges, desired (e.g., excellent) hole transport characteristics may be obtained without a substantial increase in driving voltage.

The emission auxiliary layer may increase light emission efficiency by compensating for an optical resonance distance according to the wavelength of light emitted by the emission layer. The electron blocking layer may reduce or eliminate the flow of electrons from an electron transport region. The emission auxiliary layer and the electron blocking layer may include the aforementioned materials.

p-Dopant

The hole transport region may further include a charge generating material as well as the aforementioned materials to improve conductive properties of the hole transport region. The charge generating material may be substantially homogeneously or non-homogeneously dispersed (for example, as a single layer including (e.g., consisting of) the charge generating material) in the hole transport region.

The charge generating material may include, for example, a p-dopant.

In some embodiments, a lowest unoccupied molecular orbital (LUMO) energy level of the p-dopant may be −3.5 eV or less.

In some embodiments, the p-dopant may include a quinone derivative, a cyano group-containing compound, elements EL1 and EL2-containing compound (to be described in more detail below), or any combination thereof.

Non-limiting examples of the quinone derivative may include TCNQ, F4-TCNQ, and the like.

Non-limiting examples of the cyano group-containing compound include HAT-CN, a compound represented by Formula 221, and the like:

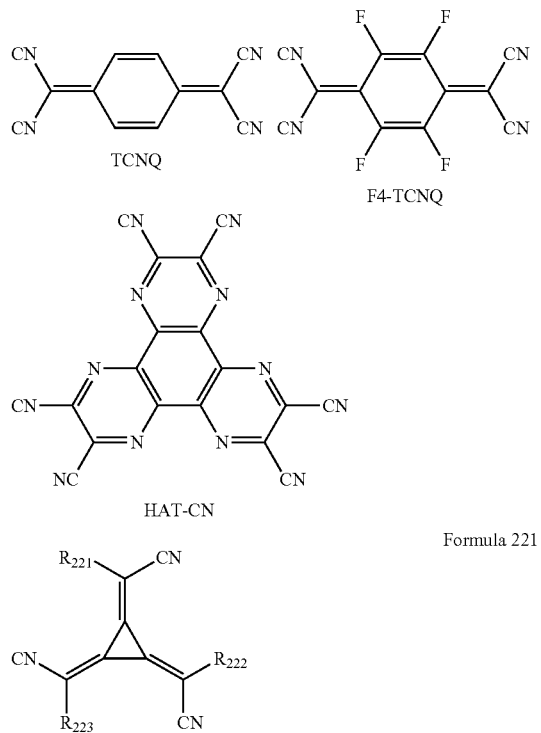

wherein, in Formula 221, $R_{221}$ to $R_{223}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, and at least one of $R_{221}$ to $R_{223}$ may each independently be: a $C_3$-$C_{60}$ carbocyclic group or a $C_1$-$C_{60}$ heterocyclic group, each substituted with a cyano group; —F; —Cl; —Br; —I; a $C_1$-$C_{20}$ alkyl group substituted with a cyano group, —F, —Cl, —Br, —I, or any combination thereof; or any combination thereof.

In the elements EL1 and EL2-containing compound, element EL1 may be a metal, a metalloid, or a combination thereof, and element EL2 may be a non-metal, a metalloid, or a combination thereof.

Non-limiting examples of the metal may include: an alkali metal (e.g., lithium (Li), sodium (Na), potassium (K), rubidium (Rb), cesium (Cs), and/or the like); an alkaline earth metal (e.g., beryllium (Be), magnesium (Mg), calcium (Ca), strontium (Sr), barium (Ba), and/or the like); a transition metal (e.g., titanium (Ti), zirconium (Zr), hafnium (Hf), vanadium (V), niobium (Nb), tantalum (Ta), chromium (Cr), molybdenum (Mo), tungsten (W), manganese (Mn), technetium (Tc), rhenium (Re), iron (Fe), ruthenium (Ru), osmium (Os), cobalt (Co), rhodium (Rh), iridium (Ir), nickel (Ni), palladium (Pd), platinum (Pt), copper (Cu), silver (Ag), gold (Au), and/or the like); post-transition metal (e.g., zinc (Zn), indium (In), tin (Sn), and/or the like); a lanthanide metal (e.g., lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), ruthenium (Lu), and/or the like); and the like.

Non-limiting examples of the metalloid may include silicon (Si), antimony (Sb), tellurium (Te), and the like.

Non-limiting examples of the non-metal may include oxygen (O), halogen (e.g., F, Cl, Br, I, and the like), and the like.

For example, the elements EL1 and EL2-containing compound may include a metal oxide, a metal halide (e.g., metal fluoride, metal chloride, metal bromide, metal iodide, and/or the like), a metalloid halide (e.g., a metalloid fluoride, a metalloid chloride, a metalloid bromide, a metalloid iodide, and/or the like), a metal telluride, or any combination thereof.

Non-limiting examples of the metal oxide may include tungsten oxide (e.g., WO, $W_2O_3$, $WO_2$, $WO_3$, $W_2O_5$, and/or the like), vanadium oxide (e.g., VO, $V_2O_3$, $VO_2$, $V_2O_5$, and/or the like), molybdenum oxide (MoO, $Mo_2O_3$, $MoO_2$, $MoO_3$, $Mo_2O_5$, and/or the like), rhenium oxide (e.g., $ReO_3$, and/or the like), and the like.

Non-limiting examples of the metal halide may include alkali metal halide, alkaline earth metal halide, transition metal halide, post-transition metal halide, lanthanide metal halide, and the like.

Non-limiting examples of the alkali metal halide may include LiF, NaF, KF, RbF, CsF, LiCl, NaCl, KCl, RbCl, CsCl, LiBr, NaBr, KBr, RbBr, CsBr, LiI, NaI, KI, RbI, CsI, and the like.

Non-limiting examples of the alkaline earth metal halide may include $BeF_2$, $MgF_2$, $CaF_2$, $SrF_2$, $BaF_2$, $BeCl_2$, $MgCl_2$, $CaCl_2$, $SrCl_2$, $BaCl_2$, $BeBr_2$, $MgBr_2$, $CaBr_2$, $SrBr_2$, $BaBr_2$, $BeI_2$, $MgI_2$, $CaI_2$, $SrI_2$, $BaI_2$, and the like.

Non-limiting examples of the transition metal halide may include titanium halide (e.g., $TiF_4$, $TiCl_4$, $TiBr_4$, $TiI_4$, and/or the like), zirconium halide (e.g., $ZrF_4$, $ZrCl_4$, $ZrBr_4$, $ZrI_4$, and/or the like), hafnium halide (e.g., $HfF_4$, $HfCl_4$, $HfBr_4$, $HfI_4$, and/or the like), vanadium halide (e.g., $VF_3$, $VCl_3$, $VBr_3$, $VI_3$, and/or the like), niobium halide (e.g., $NbF_3$, $NbCl_3$, $NbBr_3$, $NbI_3$, and/or the like), tantalum halide (e.g., $TaF_3$, $TaCl_3$, $TaBr_3$, $TaI_3$, and/or the like), chromium halide (e.g., $CrF_3$, $CrCl_3$, $CrBr_3$, $CrI_3$, and/or the like), molybdenum halide (e.g., $MoF_3$, $MoCl_3$, $MoBr_3$, $MoI_3$, and/or the like), tungsten halide (e.g., $WF_3$, $WCl_3$, $WBr_3$, $WI_3$, and/or the like), manganese halide (e.g., $MnF_2$, $MnCl_2$, $MnBr_2$, $MnI_2$, and/or the like), technetium halide (e.g., $TcF_2$, $TcCl_2$, $TcBr_2$, $TcI_2$, and/or the like), rhenium halide (e.g., $ReF_2$, $ReCl_2$, $ReBr_2$, $ReI_2$, and/or the like), iron halide (e.g., $FeF_2$, $FeCl_2$, $FeBr_2$, $FeI_2$, and/or the like), ruthenium halide (e.g., $RuF_2$, $RuCl_2$, $RuBr_2$, $RuI_2$, and/or the like), osmium halide (e.g., $OsF_2$, $OsCl_2$, $OsBr_2$, $OsI_2$, and/or the like), cobalt halide (e.g., $CoF_2$, $CoCl_2$, $CoBr_2$, $CoI_2$, and/or the like), rhodium halide (e.g., RhF$_2$, RhCl$_2$, RhBr$_2$, RhI$_2$, and/or the like), iridium halide (e.g., IrF$_2$, IrCl$_2$, IrBr$_2$, IrI$_2$, and/or the like), nickel halide (e.g., NiF$_2$, NiCl$_2$, NiBr$_2$, NiI$_2$, and/or the like), palladium halide (e.g., PdF$_2$, PdCb, PdBr$_2$, PdI$_2$, and/or the like), platinum halide (e.g., PtF$_2$, PtCl$_2$, PtBr$_2$, PtI$_2$, and/or the like), copper halide (e.g., CuF, CuCl, CuBr, CuI, and/or the like), silver halide (e.g., AgF, AgCl, AgBr, AgI, and/or the like), gold halide (e.g., AuF, AuCl, AuBr, AuI, and/or the like), and the like.

Non-limiting examples of the post-transition metal halide may include zinc halide (e.g., ZnF$_2$, ZnCl$_2$, ZnBr$_2$, ZnI$_2$, and/or the like), indium halide (e.g., InI$_3$ and/or the like), tin halide (e.g., SnI$_2$ and/or the like), and the like.

Non-limiting examples of the lanthanide metal halide may include YbF, YbF$_2$, YbF$_3$, SmF$_3$, YbCl, YbCl$_2$, YbCl$_3$, SmCl$_3$, YbBr$_2$, YbBr$_2$, YbBr$_3$, SmBr$_3$, YbI, YbI$_2$, YbI$_3$, SmI$_3$, and the like.

Non-limiting examples of the metalloid halide may include antimony halide (e.g., SbCl$_5$ and/or the like) and the like.

Non-limiting examples of the metal telluride may include alkali metal telluride (e.g., Li$_2$Te, Na$_2$Te, K$_2$Te, Rb$_2$Te, Cs$_2$Te, and/or the like), alkaline earth metal telluride (e.g., BeTe, MgTe, CaTe, SrTe, BaTe, and/or the like), transition metal telluride (e.g., TiTe$_2$, ZrTe$_2$, HfTe$_2$, V$_2$Te$_3$, Nb$_2$Te$_3$, Ta$_2$Te$_3$, Cr$_2$Te$_3$, Mo$_2$Te$_3$, W$_2$Te$_3$, MnTe, TcTe, ReTe, FeTe, RuTe, OsTe, CoTe, RhTe, IrTe, NiTe, PdTe, PtTe, Cu$_2$Te, CuTe, Ag$_2$Te, AgTe, Au$_2$Te, and/or the like), post-transition metal telluride (e.g., ZnTe and/or the like), lanthanide metal telluride (e.g., LaTe, CeTe, PrTe, NdTe, PmTe, EuTe, GdTe, TbTe, DyTe, HoTe, ErTe, TmTe, YbTe, LuTe, and/or the like), and the like.

Emission Layer in Interlayer 130

When the light-emitting device 10 is a full color light-emitting device, the emission layer may be patterned into a red emission layer, a green emission layer, and/or a blue emission layer, according to a sub-pixel. In one or more embodiments, the emission layer may have a stacked structure. The stacked structure may include two or more layers selected from a red emission layer, a green emission layer, and a blue emission layer. The two or more layers may be in direct contact with each other.

In some embodiments, the two or more layers may be separated from each other. In one or more embodiments, the emission layer may include two or more materials. The two or more materials may include a red light-emitting material, a green light-emitting material, and/or a blue light-emitting material. The two or more materials may be mixed with each other in a single layer. The two or more materials mixed with each other in the single layer may emit white light.

The emission layer may include a host and a dopant. The dopant may be a phosphorescent dopant, a fluorescent dopant, or any combination thereof.

The amount of the dopant in the emission layer may be in a range of about 0.01 parts to about 15 parts by weight based on 100 parts by weight of the host.

In some embodiments, the emission layer may include a quantum dot.

The emission layer may include a delayed fluorescent material. The delayed fluorescent material may serve as a host or a dopant in the emission layer.

The thickness of the emission layer may be in a range of about 100 Å to about 1,000 Å, and in some embodiments, about 200 Å to about 600 Å. When the thickness of the emission layer is within any of these ranges, improved luminescence characteristics may be obtained without a substantial increase in driving voltage.

Host

The host may include a compound represented by Formula 301:

$$[Ar_{301}]_{xb11}\text{-}[(L_{301})_{xb1}\text{-}R_{301}]_{xb21} \qquad \text{Formula 301}$$

wherein, in Formula 301,

Ar$_{301}$ and L$_{301}$ may each independently be a C$_3$-C$_{60}$ carbocyclic group unsubstituted or substituted with at least one R$_{10a}$ or a C$_1$-C$_{60}$ heterocyclic group unsubstituted or substituted with at least one R$_{10a}$, xb11 may be 1, 2, or 3, xb1 may be an integer from 0 to 5, R$_{301}$ may be hydrogen, deuterium, —F, —Cl, —Br, —I, a hydroxyl group, a cyano group, a nitro group, a C$_1$-C$_{60}$ alkyl group unsubstituted or substituted with at least one R$_{10a}$, a C$_2$-C$_{60}$ alkenyl group unsubstituted or substituted with at least one R$_{10a}$, a C$_2$-C$_{60}$ alkynyl group unsubstituted or substituted with at least one R$_{10a}$, a C$_1$-C$_{60}$ alkoxy group unsubstituted or substituted with at least one R$_{10a}$, a C$_3$-C$_{60}$ carbocyclic group unsubstituted or substituted with at least one R$_{10a}$, a C$_1$-C$_{60}$ heterocyclic group unsubstituted or substituted with at least one R$_{10a}$, —Si(Q$_{301}$)(Q$_{302}$)(Q$_{303}$), —N(Q$_{301}$)(Q$_{302}$), —B(Q$_{301}$)(Q$_{302}$), —C(=O)(Q$_{301}$), —S(=O)$_2$(Q$_{301}$), or —P(=O)(Q$_{301}$)(Q$_{302}$), xb21 may be an integer from 1 to 5, and Q$_{301}$ to Q$_{303}$ may each independently be understood by referring to the description of Q$_1$ provided herein.

In some embodiments, when xb11 in Formula 301 is 2 or greater, at least two Ar$_{301}$(s) may be bound via a single bond. For example, when xb11 in Formula 301 is 2 or greater, the two or more Ar$_{301}$(s) may be bound to each other via a single bond.

In some embodiments, the host may include a compound represented by Formula 301-1, a compound represented by Formula 301-2, or any combination thereof:

Formula 301-1

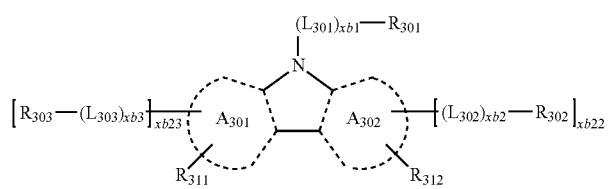

Formula 301-2

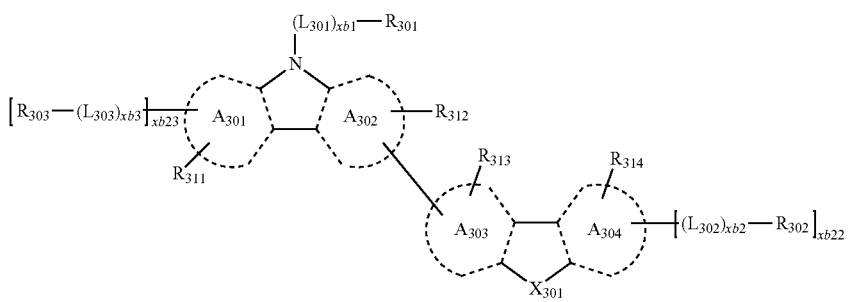

wherein, in Formulae 301-1 to 301-2,
ring $A_{301}$ to ring $A_{304}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$,
$X_{301}$ may be O, S, N-[($L_{304}$)$_{xb4}$-$R_{304}$], C($R_{304}$)($R_{305}$), or Si($R_{304}$)($R_{305}$),
xb22 and xb23 may each independently be 0, 1, or 2,
$L_{301}$, xb1, and $R_{301}$ may respectively be understood by referring to the descriptions of $L_{301}$, xb1, and $R_{301}$ provided herein,
$L_{302}$ to $L_{304}$ may each independently be understood by referring to the description of $L_{301}$ provided herein,
xb2 to xb4 may each independently be understood by referring to the descriptions of xb1 provided herein, and $R_{302}$ to $R_{305}$ and $R_{311}$ to $R_{314}$ may each independently be understood by referring to the descriptions of $R_{301}$ provided herein.

In some embodiments, the host may include an alkaline earth metal complex or zinc (Zn) complex. For example, the host may include a Be complex (e.g., Compound H55), a Mg complex, a Zn complex, or any combination thereof.

In some embodiments, the host may include one of Compounds H1 to H124, 9,10-di(2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolylbenzene (mCP), 1,3,5-tri(carbazol-9-yl)benzene (TCP), or any combination thereof:

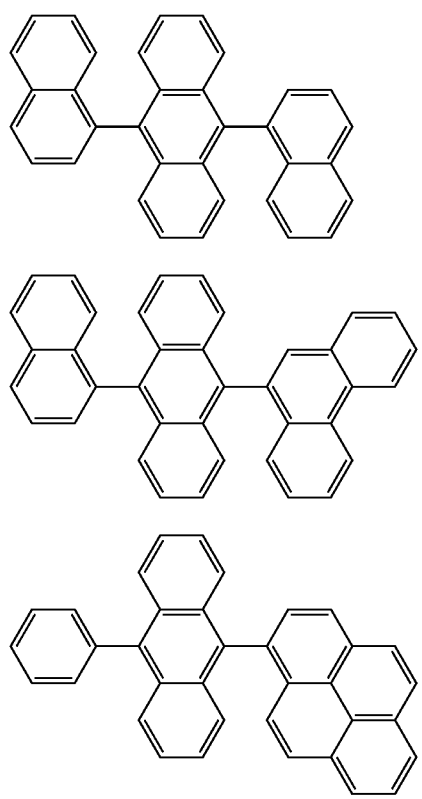

-continued
H7
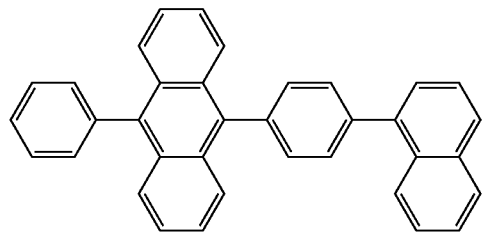
H8
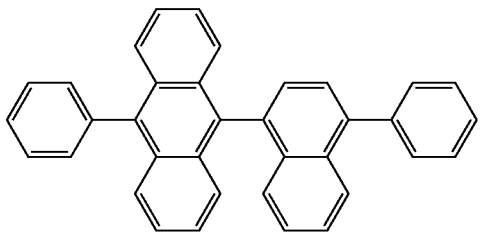
H9
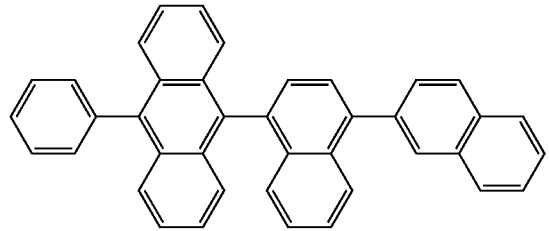
H10
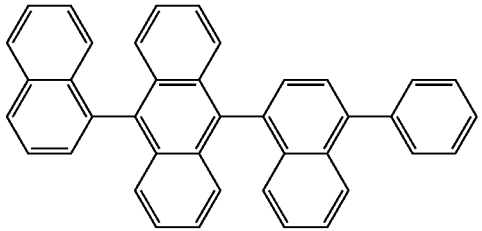
H11
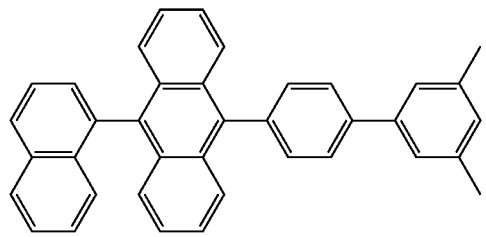
H12
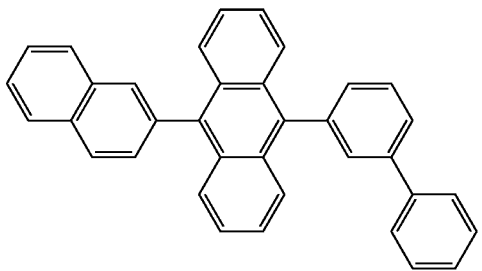
H13
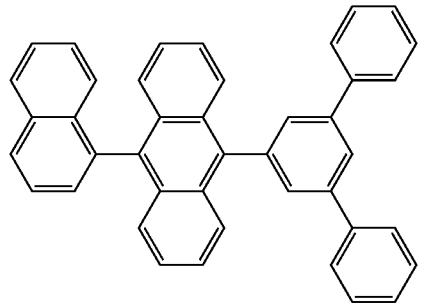
H14
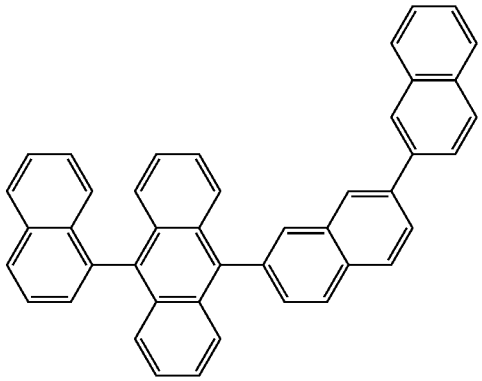
H15
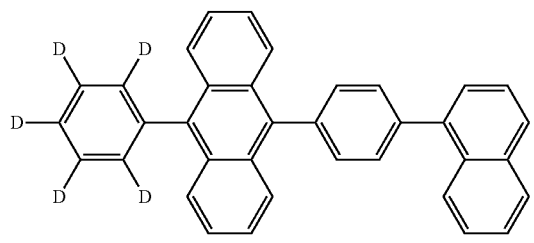
H16
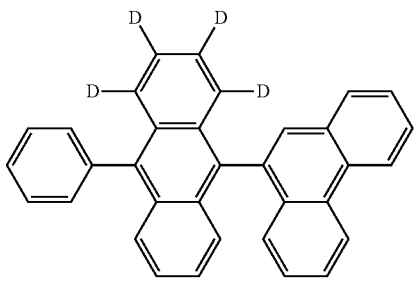

-continued
H17
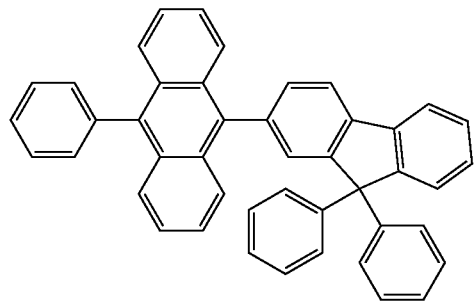
H18
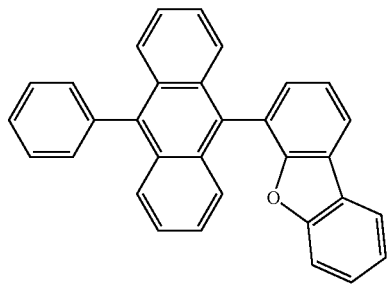
H19
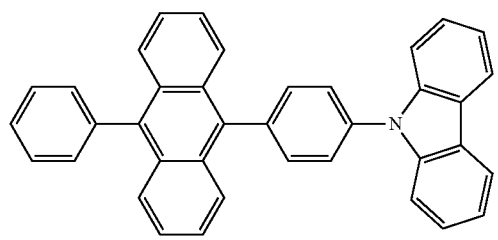
H20
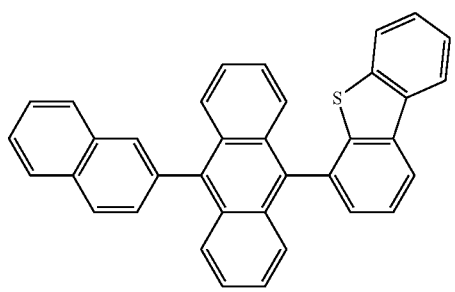
H21
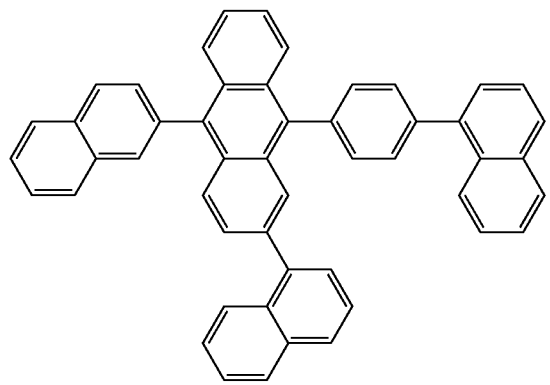
H22
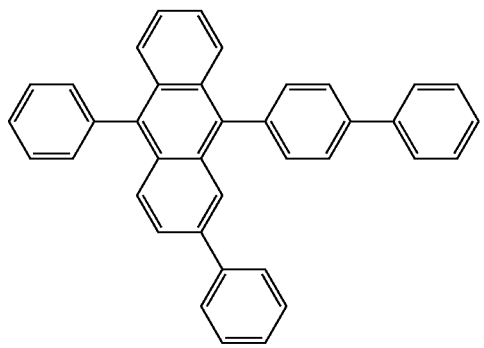
H23
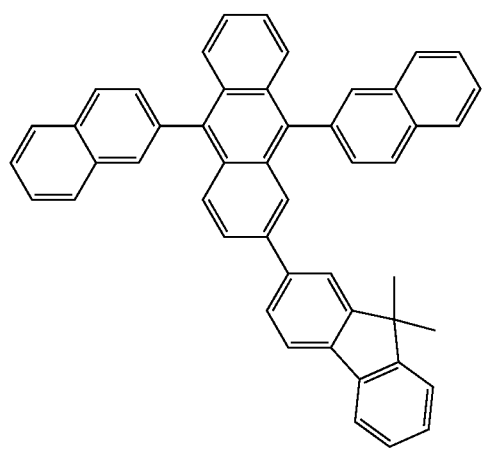
H24
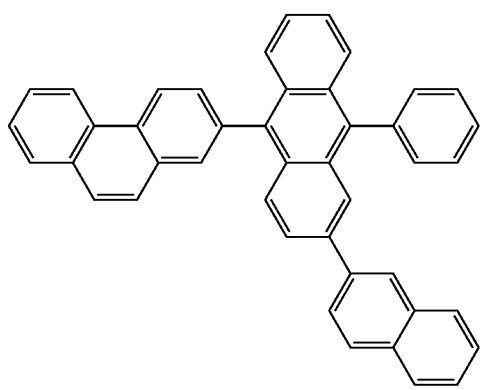

-continued
| H25 | H26 |
|---|---|
| 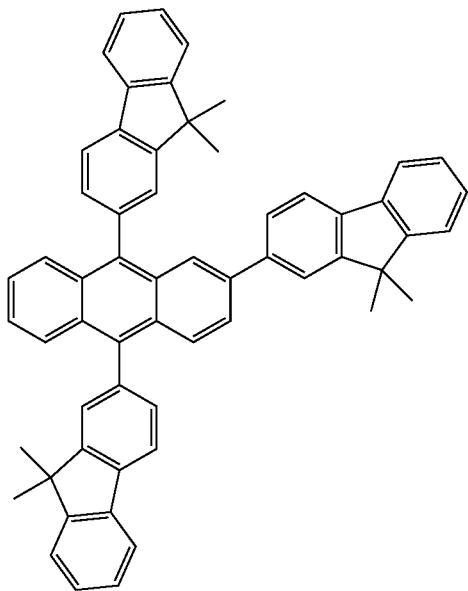 | 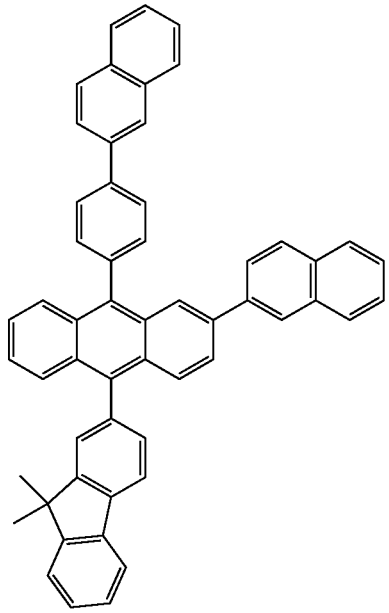 |
| H27 | H28 |
| 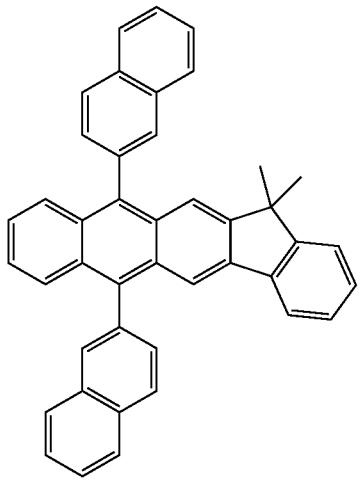 | 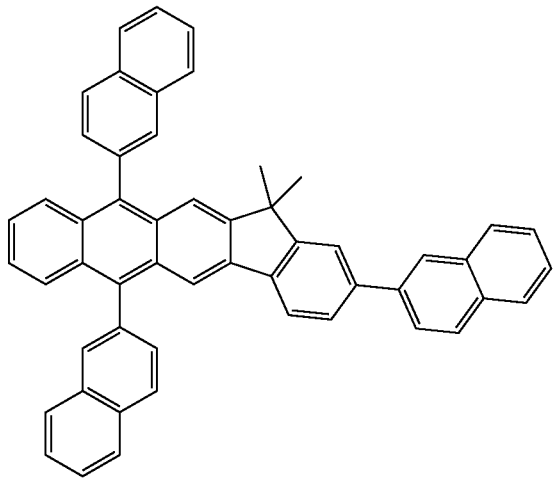 |
| H29 | H30 |
| 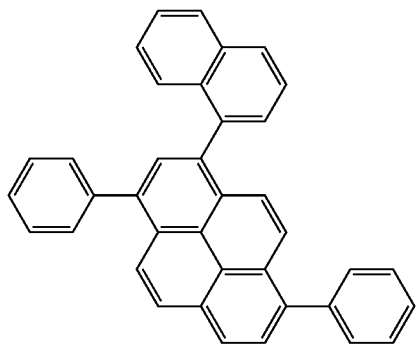 | 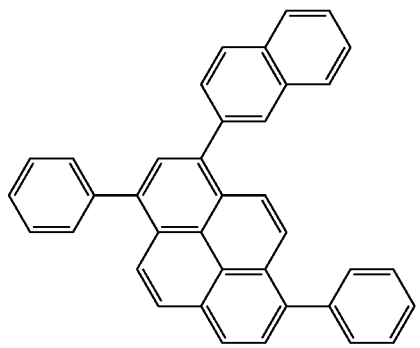 |

-continued
H31
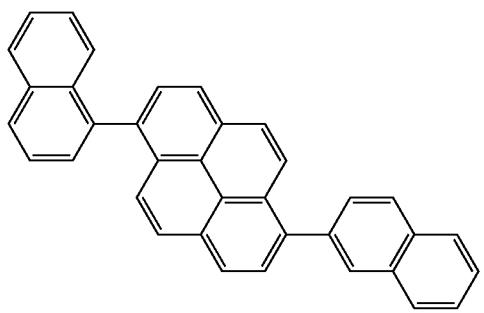
H32
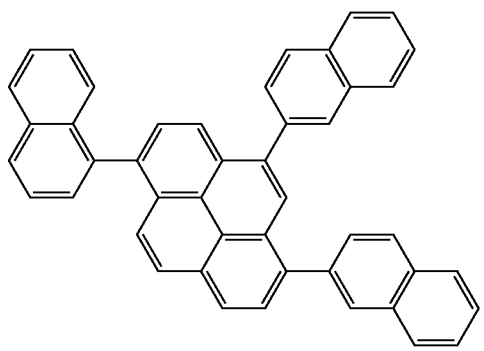
H33
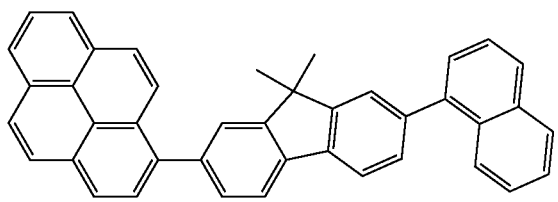
H34
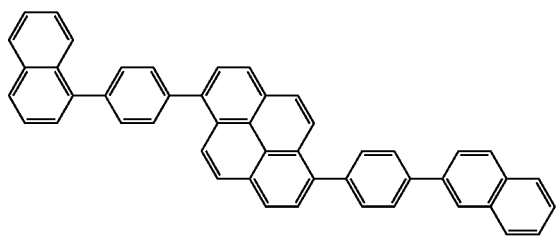
H35
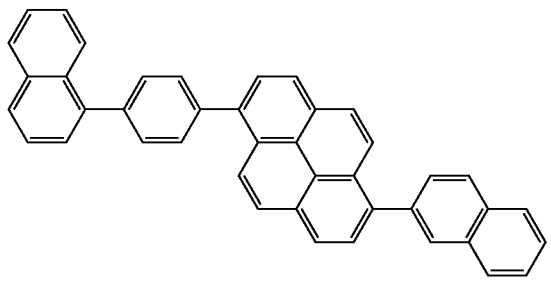
H36
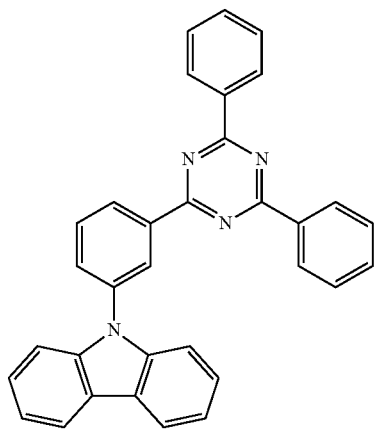
H37
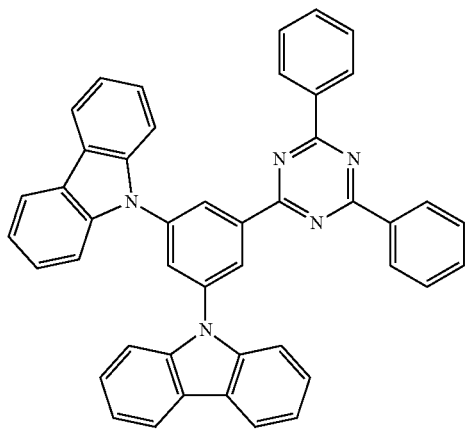
H38
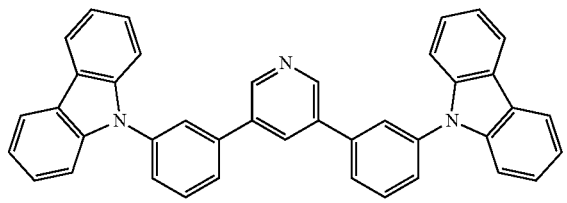

-continued
H39
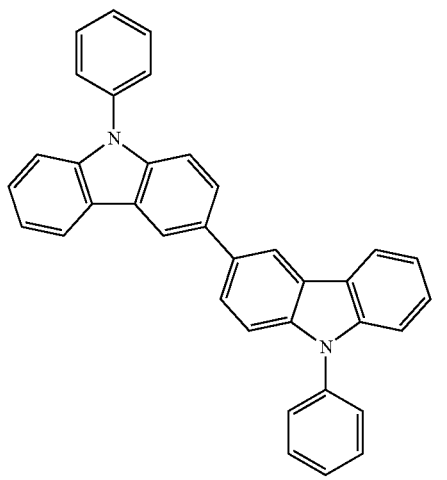
H40
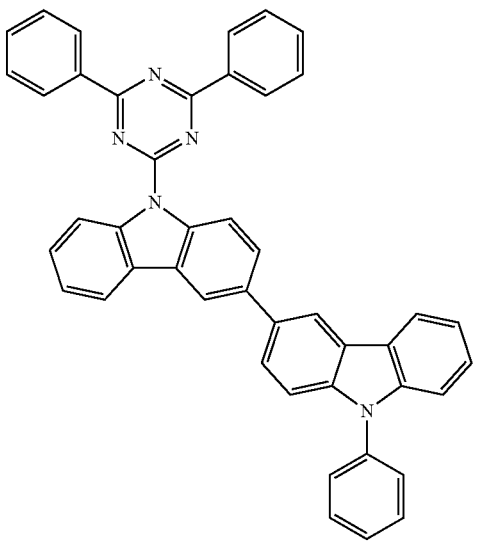
H41
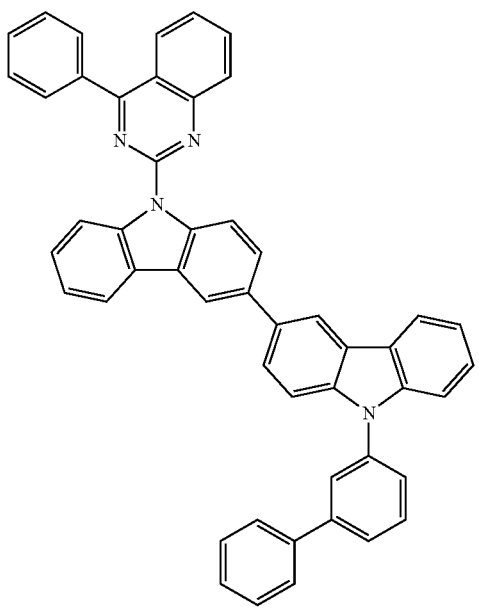
H42
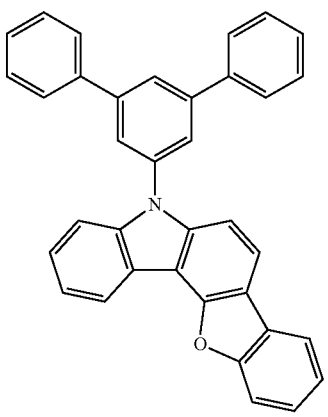
H43
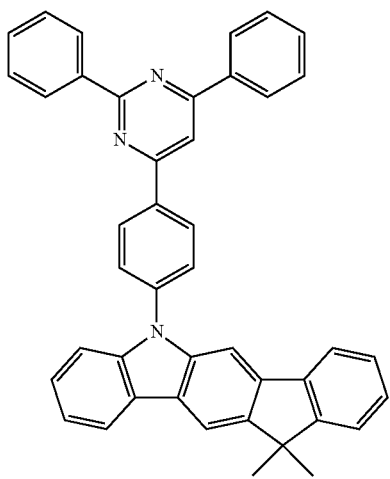
H44
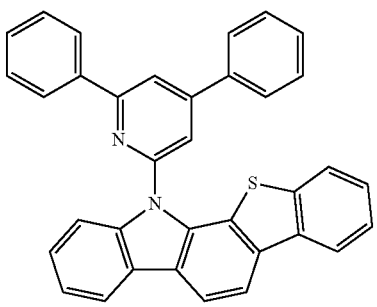

-continued
H45
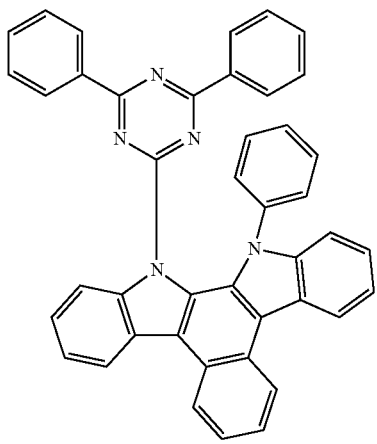
H46
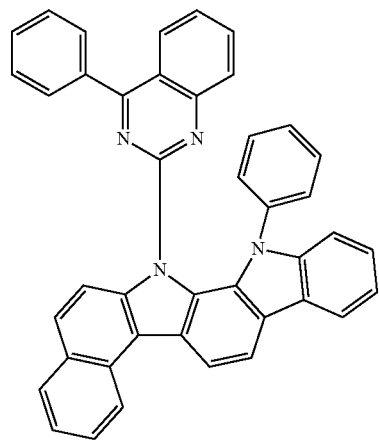
H47
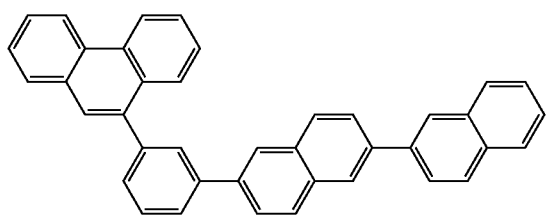
H48
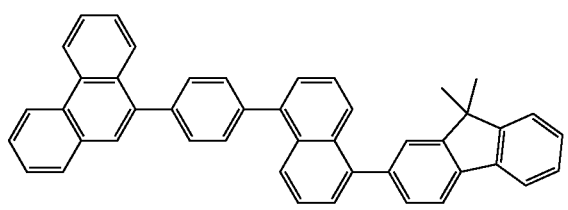
H49
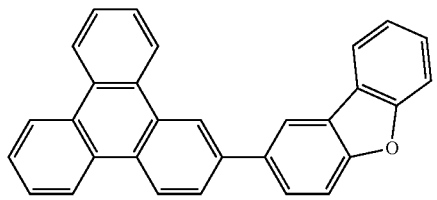
H50
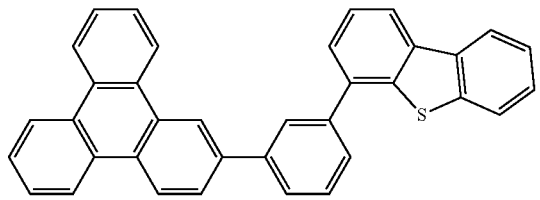
H51
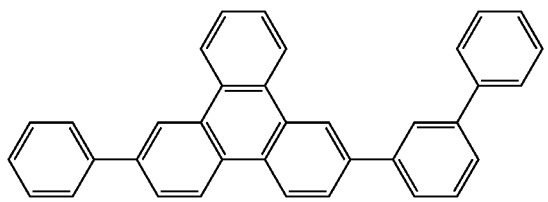
H52
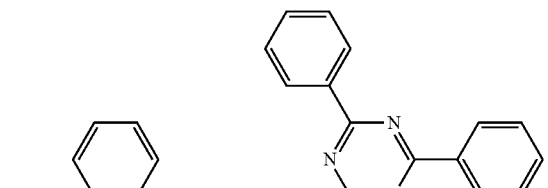
H53
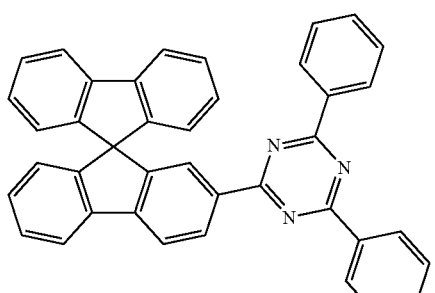
H54
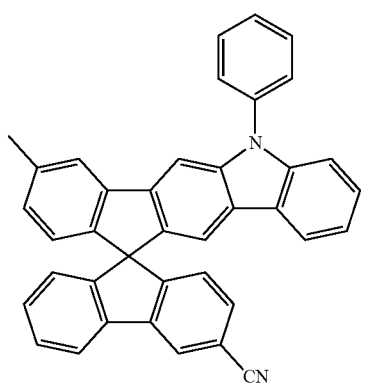

-continued
H55
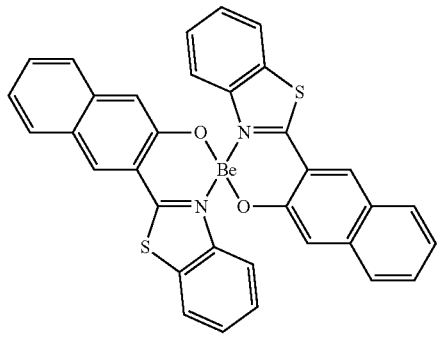
H56
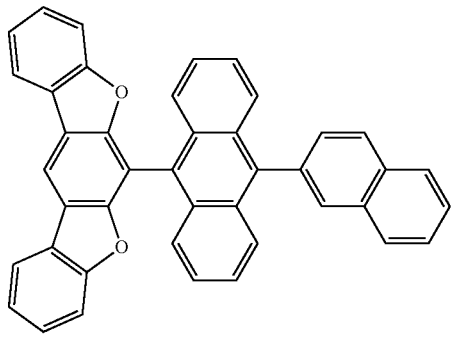
H57
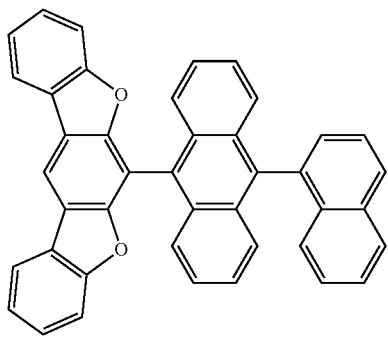
H58
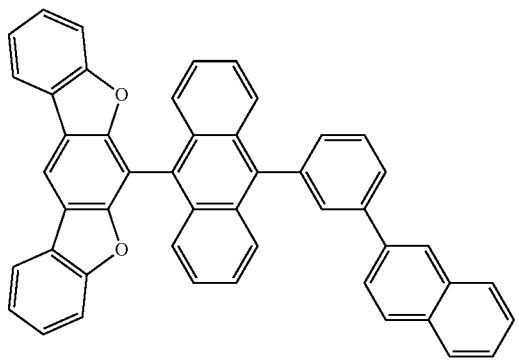
H59
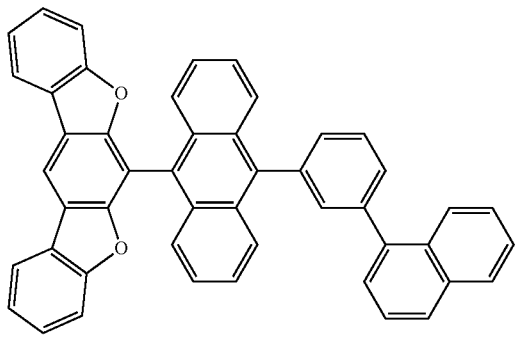
H60
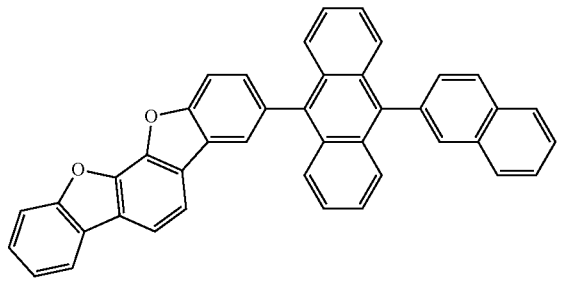
H61
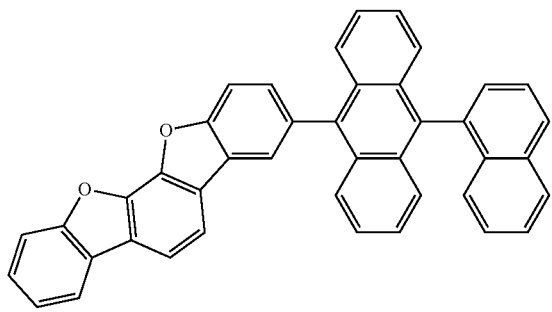
H62
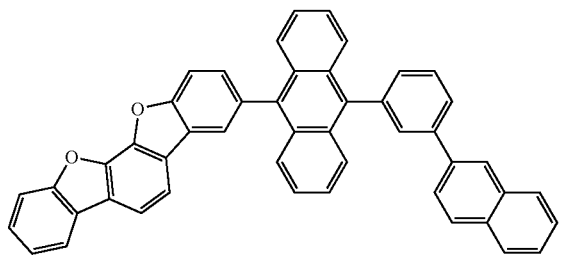

-continued
H63
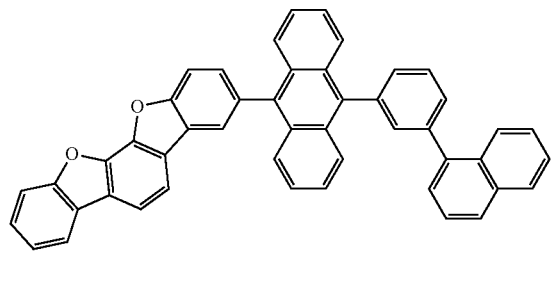
H64
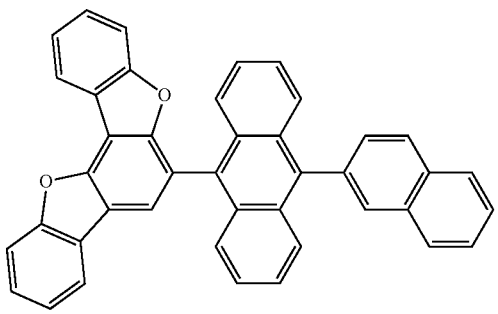
H65
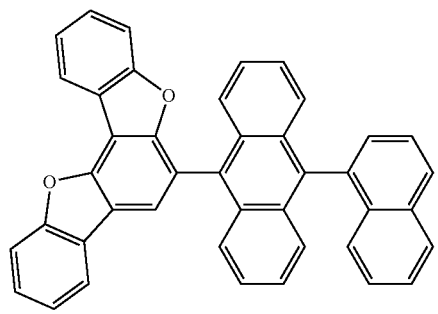
H66
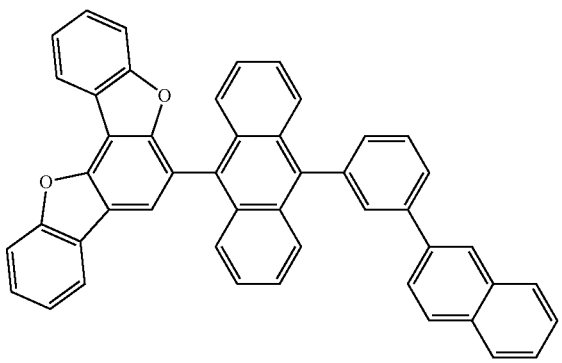
H67
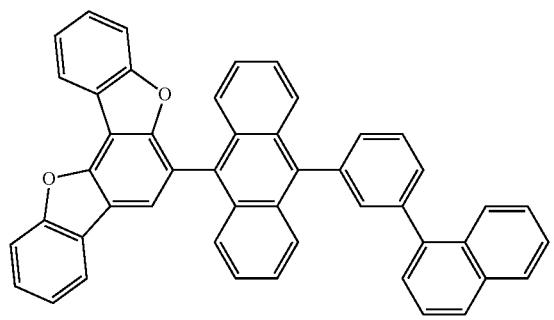
H68
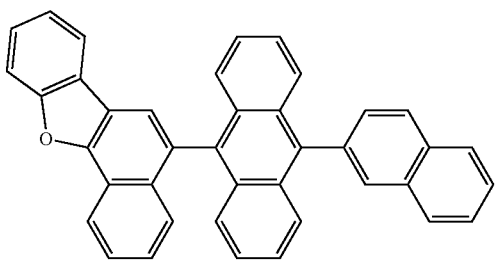
H69
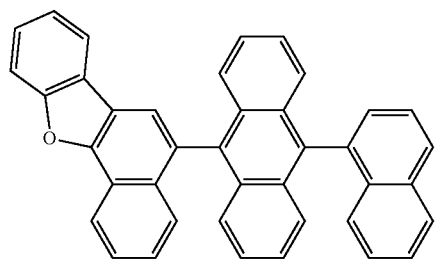
H70
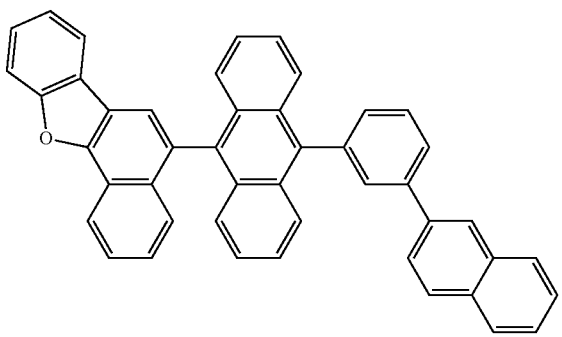

-continued
H71
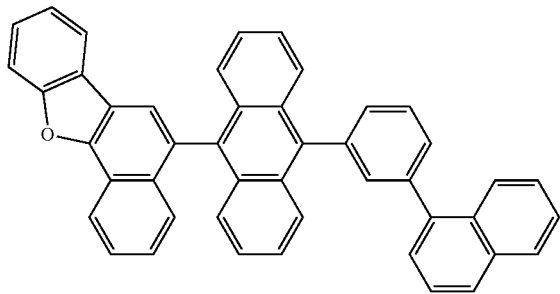
H72
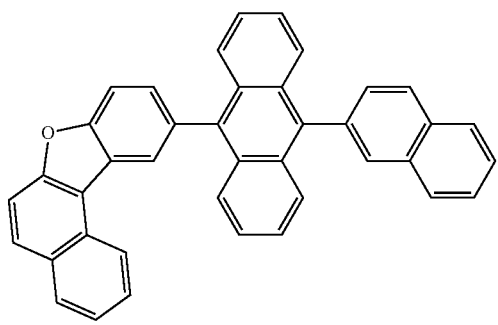
H73
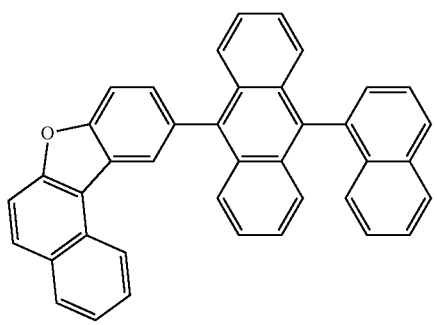
H74
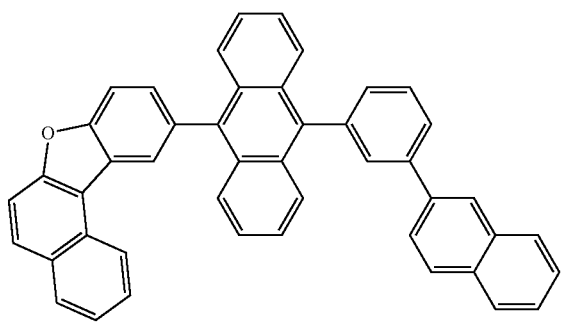
H75
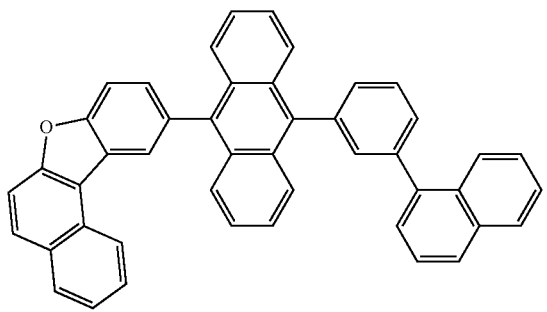
H76
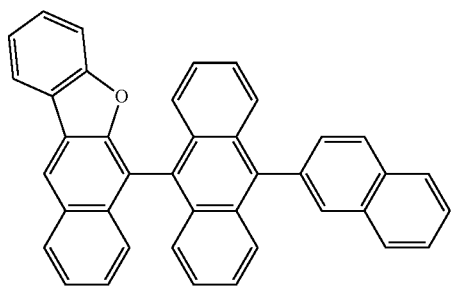
H77
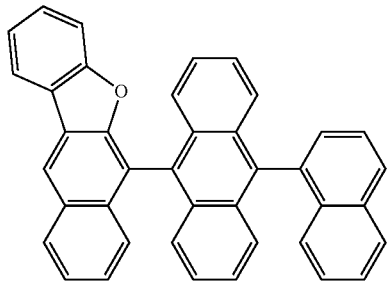
H78
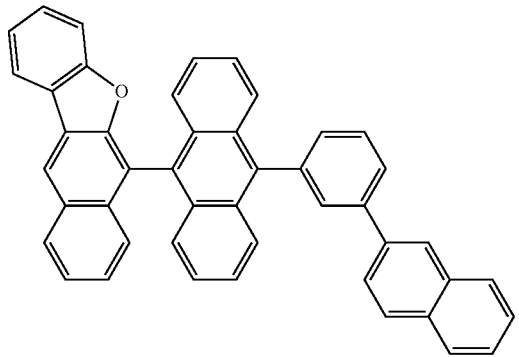

-continued
H79
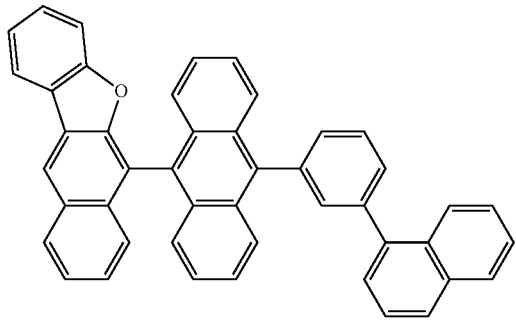
H80
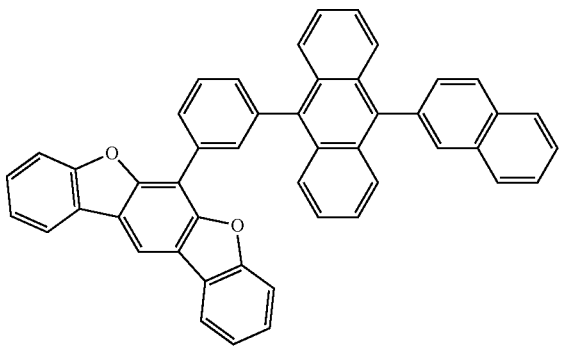
H81
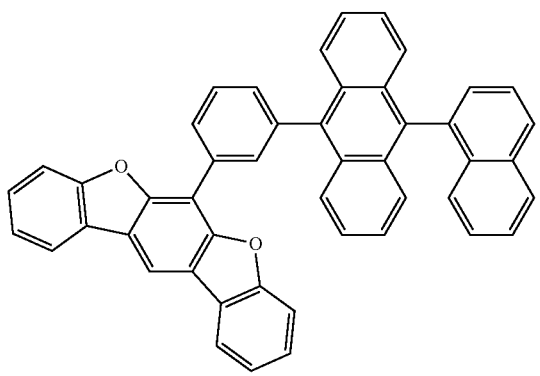
H82
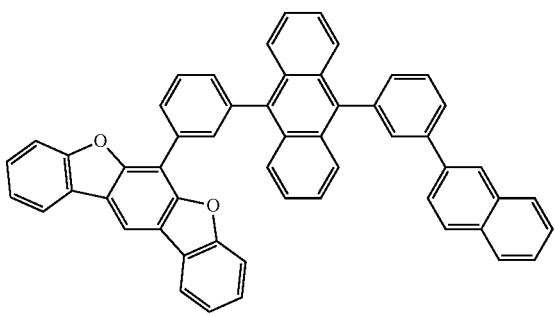
H83
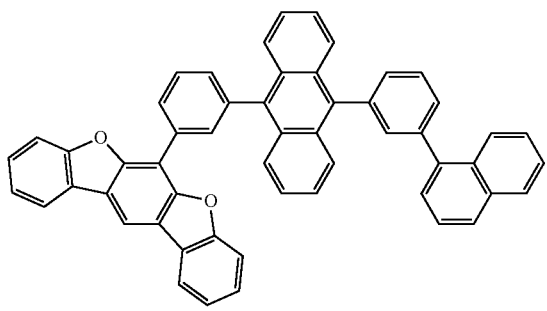
H84
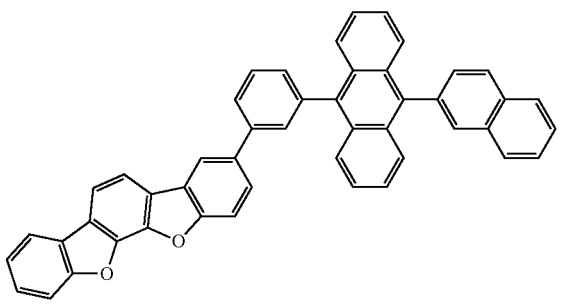
H85
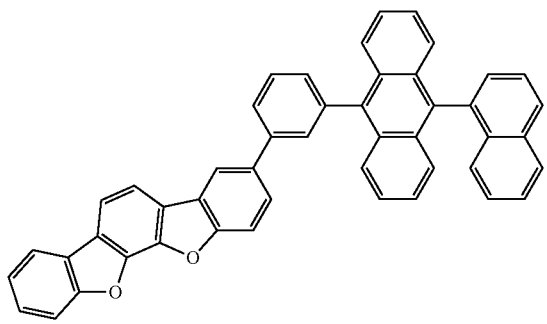
H86
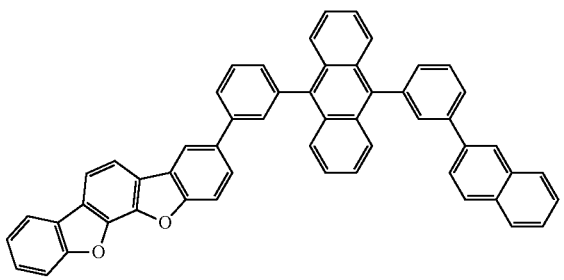

-continued
H87
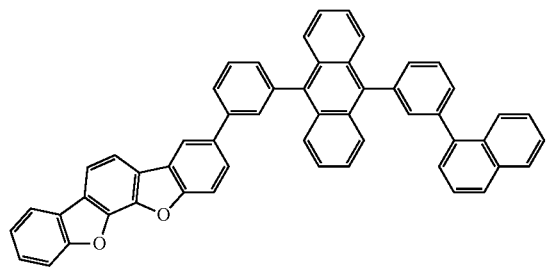
H88
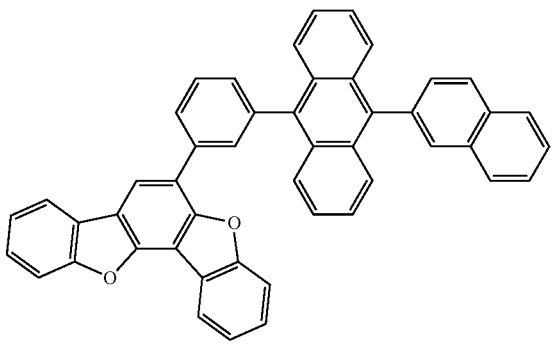
H89
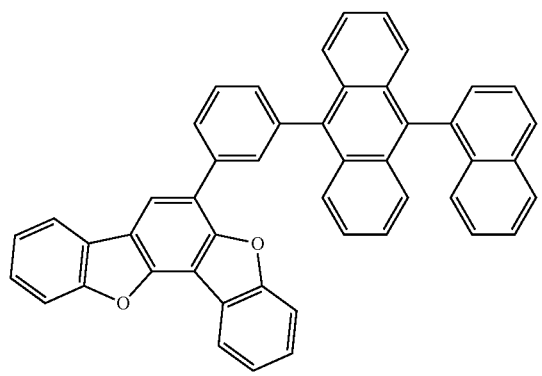
H90
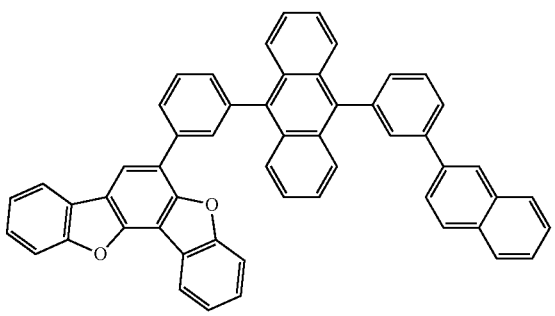
H91
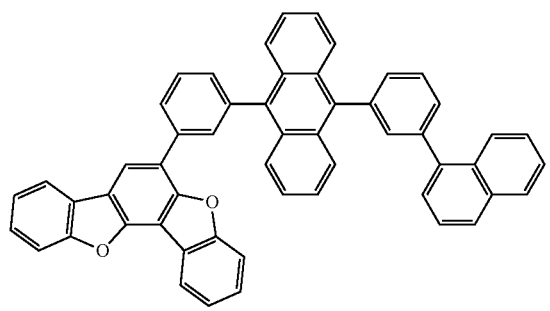
H92
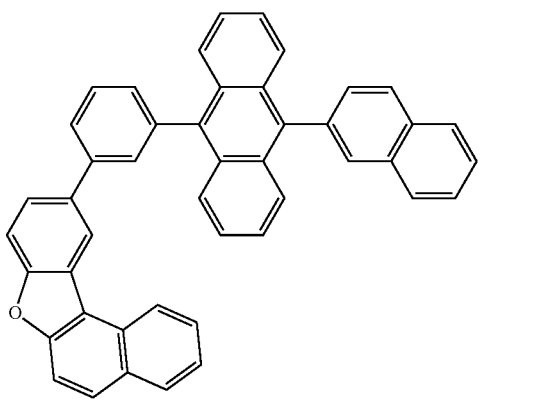
H93
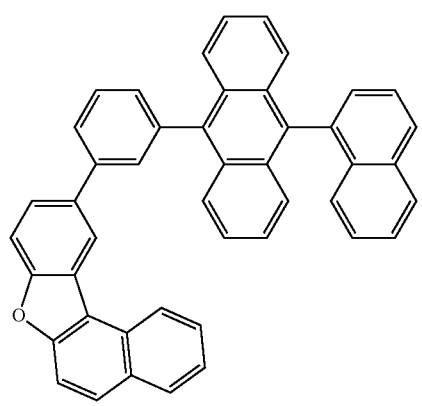
H94
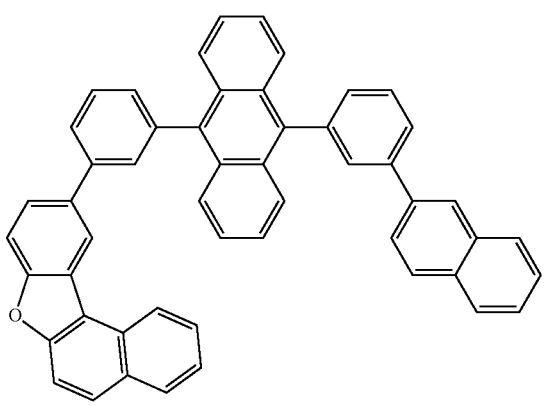

H95
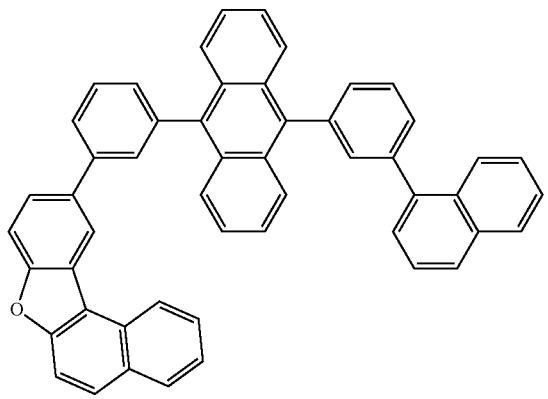
H96
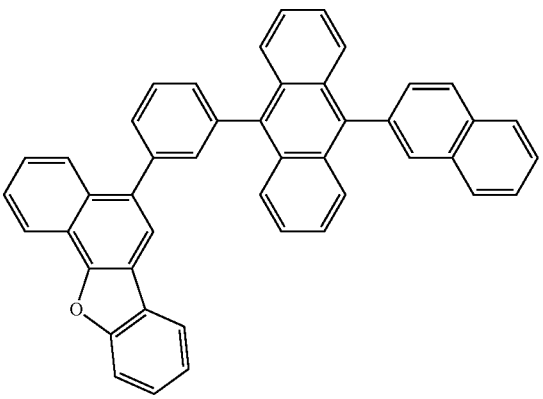
H97
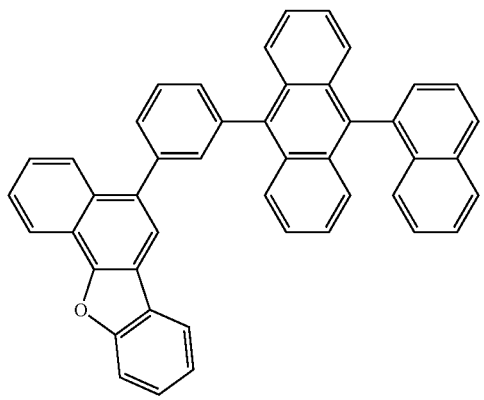
H98
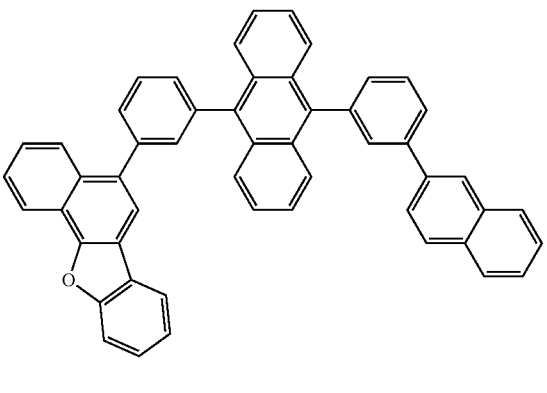
H199
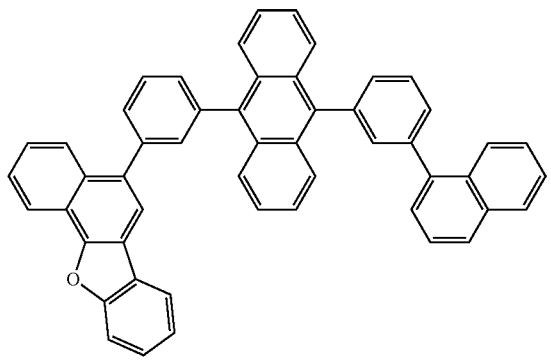
H100
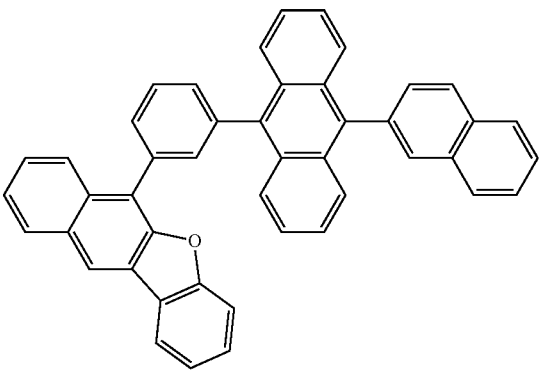
H101
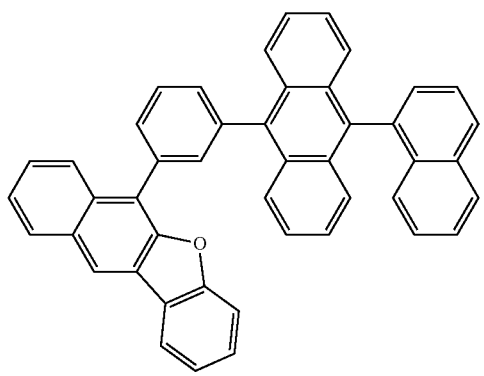
H102
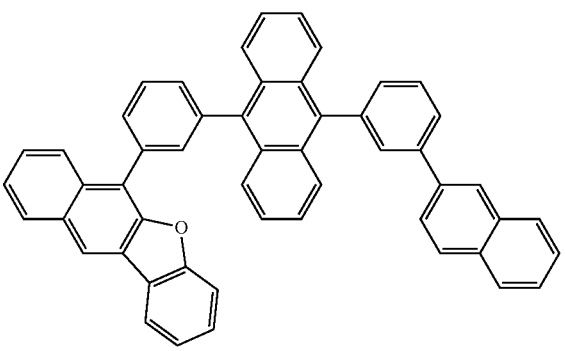

-continued
H103
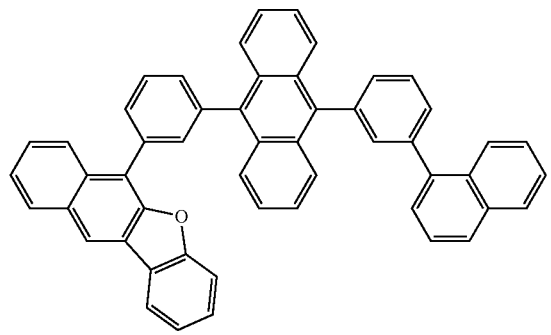
H104
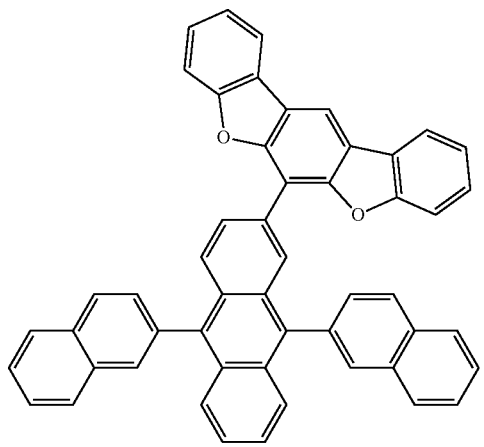
H105
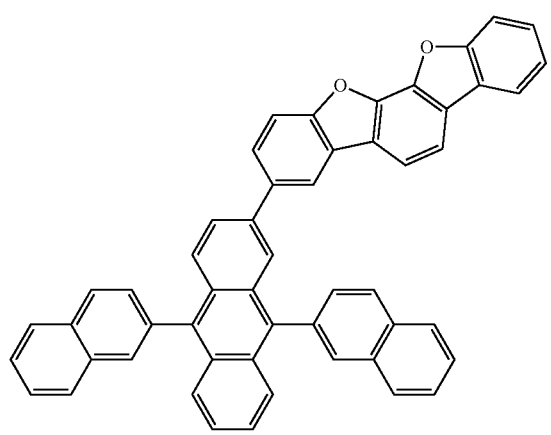
H106
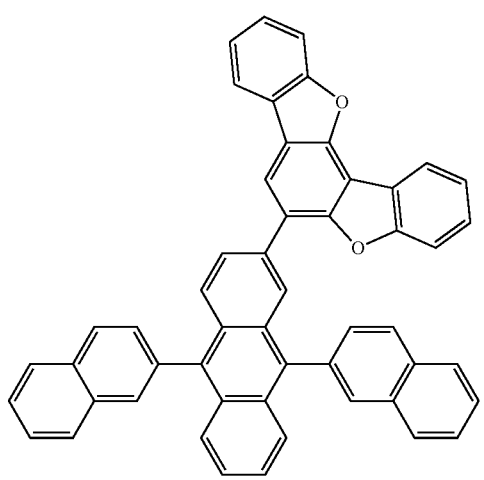
H107
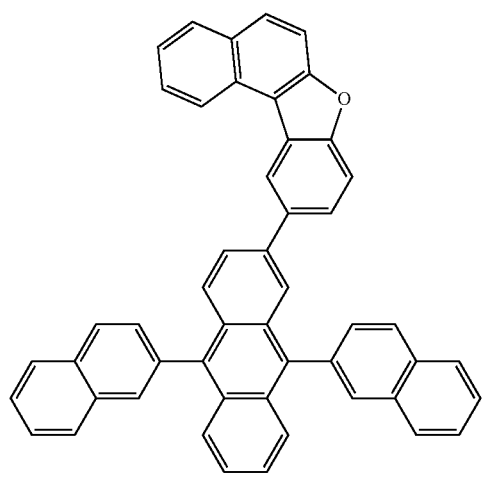
H108
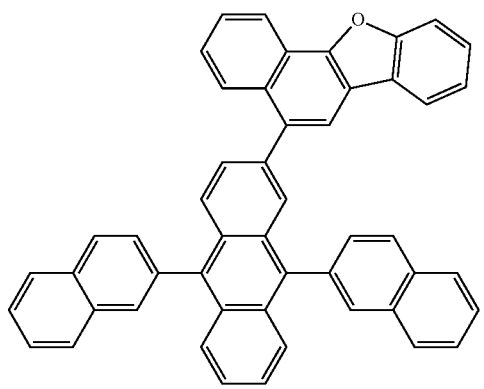

-continued
H109
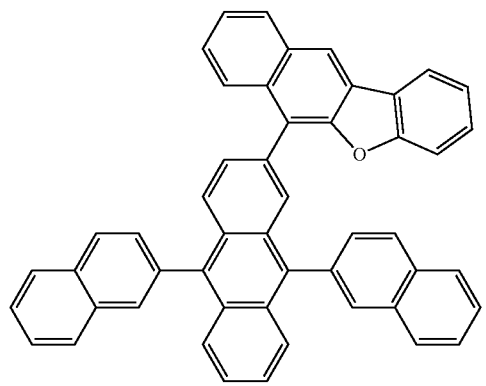
H110
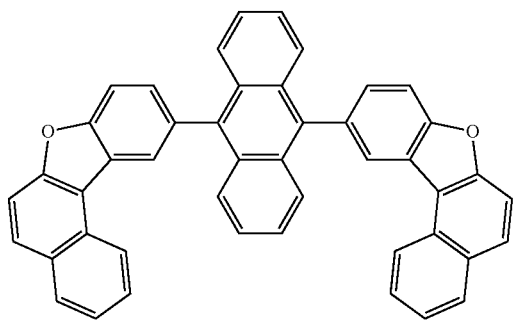
H111
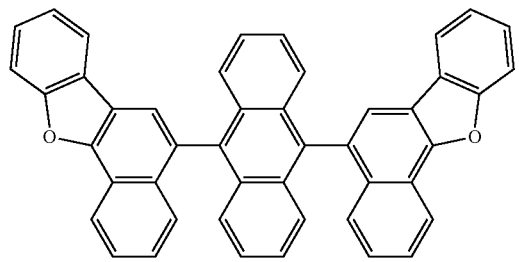
H112
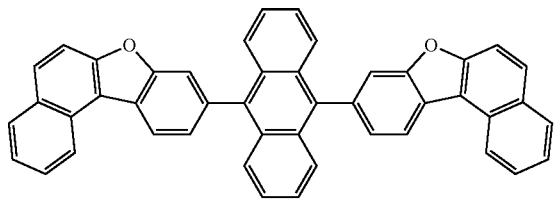
H113
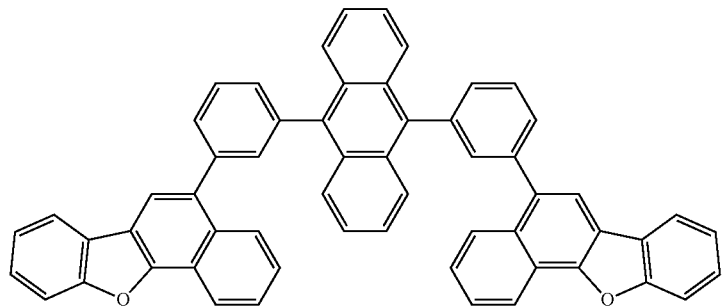
H114
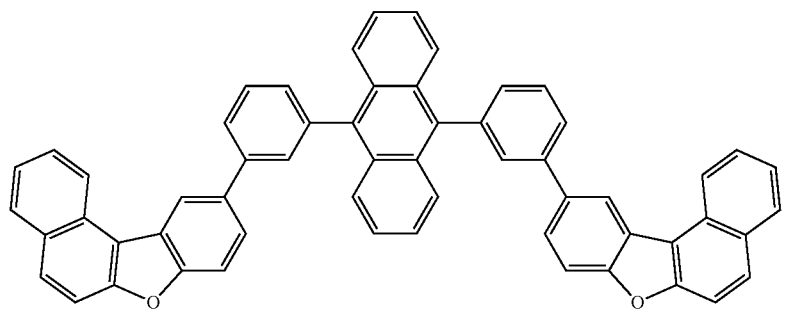

-continued
H115
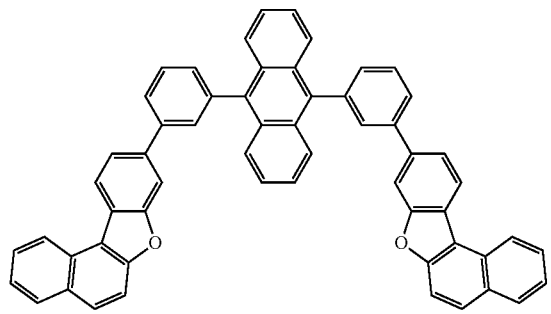
H116
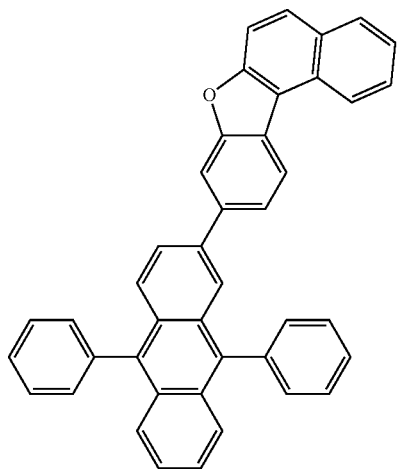
H117
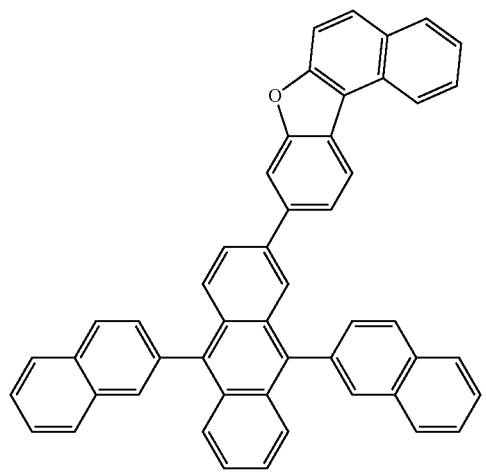
H118
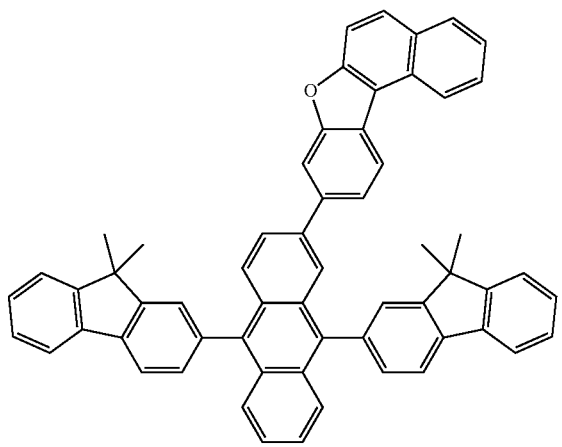
H119
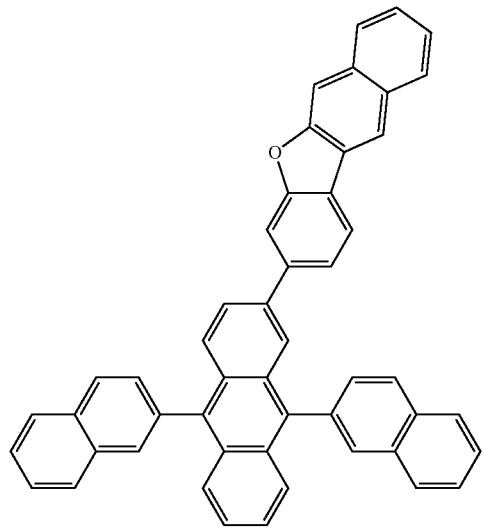
H120
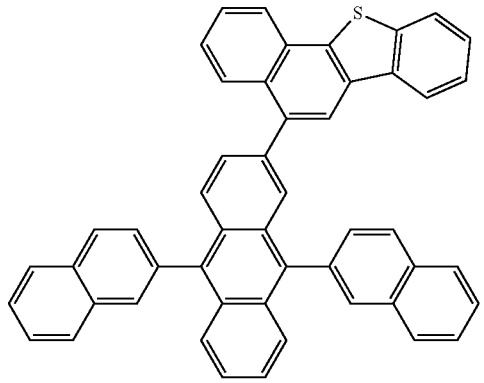

H121

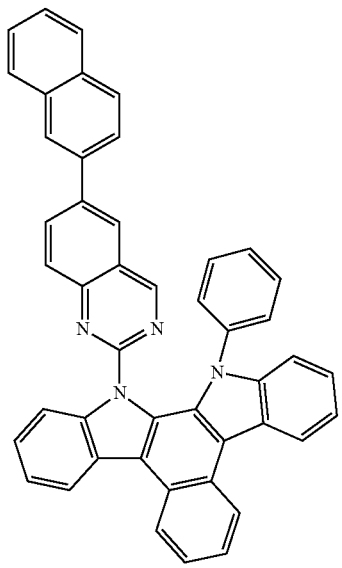

H122

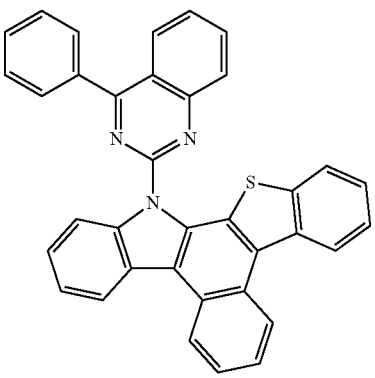

H123

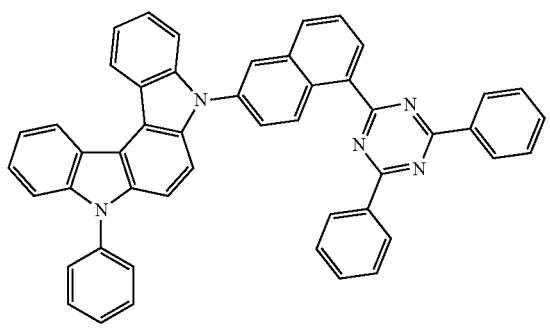

H124

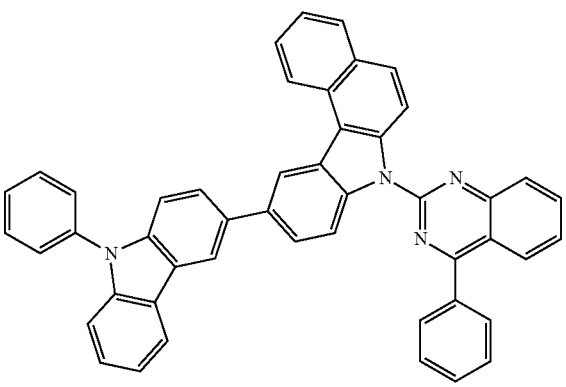

Phosphorescent Dopant

The phosphorescent dopant may include at least one transition metal as a center metal.

The phosphorescent dopant may include a monodentate ligand, a bidentate ligand, a tridentate ligand, a tetradentate ligand, a pentadentate ligand, a hexadentate ligand, or any combination thereof.

The phosphorescent dopant may be electrically neutral.

In some embodiments, the phosphorescent dopant may include an organometallic complex represented by Formula 401:

$$M(L_{401})_{xc1}(L_{402})_{xc2}$$  Formula 401

Formula 402 wherein, in Formulae 401 and 402,

M may be a transition metal (e.g., iridium (Ir), platinum (Pt), palladium (Pd), osmium (Os), titanium (Ti), gold (Au), hafnium (Hf), europium (Eu), terbium (Tb), rhodium (Rh), rhenium (Re), and/or thulium (Tm)), $L_{401}$ may be a ligand represented by Formula 402, and xc1 may be 1, 2, or 3, and when xc1 is 2 or greater, at least two $L_{401}$(s) may be identical to or different from each other, for example, when xc1 is 2 or greater, the two or more $L_{401}$(s) may be identical to or different from each other, $L_{402}$ may be an organic ligand, and xc2 may be an integer from 0 to 4, and when xc2 is 2 or greater, at least two $L_{402}$(s) may be identical to or different from each other, for example, when xc2 is 2 or greater, the two or more $L_{402}$(s) may be identical to or different from each other, $X_{401}$ and $X_{402}$ may each independently be nitrogen or carbon, ring $A_{401}$ and ring $A_{402}$ may each independently be a $C_3$-$C_{60}$ carbocyclic group or a $C_1$-$C_{60}$ heterocyclic group, $T_{401}$ may be a single bond, *—O—*', *—S—*', *—C(=O)—*', *—N($Q_{411}$)-*', *—C($Q_{411}$)($Q_{412}$)-*', *—C($Q_{411}$)=C($Q_{412}$)-*', *—C($Q_{411}$)=*', or *=C=*', $X_{403}$ and $X_{404}$ may each independently be a chemical bond (e.g., a covalent bond or a coordinate bond), O, S, N($Q_{413}$), B($Q_{413}$), P($Q_{413}$), C($Q_{413}$)($Q_{414}$), or Si($Q_{413}$)($Q_{414}$), $Q_{411}$ to $Q_{414}$ may each independently be understood by referring to the description of $Q_1$ provided herein, $R_{401}$ and $R_{402}$ may each independently be hydrogen, deuterium, —F, —Cl, —Br, —I, a hydroxyl group, a cyano group, a nitro group, a $C_1$-$C_{20}$ alkyl group unsubstituted or substituted with at least one $R_{10a}$, a $C_1$-$C_{20}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), or —P(=O)($Q_{401}$)($Q_{402}$), $Q_{401}$ to $Q_{403}$ may each independently be understood by referring to the description of $Q_1$ provided herein, xc11 and xc12 may each independently be an integer from 0 to 10, and and *' in Formula 402 each indicate a binding site to M in Formula 401.

In one or more embodiments, in Formula 402, i) $X_{401}$ may be nitrogen, and $X_{402}$ may be carbon, or ii) $X_{401}$ and $X_{402}$ may both be nitrogen.

In one or more embodiments, when xc1 in Formula 402 is 2 or greater, two ring $A_{401}$(S) of the two or more $L_{401}$(s) may optionally be bound via $T_{402}$ as a linking group, or two ring $A_{402}$(s) may optionally be bound via $T_{403}$ as a linking group (see Compounds PD1 to PD4 and PD7). $T_{402}$ and $T_{403}$ may each independently be understood by referring to the description of $T_{401}$ provided herein.

$L_{402}$ in Formula 401 may be any suitable ligand (e.g., any suitable organic ligand). For example, $L_{402}$ may be a halogen group, a diketone group (e.g., an acetylacetonate group), a carboxylic acid group (e.g., a picolinate group), —C(=O), an isonitrile group, —CN, or a phosphorus group (e.g., a phosphine group or a phosphite group).

The phosphorescent dopant may be, for example, one of Compounds PD1 to PD25, or any combination thereof:

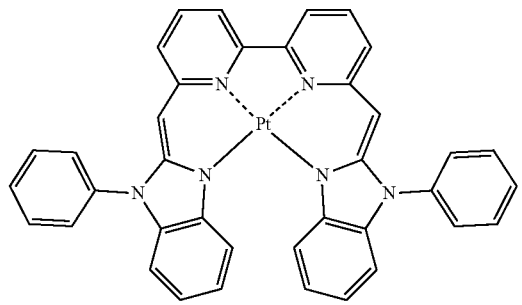
PD1

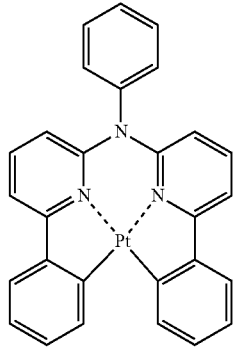
PD2

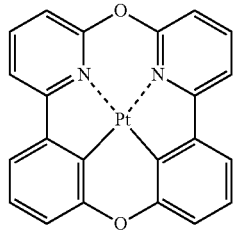
PD3

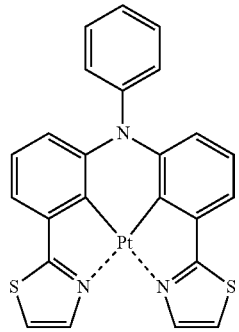
PD4

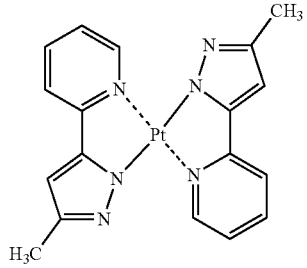
PD5

-continued
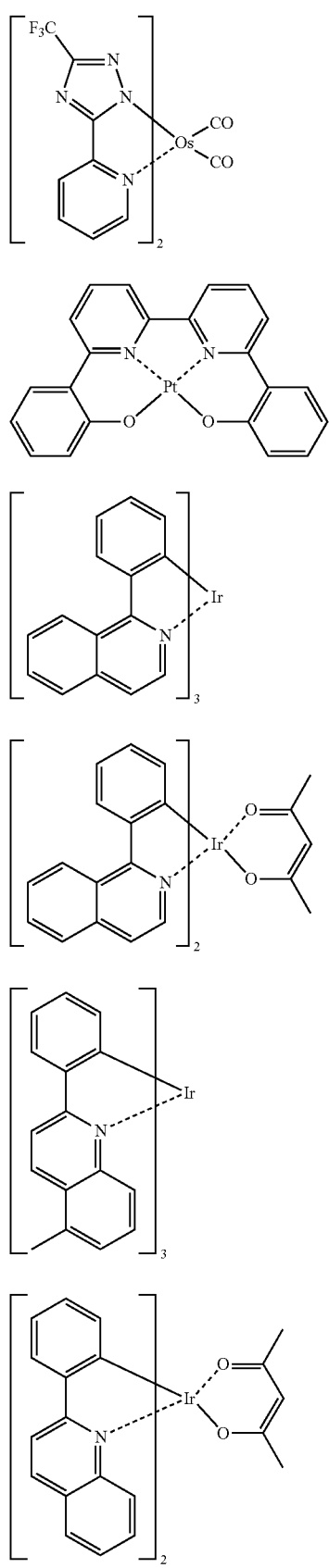
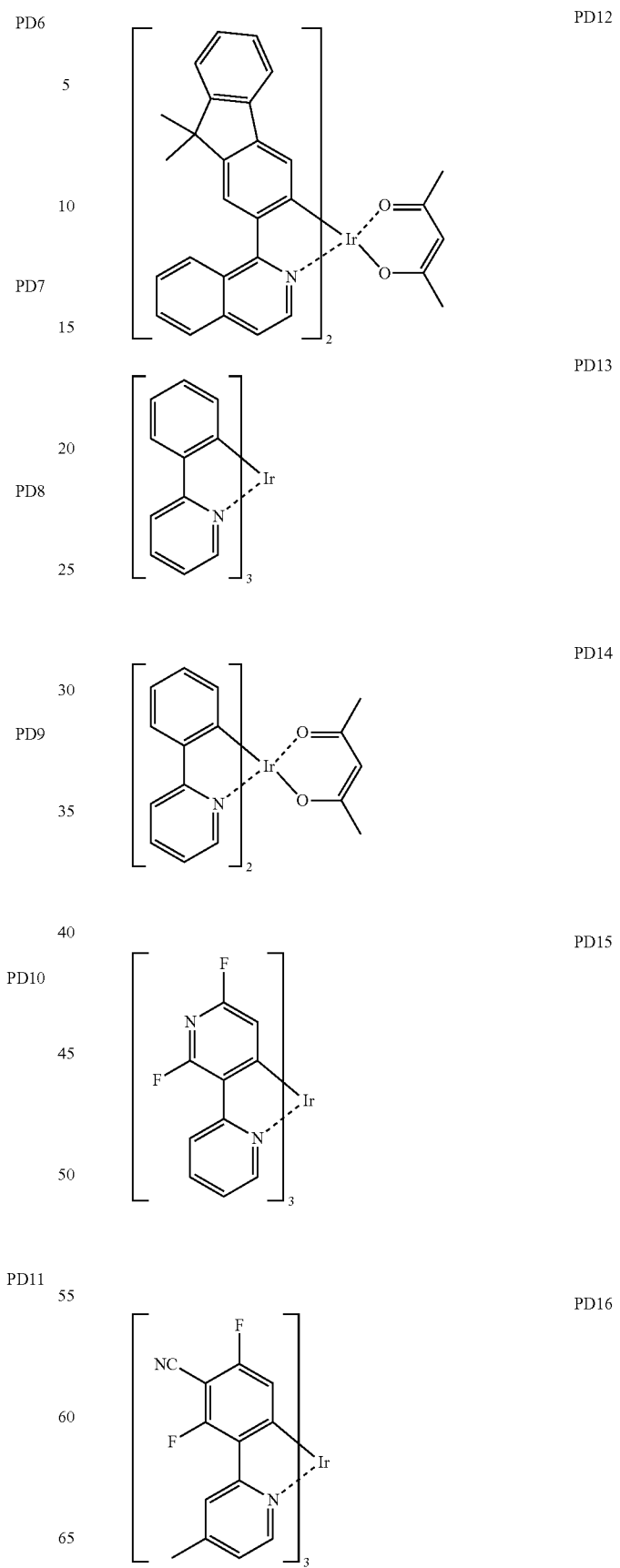

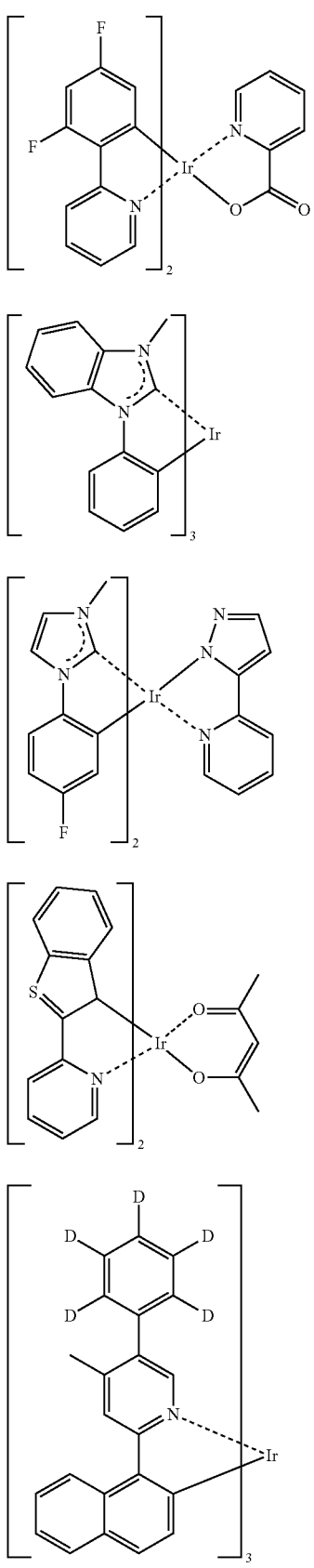
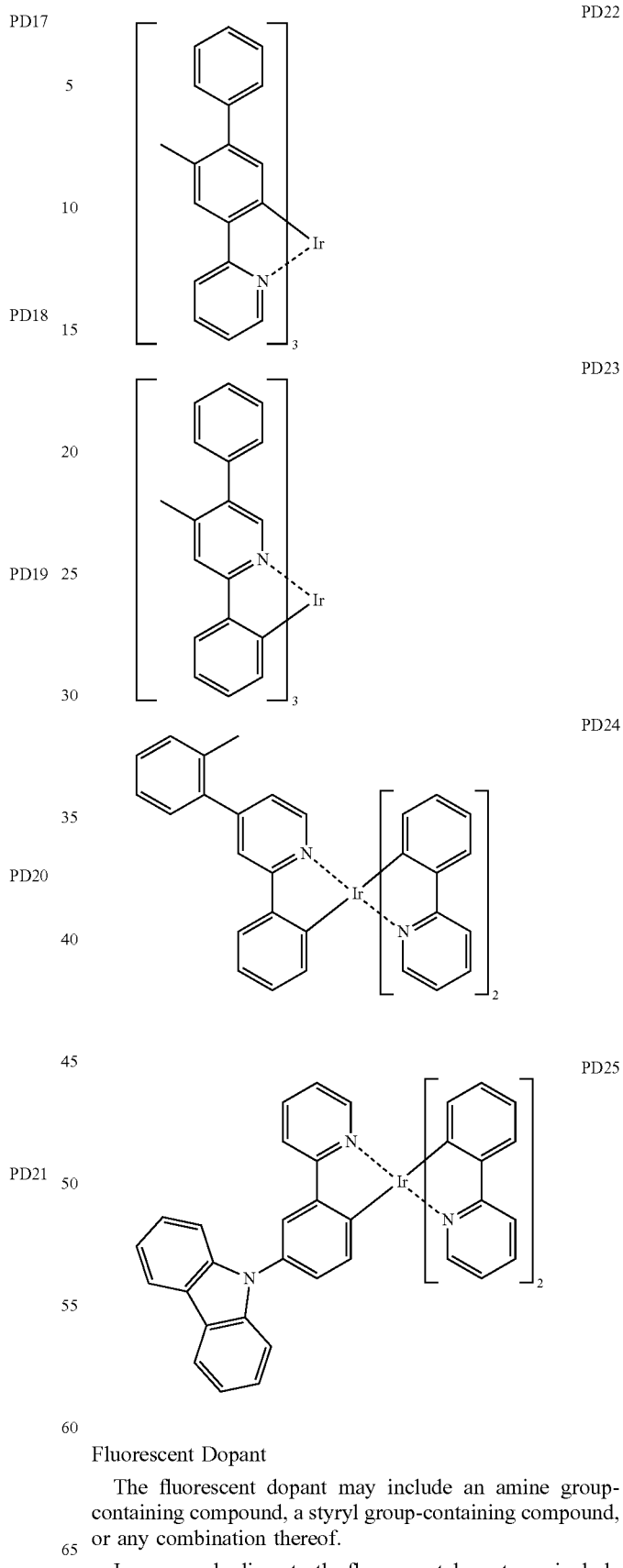
Fluorescent Dopant
The fluorescent dopant may include an amine group-containing compound, a styryl group-containing compound, or any combination thereof.
In some embodiments, the fluorescent dopant may include a compound represented by Formula 501:

Formula 501

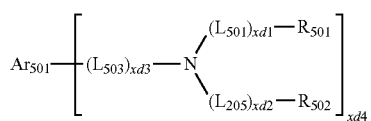

wherein, in Formula 501,
Ar$_{501}$, L$_{501}$ to L$_{503}$, R$_{501}$, and R$_{502}$ may each independently be a C$_3$-C$_{60}$ carbocyclic group unsubstituted or substituted with at least one R$_{10a}$ or a C$_1$-C$_{60}$ heterocyclic group unsubstituted or substituted with at least one R$_{10a}$, xd1 to xd3 may each independently be 0, 1, 2, or 3, and xd4 may be 1, 2, 3, 4, 5, or 6.

In some embodiments, in Formula 501, Ar$_{501}$ may include a condensed ring group (e.g., an anthracene group, a chrysene group, and/or a pyrene group) in which at least three monocyclic groups are condensed.

In some embodiments, xd4 in Formula 501 may be 2.

In some embodiments, the fluorescent dopant may include one of Compounds FD1 to FD36, DPVBi, DPAVBi, or any combination thereof:

FD1

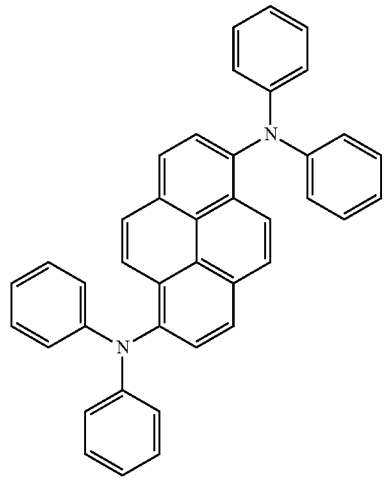

FD2

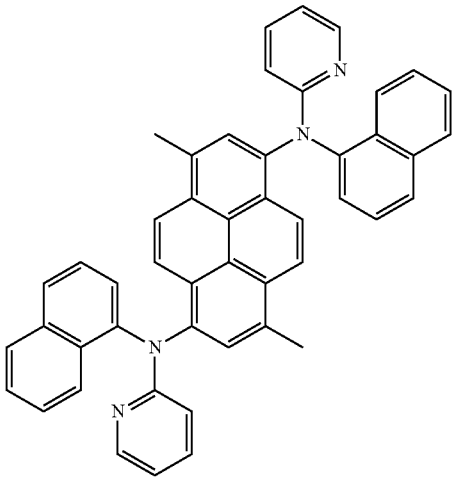

FD3

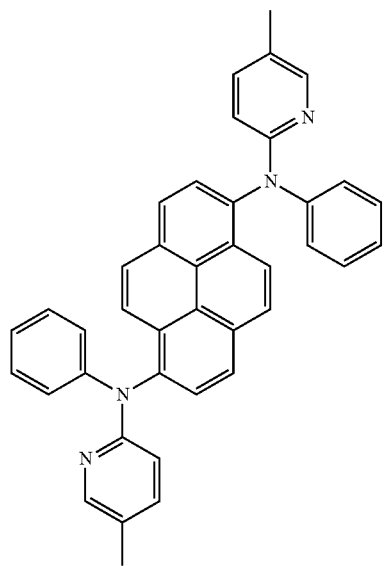

FD4

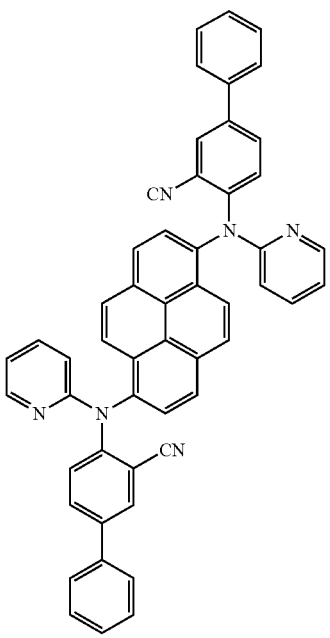

-continued
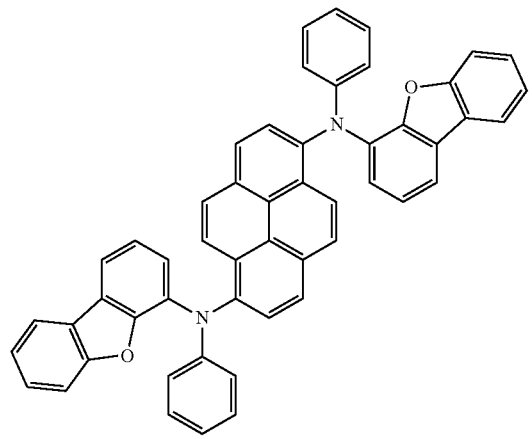
FD5
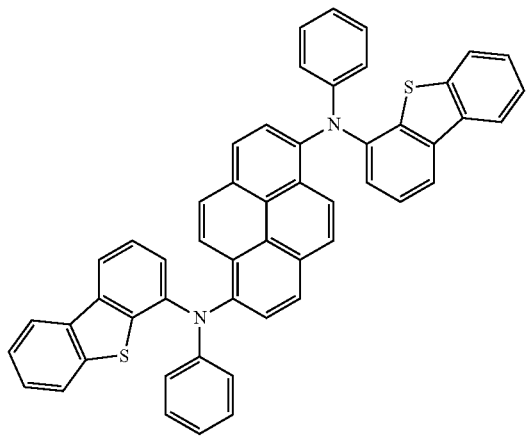
FD6
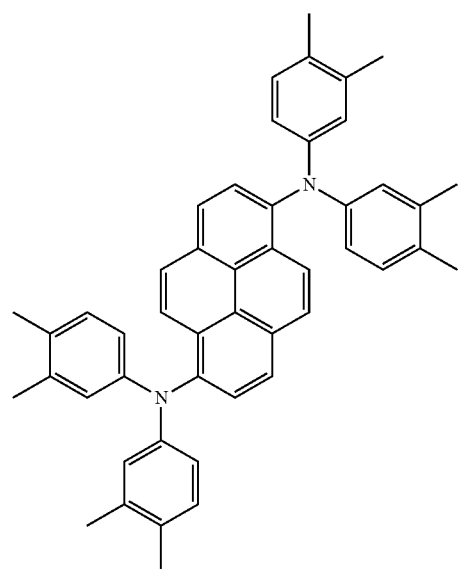
FD7
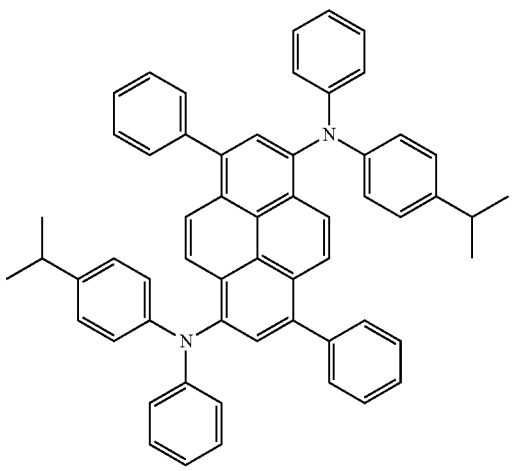
FD8
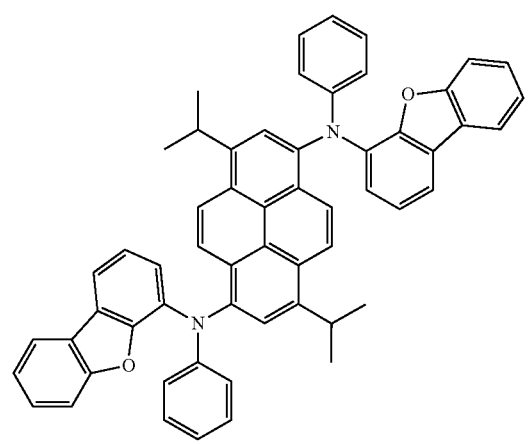
FD9
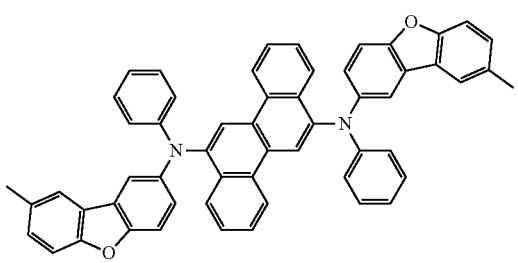
FD10

-continued
FD11
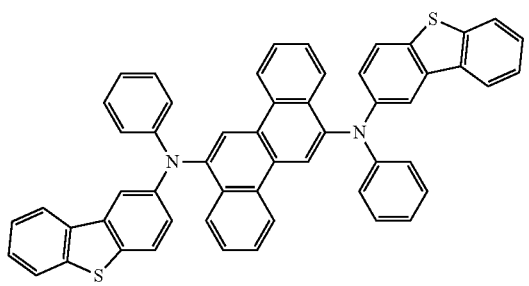
FD12
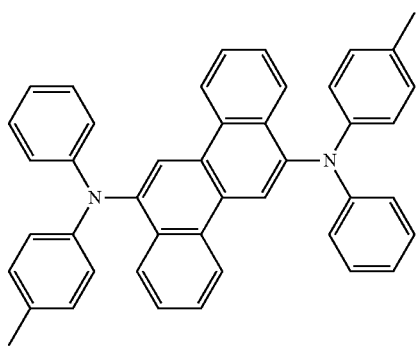
FD13
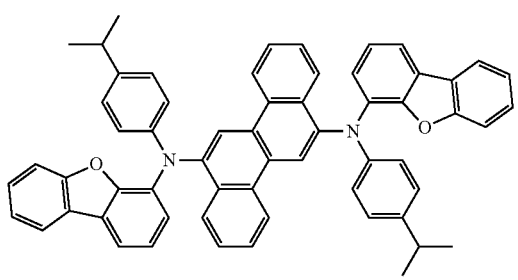
FD14
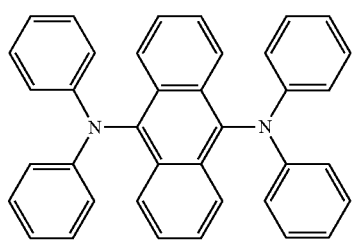
FD15
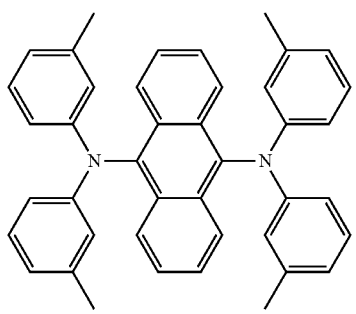
FD16
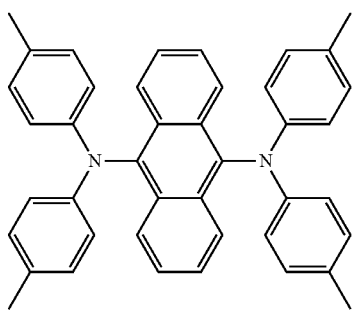
FD17
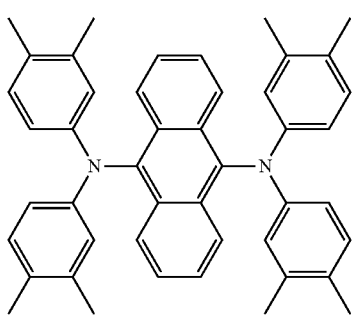
FD18
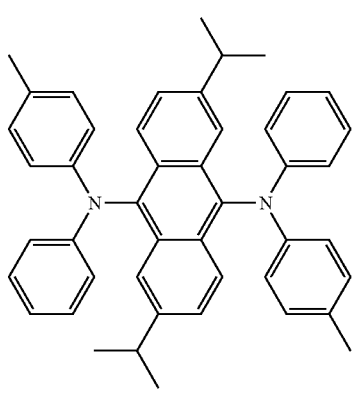

FD19
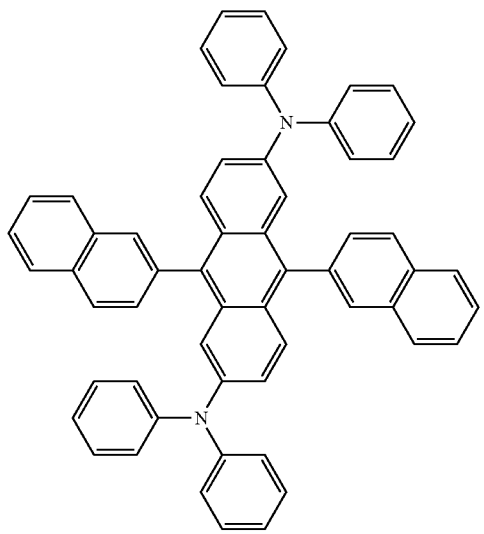
FD20
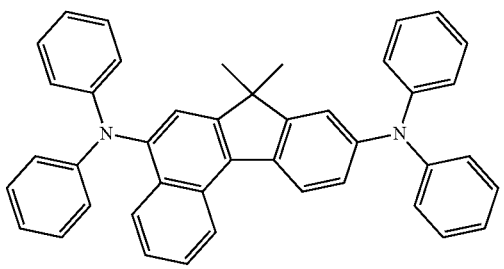
FD21
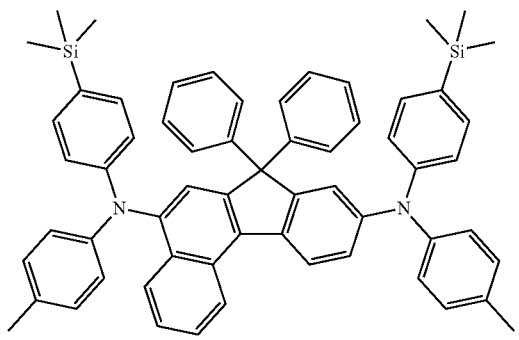
FD22
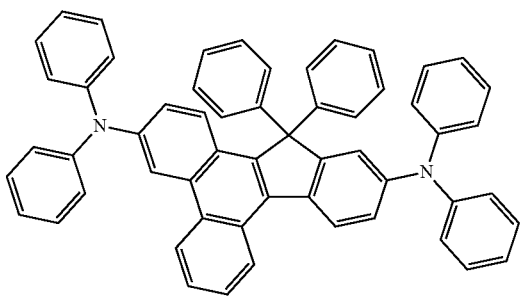
FD23
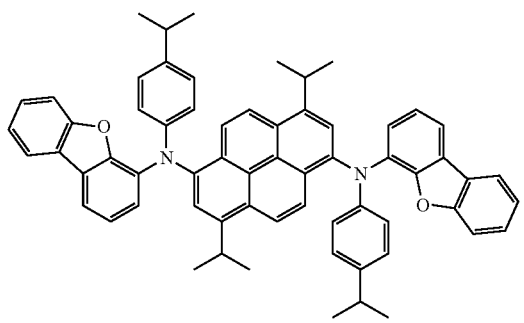
FD24
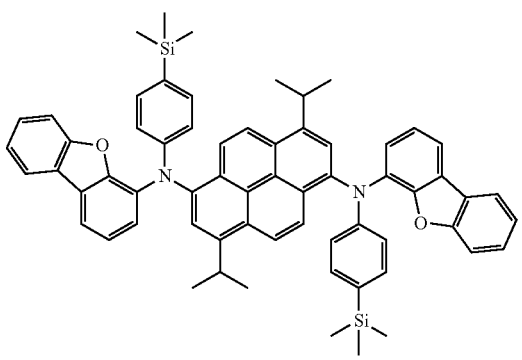
FD25
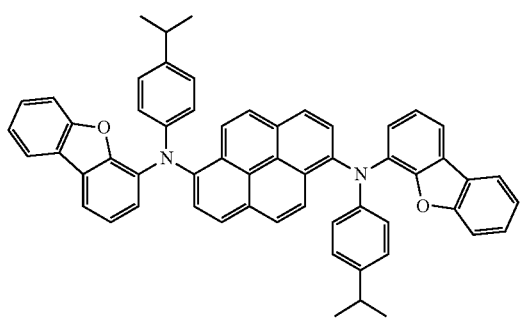
FD26
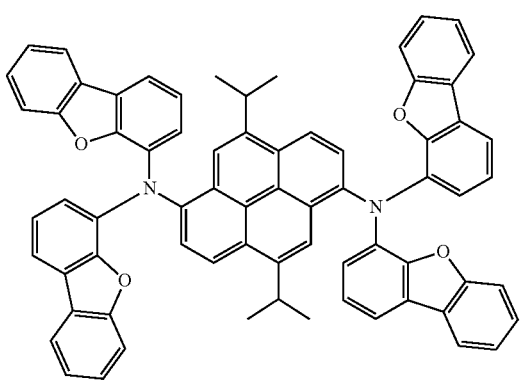

-continued
FD27
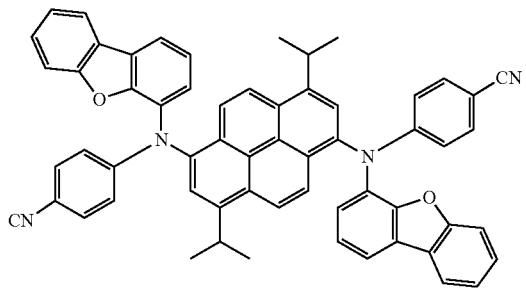
FD28
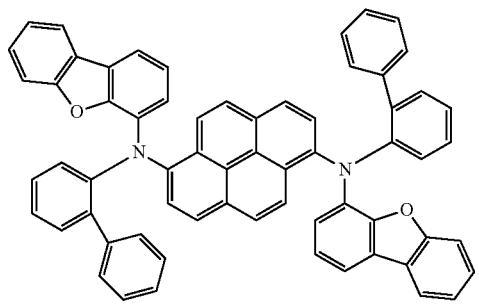
FD29
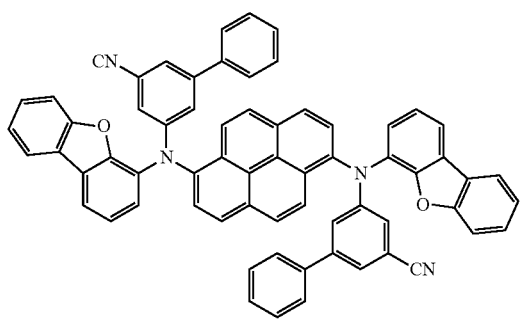
FD30
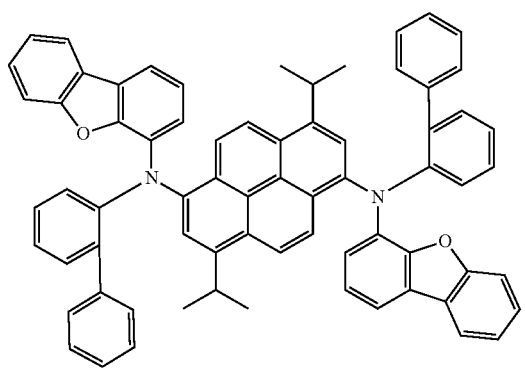
FD31
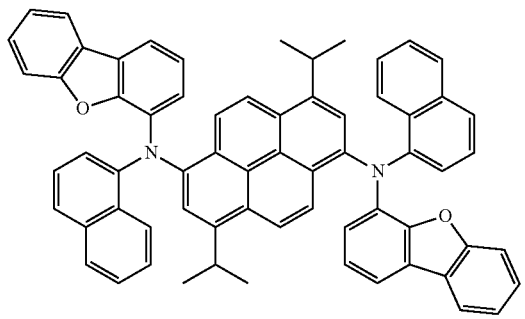
FD32
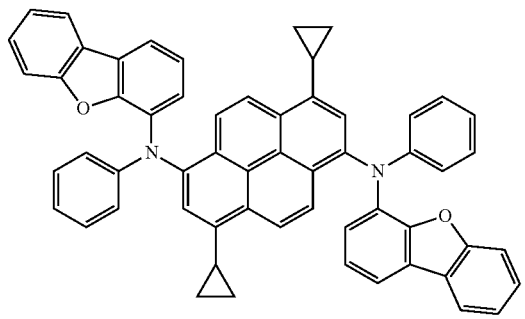
FD33
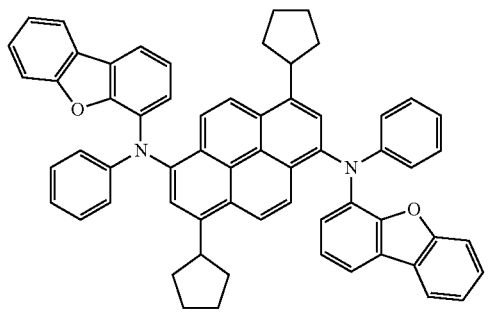
FD34
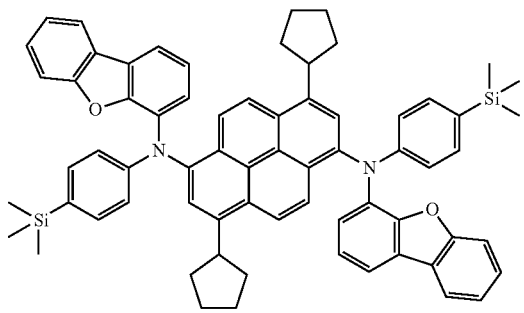

-continued

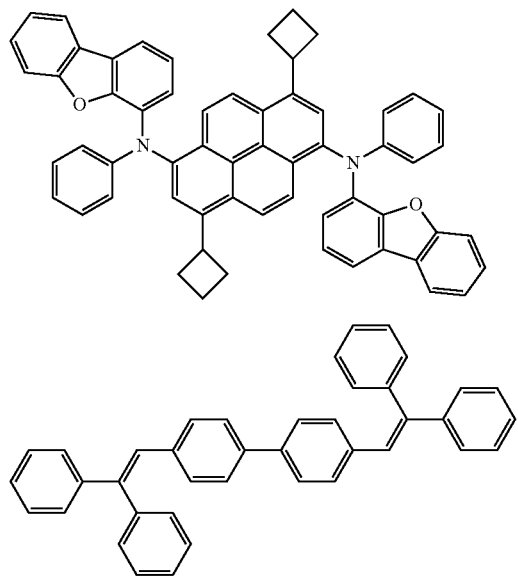
FD35

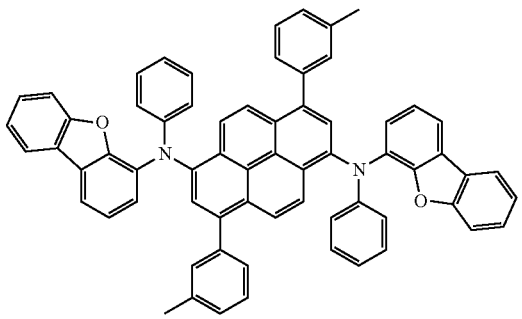
FD36

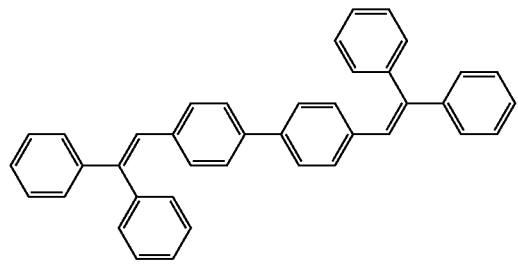
DPVBi

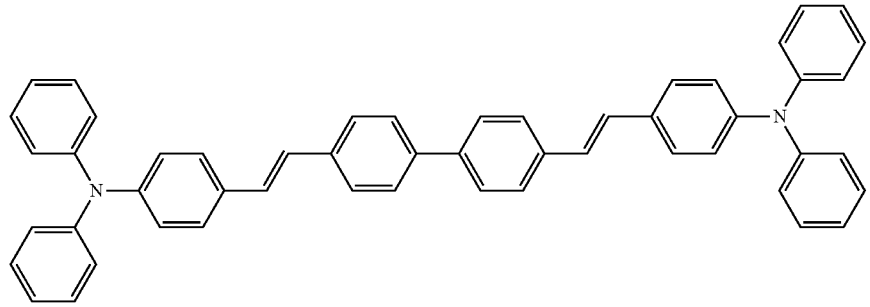
DPAVBi

Delayed Fluorescent Material

The emission layer may include a delayed fluorescent material.

The delayed fluorescent material described herein may be any suitable compound that may emit delayed fluorescence according to a delayed fluorescence emission mechanism.

The delayed fluorescent material included in the emission layer may serve as a host or a dopant, depending on the kind (e.g., types) of other materials included in the emission layer.

In some embodiments, a difference between a triplet energy level (eV) of the delayed fluorescent material and a singlet energy level (eV) of the delayed fluorescent material may be about 0 eV or greater and about 0.5 eV or smaller. When the difference between the triplet energy level (eV) of the delayed fluorescent material and the singlet energy level (eV) of the delayed fluorescent material is within this range, up-conversion from the triplet state to the singlet state in the delayed fluorescent material may occur effectively, thus improving luminescence efficiency and/or the like of the light-emitting device 10.

In some embodiments, the delayed fluorescent material may include: i) a material including at least one electron donor (e.g., a π electron-rich $C_3$-$C_{60}$ cyclic group such as a carbazole group and/or the like) and at least one electron acceptor (e.g., a sulfoxide group, a cyano group, a π electron-deficient nitrogen-containing $C_1$-$C_{60}$ cyclic group, and/or the like), ii) a material including a $C_8$-$C_{60}$ polycyclic group including at least two cyclic groups condensed to each other and sharing boron (B), and/or the like.

Examples of the delayed fluorescent material may include at least one of Compounds DF1 to DF9:

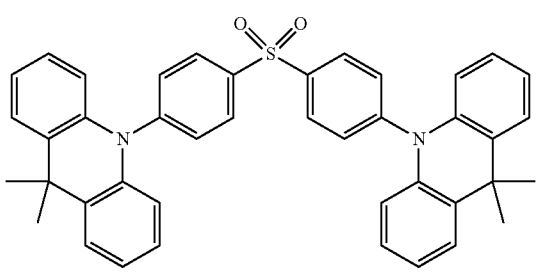
DF1(DMAC)-DPS)

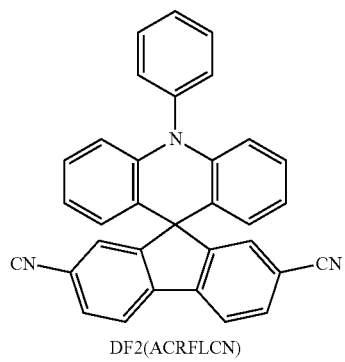
DF2(ACRFLCN)
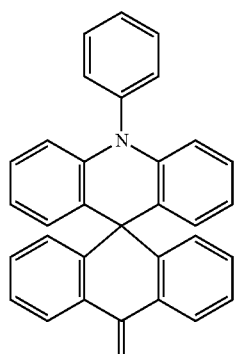
DF3(ACRSA)
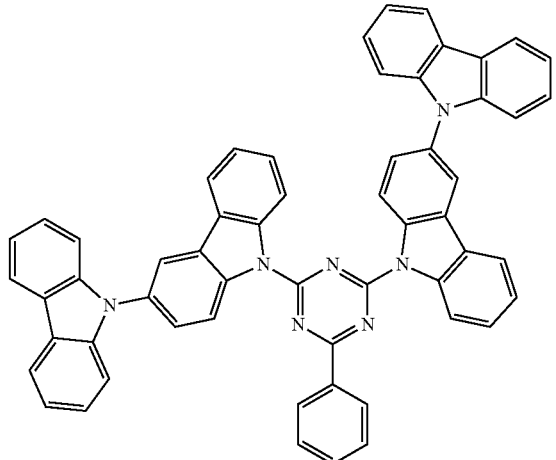
DF4(CC2TA)
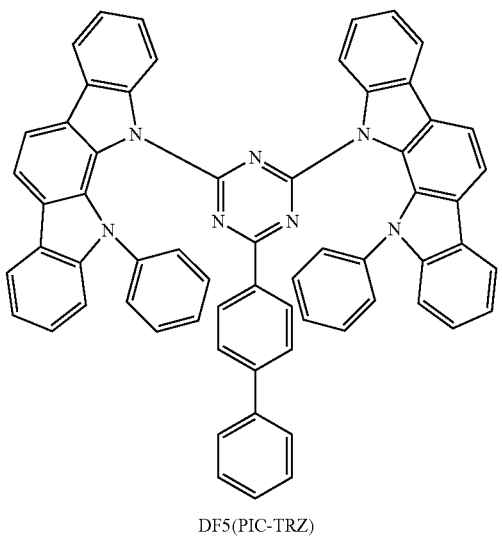
DF5(PIC-TRZ)
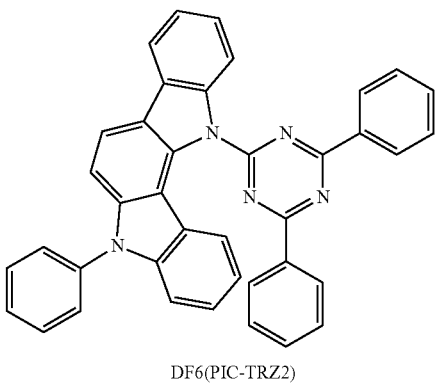
DF6(PIC-TRZ2)
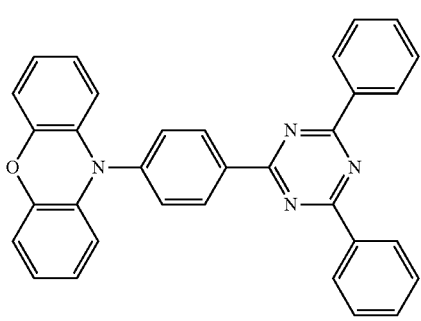
DF7(PXZ-TRZ)
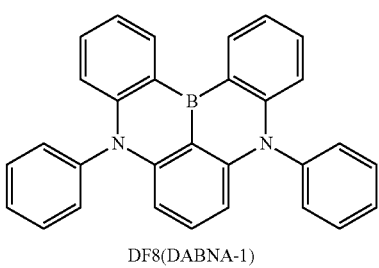
DF8(DABNA-1)

-continued

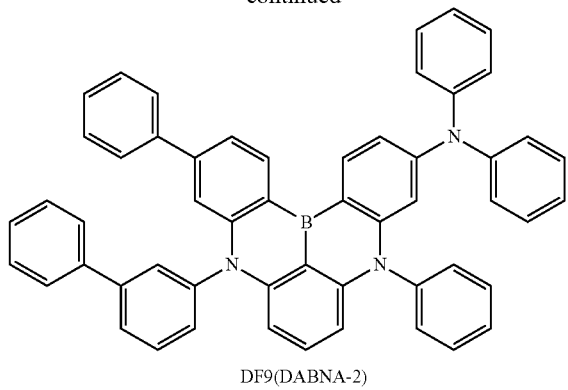

DF9(DABNA-2)

Quantum Dot

The emission layer may include quantum dots.

The term "quantum dot" as used herein refers to a crystal of a semiconductor compound and may include any suitable material capable of emitting emission wavelengths of various suitable lengths according to the size of the crystal.

The diameter of the quantum dot may be, for example, in a range of about 1 nm to about 10 nm.

Quantum dots may be synthesized by a wet chemical process, an organic metal chemical vapor deposition process, a molecular beam epitaxy process, or any similar process.

The wet chemical process is a method of growing a quantum dot particle crystal by mixing a precursor material with an organic solvent. When the crystal grows, the organic solvent may naturally serve as a dispersant coordinated on the surface of the quantum dot crystal and control the growth of the crystal. Thus, the wet chemical method may be easier than the vapor deposition process such as the metal organic chemical vapor deposition (MOCVD) or the molecular beam epitaxy (MBE) process. Further, the growth of quantum dot particles may be controlled with a lower manufacturing cost.

The quantum dot may include a group III-VI semiconductor compound; a group II-VI semiconductor compound; a group III-V semiconductor compound; a group III-VI semiconductor compound; a group I-III-VI semiconductor compound; a group IV-VI semiconductor compound; a group IV element or compound; or any combination thereof.

Non-limiting examples of the group III-VI semiconductor compound may include a binary compound such as $In_2S_3$; a ternary compound such as AgInS, $AgInS_2$, CuInS, and/or $CuInS_2$; or any combination thereof.

Non-limiting examples of the group II-VI semiconductor compound may include a binary compound such as CdS, CdSe, CdTe, ZnS, ZnSe, ZnTe, ZnO, HgS, HgSe, HgTe, MgSe, and/or MgS; a ternary compound such as CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, and/or MgZnS; a quaternary compound such as CdZnSeS, CdZnSeTe, CdZnSTe, CdHgSeS, CdHgSeTe, CdHgSTe, HgZnSeS, HgZnSeTe, and/or HgZnSTe; or any combination thereof.

Non-limiting examples of the group III-V semiconductor compound may include a binary compound such as GaN, GaP, GaAs, GaSb, AlN, AlP, AlAs, AlSb, InN, InP, InAs, and/or InSb; a ternary compound such as GaNP, GaNAs, GaNSb, GaPAs, GaPSb, AlNP, AlNAs, AlNSb, AlPAs, AlPSb, InGaP, InNP, InAlP, InNAs, InNSb, InPAs, InPSb, and/or GaAlNP; a quaternary compound such as GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, and/or InAlPSb; or any combination thereof. In some embodiments, the group III-V semiconductor compound may further include a group II element. Examples of the group III-V semiconductor compound further including the group II element may include InZnP, InGaZnP, InAlZnP, and the like.

Non-limiting examples of the group III-VI semiconductor compound may include a binary compound such as GaS, GaSe, $Ga_2Se_3$, GaTe, InS, InSe, $In_2Se_3$, InTe, and/or the like; a ternary compound such as $InGaS_3$, $InGaSe_3$, and/or the like; or any combination thereof.

Non-limiting examples of the group I-III-VI semiconductor compound may include a ternary compound such as AgInS, $AgInS_2$, CuInS, $CuInS_2$, $CuGaO_2$, $AgGaO_2$, $AgAlO_2$, or any combination thereof.

Non-limiting examples of the group IV-VI semiconductor compound may include a binary compound such as SnS, SnSe, SnTe, PbS, PbSe, and/or PbTe; a ternary compound such as SnSeS, SnSeTe, SnSTe, PbSeS, PbSeTe, PbSTe, SnPbS, SnPbSe, and/or SnPbTe; a quaternary compound such as SnPbSSe, SnPbSeTe, and/or SnPbSTe; or any combination thereof.

The group IV element or compound may be a single element compound such as Si and/or Ge; a binary compound such as SiC and/or SiGe; or any combination thereof.

Individual elements included in the multi-element compound, such as the binary compound, the ternary compound, and/or the quaternary compound, may be present in the particle thereof at a uniform or non-uniform concentration.

The quantum dot may have a single (e.g., a uniform) structure in which the concentration of each element included in the quantum dot is uniform or a core-shell double (e.g., double-layer) structure. In some embodiments, materials included in the core may be different from materials included in the shell.

The shell of the quantum dot may serve as a protective layer for reducing or preventing chemical denaturation of the core to maintain semiconductor characteristics and/or may function as a charging layer for imparting electrophoretic characteristics to the quantum dot. The shell may include a monolayer or a multilayer. An interface between the core and the shell may have a concentration gradient where a concentration of elements present in the shell decreases toward the core.

Non-limiting examples of the shell of the quantum dot include a metal oxide or a nonmetal oxide, a semiconductor compound, or a combination thereof. Non-limiting examples of the metal oxide or the nonmetal oxide may include: a binary compound such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$, and/or NiO; a ternary compound such as $MgAl_2O_4$, $CoFe_2O_4$, $NiFe_2O_4$, and/or $CoMn_2O_4$; and any combination thereof. Non-limiting examples of the semiconductor compound may include a group III-VI semiconductor compound; a group II-VI semiconductor compound; a group III-V semiconductor compound; a group III-VI semiconductor compound; a group I-III-VI semiconductor compound; a group IV-VI semiconductor compound; or any combination thereof. In some embodiments, the semiconductor compound may be CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, or any combination thereof.

The quantum dot may have a full width of half maximum (FWHM) of an emission wavelength spectrum of about 45 nm or less, about 40 nm or less, or about 30 nm or less. When the FWHM of the quantum dot is within these ranges, color purity and/or color reproducibility may be improved. In addition, because light emitted through the quantum dot is emitted in all directions, an optical viewing angle may be improved.

In addition, the quantum dot may be, for example, a spherical nanoparticle, a pyramidal nanoparticle, a multi-arm nanoparticle, a cubicnanoparticle, a nanotube particle, a nanowire particle, a nanofiber particle, or a nanoplate particle.

By adjusting the size of the quantum dot, the energy band gap may also be adjusted, thereby obtaining light of various suitable wavelengths in the quantum dot emission layer. By utilizing quantum dots of various suitable sizes, a light-emitting device that may emit light of various suitable wavelengths may be realized (e.g., produced). In some embodiments, the size of the quantum dot may be selected such that the quantum dot may emit red, green, and/or blue light. In addition, the size of the quantum dots may be selected such that the quantum dots may emit white light by combining various suitable light of colors.

Electron Transport Region in Interlayer 130

The electron transport region may have i) a single-layered structure including (e.g., consisting of) a single layer including (e.g., consisting of) a single material, ii) a single-layered structure including (e.g., consisting of) a single layer including a plurality of different materials, or iii) a multi-layered structure having a plurality of layers including a plurality of different materials.

The electron transport region may include a buffer layer, a hole blocking layer, an electron control layer, an electron transport layer, and/or an electron injection layer.

In some embodiments, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein layers of each structure are sequentially stacked on the emission layer in each stated order.

The electron transport region (e.g., a buffer layer, a hole blocking layer, an electron control layer, and/or an electron transport layer in the electron transport region) may include a metal-free compound including at least one π electron-deficient nitrogen-containing $C_1$-$C_{60}$ cyclic group.

In some embodiments, the electron transport region may include a compound represented by Formula 601:

$$[Ar_{601}]_{xe11}\text{-}[(L_{601})_{xe1}\text{-}R_{601}]_{xe21} \quad \text{Formula 601}$$

wherein, in Formula 601, $Ar_{601}$ and $L_{601}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xe11 may be 1, 2, or 3, xe1 may be 0, 1, 2, 3, 4, or 5, $R_{601}$ may be a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —Si($Q_{601}$)($Q_{602}$)($Q_{603}$), —C(=O)($Q_{601}$), —S(=O)$_2$($Q_{601}$), or —P(=O)($Q_{601}$)($Q_{602}$), $Q_{601}$ to $Q_{603}$ may each independently be understood by referring to the description of $Q_1$ provided herein, xe21 may be 1, 2, 3, 4, or 5, and at least one of $Ar_{601}$, $L_{601}$, and $R_{601}$ may each independently be a π electron-deficient nitrogen-containing $C_1$-$C_{60}$ cyclic group unsubstituted or substituted with at least one $R_{10a}$.

In some embodiments, when xe11 in Formula 601 is 2 or greater, at least two $Ar_{601}$(s) may be bound via a single bond. For example, when xe11 in Formula 601 is 2 or greater, the two or more $Ar_{601}$(s) may be bound via a single bond to each other.

In some embodiments, in Formula 601, $Ar_{601}$ may be a substituted or unsubstituted anthracene group.

In some embodiments, the electron transport region may include a compound represented by Formula 601-1:

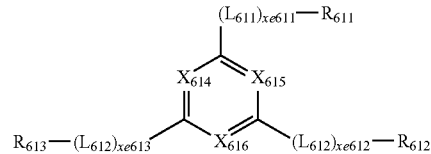

Formula 601-1 wherein, in Formula 601-1, $X_{614}$ may be N or C($R_{614}$), $X_{615}$ may be N or C($R_{615}$), $X_{616}$ may be N or C($R_{616}$), and at least one selected from $X_{614}$ to $X_{616}$ may be N, $L_{611}$ to $L_{613}$ may each independently be understood by referring to the description of $L_{601}$ provided herein, xe611 to xe613 may each independently be understood by referring to the description of xe1 provided herein, $R_{611}$ to $R_{613}$ may each independently be understood by referring to the description of $R_{601}$ provided herein, and $R_{614}$ to $R_{616}$ may each independently be hydrogen, deuterium, —F, —Cl, —Br, —I, a hydroxyl group, a cyano group, a nitro group, a $C_1$-$C_{20}$ alkyl group, a $C_1$-$C_{20}$ alkoxy group, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$.

In some embodiments, in Formulae 601 and 601-1, xe1 and xe611 to xe613 may each independently be 0, 1, or 2.

The electron transport region may include one of Compounds ET1 to ET45, 2,9-dimethyl-4,7-diphenyl-1,10-phenanthroline (BCP), 4,7-diphenyl-1,10-phenanthroline (Bphen), Alq$_3$, BAlq, TAZ, NTAZ, or any combination thereof:

143 144
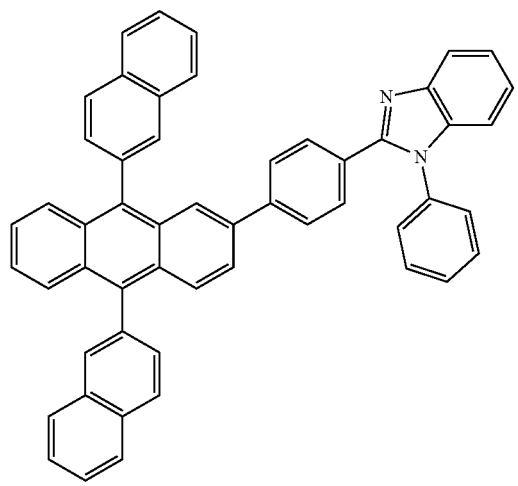
ET1
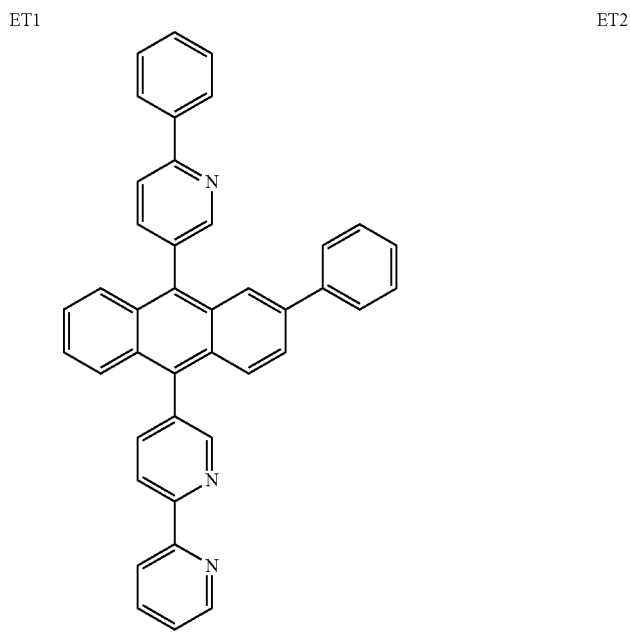
ET2
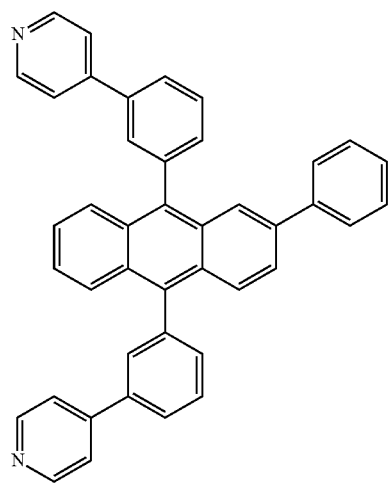
ET3
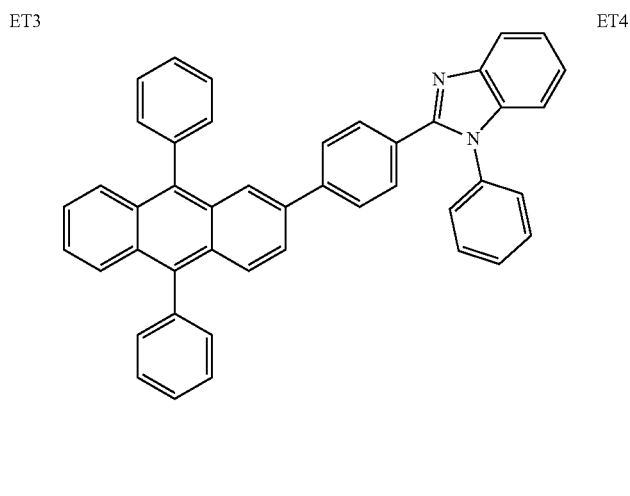
ET4
ET5 ET6
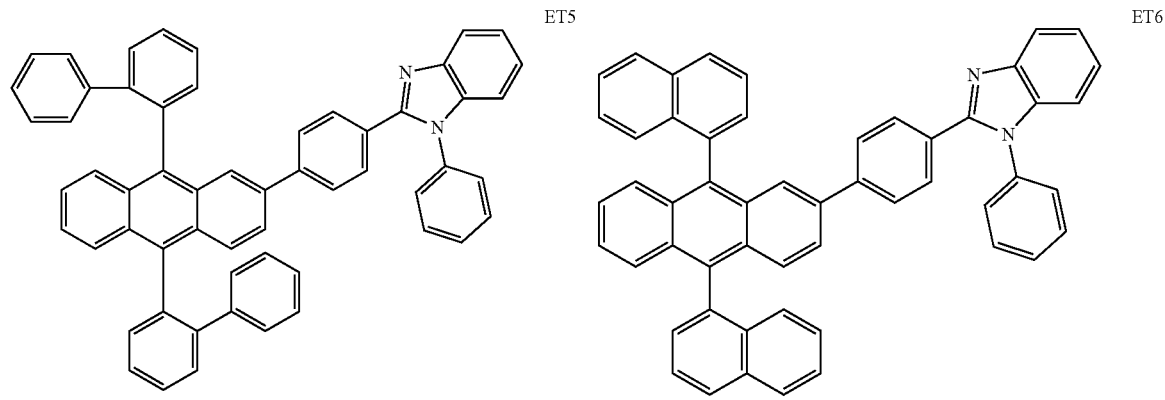

-continued
ET7
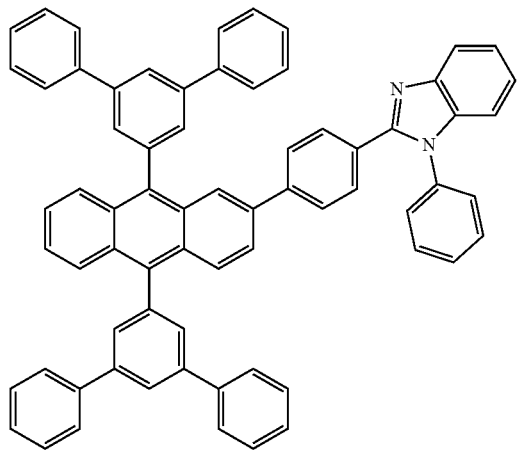
ET8
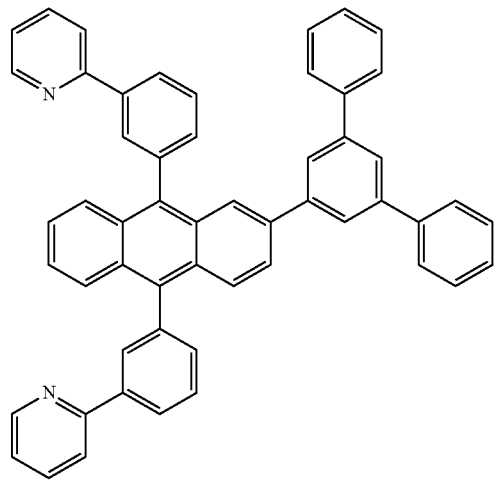
ET9
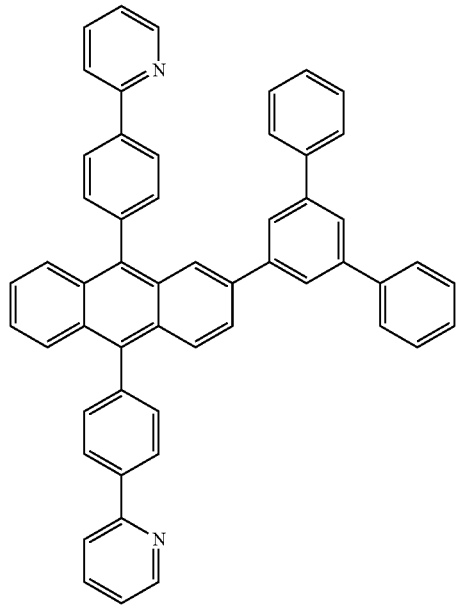
ET10
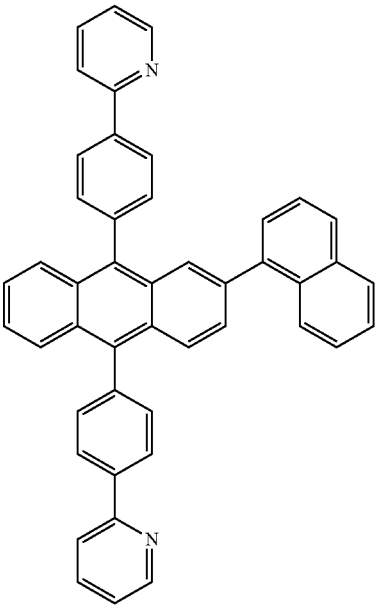
ET11
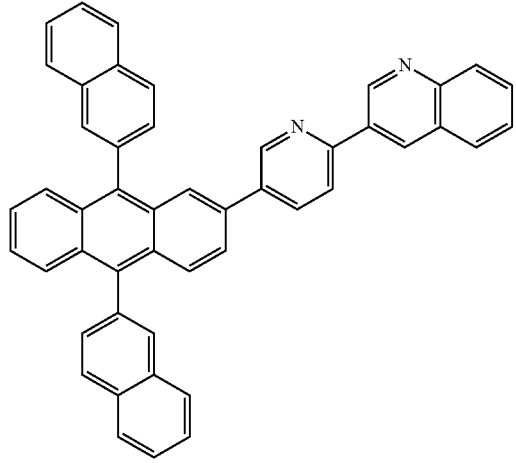
ET12
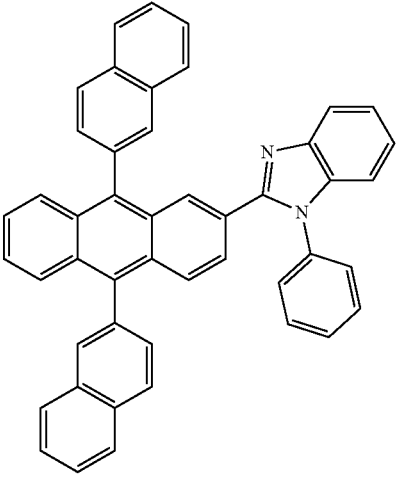

-continued
ET13
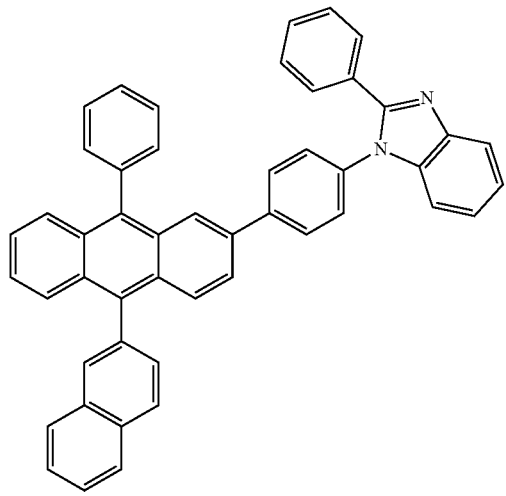
ET14
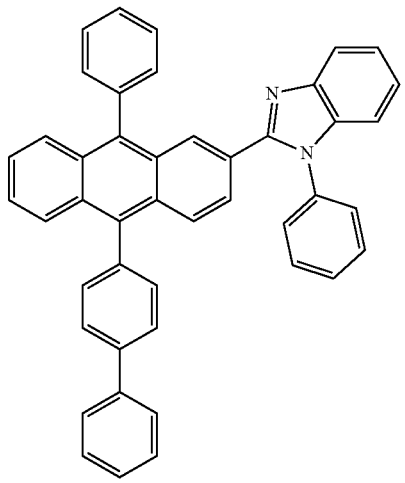
ET15
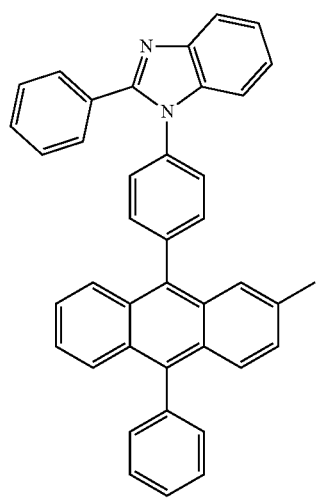
ET16
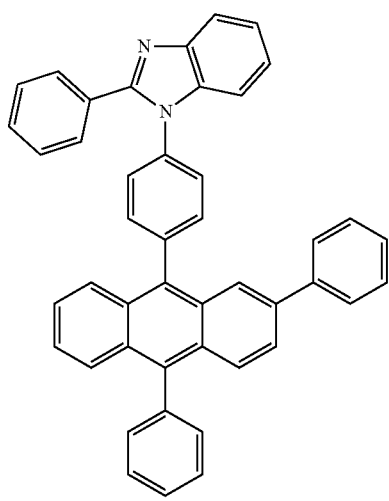
ET17
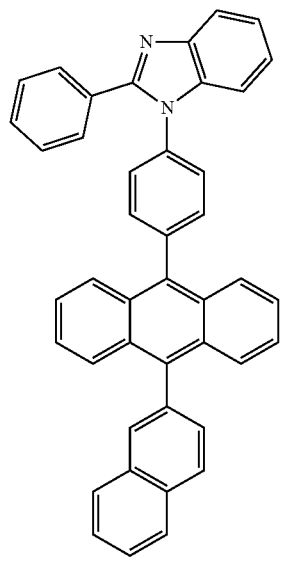
ET18
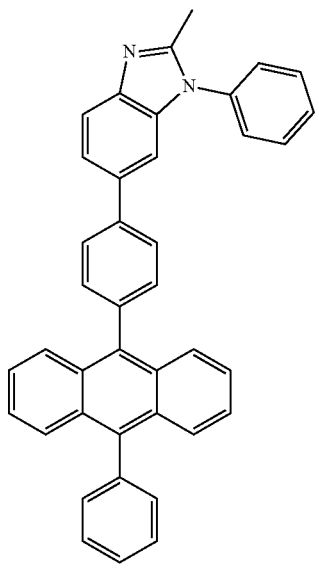

-continued
ET19
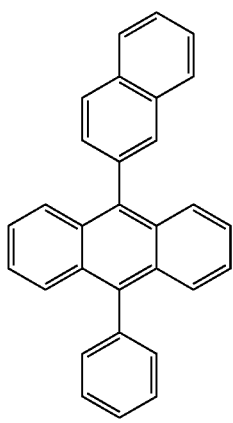
ET20
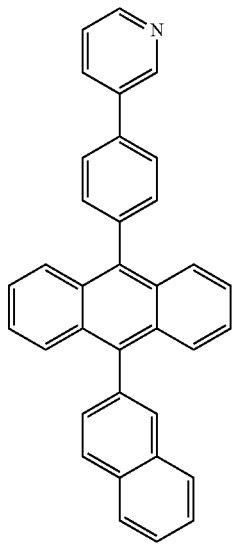
ET21
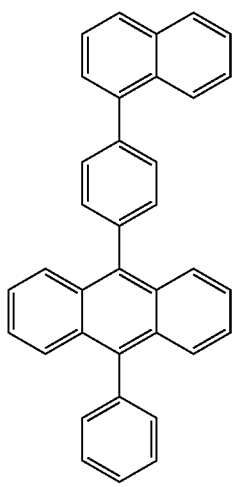
ET22
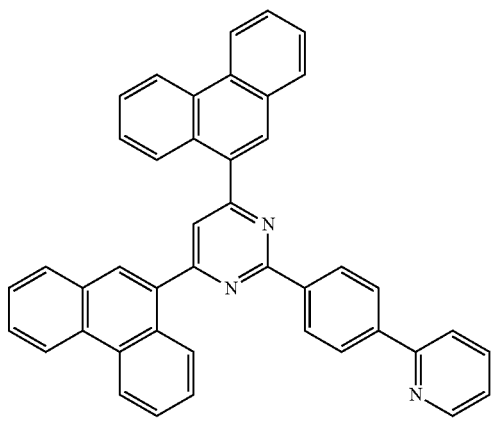
ET23
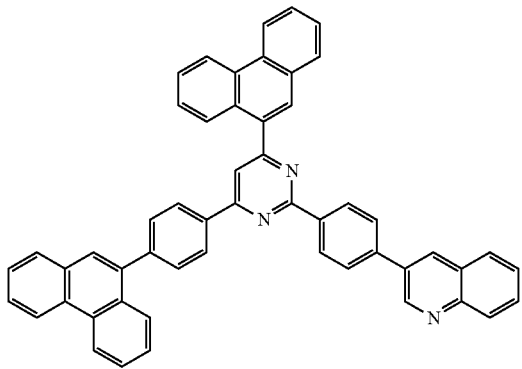
ET24
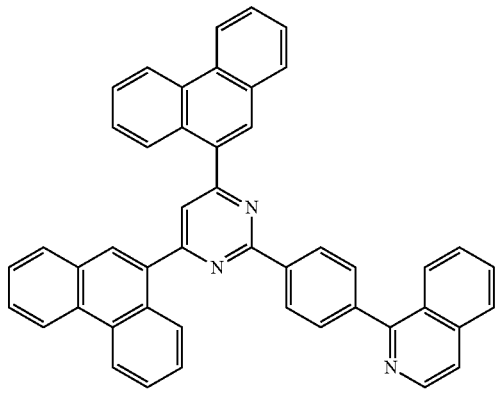

-continued
ET25
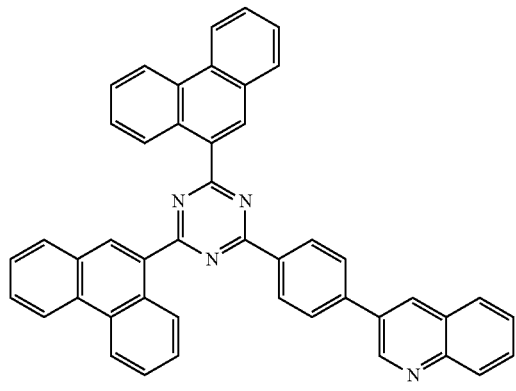
ET26
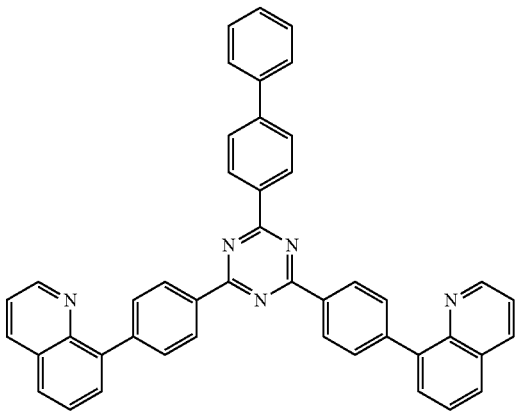
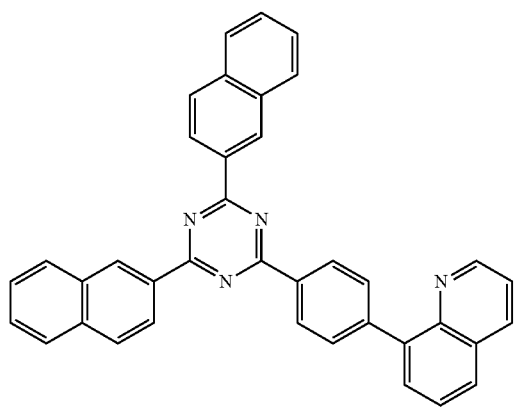
ET27
ET28
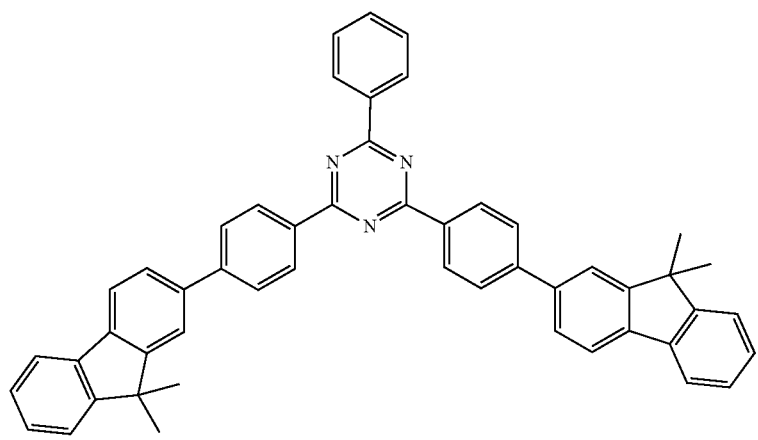

-continued
ET29
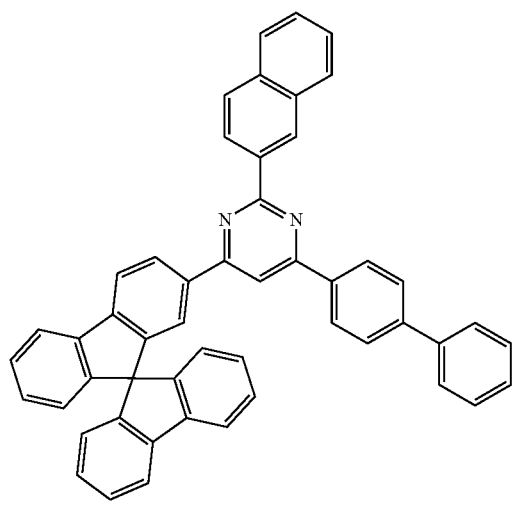
ET30
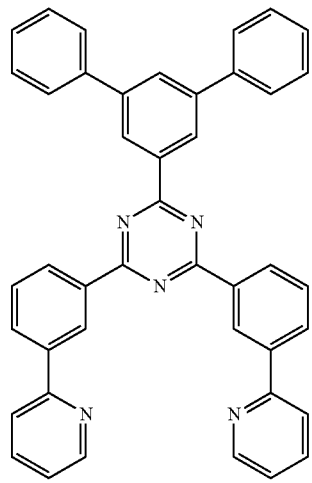
ET31
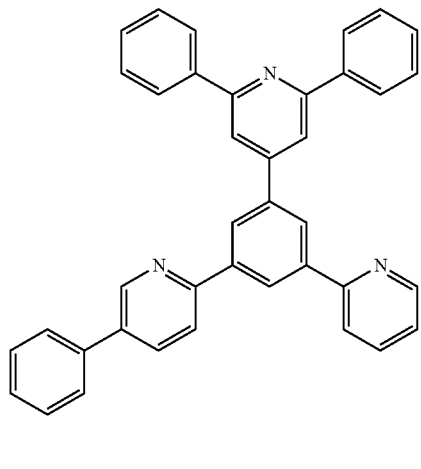
ET32
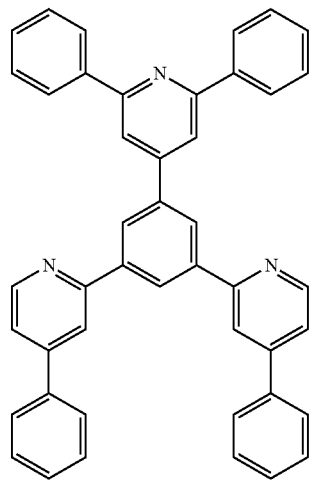
ET33
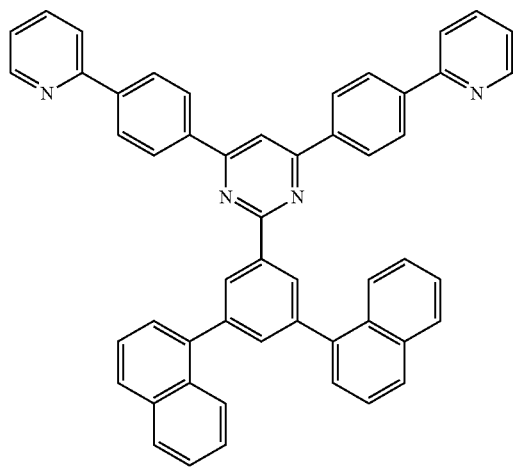
ET34
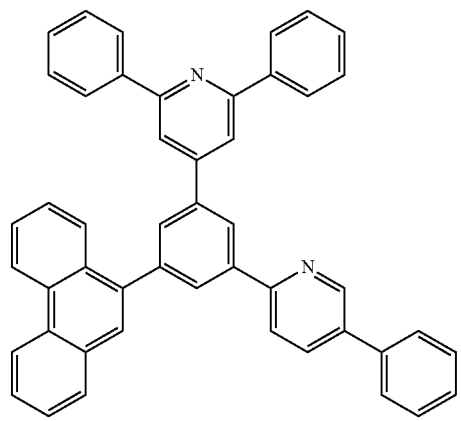

-continued
ET35
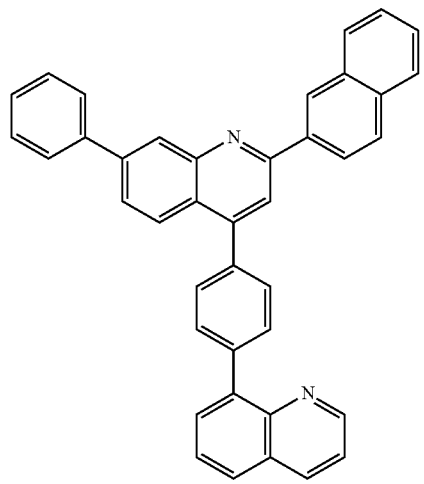
ET36
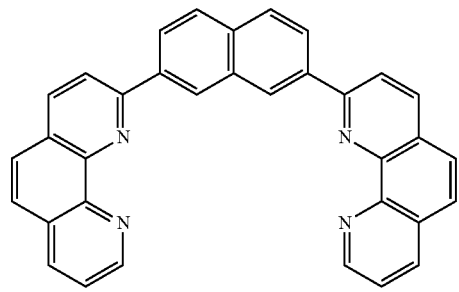
ET37
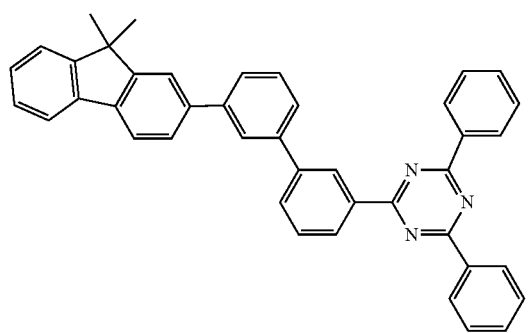
ET38
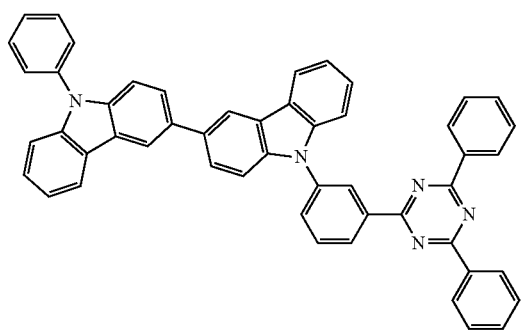
ET39
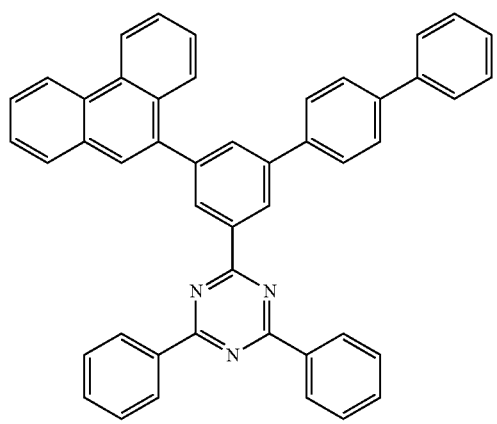
ET40
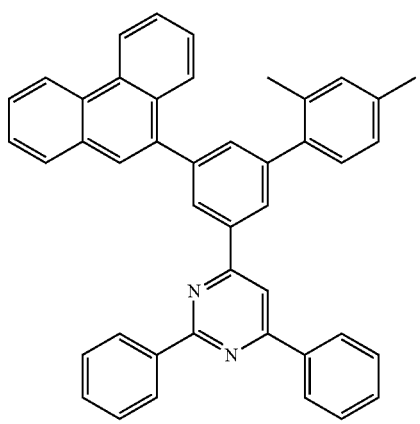

-continued
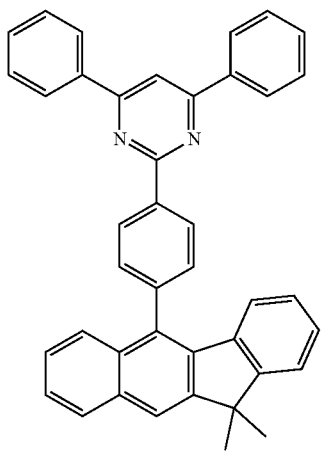
ET41
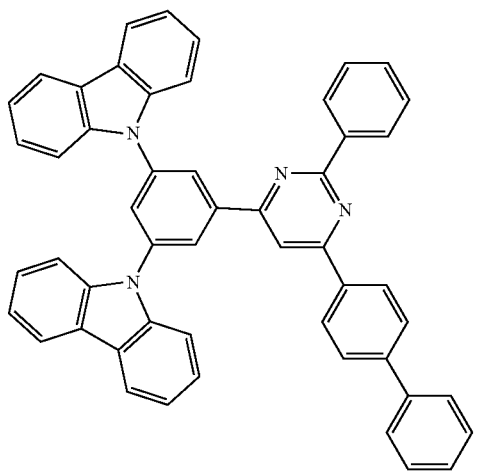
ET42
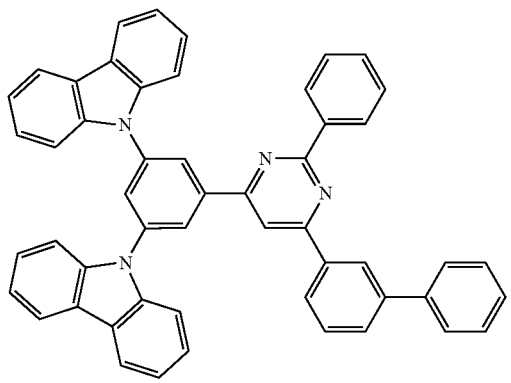
ET43
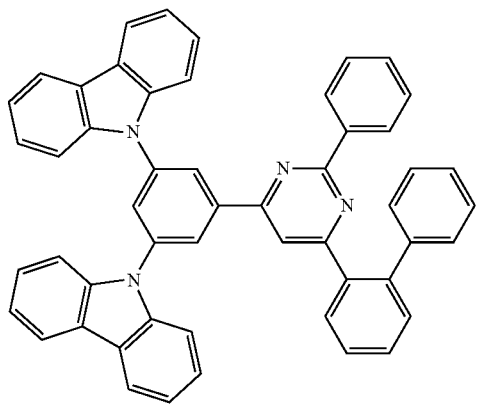
ET44
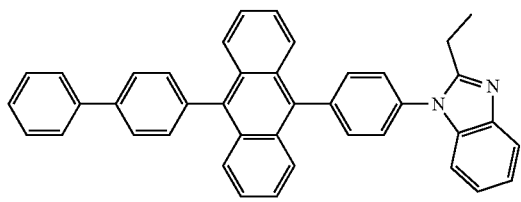
ET45
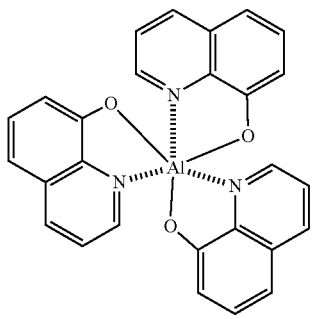
Alq₃
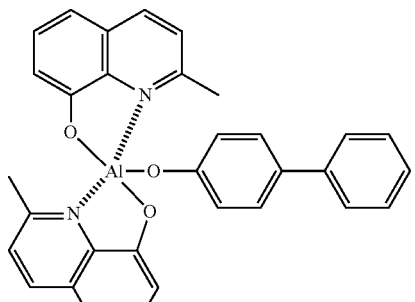
BAlq -continued

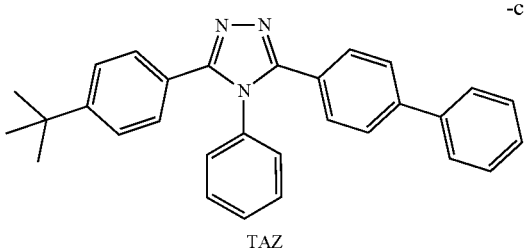

TAZ

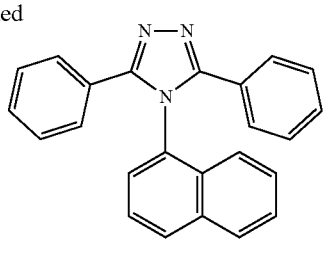

NTAZ

The thickness of the electron transport region may be in a range of about 160 Å to about 5,000 Å, and in some embodiments, about 100 Å to about 4,000 Å. When the electron transport region includes a buffer layer, a hole blocking layer, an electron control layer, an electron transport layer, or any combination thereof, the thicknesses of the buffer layer, the hole blocking layer, or the electron control layer may each independently be in a range of about 20 Å to about 1,000 Å, for example, about 30 Å to about 300 Å, and the thickness of the electron transport layer may be in a range of about 100 Å to about 1,000 Å, for example, about 150 Å to about 500 Å. When the thicknesses of the buffer layer, the hole blocking layer, the electron control layer, and/or the electron transport layer are each within these ranges, desired (e.g., excellent) electron transport characteristics may be obtained without a substantial increase in driving voltage.

The electron transport region (for example, the electron transport layer in the electron transport region) may further include, in addition to the materials described above, a metal-containing material.

The metal-containing material may include an alkali metal complex, an alkaline earth metal complex, or any combination thereof. A metal ion of the alkali metal complex may be a lithium (Li) ion, a sodium (Na) ion, a potassium (K) ion, a rubidium (Rb) ion, and/or a cesium (Cs) ion. A metal ion of the alkaline earth metal complex may be a beryllium (Be) ion, a magnesium (Mg) ion, a calcium (Ca) ion, a strontium (Sr) ion, and/or a barium (Ba) ion. Each ligand coordinated with the metal ion of the alkali metal complex and the alkaline earth metal complex may independently be hydroxyquinoline, hydroxyisoquinoline, hydroxybenzoquinoline, hydroxyacridine, hydroxyphenanthridine, hydroxyphenyloxazole, hydroxyphenylthiazole, hydroxyphenyloxadiazole, hydroxyphenylthiadiazole, hydroxyphenylpyridine, hydroxyphenylbenzimidazole, hydroxyphenylbenzothiazole, bipyridine, phenanthroline, cyclopentadiene, or any combination thereof.

For example, the metal-containing material may include a Li complex. The Li complex may include, e.g., Compound ET-D1 (LiQ) or Compound ET-D2:

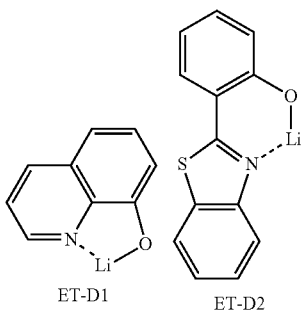

ET-D1      ET-D2

The electron transport region may include an electron injection layer that facilitates the injection of electrons from the second electrode 150. The electron injection layer may be in direct contact with the second electrode 150.

The electron injection layer may have i) a single-layered structure including (e.g., consisting of) a single layer including (e.g., consisting of) a single material, ii) a single-layered structure including (e.g., consisting of) a single layer including a plurality of different materials, or iii) a multi-layered structure having a plurality of layers including a plurality of different materials.

The electron injection layer may include an alkali metal, an alkaline earth metal, a rare earth metal, an alkali metal-containing compound, an alkaline earth metal-containing compound, a rare earth metal-containing compound, an alkali metal complex, an alkaline earth metal complex, a rare earth metal complex, or any combination thereof.

The alkali metal may be Li, Na, K, Rb, Cs or any combination thereof. The alkaline earth metal may be Mg, Ca, Sr, Ba, or any combination thereof. The rare earth metal may be Sc, Y, Ce, Tb, Yb, Gd, or any combination thereof.

The alkali metal-containing compound, the alkaline earth metal-containing compound, and the rare earth metal-containing compound may be oxide(s), halide(s) (e.g., fluoride(s), chloride(s), bromide(s), and/or iodine(s)), telluride(s), or any combination thereof of the alkali metal, the alkaline earth metal, and the rare earth metal, respectively.

The alkali metal-containing compound may be alkali metal oxide(s) (such as $Li_2O$, $CS_2O$, and/or $K_2O$), alkali metal halide(s) (such as LiF, NaF, CsF, KF, LiI, NaI, CsI, and/or KI), or any combination thereof. The alkaline earth-metal-containing compound may include alkaline earth-metal compound(s), such as BaO, SrO, CaO, $Ba_xSr_{1-x}O$ (wherein x is a real number that satisfying $0<x<1$), and/or $Ba_xCa_{1-x}O$ (wherein x is a real number that satisfying $0<x<1$). The rare earth metal-containing compound may include $YbF_3$, $ScF_3$, $Sc_2O_3$, $Y_2O_3$, $Ce_2O_3$, $GdF_3$, $TbF_3$, $YbI_3$, $ScI_3$, $TbI_3$, or any combination thereof. In some embodiments, the rare earth metal-containing compound may include a lanthanide metal telluride. Non-limiting examples of the lanthanide metal telluride may include LaTe, CeTe, PrTe, NdTe, PmTe, SmTe, EuTe, GdTe, TbTe, DyTe, HoTe, ErTe, TmTe, YbTe, LuTe, $La_2Te_3$, $Ce_2Te_3$, $Pr_2Te_3$, $Nd_2Te_3$, $Pm_2Te_3$, $Sm_2Te_3$, $Eu_2Te_3$, $Gd_2Te_3$, $Tb_2Te_3$, $Dy_2Te_3$, $Ho_2Te_3$, $Er_2Te_3$, $Tm_2Te_3$, $Yb_2Te_3$, $Lu_2Te_3$, and the like.

The alkali metal complex, the alkaline earth metal complex, and the rare earth metal complex may include: i) one of ions of the alkali metal, the alkaline earth metal, and the rare earth metal described above and ii) a ligand bound to the metal ion, e.g., hydroxyquinoline, hydroxyisoquinoline, hydroxybenzoquinoline, hydroxyacridine, hydroxyphenanthridine, hydroxyphenyloxazole, hydroxyphenylthiazole, hydroxydiaphenyloxadiazole, hydroxydiphenylthiadiazole, hydroxyphenylpyridine, hydroxyphenylbenzimidazole, hydroxyphenylbenzothiazole, bipyridine, phenanthroline, cyclopentadiene, or any combination thereof.

The electron injection layer may include (e.g., consist of) an alkali metal, an alkaline earth metal, a rare earth metal, an alkali metal-containing compound, an alkaline earth metal-containing compound, a rare earth metal-containing compound, an alkali metal complex, an alkaline earth metal complex, a rare earth metal complex, or any combination thereof, as described above. In some embodiments, the electron injection layer may further include an organic material (e.g., a compound represented by Formula 601).

In some embodiments, the electron injection layer may include (e.g., consist of) i) an alkali metal-containing compound (e.g., alkali metal halide), or ii) a) an alkali metal-containing compound (e.g., alkali metal halide); and b) an alkali metal, an alkaline earth metal, a rare earth metal, or any combination thereof. In some embodiments, the electron injection layer may be a KI:Yb co-deposition layer, a RbI:Yb co-deposition layer, and/or the like.

When the electron injection layer further includes an organic material, the alkali metal, the alkaline earth metal, the rare earth metal, the alkali metal-containing compound, the alkaline earth metal-containing compound, the rare earth metal-containing compound, the alkali metal complex, the alkaline earth metal complex, the rare earth metal complex, or any combination thereof may be homogeneously or non-homogeneously dispersed in a matrix including the organic material.

The thickness of the electron injection layer may be in a range of about 1 Å to about 100 Å, and in some embodiments, about 3 Å to about 90 Å. When the thickness of the electron injection layer is within any of these ranges, desired or excellent electron injection characteristics may be obtained without a substantial increase in driving voltage.

Second Electrode 150

The second electrode 150 may be on the interlayer 130. In an embodiment, the second electrode 150 may be a cathode that is an electron injection electrode. In this embodiment, a material for forming the second electrode 150 may be a material having a low work function, for example, a metal, an alloy, an electrically conductive compound, or any combination thereof.

The second electrode 150 may include lithium (Li), silver (Ag), magnesium (Mg), aluminum (Al), aluminum-lithium (Al—Li), calcium (Ca), magnesium-indium (Mg—In), magnesium-silver (Mg—Ag), ytterbium (Yb), silver-ytterbium (Ag—Yb), ITO, IZO, or any combination thereof. The second electrode 150 may be a transmissive electrode, a semi-transmissive electrode, or a reflective electrode.

The second electrode 150 may have a single-layered structure, or a multi-layered structure including two or more layers.

Capping Layer

A first capping layer may be located outside the first electrode 110 (e.g., on the side opposite to the second electrode), and/or a second capping layer may be located outside the second electrode 150 (e.g., on the side opposite to the first electrode). In some embodiments, the light-emitting device 10 may have a structure in which the first capping layer, the first electrode 110, the interlayer 130, and the second electrode 150 are sequentially stacked in this stated order, a structure in which the first electrode 110, the interlayer 130, the second electrode 150, and the second capping layer are sequentially stacked in this stated order, or a structure in which the first capping layer, the first electrode 110, the interlayer 130, the second electrode 150, and the second capping layer are sequentially stacked in this stated order.

In an embodiment, in the light-emitting device 10, light emitted from the emission layer in the interlayer 130 may pass through the first electrode 110 (which may be a semi-transmissive electrode or a transmissive electrode) and through the first capping layer to the outside. In an embodiment, in the light-emitting device 10, light emitted from the emission layer in the interlayer 130 may pass through the second electrode 150 (which may be a semi-transmissive electrode or a transmissive electrode) and through the second capping layer to the outside.

The first capping layer and the second capping layer may improve the external luminescence efficiency based on the principle of constructive interference. Accordingly, the optical extraction efficiency of the light-emitting device 10 may be increased, thus improving luminescence efficiency of the light-emitting device 10.

The first capping layer and the second capping layer may each include a material having a refractive index of 1.6 or higher (at 589 nm).

The first capping layer and the second capping layer may each independently be an organic capping layer including an organic material, an inorganic capping layer including an inorganic material, or a composite capping layer including an organic material and an inorganic material.

At least one of the first capping layer and the second capping layer may each independently include a carbocyclic compound, a heterocyclic compound, an amine group-containing compound, a porphine derivative, a phthalocyanine derivative, a naphthalocyanine derivative, an alkali metal complexe, an alkaline earth metal complexe, or any combination thereof. The carbocyclic compound, the heterocyclic compound, and the amine group-containing compound may optionally be substituted with a substituent of O, N, S, Se, Si, F, Cl, Br, I, or any combination thereof. In some embodiments, at least one of the first capping layer and the second capping layer may each independently include an amine group-containing compound.

In some embodiments, at least one of the first capping layer and the second capping layer may each independently include the compound represented by Formula 201, the compound represented by Formula 202, or any combination thereof.

In one or more embodiments, at least one of the first capping layer and the second capping layer may each independently include one of Compounds HT28 to HT33, one of Compounds CP1 to CP6, β-NPB, or any combination thereof:

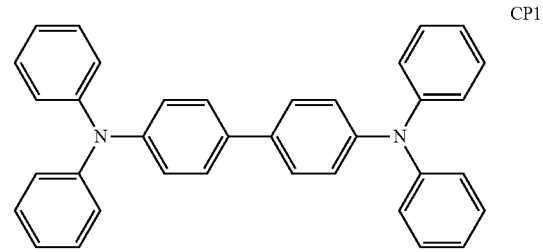

CP1

CP2

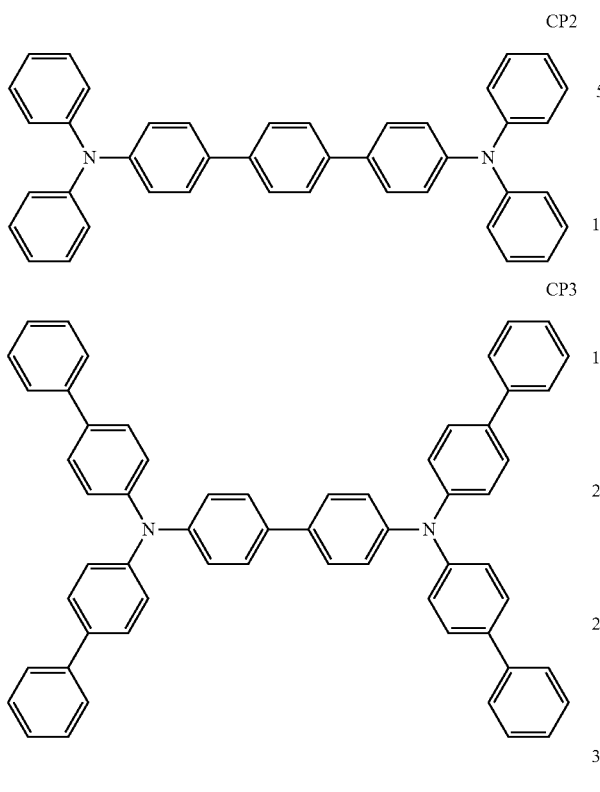

CP3

CP4

CP5

CP6

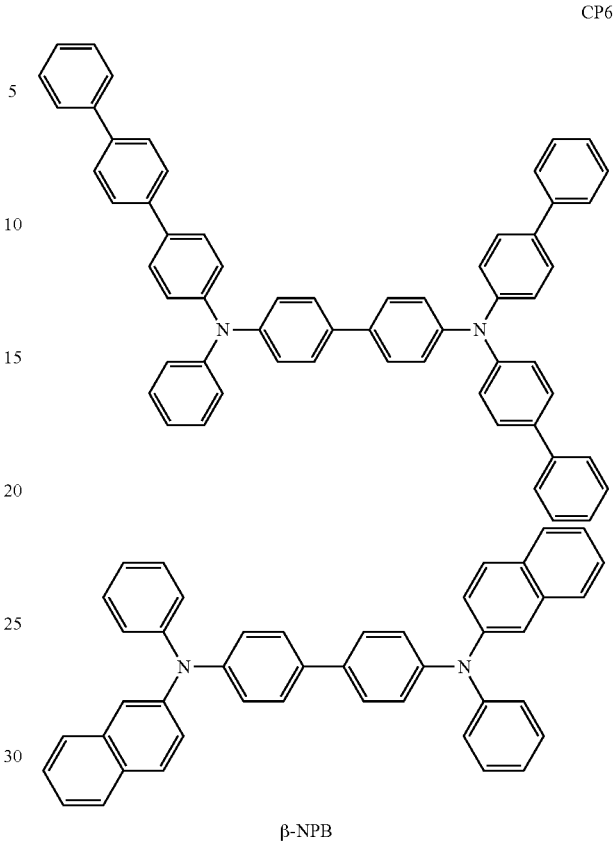

β-NPB

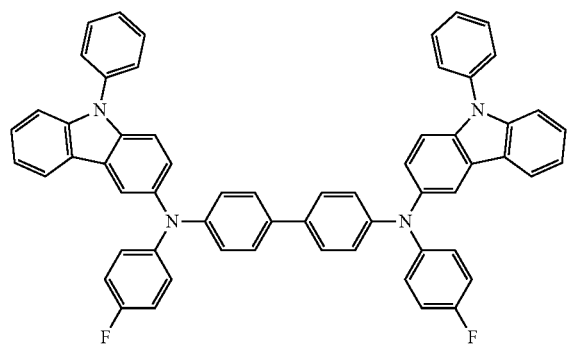

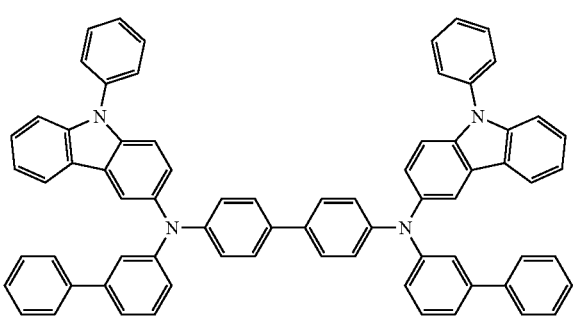

Electronic Apparatus

The light-emitting device may be included in various suitable electronic apparatuses. In some embodiments, an electronic apparatus including the light-emitting device may be an emission apparatus (e.g., light-emitting apparatus) or an authentication apparatus.

The electronic apparatus (e.g., an emission apparatus) may further include, in addition to the light-emitting device, i) a color filter, ii) a color-conversion layer, or iii) a color filter and a color-conversion layer. The color filter and/or the color-conversion layer may be disposed on at least one traveling direction of light emitted from the light-emitting device. For example, light emitted from the light-emitting device may be blue light or white light. The light-emitting device may be understood by referring to the descriptions provided herein. In some embodiments, the color-conversion layer may include a quantum dot. The quantum dot may be, for example, the quantum dot described herein.

The electronic apparatus may include a first substrate. The first substrate may include a plurality of sub-pixel areas, the color filter may include a plurality of color filter areas respectively corresponding to the plurality of sub-pixel areas, and the color-conversion layer may include a plurality of color-conversion areas respectively corresponding to the plurality of sub-pixel areas.

A pixel defining film may be located between the plurality of sub-pixel areas to define each sub-pixel area.

The color filter may further include a plurality of color filter areas and light-blocking patterns between the plurality of color filter areas, and the color-conversion layer may further include a plurality of color-conversion areas and light-blocking patterns between the plurality of color-conversion areas.

The plurality of color filter areas (or the plurality of color-conversion areas) may include: a first area emitting a first color light; a second area emitting a second color light; and/or a third area emitting a third color light, and the first color light, the second color light, and/or the third color light may have different maximum emission wavelengths. In some embodiments, the first color light may be red light, the second color light may be green light, and the third color light may be blue light. In some embodiments, the plurality of color filter areas (or the plurality of color-conversion areas) may each include a quantum dot. In some embodiments, the first area may include a red quantum dot (e.g., a red light emitting quantum dot), the second area may include a green quantum dot (e.g., a green light emitting quantum dot), and the third area may not include a quantum dot. The quantum dot may be understood by referring to the description of the quantum dot provided herein. The first area, the second area, and/or the third area may each further include an emitter.

In some embodiments, the light-emitting device may emit a first light, the first area may absorb the first light to emit 1-1 color light, the second area may absorb the first light to emit 2-1 color light, and the third area may absorb the first light to emit 3-1 color light. In this embodiment, the 1-1 color light, the 2-1 color light, and the 3-1 color light may each have a different maximum emission wavelength. In some embodiments, the first light may be blue light, the 1-1 color light may be red light, the 2-1 color light may be green light, and the 3-1 light may be blue light.

The electronic apparatus may further include a thin-film transistor, in addition to the light-emitting device. The thin-film transistor may include a source electrode, a drain electrode, and an activation layer (e.g., an active layer), wherein one of the source electrode and the drain electrode may be electrically connected to one of the first electrode and the second electrode of the light-emitting device.

The thin-film transistor may further include a gate electrode, a gate insulating film, and/or the like.

The activation layer may include a crystalline silicon, an amorphous silicon, an organic semiconductor, and/or an oxide semiconductor.

The electronic apparatus may further include a sealing portion (e.g., a sealing layer) for sealing the light-emitting device. The sealing portion may be located between the color filter and/or the color-conversion layer and the light-emitting device. The sealing portion may allow light to pass to the outside from the light-emitting device and reduce or prevent the air and moisture to permeate to the light-emitting device at the same time. The sealing portion may be a sealing substrate including a transparent glass or a plastic substrate. The sealing portion may be a thin-film encapsulating layer including organic layer(s) and/or inorganic layer(s). When the sealing portion is a thin film encapsulating layer, the electronic apparatus may be flexible.

In addition to the color filter and/or the color-conversion layer, various suitable functional layers may be disposed on the sealing portion depending on the usage of an electronic apparatus. Examples of the functional layer may include a touch screen layer, a polarization layer, and/or the like. The touch screen layer may be a resistive touch screen layer, a capacitive touch screen layer, or an infrared beam touch screen layer. The authentication apparatus may be, for example, a biometric authentication apparatus that identifies an individual according to biometric information (e.g., a fingertip, a pupil, and/or the like).

The authentication apparatus may further include a biometric information collecting unit, in addition to the light-emitting device described above.

The electronic apparatus may be applicable to various suitable displays, an optical source, lighting, a personal computer (e.g., a mobile personal computer), a cellphone, a digital camera, an electronic note, an electronic dictionary, an electronic game console, a medical device (e.g., an electronic thermometer, a blood pressure meter, a glucometer, a pulse measuring device, a pulse wave measuring device, an electrocardiograph recorder, an ultrasonic diagnosis device, an endoscope display device), a fish finder, various suitable measurement devices, gauges (e.g., gauges of an automobile, an airplane, a ship), and/or a projector.

Figure 2:
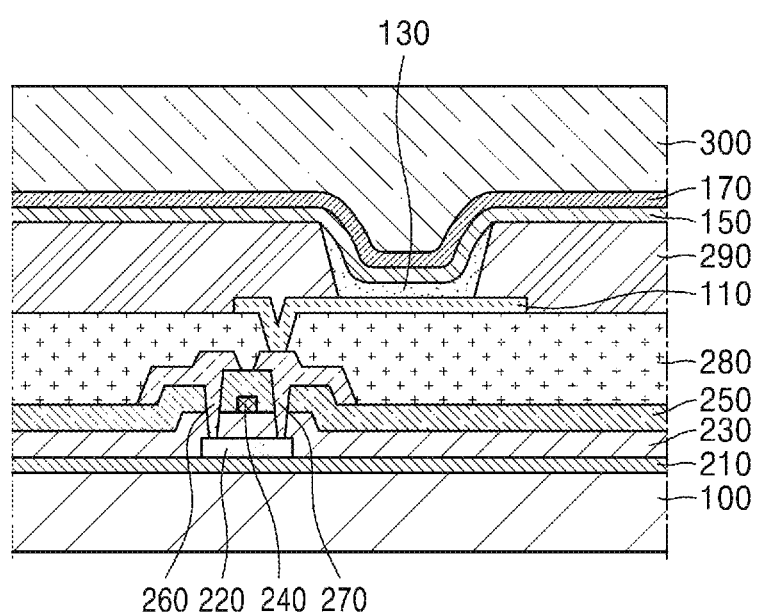
FIG. 2 is a schematic cross-sectional view of a light-emitting apparatus according to an embodiment.
Figure 3:
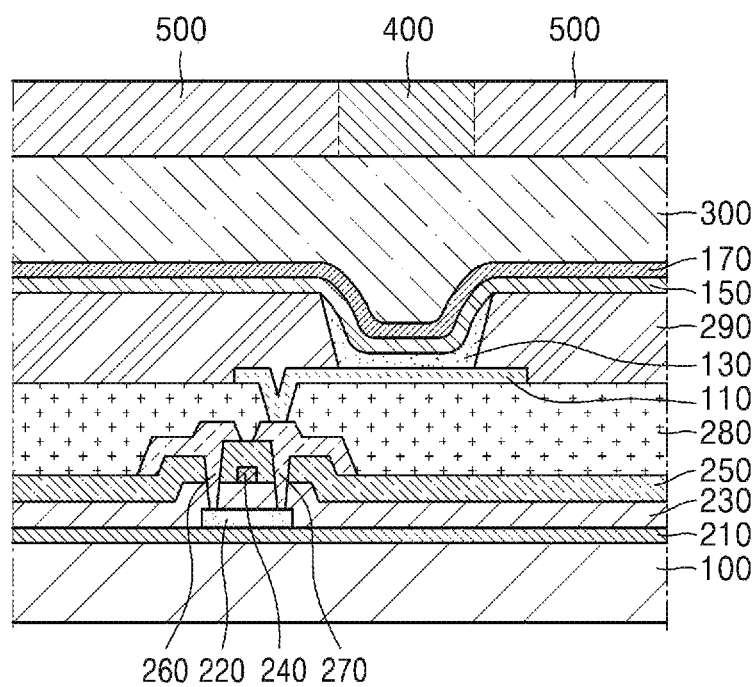
FIG. 3 is a schematic cross-sectional view of another light-emitting apparatus according to an embodiment.

Descriptions of FIGS. 2 and 3

FIG. 2 is a schematic cross-sectional view of a light-emitting apparatus according to an embodiment.

An emission apparatus (e.g., light-emitting apparatus) in FIG. 2 may include a substrate 100, a thin-film transistor, a light-emitting device, and an encapsulation unit 300 sealing the light-emitting device.

The substrate 100 may be a flexible substrate, a glass substrate, or a metal substrate. A buffer layer 210 may be on the substrate 100. The buffer layer 210 may reduce or prevent penetration of impurities through the substrate 100 and provide a flat surface on the substrate 100.

A thin-film transistor may be on the buffer layer 210. The thin-film transistor may include an active layer 220, a gate electrode 240, a source electrode 260, and a drain electrode 270.

The active layer 220 may include an inorganic semiconductor such as silicon or polysilicon, an organic semiconductor, or an oxide semiconductor, and include a source area, a drain area and a channel area.

A gate insulating film 230 for insulating the active layer 220 from the gate electrode 240 may be on the active layer 220, and the gate electrode 240 may be on the gate insulating film 230.

An interlayer insulating film 250 may be on the gate electrode 240. The interlayer insulating film 250 may be between the gate electrode 240 and the source electrode 260 and between the gate electrode 240 and the drain electrode 270 to provide insulation therebetween.

The source electrode 260 and the drain electrode 270 may be on the interlayer insulating film 250. The interlayer insulating film 250 and the gate insulating film 230 may be formed to expose the source area and the drain area of the active layer 220, and the source electrode 260 and the drain electrode 270 may be adjacent to the exposed source area and the exposed drain area of the active layer 220.

Such a thin-film transistor may be electrically connected to a light-emitting device to drive the light-emitting device and may be protected by a passivation layer 280. The passivation layer 280 may include an inorganic insulating film, an organic insulating film, or a combination thereof. A light-emitting device may be on the passivation layer 280. The light-emitting device may include a first electrode 110, an interlayer 130, and a second electrode 150.

The first electrode 110 may be on the passivation layer 280. The passivation layer 280 may not fully cover the drain electrode 270 and may expose an area (e.g., a specific area) of the drain electrode 270, and the first electrode 110 may be disposed to connect to the exposed drain electrode 270.

A pixel-defining film 290 may be on the first electrode 110. The pixel-defining film 290 may expose an area (e.g., a specific area) of the first electrode 110, and the interlayer 130 may be formed in the exposed area. The pixel-defining film 290 may be a polyimide or polyacryl organic film. In an embodiment, some higher layers (e.g., one or more layers) of the interlayer 130 may extend to the upper portion of the pixel-defining film 290 and may be disposed in the form of a common layer.

The second electrode 150 may be on the interlayer 130, and a capping layer 170 may be additionally formed on the second electrode 150. The capping layer 170 may be formed to cover the second electrode 150.

The encapsulation unit 300 may be on the capping layer 170. The encapsulation unit 300 may be on the light-emitting device to protect the light-emitting device from moisture or oxygen. The encapsulation unit 300 may include: an inorganic film including silicon nitride (SiNx), silicon oxide (SiOx), indium tin oxide, indium zinc oxide, or any combination thereof; an organic film including polyethylene terephthalate, polyethylene naphthalate, polycarbonate, polyimide, polyethylene sulfonate, polyoxy methylene, polyaryllate, hexamethyl disiloxane, an acrylic resin (e.g., polymethyl methacrylate, polyacrylic acid, and/or the like), an epoxy resin (e.g., aliphatic glycidyl ether (AGE) and/or the like), or any combination thereof; or a combination of the inorganic film and the organic film.

FIG. 3 is a schematic cross-sectional view of another light-emitting apparatus according to an embodiment.

The emission apparatus (e.g., light-emitting apparatus) shown in FIG. 3 may be substantially identical to the emission apparatus (e.g., light-emitting apparatus) shown in FIG. 2, except that a light-shielding pattern 500 and a functional area 400 are additionally located on the encapsulation unit 300. The functional area 400 may be i) a color filter area, ii) a color-conversion area, or iii) a combination of a color filter area and a color-conversion area. In some embodiments, the light-emitting device shown in FIG. 3 included in the emission apparatus (e.g., light-emitting apparatus) may be a tandem light-emitting device.

Manufacturing Method

The layers constituting the hole transport region, the emission layer, and the layers constituting the electron transport region may be formed in a certain (e.g., specific) region by utilizing one or more suitable methods such as vacuum deposition, spin coating, casting, Langmuir-Blodgett (LB) deposition, ink-jet printing, laser printing, and/or laser-induced thermal imaging.

When the layers constituting the hole transport region, the emission layer, and the layers constituting the electron transport region are each formed by vacuum deposition, the vacuum deposition may be performed at a deposition temperature in a range of about 100° C. to about 500° C. at a vacuum degree in a range of about $10^{-8}$ torr to about $10^{-3}$ torr, and at a deposition rate in a range of about 0.01 Angstroms per second (Å/sec) to about 100 Å/sec, depending on the material to be included in each layer and the structure of each layer to be formed.

General Definitions of Terms

The term "$C_3$-$C_{60}$ carbocyclic group" as used herein refers to a cyclic group consisting of only carbon atoms as a ring-forming atom and having 3 to 60 carbon atoms. The term "$C_1$-$C_{60}$ heterocyclic group" as used herein refers to a cyclic group having 1 to 60 carbon atoms in addition to a heteroatom other than carbon atoms as a ring-forming atom. The $C_3$-$C_{60}$ carbocyclic group and the $C_1$-$C_{60}$ heterocyclic group may each be a monocyclic group consisting of one ring or a polycyclic group in which at least two rings are condensed. For example, the number of ring-forming atoms in the $C_1$-$C_{60}$ heterocyclic group may be in a range of 3 to 61.

The term "cyclic group" as used herein may include the $C_3$-$C_{60}$ carbocyclic group and the $C_1$-$C_{60}$ heterocyclic group.

The term "π electron-rich $C_3$-$C_{60}$ cyclic group" as used herein refers to a cyclic group having 3 to 60 carbon atoms and not including *—N=*' as a ring-forming moiety. The term "π electron-deficient nitrogen-containing $C_1$-$C_{60}$ cyclic group" as used herein refers to a heterocyclic group having 1 to 60 carbon atoms and *—N=*' as a ring-forming moiety.

In some embodiments, the $C_3$-$C_{60}$ carbocyclic group may be i) a T1 group or ii) a group in which at least two T1 groups are condensed (e.g., with each other) (for example, a cyclopentadiene group, an adamantane group, a norbornane group, a benzene group, a pentalene group, a naphthalene group, an azulene group, an indacene group, an acenaphthylene group, a phenalene group, a phenanthrene group, an anthracene group, a fluoranthene group, a triphenylene group, a pyrene group, a chrysene group, a perylene group, a pentaphene group, a heptalene group, a naphthacene group, a picene group, a hexacene group, a pentacene group, a rubicene group, a coronene group, an ovalene group, an indene group, a fluorene group, a spiro-bifluorene group, a benzofluorene group, an indenophenanthrene group, and/or an indenoanthracene group), the $C_1$-$C_{60}$ heterocyclic group may be i) a T2 group, ii) a group in which at least two T2 groups are condensed (e.g., with each other), or iii) a group in which at least one T2 group is condensed with at least one T1 group (for example, a pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, a benzothienodibenzothiophene group, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, an azadibenzofuran group, and/or the like), the π electron-rich $C_3$-$C_{60}$ cyclic group may be i) a T1 group, ii) a condensed group in which at least two T1 groups are condensed (e.g., with each other), iii) a T3 group, iv) a condensed group in which at least two T3 groups are condensed (e.g., with each other), or v) a condensed group in which at least one T3 group is condensed with at least one T1 group (for example, a $C_3$-$C_{60}$ carbocyclic group, a pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, a benzothienodibenzothiophene group, and/or the like), and the π electron-deficient nitrogen-containing $C_1$-$C_{60}$ cyclic group may be i) a T4 group, ii) a group in which at least two T4 groups are condensed (e.g., with each other), iii) a group in which at least one T4 group is condensed with at least one T1 group, iv) a group in which at least one T4 group is condensed with at least one T3 group, or v) a group in which at least one T4 group, at least one T1 group, and at least one T3 group are condensed (e.g., with each other) (for example, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, an azadibenzofuran group, and/or the like), wherein the T1 group may be a cyclopropane group, a cyclobutane group, a cyclopentane group, a cyclohexane group, a cycloheptane group, a cyclooctane group, a cyclobutene group, a cyclopentene group, a cyclopentadiene group, a cyclohexene group, a cyclohexadiene group, a cycloheptene group, an adamantane group, a norbornane (or bicyclo[2.2.1]heptane) group, a norbornene group, a bicyclo[1.1.1]pentane group, a bicyclo[2.1.1]hexane group, a bicyclo[2.2.2]octane group, or a benzene group, the T2 group may be a furan group, a thiophene group, a 1H-pyrrole group, a silole group, a borole group, a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, or a tetrazine group, the T3 group may be a furan group, a thiophene group, a 1H-pyrrole group, a silole group, or a borole group, and the T4 group may be a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, or a tetrazine group.

The term "cyclic group", "$C_3$-$C_{60}$ carbocyclic group", "$C_1$-$C_{60}$ heterocyclic group", "π electron-rich $C_3$-$C_{60}$ cyclic group", or "π electron-deficient nitrogen-containing $C_1$-$C_{60}$ cyclic group" as used herein may each independently be a group condensed with any suitable cyclic group, a monovalent group, or a polyvalent group (e.g., a divalent group, a trivalent group, a quadrivalent group, and/or the like), depending on the structure of the formula to which the term is applied. For example, a "benzene group" may be a benzo group, a phenyl group, a phenylene group, and/or the like, and this may be understood by one of ordinary skill in the art, depending on the structure of the formula including the "benzene group".

Non-limiting examples of the monovalent $C_3$-$C_{60}$ carbocyclic group and the monovalent $C_1$-$C_{60}$ heterocyclic group may include a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group. Non-limiting examples of the divalent $C_3$-$C_{60}$ carbocyclic group and the divalent $C_1$-$C_{60}$ heterocyclic group may include a $C_3$-$C_{10}$ cycloalkylene group, a $C_1$-$C_{10}$ heterocycloalkylene group, a $C_3$-$C_{10}$ cycloalkenylene group, a $C_1$-$C_{10}$ heterocycloalkenylene group, a $C_6$-$C_{60}$ arylene group, a $C_1$-$C_{60}$ heteroarylene group, a divalent non-aromatic condensed polycyclic group, and a substituted or unsubstituted divalent non-aromatic condensed heteropolycyclic group.

The term "$C_1$-$C_{60}$ alkyl group" as used herein refers to a linear or branched aliphatic hydrocarbon monovalent group having 1 to 60 carbon atoms, and non-limiting examples thereof include a methyl group, an ethyl group, an n-propyl group, an iso-propyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, and a tert-decyl group. The term "$C_1$-$C_{60}$ alkylene group" as used herein refers to a divalent group having the same structure as the $C_1$-$C_{60}$ alkyl group.

The term "$C_2$-$C_{60}$ alkenyl group" as used herein refers to a monovalent hydrocarbon group having at least one carbon-carbon double bond in the middle or at a terminal end (e.g., the terminus) of the $C_2$-$C_{30}$ alkyl group. Non-limiting examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a monovalent hydrocarbon group having at least one carbon-carbon triple bond in the middle or at a terminal end (e.g., the terminus) of the $C_2$-$C_{30}$ alkyl group. Non-limiting examples thereof include an ethynyl group and a propynyl group. The term "$C_2$-$C_{60}$ alkynylene group" as used herein refers to a divalent group having the same structure as the $C_2$-$C_{60}$ alkynyl group.

The term "$C_1$-$C_{60}$ alkoxy group" as used herein refers to a monovalent group represented by —$OA_{101}$ (wherein $A_{101}$ is a $C_1$-$C_1$ alkyl group). Non-limiting examples thereof include a methoxy group, an ethoxy group, and an isopropyloxy group.

The term "$C_3$-$C_{10}$ cycloalkyl group" as used herein refers to a monovalent saturated hydrocarbon monocyclic group including 3 to 10 carbon atoms. Non-limiting examples of the $C_3$-$C_{10}$ cycloalkyl group include a cyclopropyl group, a cyclobutyl group, a cyclopentyl group, a cyclohexyl group, a cycloheptyl group, a cyclooctyl group, an adamantyl group, a norbornyl (bicyclo[2.2.1]heptyl) group, a bicyclo[1.1.1]pentyl group, a bicyclo[2.1.1]hexyl group, and a bicyclo[2.2.2]octyl group. The term "$C_3$-$C_{10}$ cycloalkylene group" as used herein refers to a divalent group having the same structure as the $C_3$-$C_{10}$ cycloalkyl group.

The term "$C_1$-$C_{10}$ heterocycloalkyl group" as used herein refers to a monovalent cyclic group including at least one heteroatom other than carbon atoms as a ring-forming atom and having 1 to 10 carbon atoms. Non-limiting examples thereof include a 1,2,3,4-oxatriazolidinyl group, a tetrahydrofuranyl group, and a tetrahydrothiophenyl group. The term "$C_1$-$C_{10}$ heterocycloalkylene group" as used herein refers to a divalent group having the same structure as the $C_1$-$C_{10}$ heterocycloalkyl group.

The term "$C_3$-$C_{10}$ cycloalkenyl group" as used herein refers to a monovalent cyclic group that has 3 to 10 carbon atoms and at least one carbon-carbon double bond in its ring, and is not aromatic. Non-limiting examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monovalent cyclic group including at least one heteroatom other than carbon atoms as a ring-forming atom, 1 to 10 carbon atoms, and at least one double bond in its ring. Non-limiting examples of the $C_1$-$C_{10}$ heterocycloalkenyl group include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkylene group" as used herein refers to a divalent group having the same structure as the $C_1$-$C_{10}$ heterocycloalkenyl group.

The term "$C_6$-$C_{60}$ aryl group" as used herein refers to a monovalent group having a carbocyclic aromatic system having 6 to 60 carbon atoms. The term "$C_6$-$C_{60}$ arylene group" as used herein refers to a divalent group having a carbocyclic aromatic system having 6 to 60 carbon atoms. Non-limiting examples of the $C_6$-$C_{60}$ aryl group include a phenyl group, a pentalenyl group, a naphthyl group, an azulenyl group, an indacenyl group, an acenaphthyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a heptalenyl group, a naphthacenyl group, a picenyl group, a hexacenyl group, a pentacenyl group, a rubicenyl group, a coronenyl group, a fluorenyl group and an ovalenyl group. When the $C_6$-$C_{60}$ aryl group and the $C_6$-$C_{60}$ arylene group each independently include two or more rings, the respective rings may be fused to each other.

The term "$C_1$-$C_{60}$ heteroaryl group" as used herein refers to a monovalent group having a heterocyclic aromatic system that further includes at least one heteroatom other than carbon atoms as a ring-forming atom and 1 to 60 carbon atoms. The term "$C_1$-$C_{60}$ heteroarylene group" as used herein refers to a divalent group having a heterocyclic aromatic system that further includes at least one heteroatom other than carbon atoms as a ring-forming atom and 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, a benzoquinolinyl group, an isoquinolinyl group, a benzoisoquinolinyl group, a quinoxalinyl group, a benzoquinoxalinyl group, a quinazolinyl group, a benzoquinazolinyl group, a cinnolinyl group, a phenanthrolinyl group, a phthalazinyl group, a carbazolyl group, a dibenzofuranyl group, a dibenzothiofuranyl group, and a naphthyridinyl group. When the $C_1$-$C_{60}$ heteroaryl group and the $C_1$-$C_{60}$ heteroarylene group each independently include two or more rings, the respective rings may be fused to each other.

The term "monovalent non-aromatic condensed polycyclic group" as used herein refers to a monovalent group that has two or more rings condensed with each other and only carbon atoms as the ring forming atoms (e.g., 8 to 60 carbon atoms), wherein the entire molecular structure is non-aromatic. Non-limiting examples of the monovalent non-aromatic condensed polycyclic group include an indenyl group, an indenophenanthrenyl group, an adamantyl group, and an indenoanthracenyl group. The term "divalent non-aromatic condensed polycyclic group" as used herein refers to a divalent group having substantially the same structure as the monovalent non-aromatic condensed polycyclic group.

The term "monovalent non-aromatic condensed heteropolycyclic group" as used herein refers to a monovalent group that has two or more condensed rings and at least one heteroatom other than carbon atoms (e.g., 1 to 60 carbon atoms), as a ring-forming atom, wherein the entire molecular structure is non-aromatic. Non-limiting examples of the monovalent non-aromatic condensed heteropolycyclic group include a 9H-xanthenyl group. The term "divalent non-aromatic condensed heteropolycyclic group" as used herein refers to a divalent group having substantially the same structure as the monovalent non-aromatic condensed heteropolycyclic group.

The term "$C_6$-$C_{60}$ aryloxy group" as used herein is represented by —$OA_{102}$ (wherein $A_{102}$ is the $C_6$-$C_{60}$ aryl group). The term "$C_6$-$C_{60}$ arylthio group" as used herein is represented by —$SA_{103}$ (wherein $A_{103}$ is the $C_6$-$C_{60}$ aryl group).

The term "$R_{10a}$" as used herein may be:
deuterium (-D), —F, —Cl, —Br, —I, a hydroxyl group, a cyano group, or a nitro group;
a $C_1$-$C_{60}$ alkyl group, a $C_2$-$C_{30}$ alkenyl group, a $C_2$-$C_{30}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_3$-$C_{60}$ aryloxy group, a $C_3$-$C_{60}$ arylthio group, —Si$(Q_{11})(Q_{12})(Q_{13})$, —N$(Q_{11})(Q_{12})$, —B$(Q_{11})(Q_{12})$, —C(=O)$(Q_{11})$, —S(=O)$_2(Q_{11})$, —P(=O)$(Q_{11})(Q_{12})$, or any combination thereof;
a $C_3$-$C_{60}$ carbocyclic group, a $C_1$-$C_{60}$ heterocyclic group, a $C_6$-$C_{60}$ aryloxy group, or a $C_6$-$C_{60}$ arylthio group, each unsubstituted or substituted with deuterium, —F, —Cl, —Br, —I, a hydroxyl group, a cyano group, a nitro group, a $C_1$-$C_{30}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), —P(=O)($Q_{21}$)($Q_{22}$), or any combination thereof; or
—Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$).

$Q_1$ to $Q_3$, $Q_{11}$ to $Q_{13}$, $Q_{21}$ to $Q_{23}$, and $Q_{31}$ to $Q_{33}$ may each independently be hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; or a $C_3$-$C_{60}$ carbocyclic group or a $C_1$-$C_{60}$ heterocyclic group, each unsubstituted or substituted with deuterium, —F, a cyano group, a $C_1$-$C_{30}$ alkyl group, a $C_1$-$C_{60}$ alkoxy group, a phenyl group, a biphenyl group, or any combination thereof.

The term "heteroatom" as used herein refers to any atom other than a carbon atom. Non-limiting examples of the heteroatom may include O, S, N, P, Si, B, Ge, Se, or any combination thereof.

The term "Ph" as used herein represents a phenyl group, the term "Me" as used herein represents a methyl group, the term "Et" as used herein represents an ethyl group, the term "ter-Bu" or "Bu$^t$" as used herein represents a tert-butyl group, and the term "OMe" as used herein represents a methoxy group.

The term "biphenyl group" as used herein refers to a phenyl group substituted with a phenyl group. The "biphenyl group" belongs to "a substituted phenyl group" having a "$C_6$-$C_{60}$ aryl group" as a substituent.

The term "terphenyl group" as used herein refers to a phenyl group substituted with a biphenyl group. The "terphenyl group" belongs to "a substituted phenyl group" having a "$C_6$-$C_{60}$ aryl group substituted with a $C_6$-$C_{60}$ aryl group" as a substituent.

The symbols * and *' as used herein, unless defined otherwise, refer to a binding site to an adjacent atom in a corresponding formula.

Hereinafter, compounds and a light-emitting device according to one or more embodiments will be described in more detail with reference to Synthesis Examples and Examples. The wording "B was utilized instead of A" used in describing Synthesis Examples refers to that an amount of B utilized was identical to an amount of A utilized in terms of molar equivalents. That is, an identical molar equivalent of B was utilized in place of A.

EXAMPLES

Synthesis Examples

Synthesis Example 1: Synthesis of Compound 2

Compound 2 may be synthesized according to, for example, Reaction Scheme 1:

Reaction Scheme 1

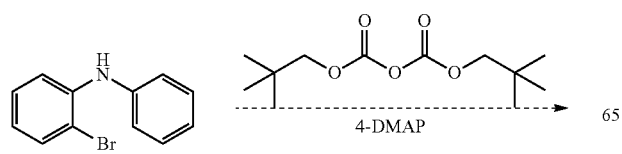

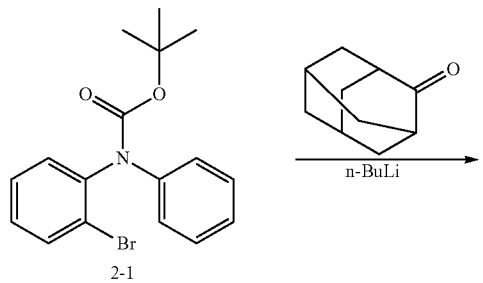

2-1

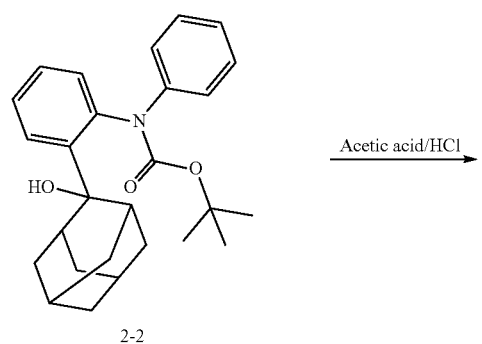

2-2

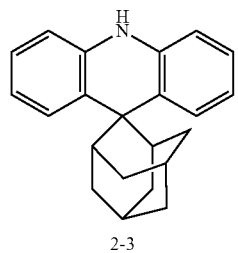

2-3

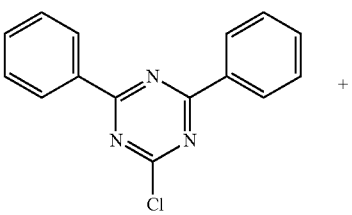

+

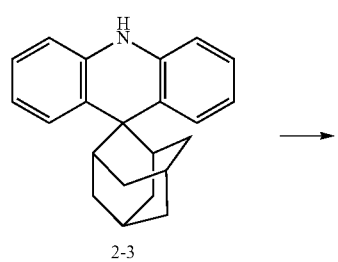

2-3

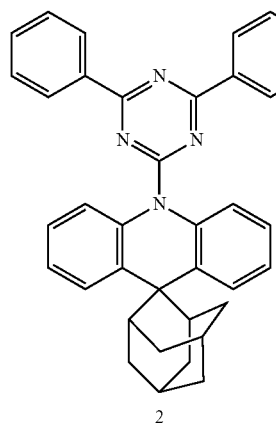

2

(Synthesis of Intermediate 2-1)

2-bromo-N-phenylaniline (CAS no. 61613-22-7), 4-(dimethylamino)pyridine (4-DMAP), and dineopentyl dicarbonate (CAS no. 24424-99-5) were reacted to obtain Intermediate 2-1. Intermediate 2-1 was subjected to liquid chromatography-mass spectrometry (LC-MS) to identify the M+1 peak value thereof.

$C_{17}H_{18}BrNO_2$: M+1 348.15

(Synthesis of Intermediate 2-2)

Intermediate 2-1 was reacted with n-BuLi and then with 2-adamantane-one (CAS no. 700-58-3) to obtain Intermediate 2-2. Intermediate 2-2 was subjected to LC-MS to identify the M+1 peak value thereof.

$C_{27}H_{33}NO_3$: M+1 420.21

(Synthesis of Intermediate 2-3)

Intermediate 2-2, acetic acid, and hydrochloric acid were reacted together to obtain Intermediate 2-3. Intermediate 2-3 was subjected to LC-MS to identify the M+1 peak value thereof.

$C_{22}H_{23}N$: M+1 302.31

(Synthesis of Compound 2)

6 grams (g) of Intermediate 2-3 and 30 milliliters (mL) of tetrahydrofuran were added to a reaction vessel, and the reaction temperature was lowered to 0° C., followed by adding 8 mL of n-butyllithium (2.5 molar (M) in hexane) dropwise. Once the reaction temperature was raised to room temperature, followed by stirring for 30 minutes, the mixture was added dropwise at a temperature of 0° C. to a reaction vessel containing 5.3 g of 2-chloro-4,6-diphenyl-1,3,5-triazine (CAS no. 3842-55-5) and 30 mL of tetrahydrofuran, followed by reflux for 24 hours at a temperature of 80° C. Once the reaction was complete, water was added to the reaction solution, followed by solid filtering (e.g., followed by filtration to obtain a dried solid). The dried solid was recrystallized utilizing dimethyl formamide to obtain 6.3 g of Compound 2 (yield: 60%). Compound 2 was identified utilizing LC-MS and $^1$H-NMR.

Synthesis Example 2: Synthesis of Compound 4

Compound 4 may be synthesized according to, for example, Reaction Scheme 2:

Reaction Scheme 2

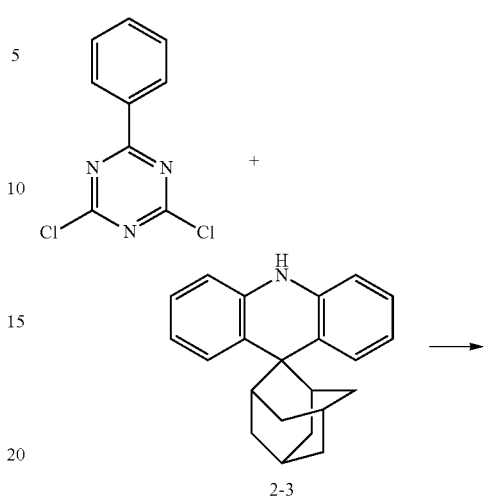

2-3

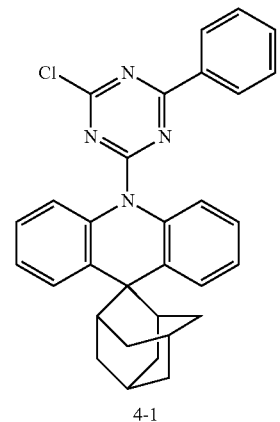

4-1

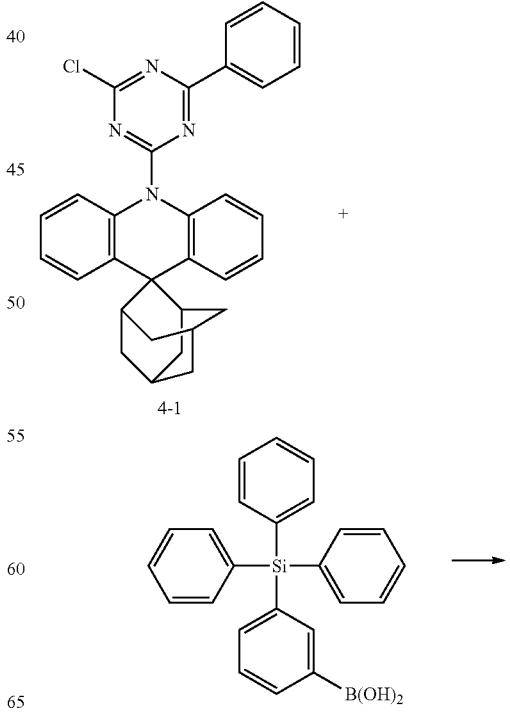

4-1

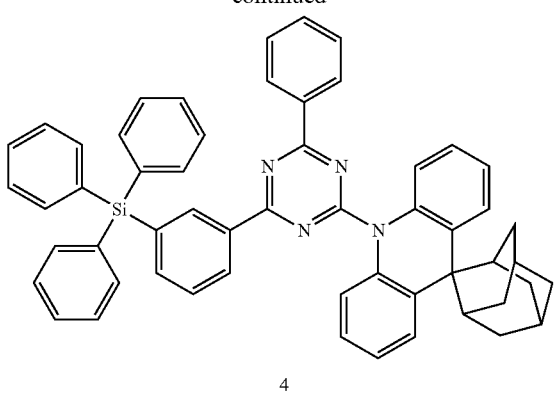

4

(Synthesis of Intermediate 4-1)

Intermediate 2-3 was reacted with n-BuLi and then with 2,4-dichloro-6-phenyl-1,3,5-triazine (CAS no. 1700-02-3) to obtain Intermediate 4-1. Intermediate 4-1 was subjected to LC-MS to identify the M+1 peak value thereof.

$C_{31}H_{27}ClN_4$: M+1 491.09

(Synthesis of Compound 4)

5 g of Intermediate 4-1, 4.3 g of (3-(triphenylsilyl)phenyl) boronic acid, 3.5 g of potassium carbonate, 0.6 g of tetrakis(triphenyl phosphine)palladium (0), 48 mL of tetrahydrofuran, and 12 mL of water were added to a reaction vessel and refluxed for 1024 hours. Once the reaction was complete, the reaction solution was subjected to extraction utilizing ethyl acetate, and the resulting organic layer was dried utilizing magnesium sulfate. Then, the solvent was removed therefrom. The residue resulting from the removal of the solvent was recrystallized utilizing dimethyl formamide to obtain 5.8 g of Compound 4 (yield: 72%). Compound 4 was identified utilizing LC-MS and $^1$H-NMR.

Synthesis Example 3: Synthesis of Compound 5

Compound 5 may be synthesized according to, for example, Reaction Scheme 3:

Reaction Scheme 3

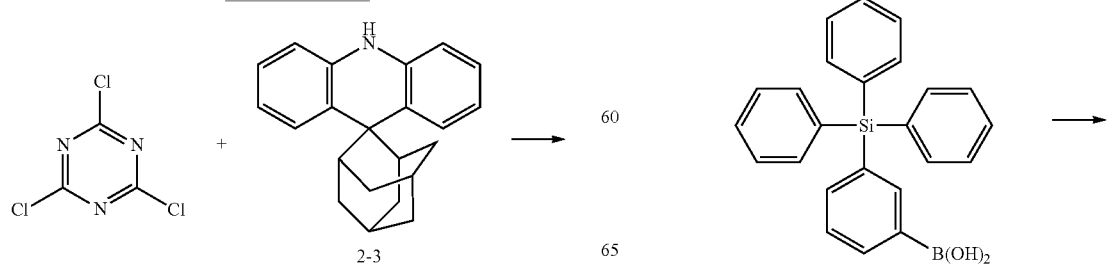

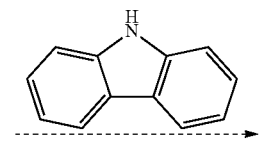

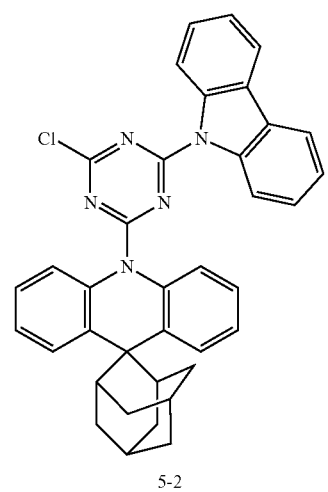

5-1

5-2

5-2

+

-continued

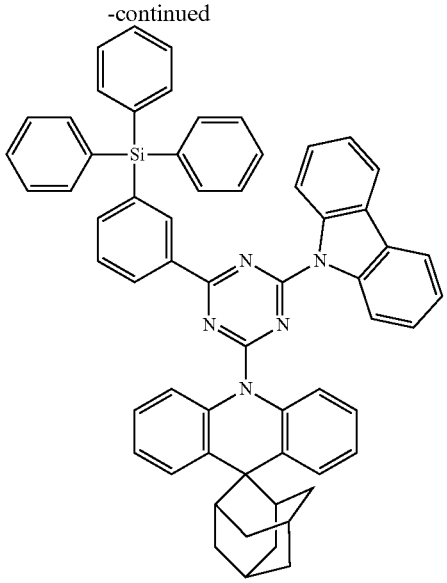

5-1

-continued

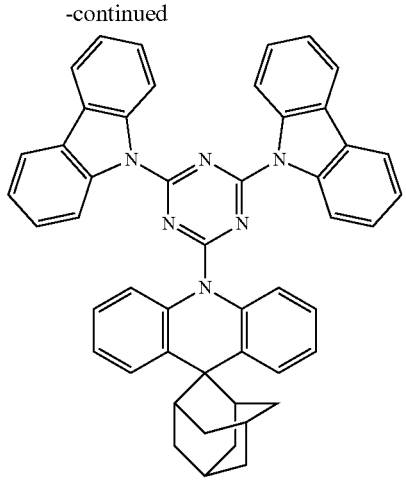

20

(Synthesis of Intermediate 5-1)

Intermediate 2-3 was reacted with n-BuLi and then with 2,4,6-trichloro-1,3,5-triazine (CAS no. 108-77-0) to obtain Intermediate 5-1. Intermediate 5-1 was subjected to LC-MS to identify the M+1 peak value thereof.

$C_{25}H_{22}Cl_2N_4$: M+1 449.13

(Synthesis of Intermediate 5-2)

9H-carbazole (CAS no. 86-74-8) was reacted with n-BuLi and then with Intermediate 5-1 to obtain Intermediate 5-2. Intermediate 5-2 was subjected to LC-MS to identify the M+1 peak value thereof.

$C_{37}H_{30}ClN_5$: M+1 580.24

(Synthesis of Compound 5)

5.1 g of Compound 5 was synthesized in substantially the same manner as in Synthesis of Compound 4, except that Intermediate 5-2 was utilized instead of Intermediate 4-1 (yield: 67%). Compound 5 was identified utilizing LC-MS and $^1$H-NMR.

Synthesis Example 4: Synthesis of Compound 20

Compound 20 may be synthesized according to, for example, Reaction Scheme 4:

(Synthesis of Compound 20)

5 g of 9H-carbazole (CAS no. 86-74-8) and 50 mL of tetrahydrofuran were added to a reaction vessel, and the temperature was lowered to 0° C. Then, 12 mL of n-butyllithium (2.5 M in hexane) was slowly added dropwise thereto. After the temperature was raised to room temperature, the reaction mixture was slowly added dropwise to a reaction vessel containing 5.8 g of Intermediate 5-1 and 25 mL of tetrahydrofuran at a temperature of 0° C., followed by reflux at 80° C. for 24 hours. Once the reaction was complete, water was added to the reaction solution, followed by solid filtering (e.g., followed by filtration to obtain a dried solid). The dried solid was recrystallized utilizing dimethyl formamide to obtain 5.3 g of Compound 20 (yield: 56%). Compound 20 was identified utilizing LC-MS and $^1$H-NMR.

Synthesis Example 5: Synthesis of Compound 22

Compound 22 may be synthesized according to, for example, Reaction Scheme 5:

Reaction Scheme 4

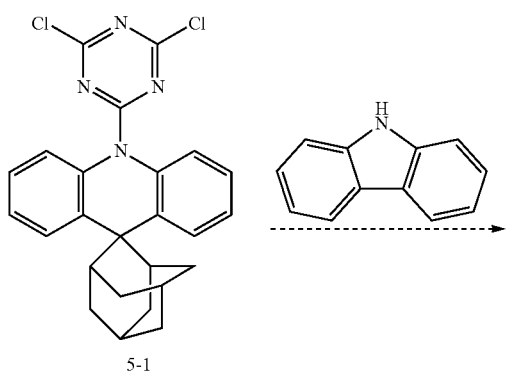

5-1

Reaction Scheme 5

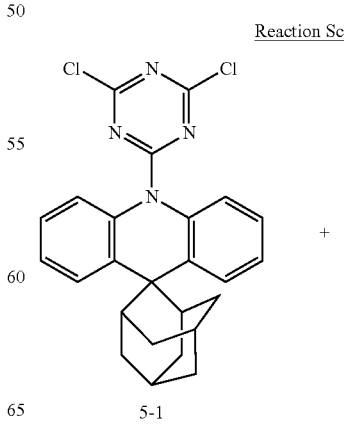

5-1

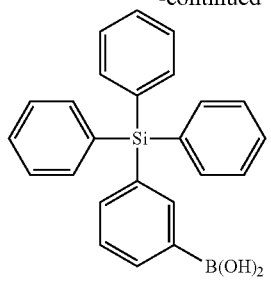

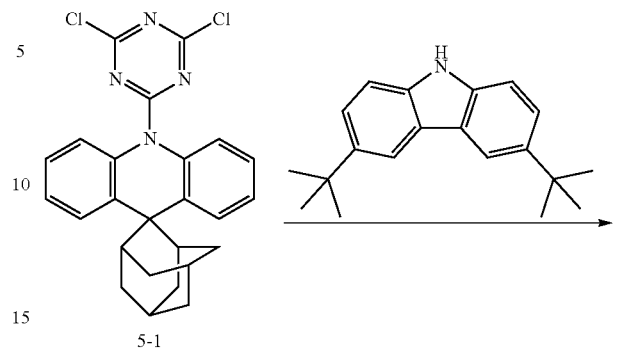

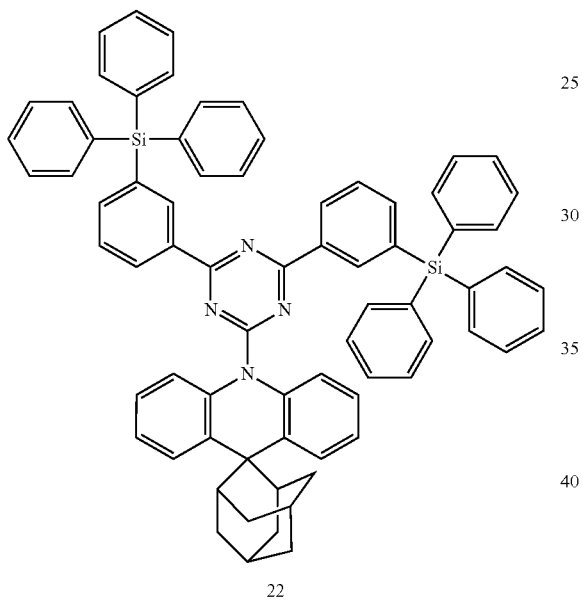

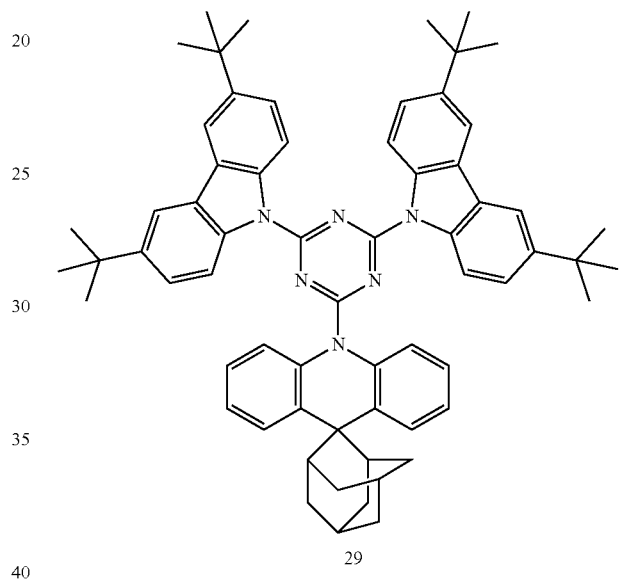

(Synthesis of Compound 22)

5 g of Intermediate 5-1, 9.3 g of (3-(triphenylsilyl)phenyl) boronic acid, 3.8 g of potassium carbonate, 0.64 g of tetrakis(triphenyl phosphine)palladium (0), 60 mL of tetrahydrofuran, and 15 mL of water were added to a reaction vessel and refluxed for 24 hours. Once the reaction was complete, the reaction solution was subjected to extraction utilizing ethyl acetate, and the resulting organic layer was dried utilizing magnesium sulfate. Then, the solvent was removed therefrom. The residue resulting from the removal of the solvent was recrystallized utilizing dimethyl formamide to obtain 7.5 g of Compound 22 (yield: 65%). Compound 22 was identified utilizing LC-MS and $^1$H-NMR.

Synthesis Example 6: Synthesis of Compound 29

Compound 29 may be synthesized according to, for example, Reaction Scheme 6:

(Synthesis of Compound 29)

6.6 g of Compound 59 was synthesized in substantially the same manner as in Synthesis of Compound 20, except that 3,6-di-tert-butyl-9H-carbazole (CAS no. 37500-95-1) was utilized instead of 9H-carbazole (CAS no. 86-74-8) (yield: 65%). Compound 29 was identified utilizing LC-MS and $^1$H-NMR.

Synthesis Example 7: Synthesis of Compound 52

Compound 52 may be synthesized according to, for example, Reaction Scheme 7:

Reaction Scheme 7

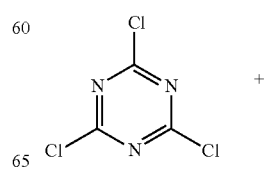

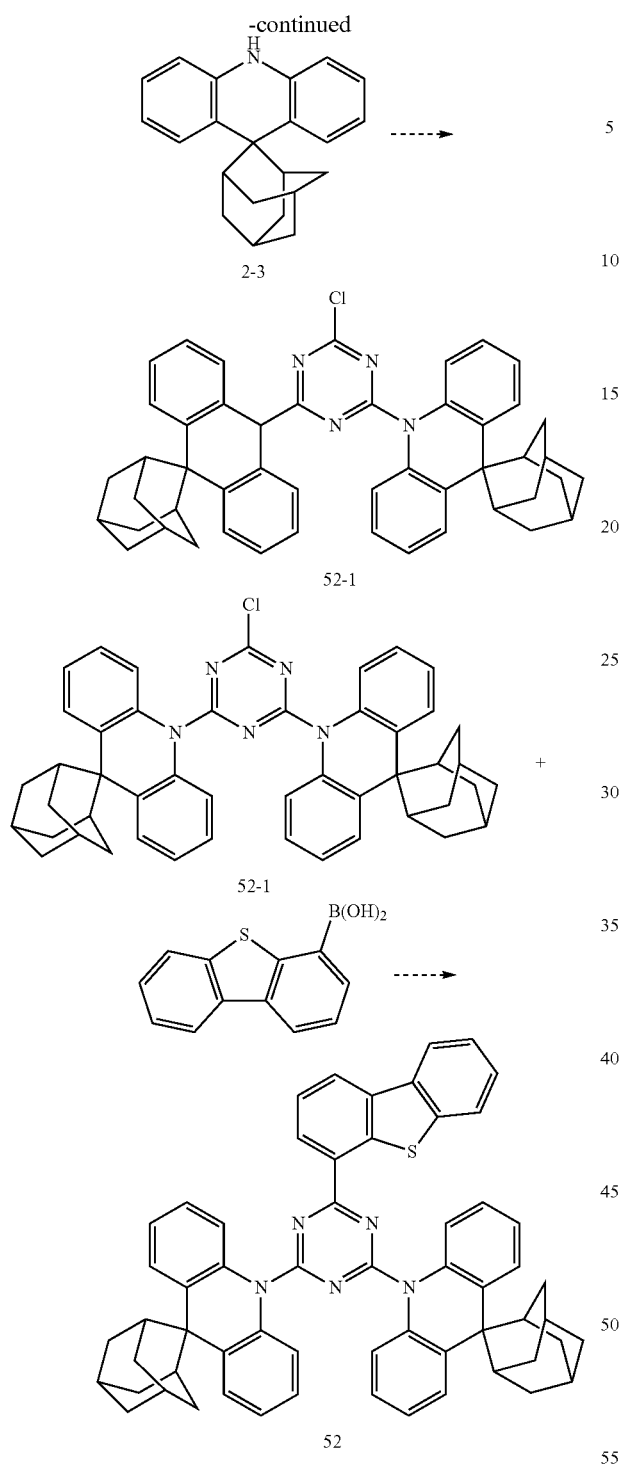

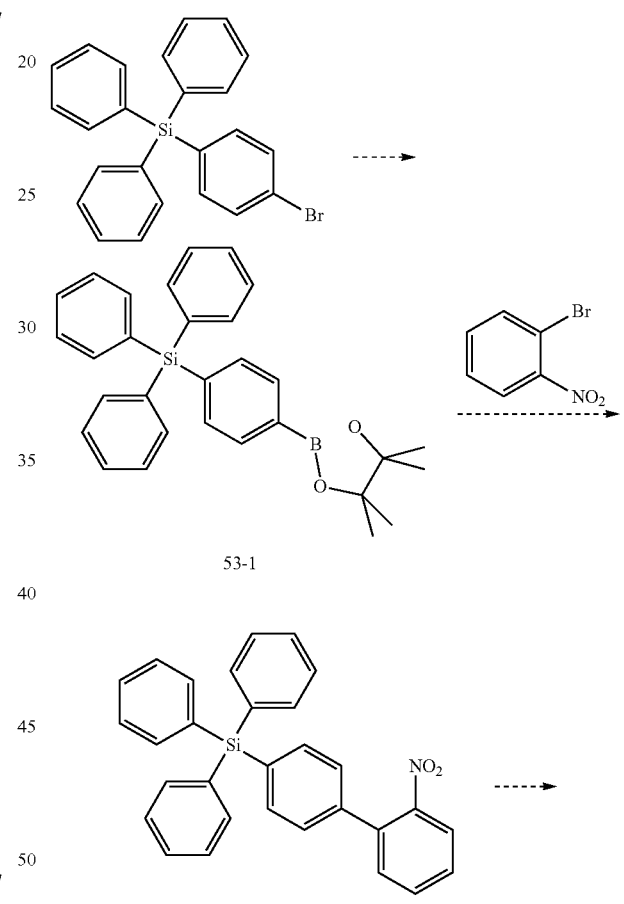

vessel and refluxed for 24 hours. Once the reaction was complete, the reaction solution was subjected to extraction utilizing ethyl acetate, and the resulting organic layer was dried utilizing magnesium sulfate. Then, the solvent was removed therefrom. The residue resulting from the removal of the solvent was recrystallized utilizing dimethyl formamide to obtain 4.2 g of Compound 52 (yield: 70%). Compound 52 was identified utilizing LC-MS and $^1$H-NMR.

Synthesis Example 8: Synthesis of Compound 53

Compound 53 may be synthesized according to, for example, Reaction Scheme 8:

(Synthesis of Intermediate 52-1)

Intermediate 2-3 was reacted with n-BuLi and then with 2,4,6-trichloro-1,3,5-triazine (CAS no. 108-77-0) to obtain Intermediate 52-1. Intermediate 52-1 was subjected to LC-MS to identify the M+1 peak value thereof.

$C_{47}H_{44}ClN_5$: M+1 714.38

(Synthesis of Compound 52)

5 g of Intermediate 52-1, 1.8 g of dibenzo[b,d]thiopen-4-ylboronic acid, 2.4 g of potassium carbonate, 0.4 g of tetrakis(triphenyl phosphine)palladium (0), 36 mL of tetrahydrofuran, and 9 mL of water were added to a reaction

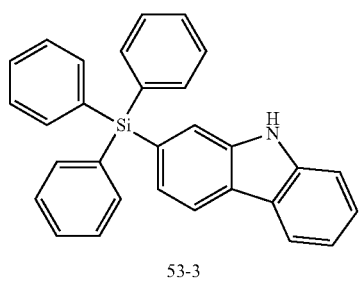

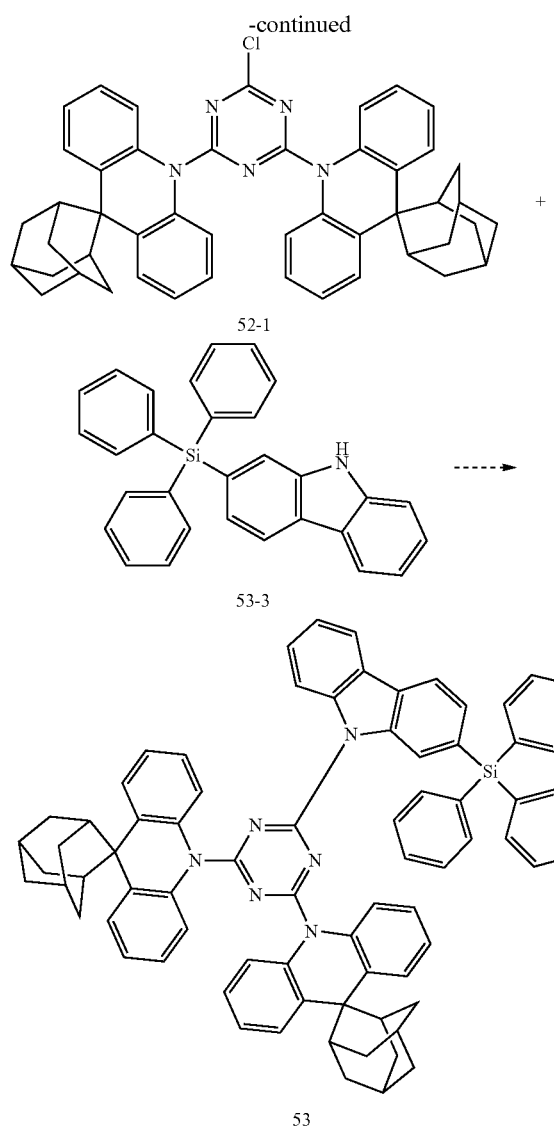

52-1

53-3

53

(Synthesis of Intermediate 53-1)

(4-bromophenyl)triphenylsilane (CAS no. 18737-40-1) was reacted with bis(pinacolato)diboron in the presence of a Pd catalyst, thereby obtaining Intermediate 2553-1. Intermediate 53-1 was subjected to LC-MS to identify the M+1 peak value thereof.

$C_{30}H_{31}BO_2Si$: M+1 463.24

(Synthesis of Intermediate 53-2)

Intermediate 53-1 was reacted with 1-bromo-2-nitrobenzene (CAS no. 577-19-5) in the presence of a Pd catalyst, thereby obtaining Intermediate 53-2. Intermediate 53-2 was subjected to LC-MS to identify the M+1 peak value thereof.

$C_{30}H_{23}NO_2Si$: M+1 458.03

(Synthesis of Intermediate 53-3)

Intermediate 53-2 was reacted with triphenyl phosphine (CAS no. 603-35-0), thereby obtaining Intermediate 53-3. Intermediate 53-3 was subjected to LC-MS to identify the M+1 peak value thereof.

$C_{30}H_{23}NSi$: M+1 426.26

(Synthesis of Compound 53)

6 g of Intermediate 53-3 and 20 mL of tetrahydrofuran were added to a reaction vessel, and the temperature was lowered to 0° C., followed by adding 5.6 mL of n-butyllithium (2.5 M in hexane) dropwise thereto. After the temperature was raised to room temperature, the reaction mixture was slowly added dropwise to a reaction vessel containing 8.4 g of Intermediate 52-1 and 20 mL of tetrahydrofuran at a temperature of 0° C., followed by reflux at 80° C. for 24 hours. Once the reaction was complete, water was added to the reaction solution, followed by solid filtering (e.g., followed by filtration to obtain a dried solid). The dried solid was recrystallized utilizing dimethyl formamide to obtain 6.4 g of Compound 53 (yield: 50%). Compound 53 was identified utilizing LC-MS and $^1$H-NMR.

Synthesis Example 9: Synthesis of Compound 56

Compound 56 may be synthesized according to, for example, Reaction Scheme 9:

Reaction Scheme 9

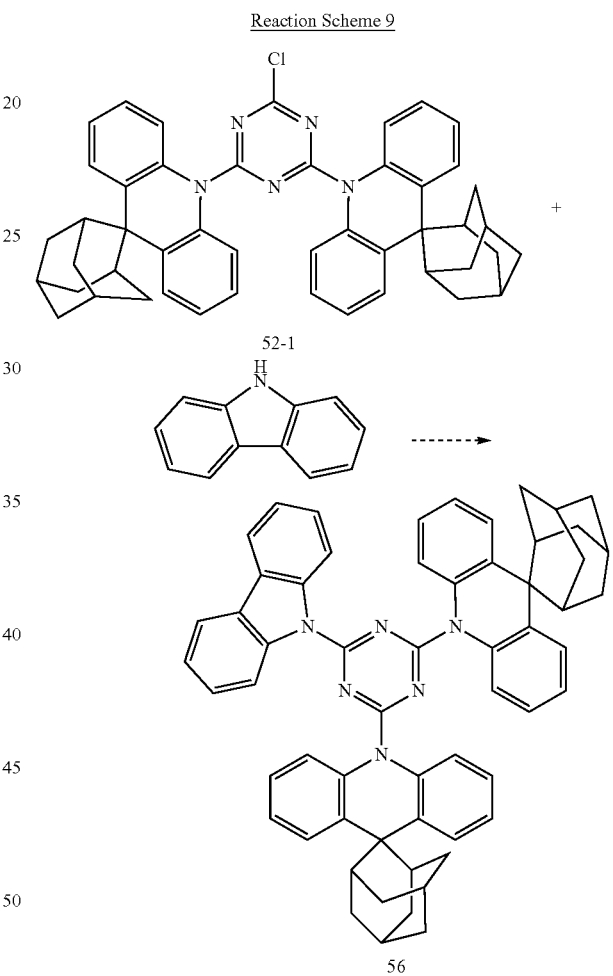

56

(Synthesis of Compound 56)

3.8 g of Compound 56 was synthesized in substantially the same manner as in Synthesis of Compound 52, except that 9H-carbazole (CAS no. 86-74-8) was utilized instead of Intermediate 53-3 (yield: 65%). Compound 56 was identified utilizing LC-MS and $^1$H-NMR.

Compounds synthesized in Synthesis Examples 1 to 9 were identified by $^1$H-NMR and mass spectroscopy/fast atom bombardment (MS/FAB). The results thereof are shown in Table 1.

Methods of synthesizing compounds other than compounds shown in Table 1 may be easily or reasonably understood to those skilled in the art by referring to the synthesis schemes and raw materials described above.

TABLE 1

| Compound | ¹H NMR (CDCl₃, 400 MHz) | MS/FAB found | MS/FAB calc. |
|---|---|---|---|
| Compound 2 | 8.36 (4H, d), 7.50 (6H, t), 7.19-7.14 (6H, m), 6.95 (2H, t), 2.10 (2H, q), 1.72 (3H, t), 1.45-1.07 (9H, m) | 533.28 | 532.26 |
| Compound 4 | 8.38-8.36 (3H, m), 7.88 (1H, s), 7.64 (1H, t), 7.50-7.38 (19H, m), 7.19-7.14 (6H, m), 6.95 (2H, t), 2.17 (2H, q), 1.72 (3H, t), 1.45-1.07 (9H, m) | 791.26 | 790.35 |
| Compound 5 | 8.55 (1H, d), 8.38 (1H, d), 8.19 (1H, d), 7.94-7.88 (2H, m), 7.58-7.38 (20H, m), 7.19-7.16 (8H, m), 6.95 (2H, d), 2.10 (2H, q), 1.72 (3H, t), 1.45-1.07 (9H, m) | 880.33 | 879.38 |
| Compound 20 | 8.55 (2H, d), 8.19 (2H, d), 7.94 (2H, d), 7.58-7.50 (4H, m), 7.35 (2H, t), 7.20-7.16 (10H, m), 6.95 (2H, t), 2.17 (2H, q), 1.72 (3H, t), 1.45-1.07 (9H, m) | 711.31 | 710.32 |
| Compound 22 | 8.38 (2H, d), 7.88 (2H, s), 7.64-7.56 (4H, m), 7.38-7.30 (30H, m), 7.19-7.17 (6H, m), 6.95 (2H, t), 2.14 (2H, q), 1.72 (3H, t), 1.45-1.07 (9H, m) | 1049.38 | 1048.44 |
| Compound 29 | 8.95 (2H, s), 8.36 (2H, s), 7.86 (2H, d), 7.62 (2H, d), 7.50 (2H, d), 7.19-7.11 (8H, m), 6.95 (2H, m), 2.17 (2H, q), 1.72 (3H, m), 1.43-1.41 (42H, m), 1.07 (3H, t) | 935.61 | 934.57 |
| Compound 52 | 8.55 (1H, d), 8.45 (1H, d), 7.93-7.91 (2H, d), 7.70 (1H, t), 7.56-7.49 (2H, m), 7.19-7.14 (12H, m), 6.95 (4H, t), 2.10 (4H, q), 1.50-1.45 (14H, m), 1.20-1.14 (10H, m) | 862.40 | 861.39 |
| Compound 53 | 8.55 (1H, d), 8.22 (1H, d), 7.94 (1H, d), 7.68 (1H, s), 7.38-7.35 (17H, m), 7.19-7.10 (13H, m), 6.95 (4H, t), 2.10 (4H, q), 1.50-1.45 (14H, m), 1.20-1.14 (10H, m) | 1103.47 | 1102.51 |
| Compound 56 | 8.55 (1H, d), 8.19 (1H, d), 7.94 (1H, d), 7.58 (1H, d), 7.50 (1H, d), 7.35 (1H, t), 7.20-7.16 (14H, m), 6.95 (4H, t), 2.10 (4H, q), 1.72 (6H, t), 1.41-1.07 (18H, m) | 845.38 | 844.43 |

Example 1

An ITO substrate having a thickness of 1,200 Å was utilized as a first electrode (anode). The ITO substrate was sonicated utilizing isopropyl alcohol and distilled water for 5 minutes each, and then irradiated with ultraviolet rays for 30 minutes and exposed to ozone for cleaning. The cleaned ITO substrate was mounted in a vacuum-deposition apparatus.

N,N'-di(1-naphthyl)-N,N'-diphenylbenzidine (NPB) was vacuum-deposited on the ITO substrate prepared by cleaning to form a hole injection layer having a thickness of 300 Å. mCP was vacuum-deposited on the hole injection layer to form a hole transport layer having a thickness of 200 Å.

Subsequently, Compound 2 (as a host) and Ir(pmp)₃ (as a dopant) were co-deposited on the hole transport layer at a weight ratio of 92:8 to form an emission layer having a thickness of 250 Å.

Then, 3-(biphenyl-4-yl)-5-(4-tert-butylphenyl)-4-phenyl-4H-1,2,4-triazole (TAZ) was deposited on the emission layer to form an electron transport layer having a thickness of 200 Å. LiF, a halogenated alkali metal, was deposited on the electron transport layer to a thickness of 10 Å to form an electron injection layer. Al was vacuum-deposited on the electron injection layer to a thickness of 100 Å to form a second electrode (cathode), thereby forming a LiF/Al electrode. HT28 was vacuum-deposited on the cathode to form a capping layer having a thickness of 700 Å, thereby completing the manufacture of a light-emitting device.

Materials utilized in preparation of the light-emitting device may be represented by the following formulae:

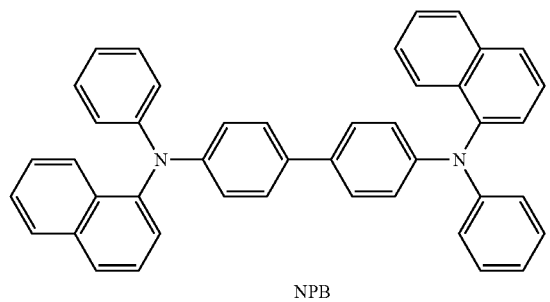

NPB

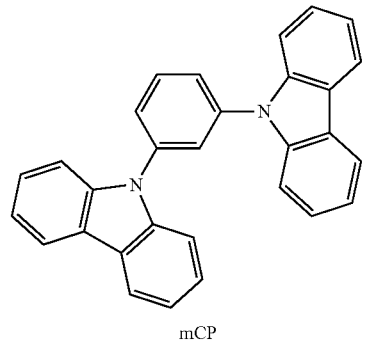

mCP

-continued

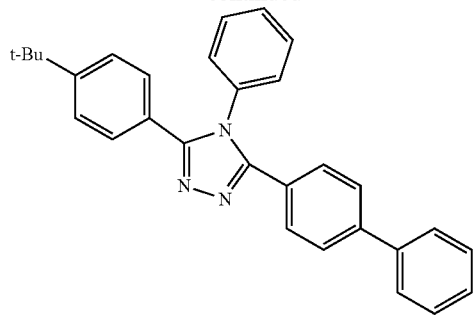

TAZ

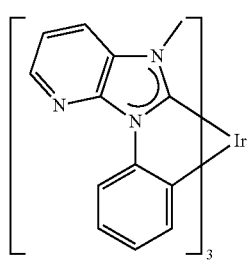

Ir(pmp)₃

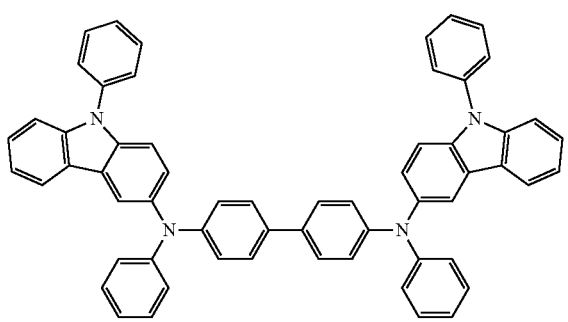

HT26

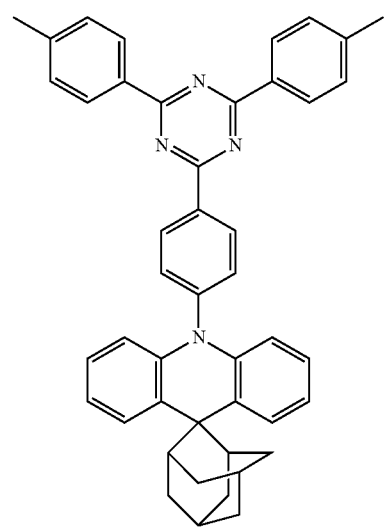

C1

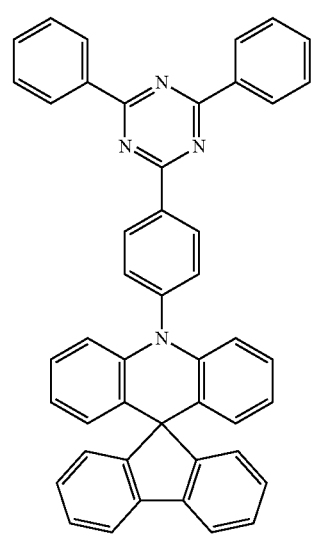

C2

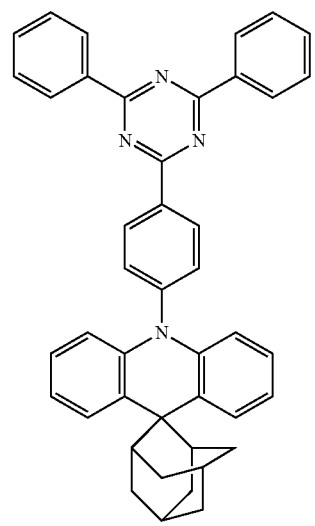

C3

Examples 2 to 9

Light-emitting devices were manufactured in substantially the same manner as in Example 1, except that the compounds shown in Table 2 instead of Compound 2 were respectively utilized in the formation of the emission layers.

Comparative Examples 1 to 3

Light-emitting devices were manufactured in substantially the same manner as in Example 1, except that Compounds $C_1$ to $C_3$ were respectively utilized in the formation of the emission layers.

To evaluate characteristics of each of the light-emitting devices manufactured in Examples 1 to 9 and Comparative Examples 1 to 3, the driving voltage, current efficiency, and maximum quantum efficiency of the light-emitting devices at a current density of 10 milliamperes per square centimeter (mA/cm$^2$) were measured. The driving voltage and the current density of each of the light-emitting devices were measured utilizing a source meter (Keithley Instrument, 2400 series). The maximum quantum efficiency of each of the light-emitting devices was measured utilizing Hamamatsu Absolute PL Quantum Yield Measurement System C9920-2-12. In evaluation of the maximum quantum efficiency, luminance/current density was measured utilizing a luminance meter that was calibrated for wavelength sensitivity, and the maximum external quantum efficiency was calculated under the assumption of an angular luminance distribution (Lambertian) assuming a complete diffusion reflecting surface. The evaluation results of the light-emitting devices are shown in Table 2.

TABLE 2

| Classification | Emission layer | Driving voltage (V) | Current density (mA/cm$^2$) | Maximum quantum efficiency (%) | Emission color |
|---|---|---|---|---|---|
| Example 1 | Compound 2 | 4.4 | 2.3 | 20.7 | Blue |
| Example 2 | Compound 4 | 4.5 | 2.3 | 20.3 | Blue |
| Example 3 | Compound 5 | 4.1 | 2.3 | 22.5 | Blue |
| Example 4 | Compound 20 | 3.9 | 2.3 | 21.2 | Blue |
| Example 5 | Compound 22 | 4.3 | 2.3 | 21.9 | Blue |
| Example 6 | Compound 29 | 3.7 | 2.3 | 20.5 | Blue |
| Example 7 | Compound 52 | 4.1 | 2.3 | 21.4 | Blue |
| Example 8 | Compound 53 | 4.3 | 2.3 | 21.5 | Blue |
| Example 9 | Compound 56 | 3.8 | 2.3 | 20.5 | Blue |
| Comparative Example 1 | Compound C1 | 4.6 | 2.3 | 19.7 | Blue |
| Comparative Example 2 | Compound C2 | 4.7 | 2.3 | 18.5 | Blue |
| Comparative Example 3 | Compound C3 | 4.6 | 2.3 | 17.9 | Blue |

As shown in the results of Table 2, the light-emitting devices of Examples 1 to 9 were each found to have a lower driving voltage and a higher maximum quantum efficiency, as compared with the light-emitting devices of Comparative Examples 1 to 3.

As should be apparent from the foregoing description, a light-emitting device including the heterocyclic compound of the present disclosure may have a low driving voltage, a high efficiency, and/or a high maximum quantum efficiency.

The use of "may" when describing embodiments of the present invention refers to "one or more embodiments of the present invention."

As used herein, the term "substantially," "about," and similar terms are used as terms of approximation and not as terms of degree, and are intended to account for the inherent deviations in measured or calculated values that would be recognized by those of ordinary skill in the art. Moreover, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited this specification is intended to include all higher numerical limitations subsumed therein. Accordingly, Applicant reserves the right to amend this specification, including the claims, to expressly recite any sub-range subsumed within the ranges expressly recited herein. All such ranges are intended to be inherently described in this specification such that amending to expressly recite any such subranges would comply with the requirements of 35 U.S.C. § 112(a), and 35 U.S.C. § 132(a).

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims, and equivalents thereof.

What is claimed is:

1. A light-emitting device comprising:
   a first electrode;
   a second electrode facing the first electrode; and
   an interlayer between the first electrode and the second electrode and comprising an emission layer, and
   the light-emitting device comprises at least one heterocyclic compound represented by Formula 1:

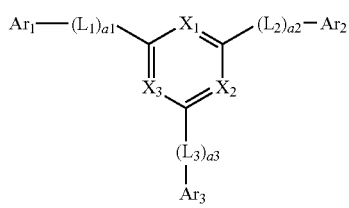

Formula 1

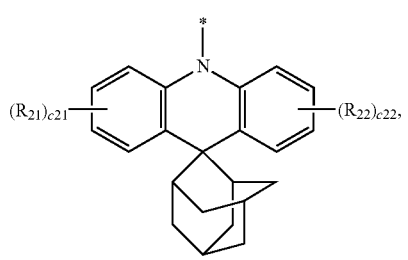

Formula 2 wherein, in Formulae 1 and 2,
$X_1$ is N or C-$(L_4)_{a4}$-$(R_1)_{c1}$, $X_2$ is N or C-$(L_5)_{a5}$-$(R_2)_{c2}$, and $X_3$ is N or C-$(L_6)_{a6}$-$(R_3)_{c3}$, provided that at least one of $X_1$ to $X_3$ is N,
$L_1$ to $L_6$ are each independently a single bond, a $C_5$-$C_{60}$ carbocyclic group unsubstituted or substituted with at least one $R_{10a}$, or a $C_1$-$C_{60}$ heterocyclic group unsubstituted or substituted with at least one $R_{10a}$,
a1 to a6 are each independently an integer from 1 to 5,
$Ar_1$ to $Ar_3$ are each independently a group represented by Formula 2, deuterium, —F, —Cl, —Br, —I, a hydroxyl group, a cyano group, a nitro group, an amino group, an amidino group, a hydrazino group, a hydrazono group, a carboxylic acid group or a salt thereof, a sulfonic acid group or a salt thereof, a phosphoric acid group or a salt thereof, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{10}$ cycloalkyl group unsubstituted or substituted with at least one $R_{10a}$, a $C_1$-$C_{10}$ heterocycloalkyl group unsubstituted or substituted with at least one $R_{10a}$, a $C_3$-$C_{10}$ cycloalkenyl group unsubstituted or substituted with at least one $R_{10a}$, a $C_1$-$C_{10}$ heterocycloalkenyl group unsubstituted or substituted with at least one $R_{10a}$, a $C_6$-$C_{60}$ aryl group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, a $C_1$-$C_{60}$ heteroaryl group unsubstituted or substituted with at least one $R_{10a}$, a monovalent non-aromatic condensed polycyclic group unsubstituted or substituted with at least one $R_{10a}$, a monovalent non-aromatic condensed heteropolycyclic group unsubstituted or substituted with at least one $R_{10a}$, —Si$(Q_1)(Q_2)(Q_3)$, —N$(Q_1)(Q_2)$, —B$(Q_1)(Q_2)$, —S$(=O)_2(Q_1)$, or —P$(=O)(C_{21})(Q_2)$, provided that at least one of $Ar_1$ to $Ar_3$ is the group represented by Formula 2, $R_1$ to $R_3$, $R_{21}$, and $R_{22}$ are each independently hydrogen, deuterium, —F, —Cl, —Br, —I, a hydroxyl group, a cyano group, a nitro group, an amino group, an amidino group, a hydrazino group, a hydrazono group, a carboxylic acid group or a salt thereof, a sulfonic acid group or a salt thereof, a phosphoric acid group or a salt thereof, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{10}$ cycloalkyl group unsubstituted or substituted with at least one $R_{10a}$, a $C_1$-$C_{10}$ heterocycloalkyl group unsubstituted or substituted with at least one $R_{10a}$, a $C_3$-$C_{10}$ cycloalkenyl group unsubstituted or substituted with at least one $R_{10a}$, a $C_1$-$C_{10}$ heterocycloalkenyl group unsubstituted or substituted with at least one $R_{10a}$, a $C_6$-$C_{60}$ aryl group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, a $C_1$-$C_{60}$ heteroaryl group unsubstituted or substituted with at least one $R_{10a}$, a monovalent non-aromatic condensed polycyclic group unsubstituted or substituted with at least one $R_{10a}$, a monovalent non-aromatic condensed heteropolycyclic group unsubstituted or substituted with at least one $R_{10a}$, —Si$(Q_1)(Q_2)(Q_3)$, —N$(Q_1)(Q_2)$, —B$(Q_1)(Q_2)$, —S$(=O)_2(Q_1)$, or —P$(=O)(Q_1)(Q_2)$, c1 to c3 are each independently an integer from 1 to 5, c21 and c22 are each independently an integer from 1 to 4, provided that:

when $Ar_1$ is the group represented by Formula 2, and *-$(L_2)_{a2}$-$Ar_2$ and *-$(L_3)_{a3}$-$Ar_3$ are each a substituted or unsubstituted phenyl group, $L_1$ is a single bond, when $Ar_2$ is the group represented by Formula 2, and *-$(L_1)_{a1}$-$Ar_1$ and *-$(L_3)_{a3}$-$Ar_3$ are each a substituted or unsubstituted phenyl group, $L_2$ is a single bond, and when $Ar_3$ is the group represented by Formula 2, and *-$(L_1)_{a1}$-$Ar_1$ and *-$(L_2)_{a2}$-$Ar_2$ are each a substituted or unsubstituted phenyl group, $L_3$ is a single bond, and $R_{10a}$ is:

deuterium (-D), —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si$(Q_{11})(Q_{12})(Q_{13})$, —N$(Q_{11})(Q_{12})$, —B$(Q_{11})(Q_{12})$, —C$(=O)(Q_{11})$, —S$(=O)_2(Q_{11})$, —P$(=O)(Q_{11})(Q_{12})$, or any combination thereof;

a $C_3$-$C_{60}$ carbocyclic group, a $C_1$-$C_{60}$ heterocyclic group, a $C_6$-$C_{60}$ aryloxy group, or a $C_6$-$C_{60}$ arylthio group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si$(Q_{21})(Q_{22})(Q_{23})$, —N$(Q_{21})(Q_{22})$, —B$(Q_{21})(Q_{22})$, —C$(=O)(Q_{21})$, —S$(=O)_2(Q_{21})$, —P$(=O)(Q_{21})(Q_{22})$, or any combination thereof; or —Si$(Q_{31})(Q_{32})(Q_{33})$, —N$(Q_{31})(Q_{32})$, —B$(Q_{31})(Q_{32})$, —C$(=O)(Q_{31})$, —S$(=O)_2(Q_{31})$, or —P$(=O)(Q_{31})(Q_{32})$, and wherein $Q_1$ to $Q_3$, $Q_{11}$ to $Q_{13}$, $Q_{21}$ to $Q_{23}$, and $Q_{31}$ to $Q_{33}$ are each independently hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; or a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof, and

* indicates a binding site to an adjacent atom.

2. The light-emitting device of claim 1, wherein the emission layer comprises the at least one heterocyclic compound.

3. The light-emitting device of claim 2, wherein the emission layer comprises a host and a dopant, and the host in the emission layer is greater in content than the dopant in the emission layer, and wherein the host comprises the at least one heterocyclic compound, and the dopant is a phosphorescent dopant or a thermally activated delayed fluorescent (TADF) dopant.

4. The light-emitting device of claim 2, wherein the emission layer is to emit blue light having a maximum emission wavelength in a range of about 390 nanometers (nm) to 440 nm.

5. The light-emitting device of claim 1, wherein the first electrode is an anode, the second electrode is a cathode, and the interlayer further comprises a hole transport region between the first electrode and the emission layer and an electron transport region between the emission layer and the second electrode, the hole transport region comprises a hole injection layer, a hole transport layer, an emission auxiliary layer, an electron blocking layer, or any combination thereof, and the electron transport region comprises a buffer layer, a hole blocking layer, an electron control layer, an electron transport layer, an electron injection layer, or any combination thereof.

6. The light-emitting device of claim 5, wherein the hole transport region comprises a compound represented by Formula 201, a compound represented by Formula 202, or any combination thereof:

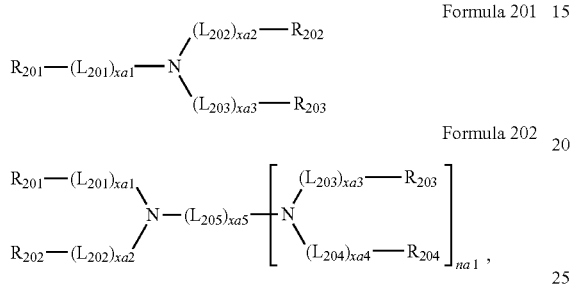

Formula 201

Formula 202 and
wherein, in Formulae 201 and 202, $L_{201}$ to $L_{204}$ are each independently a $C_3$-$C_{60}$ carbocyclic group unsubstituted or substituted with at least one $R_{10a}$ or a $C_1$-$C_{60}$ heterocyclic group unsubstituted or substituted with at least one R10a, $L_{205}$ is *—O—*I, *—S—*I, *—N($Q_{201}$)-*I, a $C_1$-$C_{20}$ alkylene group unsubstituted or substituted with at least one $R_{10a}$, a $C_2$-$C_{20}$ alkenylene group unsubstituted or substituted with at least one $R_{10a}$, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, xa1 to xa4 are each independently an integer from 0 to 5,
xa5 is an integer from 1 to 10, $R_{201}$ to $R_{204}$ and $Q_{201}$ are each independently a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $R_{201}$ and $R_{202}$ are optionally bound to each other via a single bond, a $C_1$-$C_5$ alkylene group unsubstituted or substituted with at least one $R_{10a}$, or a $C_2$-$C_5$ alkenylene group unsubstituted or substituted with at least one $R_{10a}$ to form a $C_8$-$C_{60}$ polycyclic group unsubstituted or substituted with at least one $R_{10a}$, $R_{203}$ and $R_{204}$ are optionally bound to each other via a single bond, a $C_1$-$C_5$ alkylene group unsubstituted or substituted with at least one $R_{10a}$, or a $C_2$-$C_5$ alkenylene group unsubstituted or substituted with at least one $R_{10a}$ to form a $C_8$-$C_{60}$ polycyclic group unsubstituted or substituted with at least one $R_{10a}$, na1 is an integer from 1 to 4, and $R_{10a}$ is:
deuterium (-D), —F, —Cl, —Br, —I, a hydroxyl group, a cyano group, or a nitro group;
a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), —P(=O)($Q_{11}$)($Q_{12}$), or any combination thereof;

a $C_3$-$C_{60}$ carbocyclic group, a $C_1$-$C_{60}$ heterocyclic group, a $C_6$-$C_{60}$ aryloxy group, or a $C_6$-$C_{60}$ arylthio group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), —P(=O)($Q_{21}$)($Q_{22}$), or any combination thereof; or —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$), and wherein $Q_1$ to $Q_3$, $Q_{11}$ to $Q_{13}$, $Q_{21}$ to $Q_{23}$, and $Q_{31}$ to $Q_{33}$ are each independently hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; or a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof.

7. The light-emitting device of claim 1, wherein
the light-emitting device further comprises at least one of a first capping layer located outside the first electrode or a second capping layer located outside the second electrode, and
the at least one of the first capping layer or the second capping layer has a refractive index of 1.6 or higher at a wavelength of 589 nanometers (nm).

8. A heterocyclic compound represented by Formula 1:

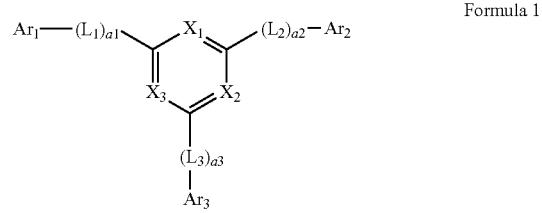

Formula 1

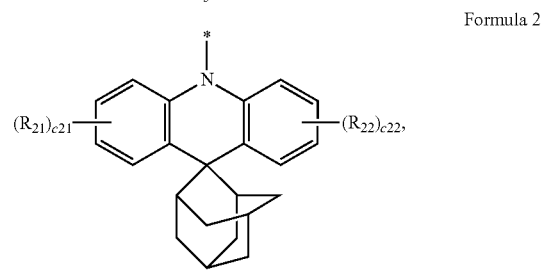

Formula 2 wherein, in Formulae 1 and 2, $X_1$ is N or C-($L_4$)$_{a4}$-($R_1$)$_{c1}$, $X_2$ is N or C-($L_5$)$_{a5}$-($R_2$)$_{c2}$, and $X_3$ is N or C-($L_6$)$_{a6}$-($R_3$)$_{c3}$, provided that at least one of $X_1$ to $X_3$ is N, $L_1$ to $L_6$ are each independently a single bond, a $C_6$-$C_{60}$ carbocyclic group unsubstituted or substituted with at least one $R_{10a}$, or a $C_1$-$C_{60}$ heterocyclic group unsubstituted or substituted with at least one $R_{10a}$, a1 to a6 are each independently an integer from 1 to 5, Ar$_1$ to Ar$_3$ are each independently a group represented by Formula 2, deuterium, —F, —Cl, —Br, —I, a hydroxyl group, a cyano group, a nitro group, an amino group, an amidino group, a hydrazino group, a hydrazono group, a carboxylic acid group or a salt thereof, a sulfonic acid group or a salt thereof, a phosphoric acid group or a salt thereof, a C$_1$-C$_{60}$ alkyl group unsubstituted or substituted with at least one R$_{10a}$, a C$_2$-C$_{60}$ alkenyl group unsubstituted or substituted with at least one R$_{10a}$, a C$_2$-C$_{60}$ alkynyl group unsubstituted or substituted with at least one R$_{10a}$, a C$_1$-C$_{60}$ alkoxy group unsubstituted or substituted with at least one R$_{10a}$, a C$_3$-C$_{10}$ cycloalkyl group unsubstituted or substituted with at least one R$_{10a}$, a C$_1$-C$_{10}$ heterocycloalkyl group unsubstituted or substituted with at least one R$_{10a}$, a C$_3$-C$_{10}$ cycloalkenyl group unsubstituted or substituted with at least one R$_{10a}$, a C$_1$-C$_{10}$ heterocycloalkenyl group unsubstituted or substituted with at least one R$_{10a}$, a C$_6$-C$_{60}$ aryl group unsubstituted or substituted with at least one R$_{10a}$, a C$_6$-C$_{60}$ aryloxy group unsubstituted or substituted with at least one R$_{10a}$, a C$_6$-C$_{60}$ arylthio group unsubstituted or substituted with at least one R$_{10a}$, a C$_1$-C$_{60}$ heteroaryl group unsubstituted or substituted with at least one R$_{10a}$, a monovalent non-aromatic condensed polycyclic group unsubstituted or substituted with at least one R$_{10a}$, a monovalent non-aromatic condensed heteropolycyclic group unsubstituted or substituted with at least one R$_{10a}$, —Si(Q$_1$)(Q$_2$)(Q$_3$), —N(Q$_1$)(Q$_2$), —B(Q$_1$)(Q$_2$), —S(=O)$_2$(Q$_1$), or —P(=O)(Q$_1$)(Q$_2$), provided that at least one of Ar$_1$ to Ar$_3$ is the group represented by Formula 2, R$_1$ to R$_3$, R$_{21}$, and R$_{22}$ are each independently hydrogen, deuterium, —F, —Cl, —Br, —I, a hydroxyl group, a cyano group, a nitro group, an amino group, an amidino group, a hydrazino group, a hydrazono group, a carboxylic acid group or a salt thereof, a sulfonic acid group or a salt thereof, a phosphoric acid group or a salt thereof, a C$_1$-C$_{60}$ alkyl group unsubstituted or substituted with at least one R$_{10a}$, a C$_2$-C$_{60}$ alkenyl group unsubstituted or substituted with at least one R$_{10a}$, a C$_2$-C$_{60}$ alkynyl group unsubstituted or substituted with at least one R$_{10a}$, a C$_1$-C$_{60}$ alkoxy group unsubstituted or substituted with at least one R$_{10a}$, a C$_3$-C$_{10}$ cycloalkyl group unsubstituted or substituted with at least one R$_{10a}$, a C$_1$-C$_{10}$ heterocycloalkyl group unsubstituted or substituted with at least one R$_{10a}$, a C$_3$-C$_{10}$ cycloalkenyl group unsubstituted or substituted with at least one R$_{10a}$, a C$_1$-C$_{10}$ heterocycloalkenyl group unsubstituted or substituted with at least one R$_{10a}$, a C$_6$-C$_{60}$ aryl group unsubstituted or substituted with at least one R$_{10a}$, a C$_6$-C$_{60}$ aryloxy group unsubstituted or substituted with at least one R$_{10a}$, a C$_6$-C$_{60}$ arylthio group unsubstituted or substituted with at least one R$_{10a}$, a C$_1$-C$_{60}$ heteroaryl group unsubstituted or substituted with at least one R$_{10a}$, a monovalent non-aromatic condensed polycyclic group unsubstituted or substituted with at least one R$_{10a}$, a monovalent non-aromatic condensed heteropolycyclic group unsubstituted or substituted with at least one R$_{10a}$, —Si(Q$_1$)(Q$_2$)(Q$_3$), —N(Q$_1$)(Q$_2$), —B(Q$_1$)(Q$_2$), —S(=O)$_2$(Q$_1$), or —P(=O)(Q$_1$)(Q$_2$), c1 to c3 are each independently an integer from 1 to 5,
c21 and c22 are each independently an integer from 1 to 4, provided that
when Ar$_1$ is the group represented by Formula 2, and *-(L$_2$)$_{a2}$-Ar$_2$ and *-(L$_3$)$_{a3}$-Ar$_3$ are each a substituted or unsubstituted phenyl group, L$_1$ is a single bond,
when Ar$_2$ is the group represented by Formula 2, and *-(L$_1$)$_{a1}$-Ar$_1$ and *-(L$_3$)$_{a3}$-Ar$_3$ are each a substituted or unsubstituted phenyl group, L$_2$ is a single bond, and
when Ar$_3$ is the group represented by Formula 2, and *-(L$_1$)$_{a1}$-Ar$_1$ and *-(L$_2$)$_{a2}$-Ar$_2$ are each a substituted or unsubstituted phenyl group, L$_3$ is a single bond, and R$_{10a}$ is:
deuterium (-D), —F, —Cl, —Br, —I, a hydroxyl group, a cyano group, or a nitro group;

a C$_1$-C$_{60}$ alkyl group, a C$_2$-C$_{60}$ alkenyl group, a C$_2$-C$_{60}$ alkynyl group, or a C$_1$-C$_{60}$ alkoxy group, each unsubstituted or substituted with deuterium, —F, —Cl, —Br, —I, a hydroxyl group, a cyano group, a nitro group, a C$_3$-C$_{60}$ carbocyclic group, a C$_1$-C$_{60}$ heterocyclic group, a C$_6$-C$_{60}$ aryloxy group, a C$_6$-C$_{60}$ arylthio group, —Si(Q$_{11}$)(Q$_{12}$)(Q$_{13}$), —N(Q$_{11}$)(Q$_{12}$), —B(Q$_{11}$)(Q$_{12}$), —C(=O)(Q$_{11}$), —S(=O)$_2$(Q$_{11}$), —P(=O)(Q$_{11}$)(Q$_{12}$), or any combination thereof;

a C$_3$-C$_{60}$ carbocyclic group, a C$_1$-C$_{60}$ heterocyclic group, a C$_6$-C$_{60}$ aryloxy group, or a C$_6$-C$_{60}$ arylthio group, each unsubstituted or substituted with deuterium, —F, —Cl, —Br, —I, a hydroxyl group, a cyano group, a nitro group, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{60}$ carbocyclic group, a C$_1$-C$_{60}$ heterocyclic group, a C$_{6-60}$ aryloxy group, a C$_6$-C$_{60}$ arylthio group, —Si(Q$_{21}$)(Q$_{22}$)(Q$_{23}$), —N(Q$_{21}$)(Q$_{22}$), —B(Q$_{21}$)(Q$_{22}$), —C(=O)(Q$_{21}$), —S(=O)$_2$(Q$_{21}$), —P(=O)(Q$_{21}$)(Q$_{22}$), or any combination thereof; or —Si(Q$_{31}$)(Q$_{32}$)(Q$_{33}$), —N(Q$_{31}$)(Q$_{32}$), —B(Q$_{31}$)(Q$_{32}$), —C(=O)(Q$_{31}$), —S(=O)$_2$(Q$_{31}$), or —P(=O)(Q$_{31}$)(Q$_{32}$), and wherein Q$_1$ to Q$_3$, Q$_{11}$ to Q$_{13}$, Q$_{21}$ to Q$_{23}$, and Q$_{31}$ to Q$_{33}$ are each independently hydrogen; deuterium; —F; —Cl; —Br; —I; a hydroxyl group; a cyano group; a nitro group; a C$_1$-C$_{60}$ alkyl group; a C$_2$-C$_{60}$ alkenyl group; a C$_2$-C$_{60}$ alkynyl group; a C$_1$-C$_{60}$ alkoxy group; or a C$_3$-C$_{60}$ carbocyclic group or a C$_1$-C$_{60}$ heterocyclic group, each unsubstituted or substituted with deuterium, —F, a cyano group, a C$_1$-C$_{60}$ alkyl group, a C$_1$-C$_{60}$ alkoxy group, a phenyl group, a biphenyl group, or any combination thereof, and

* indicates a binding site to an adjacent atom.

9. The heterocyclic compound of claim 8, wherein
X$_1$ to X$_3$ are each N,
X$_1$ and X$_2$ are each N, and X$_3$ is C-(L$_6$)$_{a6}$-(R$_3$)$_{c3}$,
X$_1$ and X$_3$ are each N, and X$_2$ is C-(L$_5$)$_{a5}$-(R$_2$)$_{c2}$, or
X$_2$ and X$_3$ are each N, and X$_1$ is C-(L$_4$)$_{a4}$-(R$_1$)$_{c1}$.

10. The heterocyclic compound of claim 8, wherein L$_1$ to L$_6$ are each independently:
a single bond; or
a benzene group, a pentalene group, an indene group, a naphthalene group, an azulene group, a heptalene group, an indacene group, an acenaphthalene group, a fluorene group, a spiro-bifluorene group, a spiro-benzofluorene-fluorene group, a benzofluorene group, a dibenzofluorene group, a phenalene group, a phenanthrene group, an anthracene group, a fluoranthene group, a pyrene group, a chrysene group, a naphthacene group, a picene group, a perylene group, a pyrrole group, a thiophene group, a furan group, a silole group, an imidazole group, a pyrazole group, a thiazole group, an isothiazole group, an oxazole group, an isoxazole group, a pyridine group, a pyrazine group, a pyrimidine group, a pyridazine group, a triazine group, a benzofuran group, a benzothiophene group, a dibenzofuran group, a dibenzothiophene group, a carbazole group, a benzosilole group, a dibenzosilole group, a quinoline group, an isoquinoline group, a benzimidazole group, an imidazopyridine group, or an imidazopyrimidine group, each unsubstituted or substituted with deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a spiro-benzofluorene-fluorenyl group, a benzofluorenyl group, a dibenzofluorenyl group, a phenalenyl group, a phenanthrenyl group, an anthracenyl group, a fluoranthenyl group, a pyrenyl group, a chrysenyl group, a naphthacenyl group, a picenyl group, a perylenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a triazinyl group, a benzofuranyl group, a benzothiophenyl group, a dibenzofuranyl group, a dibenzothiophenyl group, a carbazolyl group, a benzosilolyl group, a dibenzosilolyl group, a quinolinyl group, an isoquinolinyl group, a benzimidazolyl group, an imidazopyridinyl group, an imidazopyrimidinyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), —P(=O)($Q_{31}$)($Q_{32}$), or any combination thereof, and wherein $Q_{31}$ to $Q_{33}$ are each independently a $C_1$-$C_{10}$ alkyl group, a $C_1$-$C_{10}$ alkoxy group, a phenyl group, a biphenyl group, a terphenyl group, a naphthyl group, or a phenyl group substituted with a cyano group.

11. The heterocyclic compound of claim 8, wherein $L_1$ to $L_6$ are each independently a single bond or a group represented by one of Formulae 3-1 to 3-24:

3-1

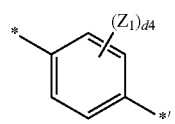

3-2

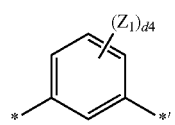

3-3

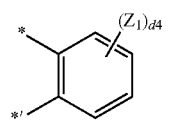

3-4

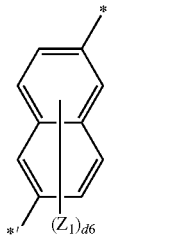

3-5

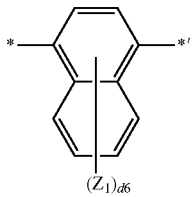

3-6

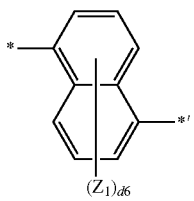

3-7

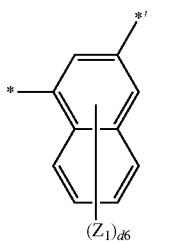

3-8

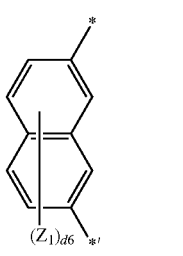

3-9

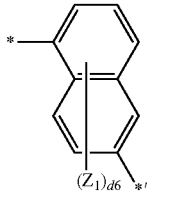

3-10

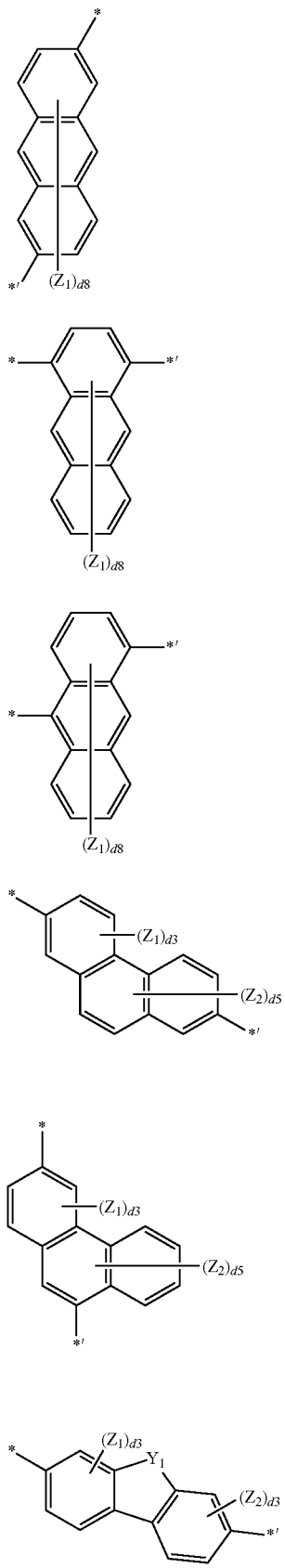
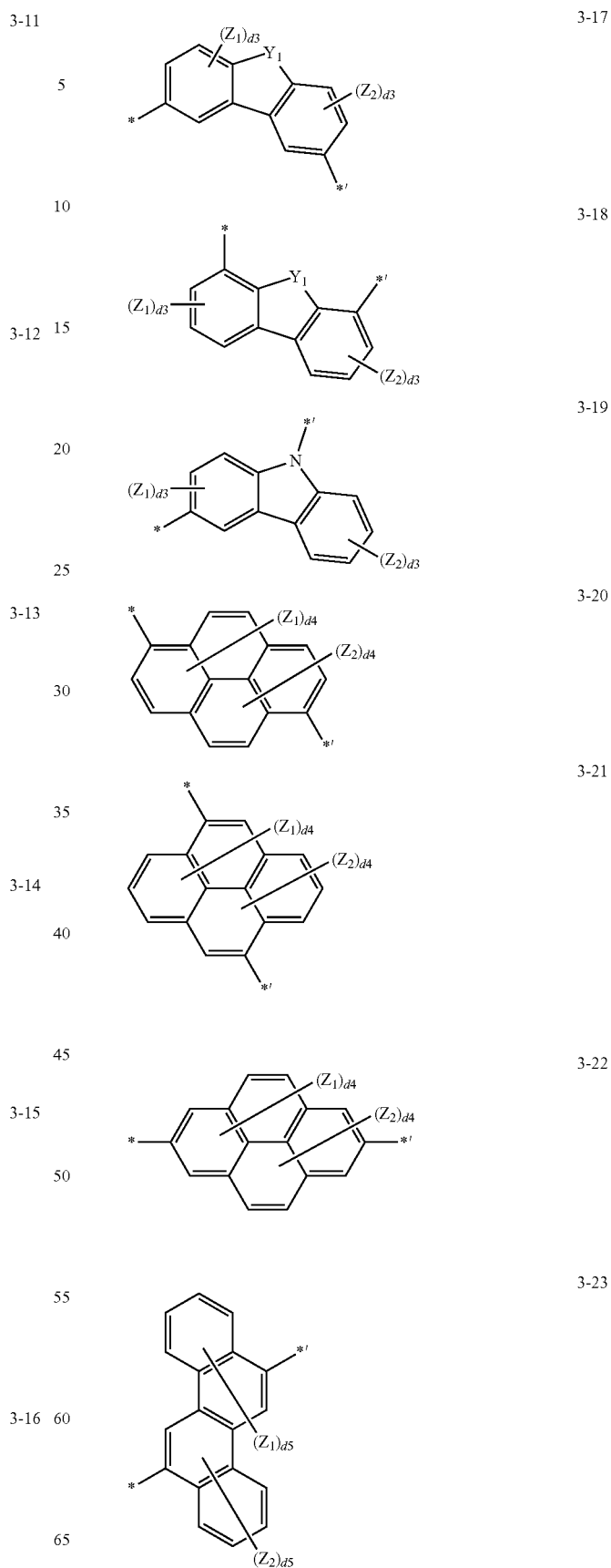

-continued 2-34

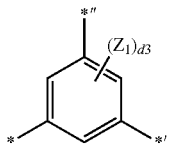

wherein, in Formulae 3-1 to 3-24,
$Y_1$ is O, S, $C(Z_3)(Z_4)$, $N(Z_5)$, or $Si(Z_6)(Z_7)$,
$Z_1$ to $Z_7$ are each independently hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a spiro-benzofluorene-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a triazinyl group, a benzofuranyl group, a benzothiophenyl group, a dibenzofuranyl group, a dibenzothiophenyl group, a carbazolyl group, a benzosilolyl group, a dibenzosilolyl group, a quinolinyl group, an isoquinolinyl group, a benzimidazolyl group, —Si$(Q_{31})(Q_{32})(Q_{33})$, —N$(Q_{31})(Q_{32})$, or —B$(Q_{31})(Q_{32})$, and
wherein $Q_{31}$ to $Q_{33}$ are each independently a $C_1$-$C_{10}$ alkyl group, a $C_1$-$C_{10}$ alkoxy group, a phenyl group, a biphenyl group, a terphenyl group, a naphthyl group, or a phenyl group substituted with a cyano group,
d3 is an integer from 0 to 3,
d4 is an integer from 0 to 4,
d5 is an integer from 0 to 5,
d6 is an integer from 0 to 6,
d8 is an integer from 0 to 8, and
* and *' each indicate a binding site to an adjacent atom.

12. The heterocyclic compound of claim 8, wherein
when $Ar_1$ is the group represented by Formula 2, $L_1$ is a single bond,
when $Ar_2$ is the group represented by Formula 2, $L_2$ is a single bond, and
when $Ar_3$ is the group represented by Formula 3, $L_3$ is a single bond.

13. The heterocyclic compound of claim 8, wherein one or two of $Ar_1$ to $Ar_3$ are each the group represented by Formula 2.

14. The heterocyclic compound of claim 8, wherein $Ar_1$ to $Ar_3$ are each independently:
the group represented by Formula 2, a $C_1$-$C_{20}$ alkyl group, a $C_1$-$C_{20}$ alkyl group substituted with at least one phenyl group, or a $C_1$-$C_{20}$ alkoxy group;
a cyclopentyl group, a cyclohexyl group, a cycloheptyl group, a cyclopentenyl group, a cyclohexenyl group, a phenyl group, a biphenyl group, a terphenyl group, a naphthyl group, a fluorenyl group, a spiro-bifluorenyl group, a spiro-fluorene-benzofluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a triazinyl group, an indolyl group, an isoindolyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a dibenzofuranyl group, a dibenzothiophenyl group, a dibenzosilolyl group, a carbazolyl group, a benzocarbazolyl group, a dibenzocarbazolyl group, an azafluorenyl group, an azaspirobifluorenyl group, an azacarbazolyl group, a diazacarbazolyl group, an azadibenzofuranyl group, an azadibenzothiophenyl group, an azadibenzosilolyl group, an imidazopyridinyl group, or an imidazopyrimidinyl group, each unsubstituted or substituted with deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkyl group substituted with at least one phenyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a naphthyl group, a fluorenyl group, a spiro-bifluorenyl group, a spiro-fluorene-benzofluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a triazinyl group, an indolyl group, an isoindolyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a dibenzofuranyl group, a dibenzothiophenyl group, a dibenzosilolyl group, a carbazolyl group, a benzocarbazolyl group, a dibenzocarbazolyl group, an azafluorenyl group, an azaspiro-bifluorenyl group, an azacarbazolyl group, a diazacarbazolyl group, an azadibenzofuranyl group, an azadibenzothiophenyl group, an azadibenzosilolyl group, an imidazopyridinyl group, an imidazopyrimidinyl group, —Si$(Q_{31})(Q_{32})(Q_{33})$, —N$(Q_{31})(Q_{32})$, —B$(Q_{31})(Q_{32})$, —C(=O)$(Q_{31})$, —S(=O)$_2(Q_{31})$, —P(=O)$(Q_{31})(Q_{32})$, or any combination thereof; or
—Si$(Q_1)(Q_2)(Q_3)$, —N$(Q_1)(Q_2)$, or —B$(Q_1)(Q_2)$, and
wherein $Q_1$ to $Q_3$ and $Q_{31}$ to $Q_{33}$ are each independently a $C_1$-$C_{10}$ alkyl group, a alkoxy group, a phenyl group, a biphenyl group, a terphenyl group, a naphthyl group, or a phenyl group substituted with a cyano group.

15. The heterocyclic compound of claim 8, wherein $Ar_1$ to $Ar_3$ are each independently the group represented by Formula 2, a $C_1$-$C_{20}$ alkyl group, a $C_1$-$C_{20}$ alkyl group substituted with at least one phenyl group, a $C_1$-$C_{20}$ alkoxy group, a group represented by one of Formulae 5-1 to 5-21, or —Si$(C_{21})(Q_2)(Q_3)$:

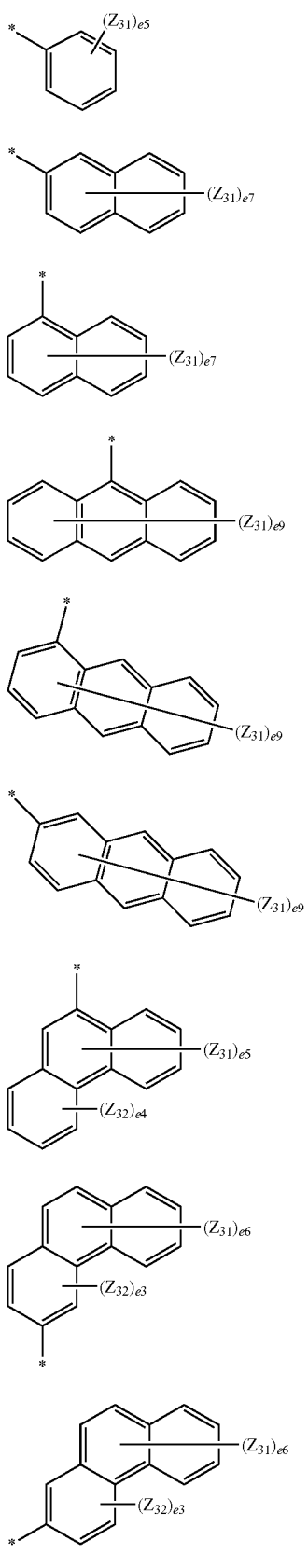
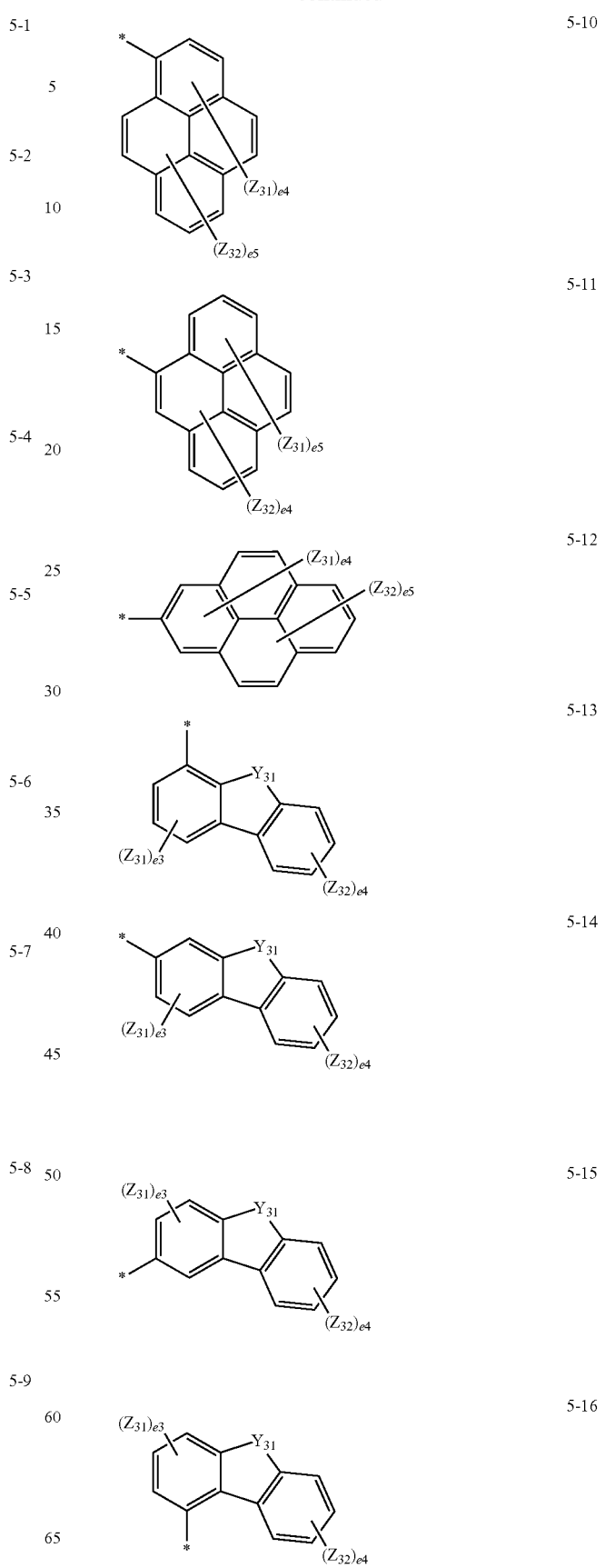

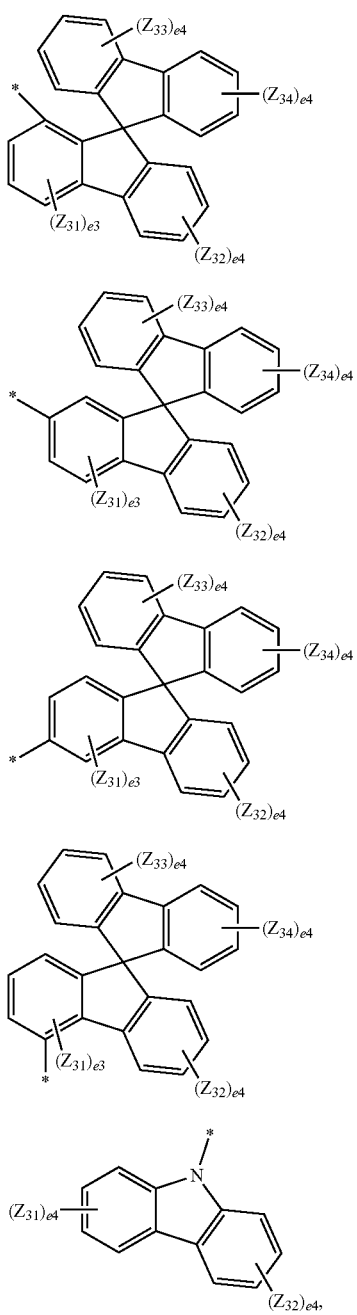

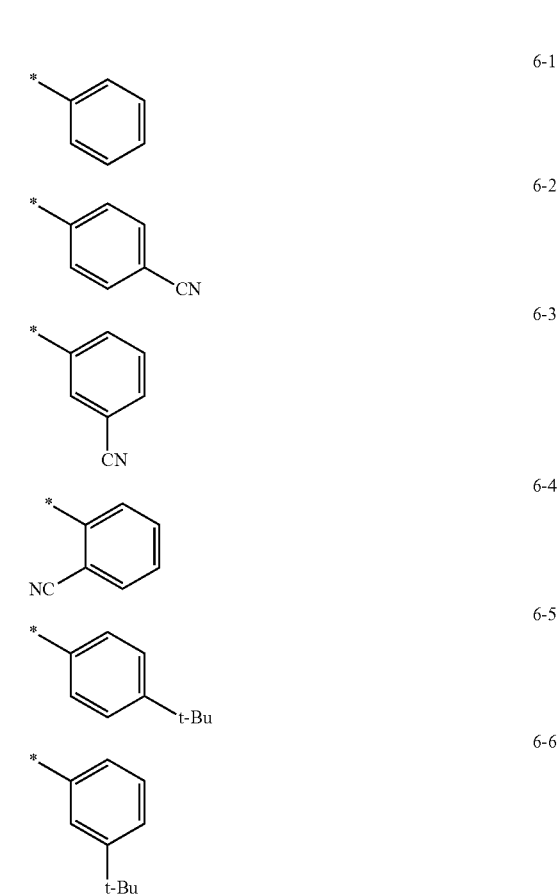

wherein, in Formulae 5-1 to 5-21, $Y_{31}$ is O, S, $N(Z_{35})$, $C(Z_{33})(Z_{34})$, or $Si(Z_{36})(Z_{37})$, $Z_{31}$ to $Z_{37}$ are each independently hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkyl group substituted with at least one phenyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a naphthyl group, a fluorenyl group, a spiro-bifluorenyl group, a spiro-fluorene-benzofluorenyl group, a benzofluorenyl group, a dibenzofluorenyl group, a phenalenyl group, a phenanthrenyl group, an anthracenyl group, a fluoranthenyl group, a triphenylenyl group, a pyridinyl group, a pyrimidinyl group, a pyrazinyl group, a triazinyl group, a quinolinyl group, an isoquinolinyl group, a benzoquinolinyl group, a naphthyridinyl group, a quinoxalinyl group, a quinazolinyl group, a carbazolyl group, a phenanthridinyl group, an acridinyl group, a phenanthrolinyl group, a phenazinyl group, a dibenzofuranyl group, a dibenzothiophenyl group, a dibenzosilolyl group, —Si($Q_{31}$)($Q_{32}$)($Q_{33}$), —N($Q_{31}$)($Q_{32}$), or —B($Q_{31}$)($Q_{32}$), e2 is 1 or 2, e3 is an integer from 1 to 3, e4 is an integer from 1 to 4, e5 is an integer from 1 to 5, e6 is an integer from 1 to 6, e7 is an integer from 1 to 7, and e9 is an integer from 1 to 9, and wherein $Q_1$ to $Q_3$ and $Q_{31}$ to $Q_{33}$ are each independently a $C_1$-$C_{10}$ alkyl group, a $C_1$-$C_{10}$ alkoxy group, a phenyl group, a biphenyl group, a terphenyl group, a naphthyl group, or a phenyl group substituted with a cyano group, and

* indicates a binding site to an adjacent atom.

16. The heterocyclic compound of claim 8, wherein $Ar_1$ to $Ar_3$ are each independently the group represented by Formula 2 or a group represented by one of Formulae 6-1 to 6-61:

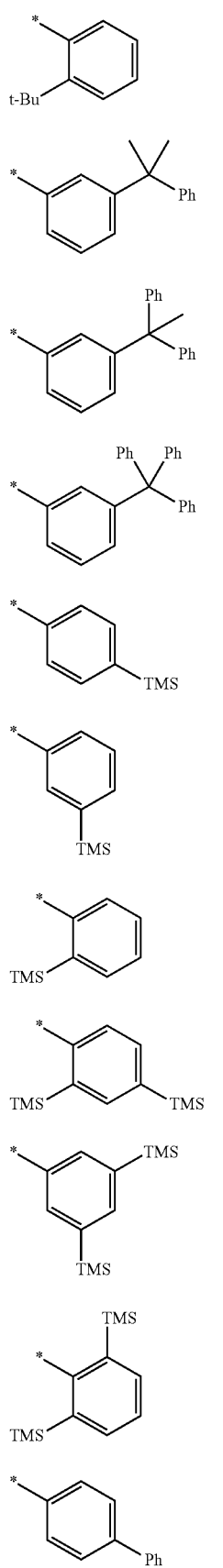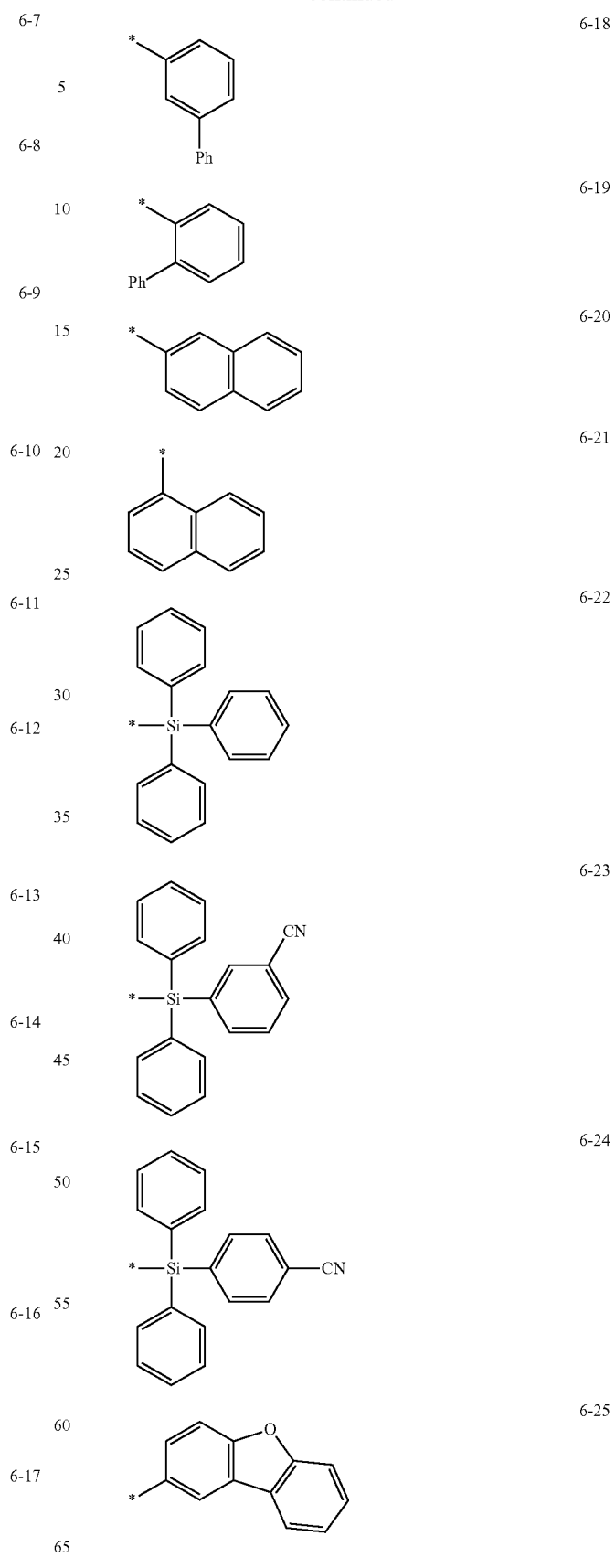

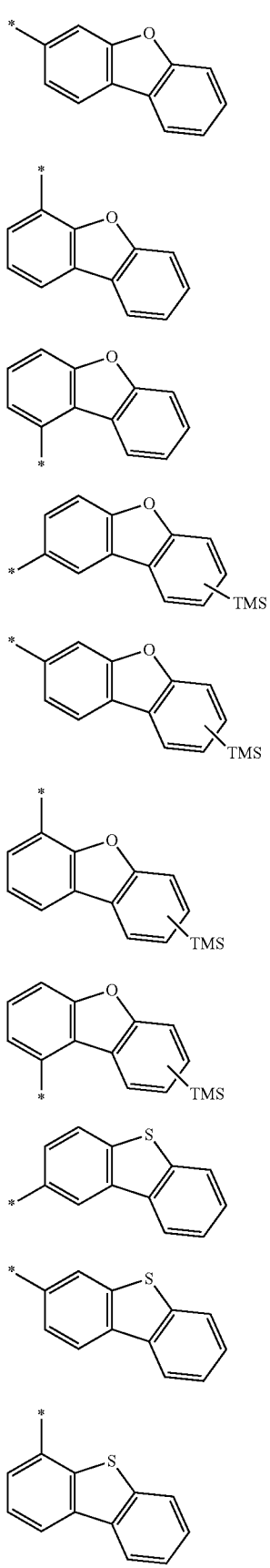
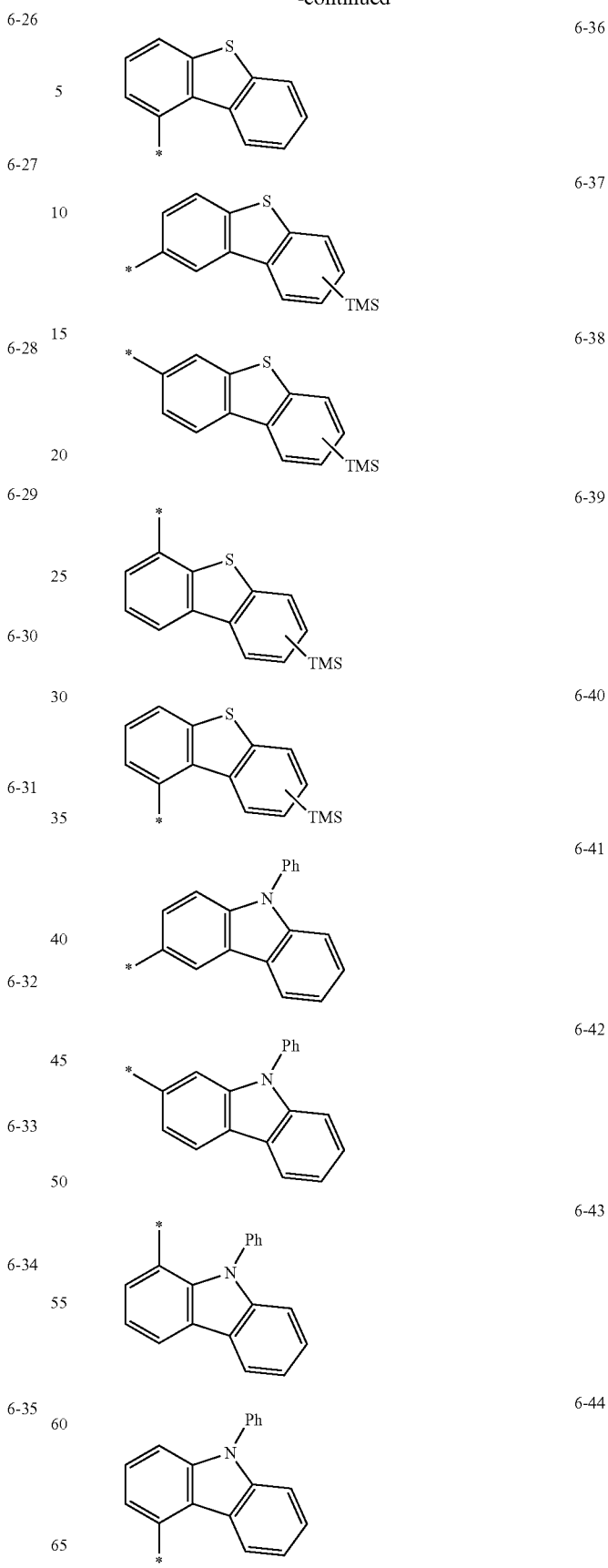

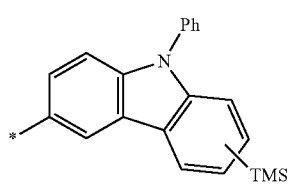
6-45
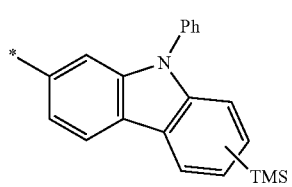
6-46
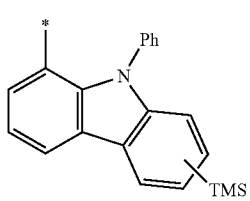
6-47
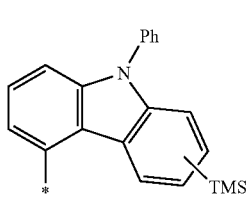
6-48
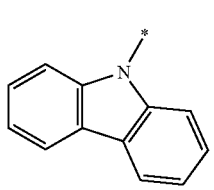
6-49
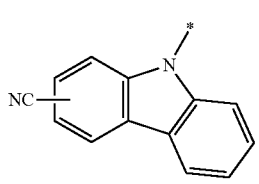
6-50
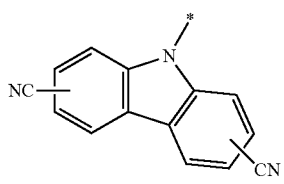
6-51
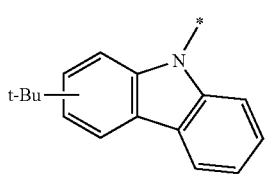
6-52
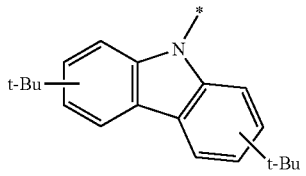
6-53
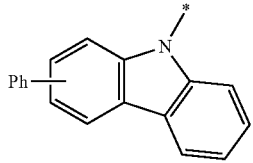
6-54
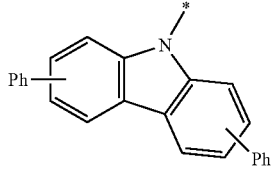
6-55
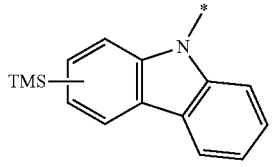
6-56
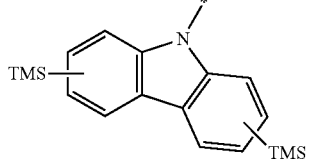
6-57
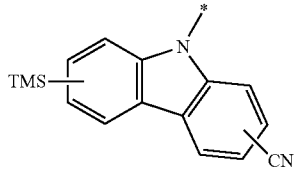
6-58
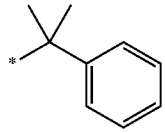
6-59
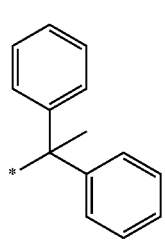
6-60

6-61

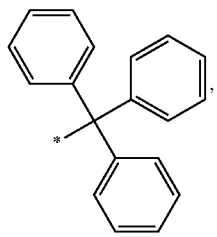

wherein, in Formulae 6-1 to 6-61,

"t-Bu" represents a tert-butyl group,

"Ph" represents a phenyl group,

"TMS" represents a trimethylsilyl group, and

* indicates a binding site to an adjacent atom.

17. The heterocyclic compound of claim 8, wherein at least one selected from $Ar_1$ to $Ar_3$ is the group represented by Formula 2, and at least one selected from a rest of $Ar_1$ to $Ar_3$ is:

a $C_1$-$C_{20}$ alkyl group, a $C_1$-$C_{20}$ alkyl group substituted with at least one phenyl group, or a $C_1$-$C_{20}$ alkoxy group; or a phenyl group, a dibenzofuranyl group, a dibenzothiophenyl group, or a carbazolyl group, each unsubstituted or substituted with a cyano group, a $C_1$-$C_{20}$ alkyl group, a $C_1$-$C_{20}$ alkyl group substituted with at least one phenyl group, a $C_1$-$C_{20}$ alkoxy group, a phenyl group, a dibenzofuranyl group, a dibenzothiophenyl group, a carbazolyl group, —$Si(Q_{31})(Q_{32})(Q_{33})$, or any combination thereof, and wherein $Q_{31}$ to $Q_{33}$ are each independently a $C_1$-$C_{10}$ alkyl group, a $C_1$-$C_{10}$ alkoxy group, a phenyl group, a biphenyl group, terphenyl group, a naphthyl group, or a phenyl group substituted with a cyano group.

18. The heterocyclic compound of claim 8, wherein $R_{21}$ and $R_{22}$ are each hydrogen.

19. A heterocyclic compound represented by one of Formulae 1-1 to 1-6:

1-1

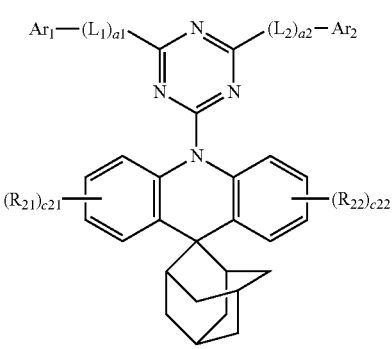

1-2

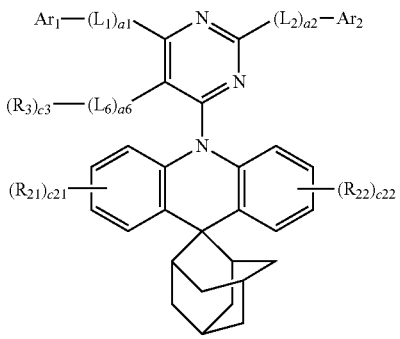

1-3

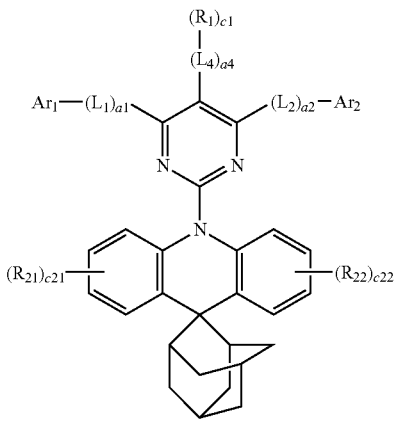

1-4

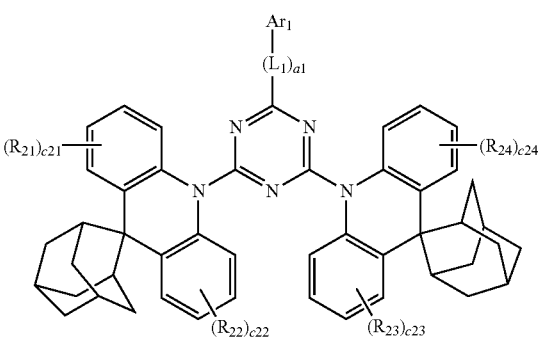

1-5

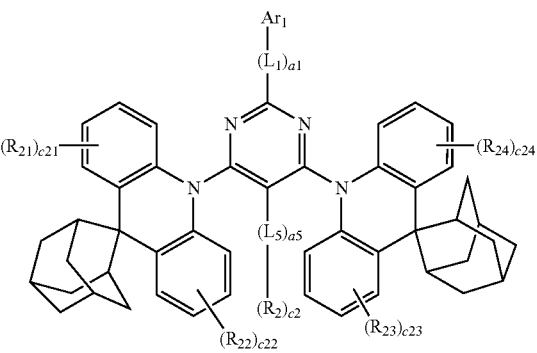

-continued 1-6

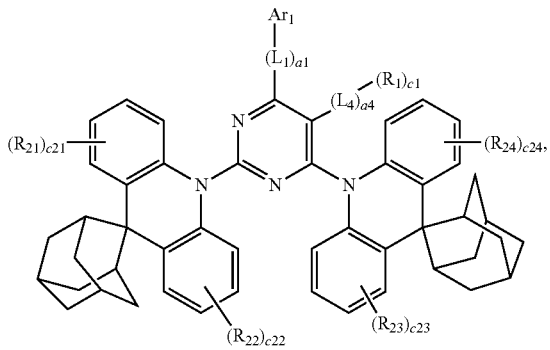

and

Formula 2

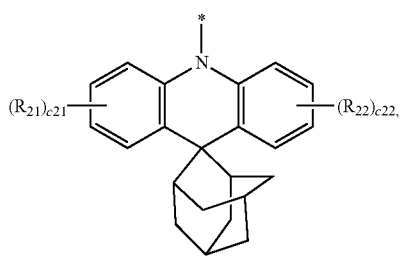

wherein, in Formulae 1-1 to 1-6 and Formula 2, $R_1$ to $R_3$, $R_{21}$, $R_{22}$, $R_{23}$ and $R_{24}$ are each independently hydrogen, deuterium, —F, —Cl, —Br, —I, a hydroxyl group, a cyano group, a nitro group, an amino group, an amidino group, a hydrazino group, a hydrazono group, a carboxylic acid group or a salt thereof, a sulfonic acid group or a salt thereof, a phosphoric acid group or a salt thereof, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{10}$ cycloalkyl group unsubstituted or substituted with at least one $R_{10a}$, a $C_1$-$C_{10}$ heterocycloalkyl group unsubstituted or substituted with at least one $R_{10a}$, a $C_3$-$C_{10}$ cycloalkenyl group unsubstituted or substituted with at least one $R_{10a}$, a $C_1$-$C_{10}$ heterocycloalkenyl group unsubstituted or substituted with at least one $R_{10a}$, a $C_6$-$C_{60}$ aryl group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, a $C_1$-$C_{60}$ heteroaryl group unsubstituted or substituted with at least one $R_{10a}$, a monovalent non-aromatic condensed polycyclic group unsubstituted or substituted with at least one $R_{10a}$, a monovalent non-aromatic condensed heteropolycyclic group unsubstituted or substituted with at least one $R_{10a}$, —Si($Q_1$)($Q_2$)($Q_3$), —N($Q_1$)($Q_2$), —B($Q_1$)($Q_2$), —S(=O)$_2$($Q_1$), or —P(=O)($Q_1$)($Q_2$), c23 and c24 are each independently an integer from 1 to 4, and $L_1$, $L_2$, and $L_4$ to $L_6$ are each independently a single bond, a $C_5$-$C_{60}$ carbocyclic group unsubstituted or substituted with at least one $R_{10a}$, or a $C_1$-$C_{60}$ heterocyclic group unsubstituted or substituted with at least one $R_{10a}$, a1, a2 and a4 to a6 are each independently an integer from 1 to 5, $Ar_1$ and $Ar_2$ are each independently a group represented by Formula 2, deuterium, —F, —Cl, —Br, —I, a hydroxyl group, a cyano group, a nitro group, an amino group, an amidino group, a hydrazino group, a hydrazono group, a carboxylic acid group or a salt thereof, a sulfonic acid group or a salt thereof, a phosphoric acid group or a salt thereof, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{10}$ cycloalkyl group unsubstituted or substituted with at least one $R_{10a}$, a $C_1$-$C_{10}$ heterocycloalkyl group unsubstituted or substituted with at least one $R_{10a}$, a $C_3$-$C_{10}$ cycloalkenyl group unsubstituted or substituted with at least one $R_{10a}$, a $C_1$-$C_{10}$ heterocycloalkenyl group unsubstituted or substituted with at least one $R_{10a}$, a $C_6$-$C_{60}$ aryl group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, a $C_1$-$C_{60}$ heteroaryl group unsubstituted or substituted with at least one $R_{10a}$, a monovalent non-aromatic condensed polycyclic group unsubstituted or substituted with at least one $R_{10a}$, a monovalent non-aromatic condensed heteropolycyclic group unsubstituted or substituted with at least one $R_{10a}$, —Si($Q_1$)($Q_2$)($Q_3$), —N($Q_1$)($Q_2$), —B($Q_1$)($Q_2$), —S(=O)$_2$($Q_1$), or —P(=O)($Q_1$)($Q_2$), c1 to c3 are each independently an integer from 1 to 5, c21 and c22 are each independently an integer from 1 to 4, and $R_{10a}$ is:

deuterium (-D), —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{11}$)($Q_{212}$)($Q_{13}$), —N($Q_{11}$)($Q_{12}$), —B($Q_{11}$)($Q_{12}$), —C(=O)($Q_{11}$), —S(=O)$_2$($Q_{11}$), —P(=O)($Q_{11}$)($Q_{12}$), or any combination thereof;

a $C_3$-$C_{60}$ carbocyclic group, a $C_1$-$C_{60}$ heterocyclic group, a $C_6$-$C_{60}$ aryloxy group, or a $C_6$-$C_{60}$ arylthio group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_{6-60}$ aryloxy group, a $C_6$-$C_{60}$ arylthio group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), —P(=O)($Q_{21}$)($Q_{22}$), or any combination thereof; or —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$), and wherein $Q_1$ to $Q_3$, $Q_{11}$ to $Q_{13}$, $Q_{21}$ to $Q_{23}$, and $Q_{31}$ to $Q_{33}$ are each independently hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; or a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof, and

* indicates a binding site to an adjacent atom.

20. The heterocyclic compound of claim 8, wherein the heterocyclic compound is selected from Compounds 1 to 60:

1

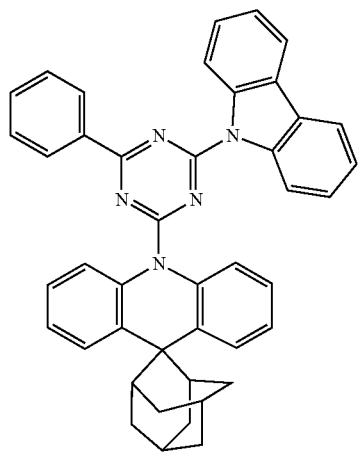

2

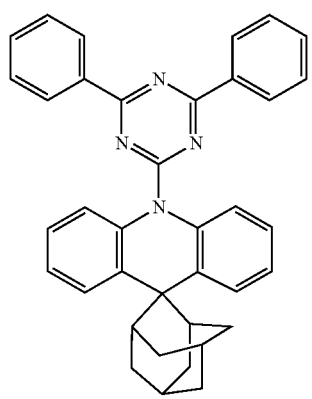

3

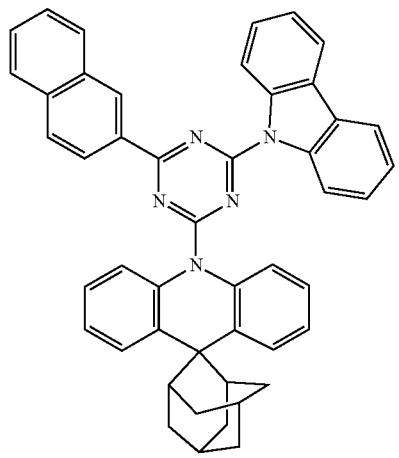

-continued

4

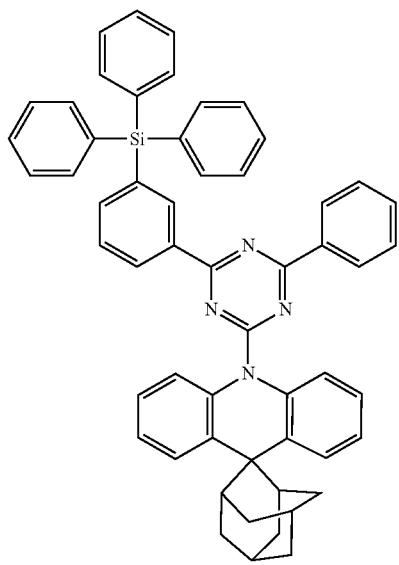

5

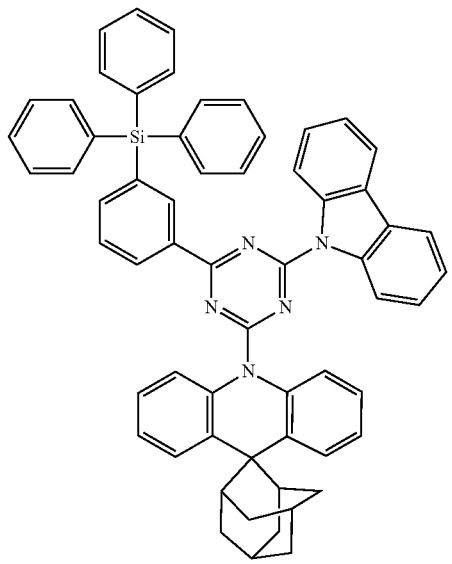

221
-continued
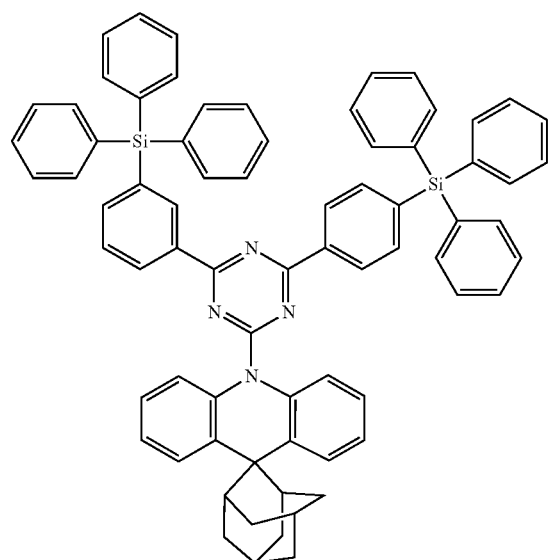
6
222
-continued
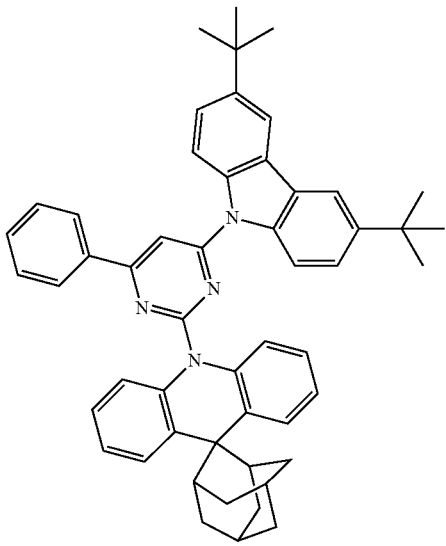
8
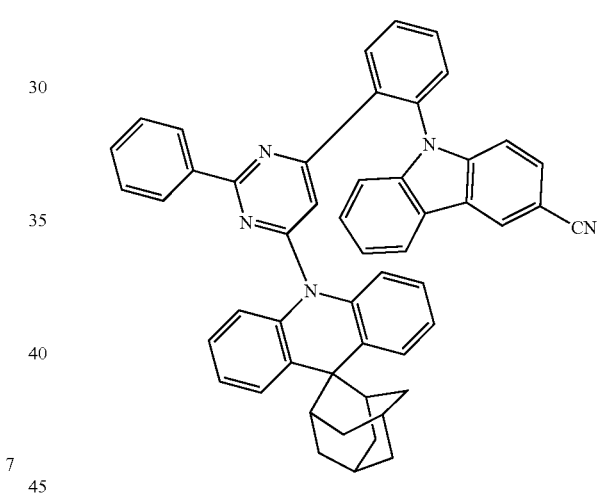
9
7
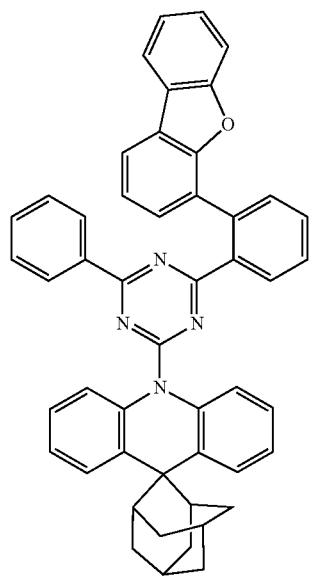
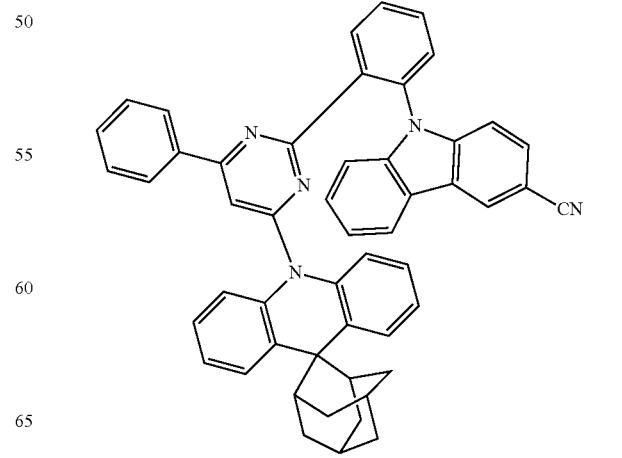
10

11
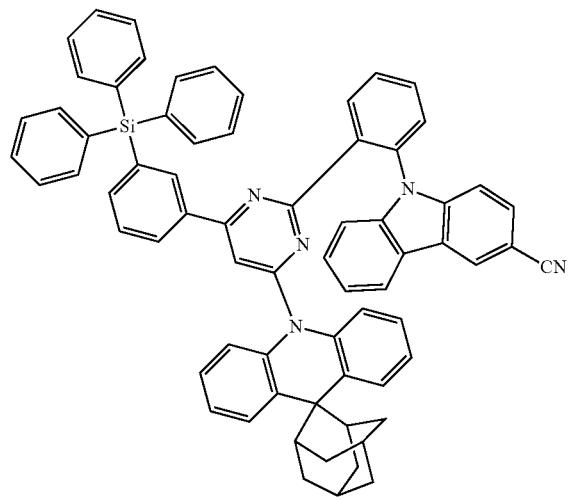
12
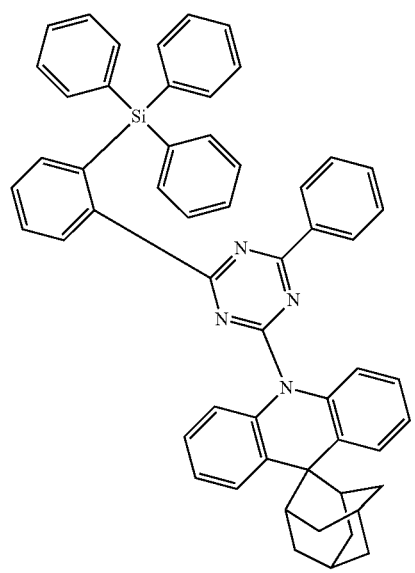
13
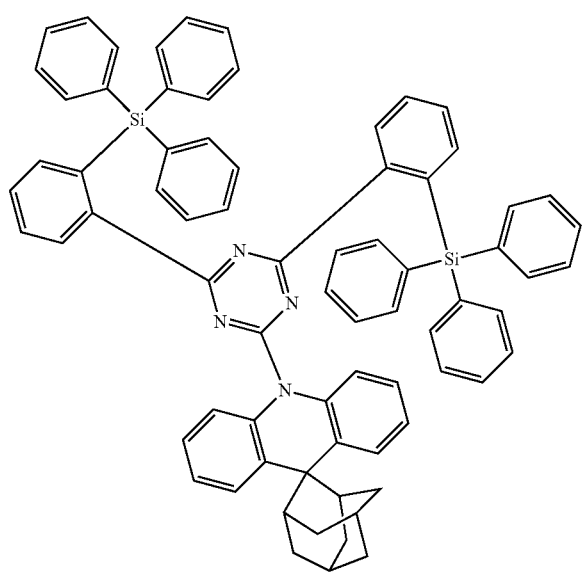
14
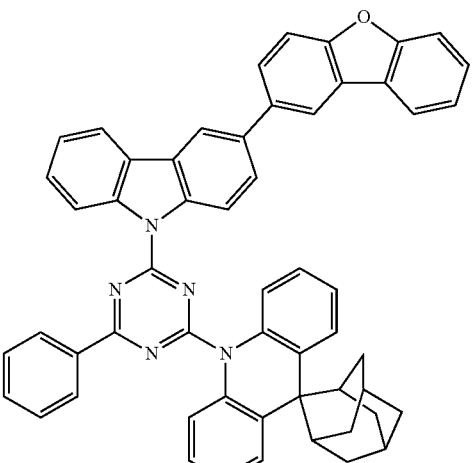
15
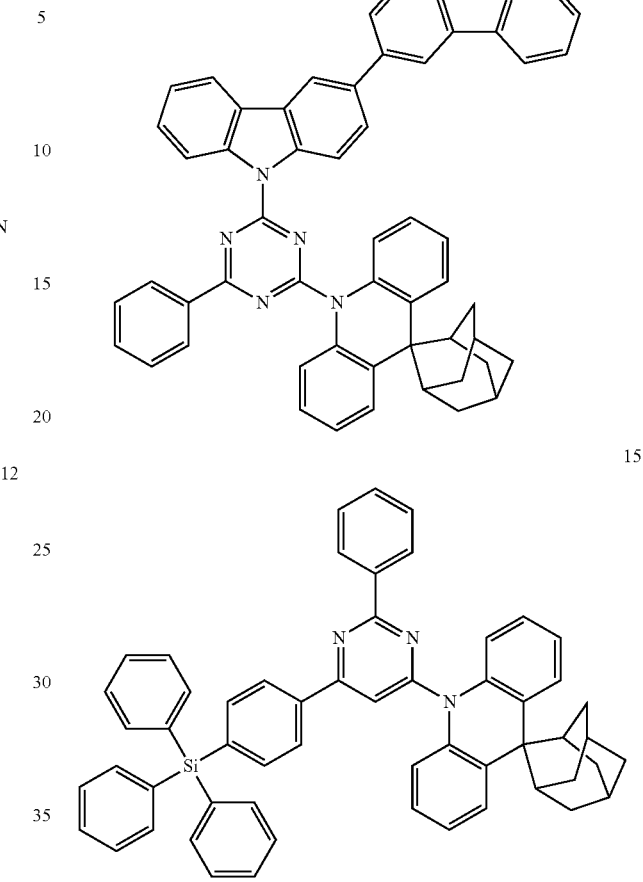
16
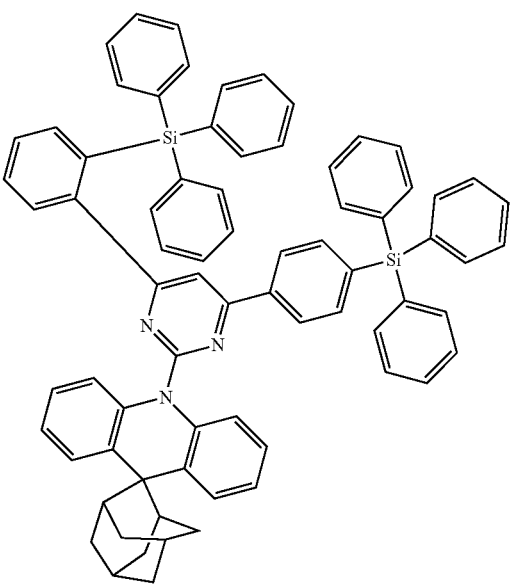

17
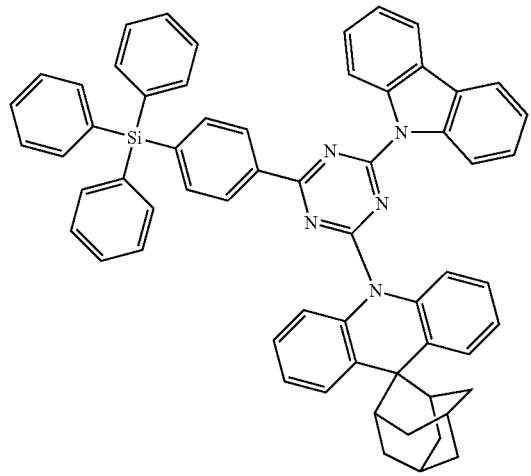
18
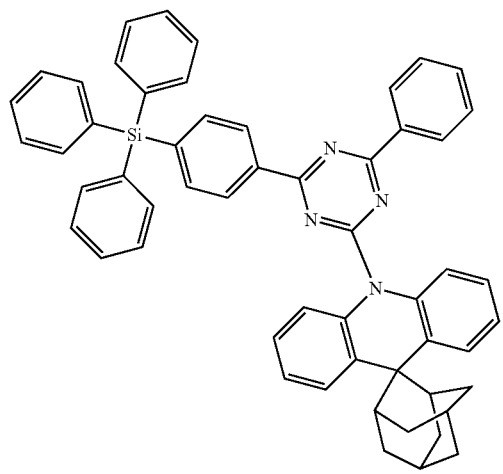
19
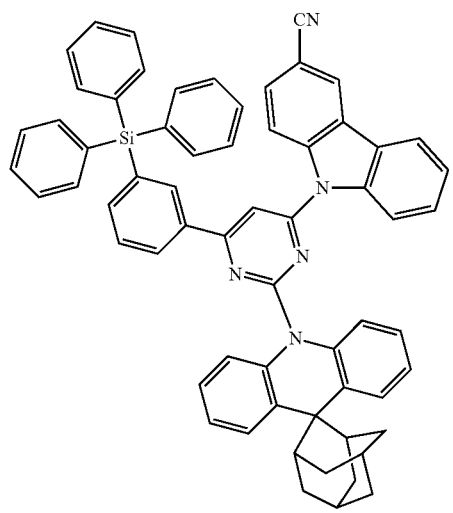
20
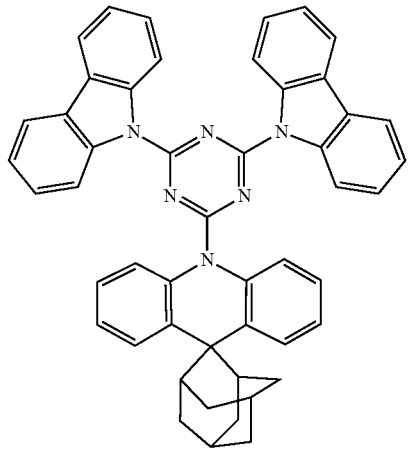
21
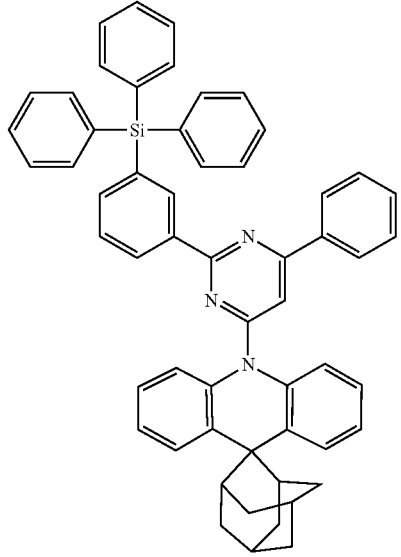
22
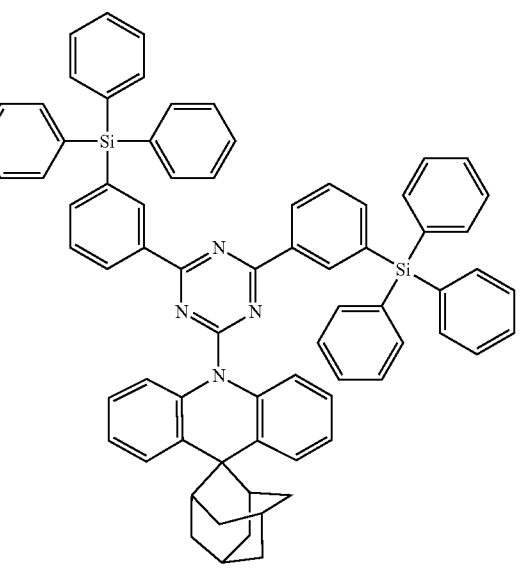

227 -continued
23
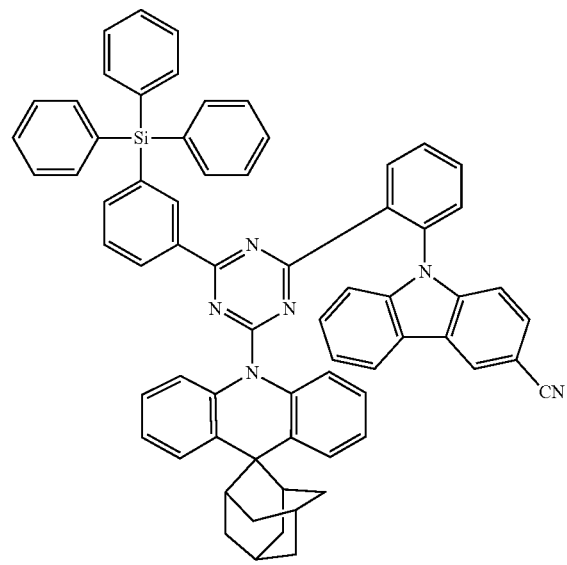
24
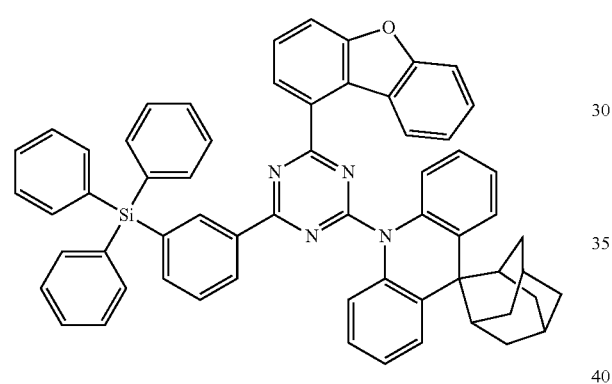
25
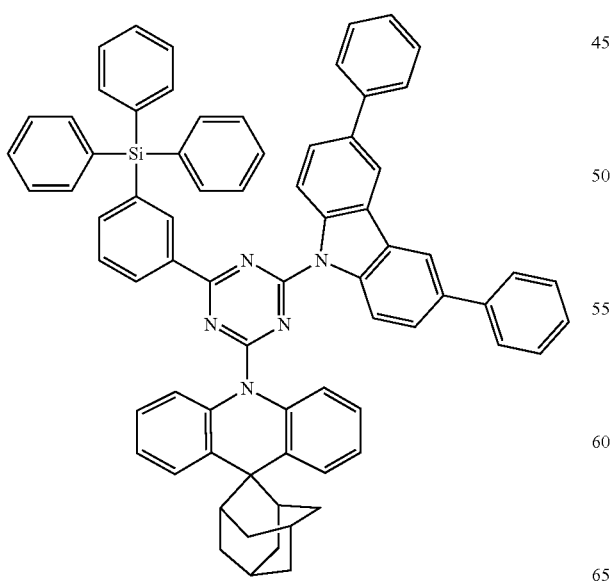
228 -continued
26
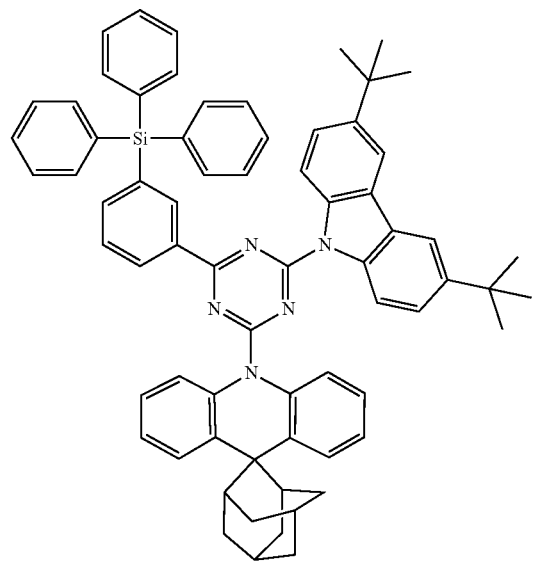
27
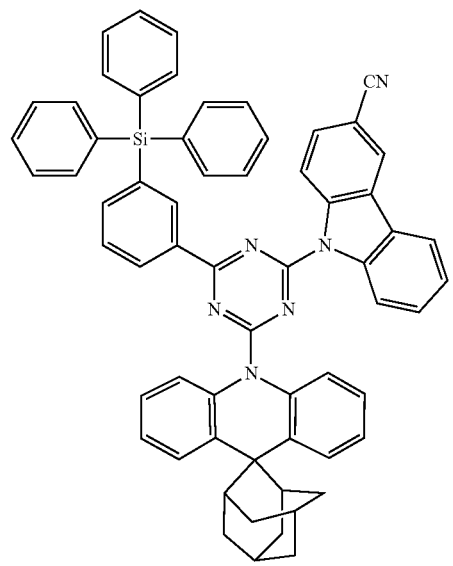

28
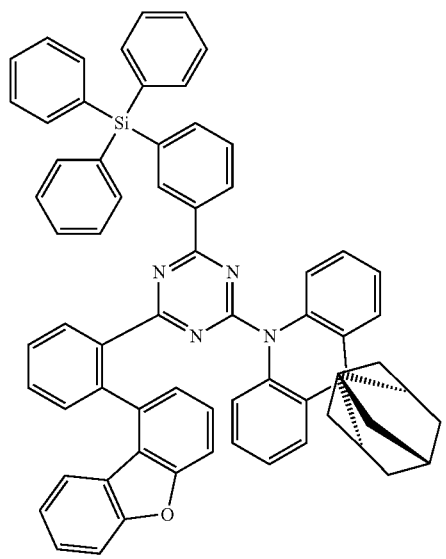
29
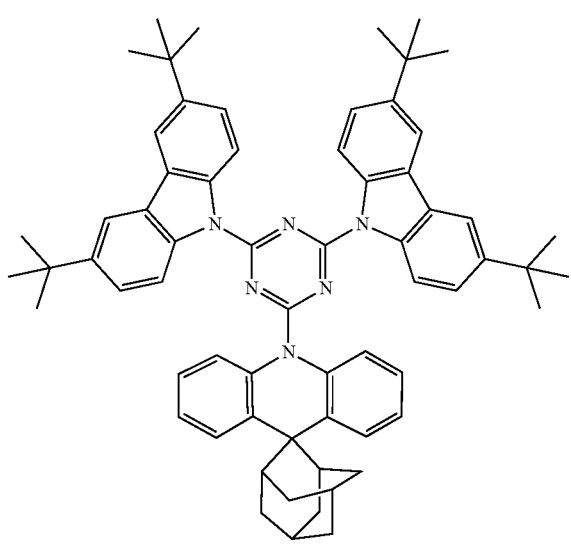
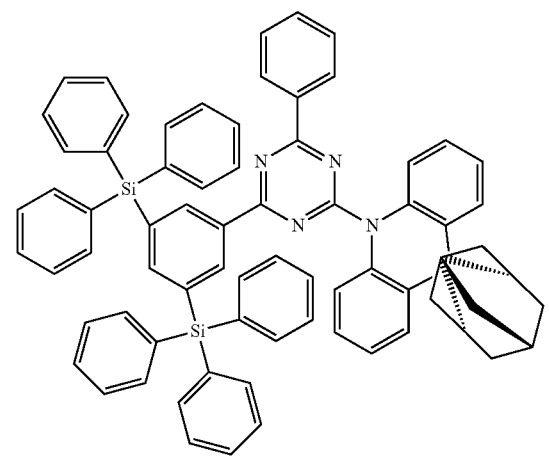
31
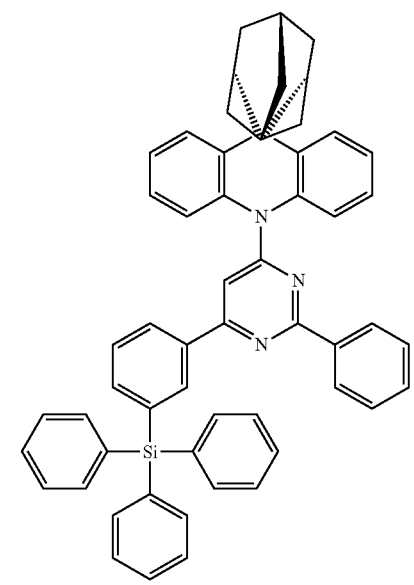
32
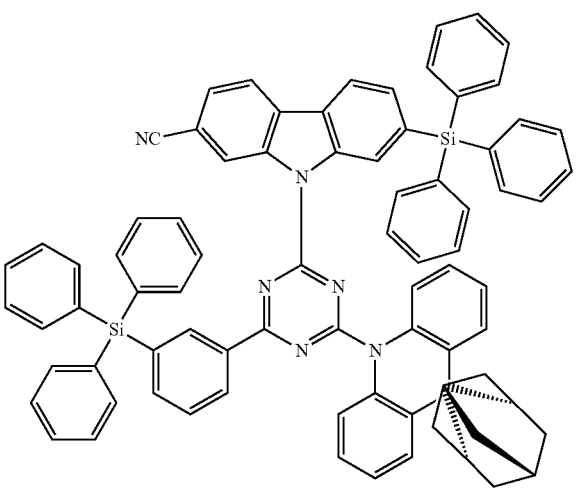
33
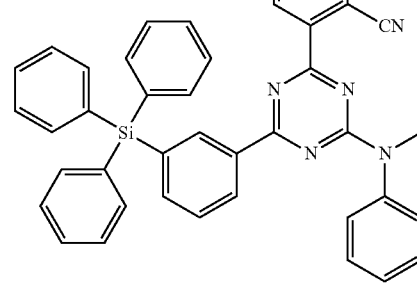

231
-continued
34
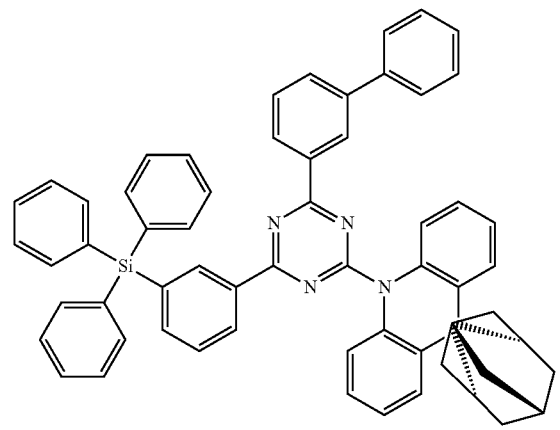
35
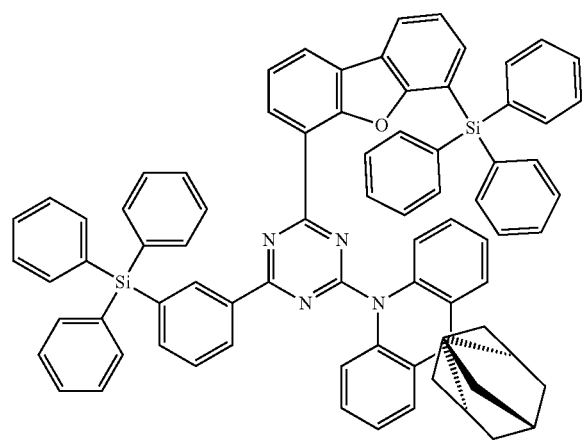
36
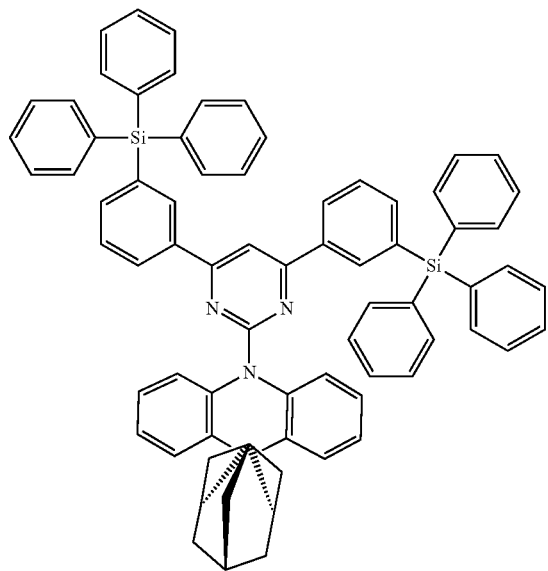
232
-continued
37
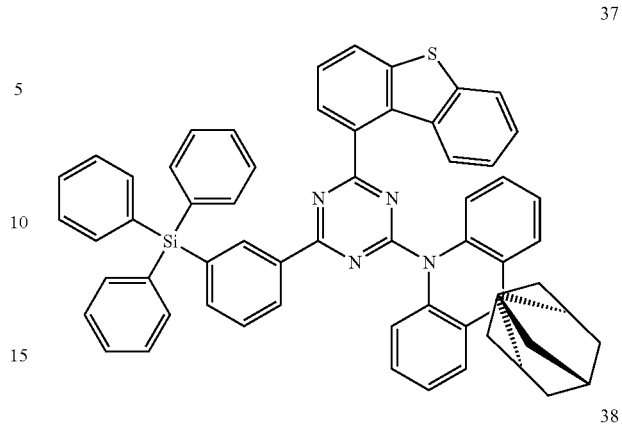
38
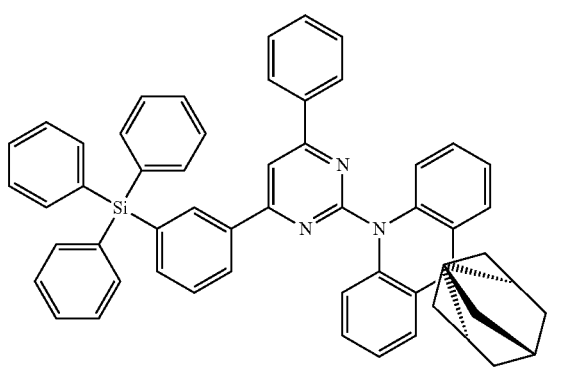
39
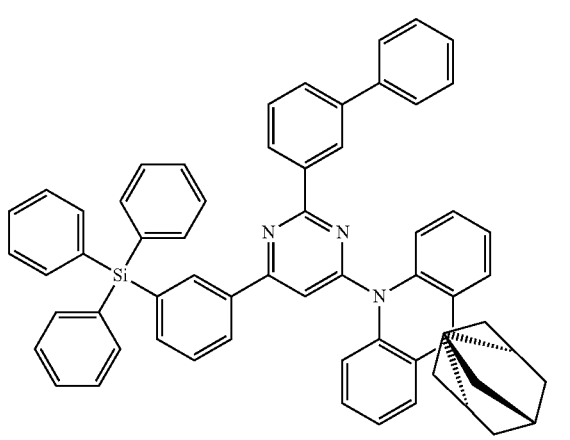
40
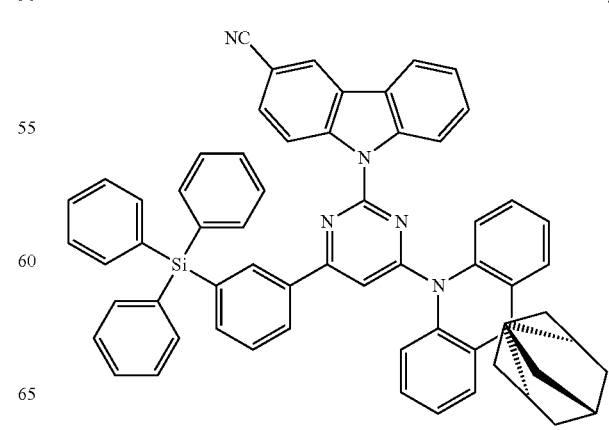

233
-continued
234
-continued
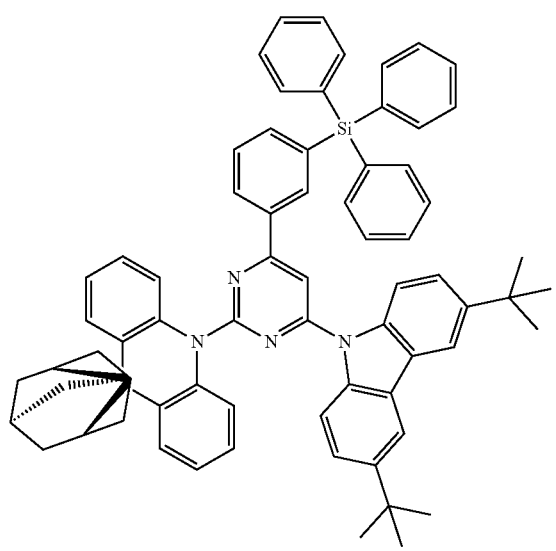
41
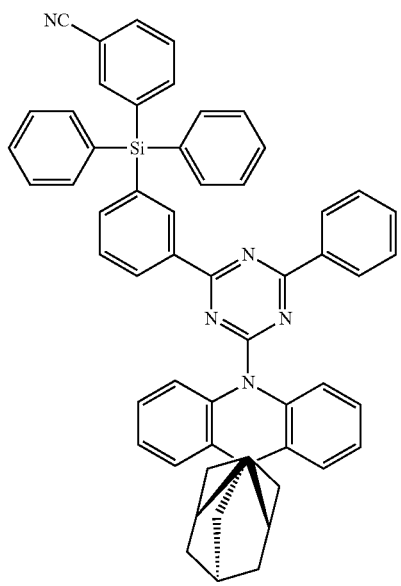
43
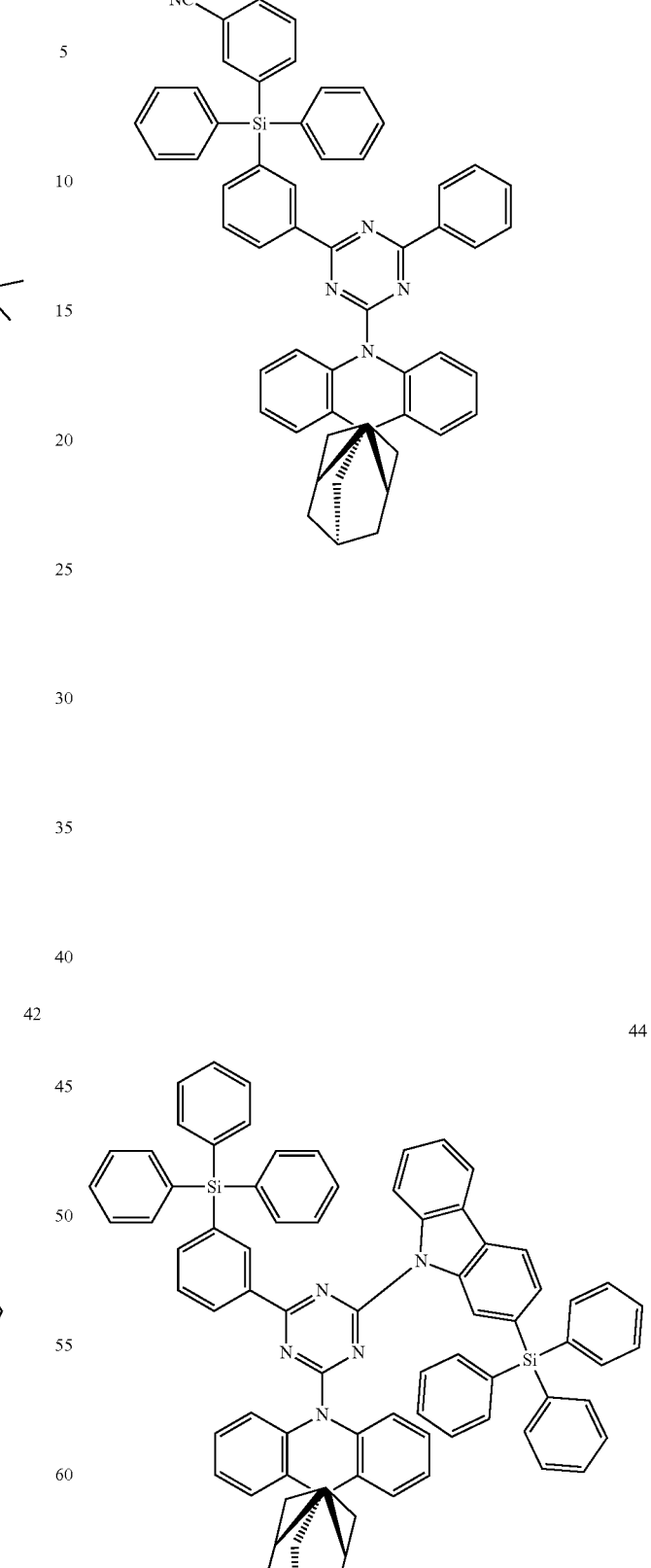

45
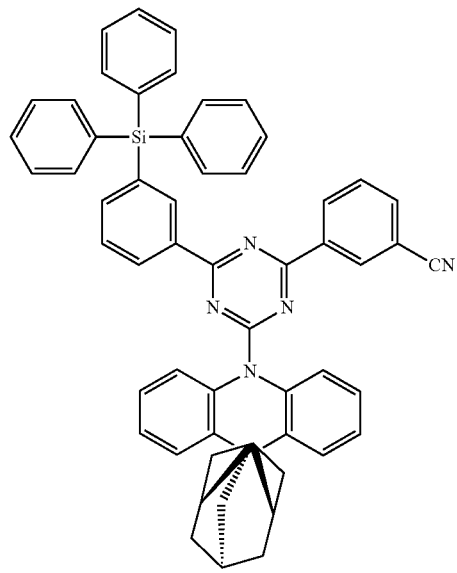
46
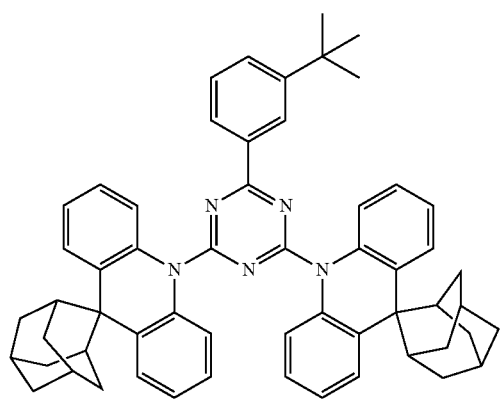
47
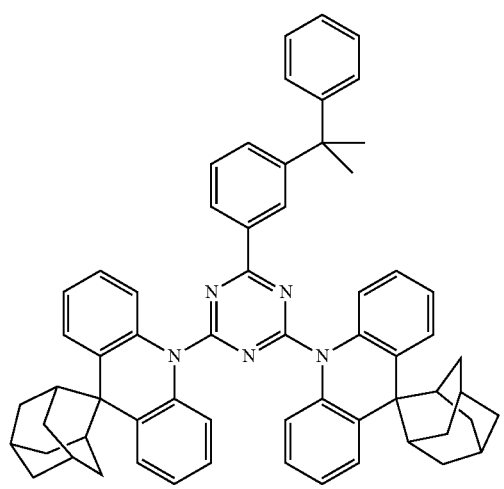
48
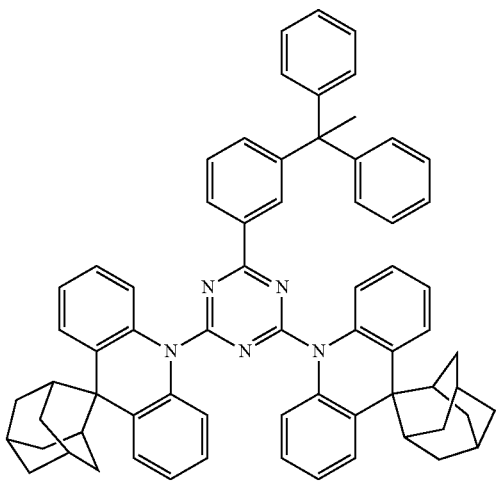
49
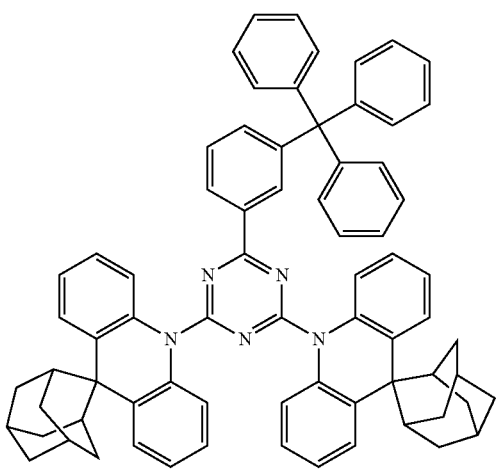
50
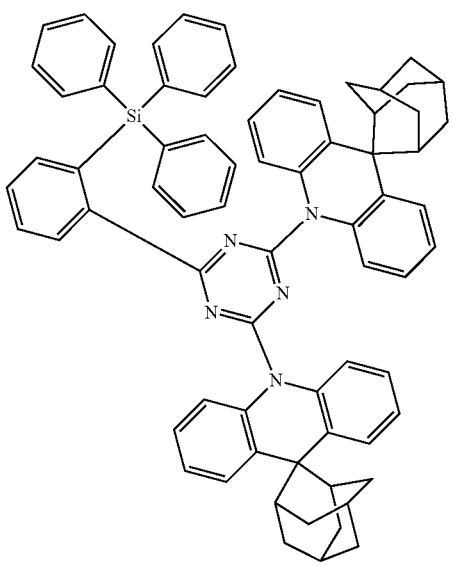

-continued
51
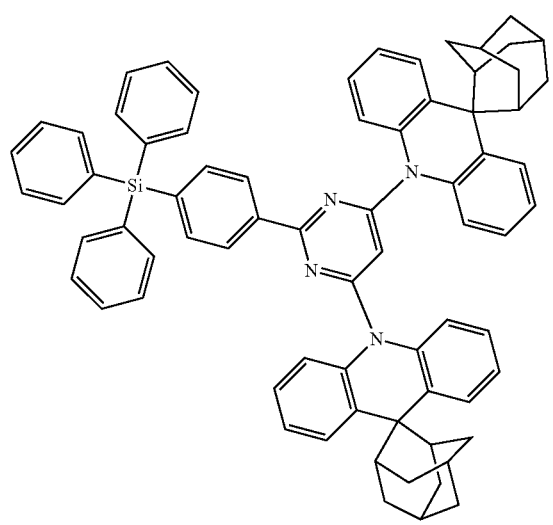
52
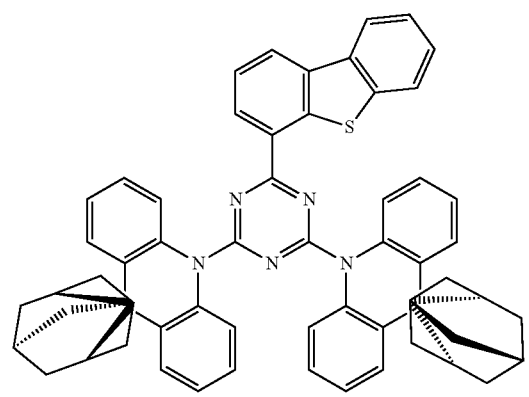
53
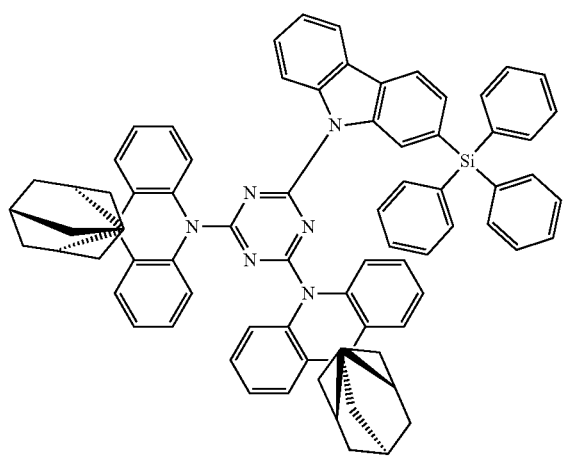
-continued
54
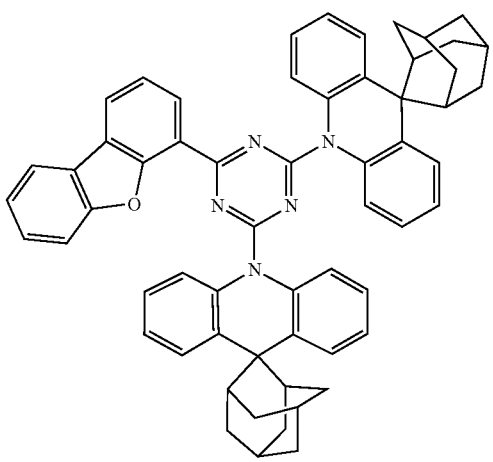
55
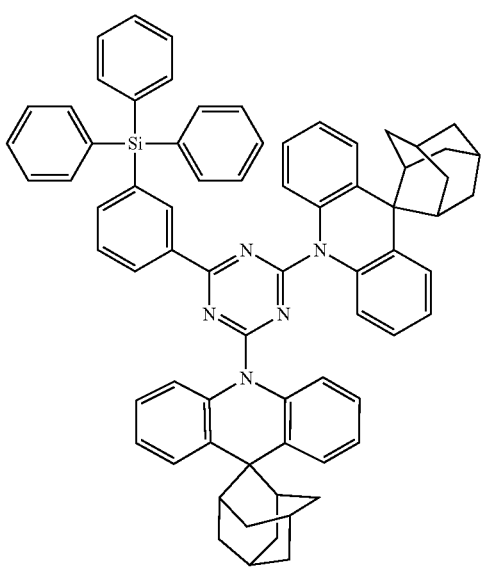
56
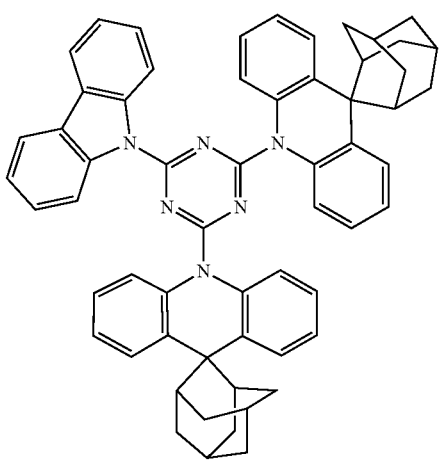

57
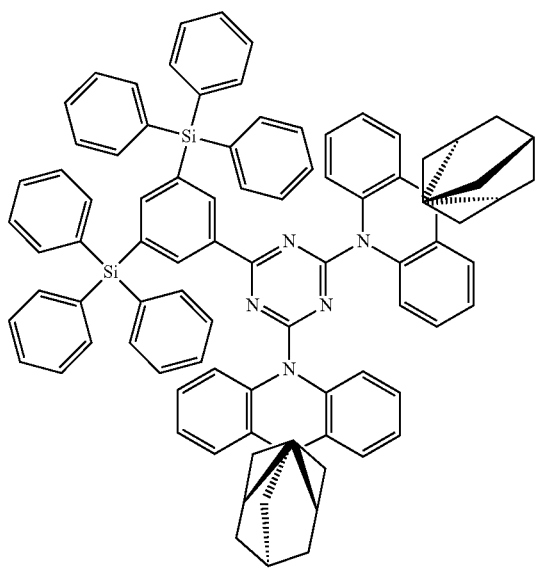
58
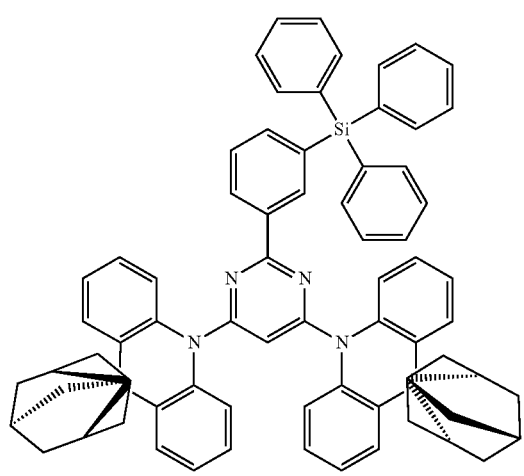
59
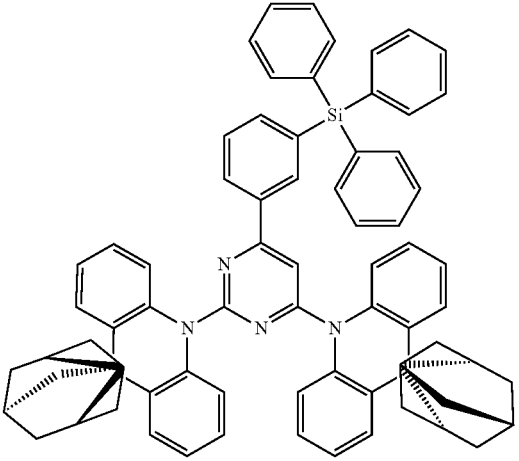
60
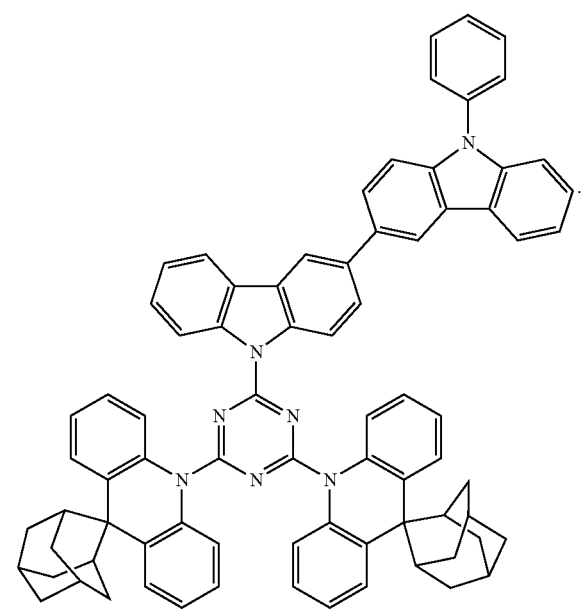
* * * * *